US010844400B2

(12) United States Patent
De Framond et al.

(10) Patent No.: US 10,844,400 B2
(45) Date of Patent: *Nov. 24, 2020

(54) CORN EVENT 5307

(71) Applicant: Syngenta Participations AG, Basel (CH)

(72) Inventors: Annick Jeanne De Framond, Durham, NC (US); Moez Rajabali Meghji, St. Louis, MO (US); Stephen L. New, Cary, NC (US); Anna Underwood Prairie, Durham, NC (US)

(73) Assignee: Syngenta Participation AG, Basel (CH)

( * ) Notice: Subject to any disclaimer, the term of this patent is extended or adjusted under 35 U.S.C. 154(b) by 27 days.

This patent is subject to a terminal disclaimer.

(21) Appl. No.: 16/126,171

(22) Filed: Sep. 10, 2018

(65) Prior Publication Data

US 2018/0371555 A1     Dec. 27, 2018

Related U.S. Application Data

(62) Division of application No. 14/815,345, filed on Jul. 31, 2015, now Pat. No. 10,100,371, which is a division of application No. 13/140,429, filed as application No. PCT/US2009/067873 on Dec. 14, 2009, now Pat. No. 9,133,474.

(60) Provisional application No. 61/122,885, filed on Dec. 16, 2008.

(51) Int. Cl.
*C12N 15/82*     (2006.01)

(52) U.S. Cl.
CPC .............................. *C12N 15/8286* (2013.01)

(58) Field of Classification Search
CPC .................................................. C12N 15/8286
See application file for complete search history.

(56) References Cited

U.S. PATENT DOCUMENTS

| | | | |
|---|---|---|---|
| 5,495,068 A | 2/1996 | Foley | |
| 5,736,131 A | 4/1998 | Bosch et al. | |
| 8,309,516 B2 * | 11/2012 | Hart | C07K 14/325 514/4.5 |
| 8,466,346 B2 * | 6/2013 | DeFramond | C12Q 1/6895 800/302 |
| 9,133,474 B2 | 9/2015 | Deframond et al. | |
| 2006/0141495 A1 | 6/2006 | Wu et al. | |
| 2010/0017914 A1 | 1/2010 | Hart et al. | |
| 2018/0112279 A1 | 4/2018 | De Framond et al. | |

FOREIGN PATENT DOCUMENTS

| | | |
|---|---|---|
| EP | 0942985 B1 | 9/2004 |
| EP | 2373153 | 5/2017 |
| WO | 9822595 A1 | 5/1998 |
| WO | 2007142840 A2 | 12/2007 |
| WO | 2008121633 A1 | 10/2008 |
| WO | 2010077816 A1 | 7/2010 |
| WO | 2011041256 A2 | 4/2011 |

OTHER PUBLICATIONS

Grimanelli et al., "Timing of the Maternal-to-Zygotic Transition during Early Seed Development in Maize," The Plant Cell, vol. 17, 1061-1072, Apr. 2005, Supplementary Table 1.
Corresponding to GenBank/EMBL Accession No. T14727 [Retrieved from the internet Oct. 18, 2013:<URL:http://ftp.gramene.org/archives/release26/data/maps/ibm2n04.tab] in entirety, 59 pp.
Song et al., Gene expression of a gene family in maize based on noncollinear haplotypes, Proceedings of the National Academy of Sciences of the United States of America (PNAS), Jul. 22, 2003, vol. 100, No. 15, pp. 9055-9060, ISSN: 0027-8424.
Genbank AC125584.2. Rattus norvegicus clone CH230-1 F2. Oct. 9, 2002. [Retrieved from the internet Oct. 5, 2011:<URL://www.ncbi.nlm.nih.gov/nuccore/2326310>] in entirety.
Genbank AC202540.4. Zea mays chromosome 3 clone ZMMBBb-133C10; ZMMBBb0133c10, *Sequencing in Progress *, 4 unordered pieces. Jun. 27, 2008. [Retrieved from the internet Oct. 5, 2011:<URL://www.ncbi.nlm.nih.gov/nuccore/160688634>] in entirety.
Genbank AC208695.3. Zea mays chromosome 4 clone ZMMBBb-318B2; ZMMBBb0318B02, * Sequencing in Progress *, 4 unordered pieces. Jun. 27, 2008 [Retrieved from the internet Oct. 5, 2011:<URL://www.ncbi.nlm.nih.gov/nuccore/189908068>] in entirety.
Fu et al., 2002, Proceedings of the National Academy of Science, USA, 99, 14, 9573-9578.
R.K. Wilson, Sep. 2013, GenBank Accession No. AC202955.4 (version 4), National Center for Biotechnology Information, National Institutes of Health, U.S.A.

* cited by examiner

*Primary Examiner* — David H Kruse
(74) *Attorney, Agent, or Firm* — Karen A. Magri

(57) ABSTRACT

A novel transgenic corn event designated 5307, is disclosed. The invention relates to DNA sequences of the recombinant constructs inserted into the corn genome and of genomic sequences flanking the insertion site that resulted in the 5307 event. The invention further relates to assays for detecting the presence of the DNA sequences of event 5307, to corn plants and corn seeds comprising the genotype of and to methods for producing a corn plant by crossing a corn plant comprising the event 5307 genotype with itself or another corn variety.

7 Claims, 2 Drawing Sheets

Specification includes a Sequence Listing.

Plasmid map of pSYN12274.

Insert map of Event 5307.

CORN EVENT 5307

RELATED APPLICATION INFORMATION

This application is a divisional of co-pending U.S. patent application Ser. No. 14/815,345 filed Jul. 31, 2015 (allowed), which is a divisional of U.S. patent application Ser. No. 13/140,429 (now U.S. Pat. No. 9,133,474 B2), which is a national stage filing under 35 U.S.C. § 371 of International Application No. PCT/US2009/067873, filed Dec. 14, 2009 and published Jul. 8, 2010 as WO 2010/077816, which claims the benefit of U.S. Provisional Application Ser. No. 61/122,885, filed Dec. 16, 2008, the contents of each of which are incorporated herein by reference in their entireties.

STATEMENT REGARDING ELECTRONIC SUBMISSION OF A SEQUENCE LISTING

A sequence listing in ASCII text format, submitted under 37 C.F.R. § 1.821, entitled "71922-US-REG-D-P-4_SEQ LIST_ST25.txt", 445 KB in size, generated on Sep. 7, 2018, and filed via EFS-Web is provided in lieu of a paper copy. This sequence listing is hereby incorporated by reference into the specification for its disclosures.

FIELD OF THE INVENTION

The invention relates generally to the field of plant molecular biology, plant transformation, and plant breeding. More specifically, the invention relates to insect resistant transgenic corn plants comprising a novel transgenic genotype and to methods of detecting the presence of the corn plant DNA in a sample and compositions thereof.

BACKGROUND

Plant pests are a major factor in the loss of the world's important agricultural crops. About $8 billion are lost every year in the U.S. alone due to infestations of non-mammalian pests including insects. Species of corn rootworm are considered the most destructive corn pests. Important rootworm pest species include *Diabrotica virgifera virgifera*, the western corn rootworm; *D. longicornis barberi*, the northern corn rootworm, *D. undecimpunctata howardi*, the southern corn rootworm, and *D. virgifera zeae*, the Mexican corn rootworm.

Corn rootworm is mainly controlled by intensive applications of chemical pesticides. Good corn rootworm control can thus be reached, but these chemicals can sometimes also affect beneficial organisms. Another problem resulting from the wide use of chemical pesticides is the appearance of resistant insect varieties. This has been partially alleviated by various resistance management practices, but there is an increasing need for alternative pest control strategies. One such alternative includes the expression of foreign genes encoding insecticidal proteins in transgenic plants. This approach has provided an efficient means of protection against selected insect pests, and transgenic plants expressing insecticidal toxins have been commercialized, allowing farmers to reduce applications of chemical insecticides.

The expression of foreign genes in plants can to be influenced by their chromosomal position, perhaps due to chromatin structure or the proximity of transcriptional regulation elements close to the integration site (See for example, Weising et al., 1988, "Foreign Genes in Plants," Ann. Rev. Genet. 22:421-477). Therefore, it is common to produce hundreds of different events and screen those events for a single event that has desired transgene expression levels and patterns for commercial purposes. An event that has desired levels or patterns of transgene expression is useful for introgressing the transgene into other genetic backgrounds by sexual outcrossing using conventional breeding methods. Progeny of such crosses maintain the transgene expression characteristics of the original transformant. This strategy is used to ensure reliable gene expression in a number of varieties that are well adapted to local growing conditions.

It would be advantageous to be able to detect the presence of a particular event in order to determine whether progeny of a sexual cross contain a transgene of interest. In addition, a method for detecting a particular event would be helpful for complying with regulations requiring the pre-market approval and labeling of foods derived from recombinant crop plants, for example. It is possible to detect the presence of a transgene by any well-known nucleic acid detection method including but not limited to thermal amplification (polymerase chain reaction (PCR)) using polynucleotide primers or DNA hybridization using nucleic acid probes. Typically, for the sake of simplicity and uniformity of reagents and methodologies for use in detecting a particular DNA construct that has been used for transforming various plant varieties, these detection methods generally focus on frequently used genetic elements, for example, promoters, terminators, and marker genes, because for many DNA constructs, the coding sequence region is interchangeable. As a result, such methods may not be useful for discriminating between constructs that differ only with reference to the coding sequence. In addition, such methods may not be useful for discriminating between different events, particularly those produced using the same DNA construct unless the sequence of chromosomal DNA adjacent to the inserted heterologous DNA ("flanking DNA") is known.

The invention includes an insect resistant transgenic corn event that has incorporated into its genome a FR8a gene, disclosed in International Publication No. WO 08/121633, published Oct. 9, 2008, which is herein incorporated by reference, encoding a FR8a insecticidal toxin, useful in controlling *Diabrotica* spp. insect pests. The transgenic corn event also has incorporated in its genome a PMI gene, encoding a phosphomannose isomerase enzyme (PMI), disclosed in U.S. Pat. No. 5,767,378, which is herein incorporated by reference, useful as a selectable marker, which allows the plant to utilize mannose as a carbon source. The invention further includes novel isolated nucleic acid sequences which are unique to the transgenic corn event, useful for identifying the transgenic corn event and for detecting nucleic acids from the transgenic corn event in a biological sample, as well as kits comprising the reagents necessary for use in detecting these nucleic acids in a biological sample.

SUMMARY

The invention is drawn to a transgenic corn event, designated 5307, comprising a novel transgenic genotype that comprises a FR8a gene and a PMI gene which confers insect resistance and the ability to utilize mannose as a carbon source, respectively, to the 5307 corn event and progeny thereof. The invention also provides transgenic corn plants comprising the genotype of the invention, seed from transgenic corn plants comprising the genotype of the invention, and to methods for producing a transgenic corn plant comprising the genotype of the invention by crossing a corn inbred comprising the genotype of the invention with itself or another corn line of a different genotype. The transgenic corn plants of the invention may have essentially all of the morphological and physiological characteristics of the corresponding isogenic non-transgenic corn plant in addition to those conferred upon the corn plant by the novel genotype of the invention. The invention also provides compositions and methods for detecting the presence of nucleic acids from event 5307 based on the DNA sequence of the recombinant expression cassettes inserted into the corn genome that resulted in the 5307 event and of genomic sequences flanking the insertion site. The 5307 event can be further characterized by analyzing expression levels of FR8a and PMI proteins as well as by testing efficacy against corn rootworm.

According to one aspect, the invention provides a preferably isolated nucleic acid molecule comprising at least 10 contiguous nucleotides of a heterologous DNA sequence inserted into the corn plant genome of corn event 5307 and at least 10 contiguous nucleotides of a corn plant genome DNA flanking the point of insertion of a heterologous DNA sequence inserted into the corn plant genome of corn event 5307. The preferably isolated nucleic acid molecule according to this aspect may comprise at least 20 or at least 50 contiguous nucleotides of a heterologous DNA sequence inserted into the corn plant genome of corn event 5307 and at least 20 or at least 50 contiguous nucleotides of a corn plant genome DNA flanking the point of insertion of a heterologous DNA sequence inserted into the corn plant genome of corn event 5307.

According to another aspect, the invention provides a preferably isolated nucleic acid molecule comprising at least one junction sequence of event 5307 selected from the group consisting of SEQ ID NO: 1 and SEQ ID NO: 2, and complements thereof. A junction sequence spans the junction between the heterologous DNA comprising the expression cassettes inserted into the corn genome and DNA from the corn genome flanking the insertion site and is diagnostic for the 5307 event.

According to another aspect, the invention provides a preferably isolated nucleic acid linking a heterologous DNA molecule to the corn plant genome in corn event 5307 comprising a sequence of from about 11 to about 20 contiguous nucleotides selected from the group consisting of SEQ ID NO: 1, SEQ ID NO: 2, and complements thereof.

According to another aspect, the invention provides a preferably isolated nucleic acid molecule comprising a nucleotide sequence selected from the group consisting of SEQ ID NO: 1, SEQ ID NO: 2, SEQ ID NO: 3, SEQ ID NO: 4, and complements thereof.

According to another aspect of the invention, an amplicon comprising a nucleic acid molecule of the invention is provided.

According to still another aspect of the invention, flanking sequence primers for detecting event 5307 are provided. Such flanking sequence primers comprise a preferably isolated nucleic acid sequence comprising at least 10-15 contiguous nucleotides from nucleotides 1-1348 as set forth in SEQ ID NO: 5 (arbitrarily designated herein as the 5' flanking sequence), or the complements thereof, also disclosed as SEQ ID NO: 111. In one embodiment of this aspect the flanking sequence primers are selected from the group consisting of SEQ ID NO: 9 through SEQ ID NO: 14, and complements thereof.

In another aspect of the invention, the flanking sequences primers comprise a preferably isolated nucleic acid sequence comprising at least 10-15 contiguous nucleotides from nucleotides 1-1093 as set forth in SEQ ID NO: 6 (arbitrarily designated herein as the 3' flanking sequence), or the complements thereof. In one embodiment of this aspect the flanking sequence primers are selected from the group consisting of SEQ ID NO: 69 through SEQ ID NO: 72, and complements thereof.

According to another aspect of the invention, primer pairs that are useful for nucleic acid amplification, for example, are provided. Such primer pairs comprise a first primer comprising a nucleotide sequence of at least 10-15 contiguous nucleotides in length which is or is complementary to one of the above-described genomic flanking sequences (SEQ ID NO: 5, or SEQ ID NO: 6) and a second primer comprising a nucleotide sequence of at least 10-15 contiguous nucleotides of heterologous DNA inserted into the event 5307 genome. The second primer preferably comprises a nucleotide sequence which is or is complementary to the insert sequence adjacent to the plant genomic flanking DNA sequence as set forth in SEQ ID NO: 7. In one embodiment of this aspect the insert sequence primers are selected from the group consisting of SEQ ID NO: 15 through SEQ ID NO: 68, and complements thereof.

According to another aspect of the invention, methods of detecting the presence of DNA corresponding to event 5307 in a biological sample are provided. Such methods comprise: (a) contacting the sample comprising DNA with a pair of primers that, when used in a nucleic acid amplification reaction with genomic DNA from corn event 5307; produces an amplicon that is diagnostic for corn event 5307; (b) performing a nucleic acid amplification reaction, thereby producing the amplicon; and (c) detecting the amplicon. In one embodiment of this aspect, the amplicon comprises a nucleotide sequence selected from the group consisting of SEQ ID NO: 1, SEQ ID NO: 2, SEQ ID NO: 3, SEQ ID NO: 4, SEQ ID NO: 5, SEQ ID NO: 6, and complements thereof.

According to another aspect, the invention provides methods of detecting the presence of a DNA corresponding to the 5307 event in a biological sample. Such methods comprise: (a) contacting the sample comprising DNA with a probe that hybridizes under high stringency conditions with genomic DNA from corn event 5307 and does not hybridize under high stringency conditions with DNA of a control corn plant; (b) subjecting the sample and probe to high stringency hybridization conditions; and (c) detecting hybridization of the probe to the DNA. The detected hybridized DNA sequence includes at least one polynucleotide sequence comprising SEQ ID NO: 1, SEQ ID NO: 2, SEQ ID NO: 3, SEQ ID NO: 4, SEQ ID NO: 5, SEQ ID NO: 6, and complements thereof.

According to another aspect of the invention, a kit is provided for the detection of event 5307 nucleic acids in a biological sample. The kit includes at least one DNA sequence comprising a sufficient length of polynucleotides which is or is complementary to SEQ ID NO: 1, SEQ ID NO: 2, SEQ ID NO: 3, SEQ ID NO: 4, SEQ ID NO: 5 or SEQ ID NO: 6, wherein the DNA sequences are useful as primers or probes that hybridize to isolated DNA from event 5307, and which, upon amplification of or hybridization to a nucleic acid sequence in a sample followed by detection of the amplicon or hybridization to the target sequence, are diagnostic for the presence of nucleic acid sequences from event 5307 in the sample. The kit further includes other materials necessary to enable nucleic acid hybridization or amplification methods.

In another aspect, the invention provides a method of detecting corn event 5307 protein in a biological sample comprising: (a) extracting protein from a sample of corn event 5307 tissue; (b) assaying the extracted protein using an immunological method comprising antibody specific for the insecticidal or selectable marker protein produced by the 5307 event; and (c) detecting the binding of said antibody to the insecticidal or selectable marker protein.

In another aspect, the invention provides a biological sample derived from a event 5307 corn plant, tissue, or seed, wherein the sample comprises a nucleic acid comprising a nucleotide sequence which is or is complementary to a sequence selected from the group consisting of SEQ ID NO: 1 and SEQ ID NO: 2, and wherein the sequence is detectable in the sample using a nucleic acid amplification or nucleic acid hybridization method. In one embodiment of this aspect, the sample is selected from the group consisting of corn flour, corn meal, corn syrup, corn oil, cornstarch, and cereals manufactured in whole or in part to contain corn by-products.

In another aspect, the invention provides an extract derived from a event 5307 corn plant, tissue, or seed comprising a nucleotide sequence which is or is complementary to a nucleotide sequence selected from the group consisting of SEQ ID NO: 1 and SEQ ID NO: 2. In one embodiment of this aspect, the sequence is detectable in the extract using a nucleic acid amplification or nucleic acid hybridization method. In another embodiment of this aspect, the sample is selected from the group consisting of corn flour, corn meal, corn syrup, corn oil, cornstarch, and cereals manufactured in whole or in part to contain corn by-products.

According to another aspect of the invention, corn plants and seeds comprising the nucleic acid molecules of the invention are provided. In one embodiment of the invention, a deposit of event 5307 corn seed was made to the American Type Culture Collection (ATCC) in accordance with the Budapest Treaty on 15 Oct. 2008. An example of said seed being deposited as ATCC Accession No: PTA-9561.

According to another aspect, the invention provides a method for producing a corn plant resistant to at least corn rootworm infestation comprising: (a) sexually crossing a first parent corn plant with a second parent corn plant, wherein first or second parent corn plant comprises corn event 5307 DNA, thereby producing a plurality of first generation progeny plants; (b) selecting a first generation progeny plant that is resistant to at least corn rootworm infestation; (c) selfing the first generation progeny plant, thereby producing a plurality of second generation progeny plants; (d) selecting from the second generation progeny plants, a plant that is at least resistant to corn rootworm infestation; wherein the second generation progeny plants comprise a nucleotide sequence selected from the group consisting of SEQ ID NO: 1, SEQ ID NO: 2, SEQ ID NO: 3 and SEQ ID NO: 4.

According to yet another aspect, the invention provides a method for producing corn seed comprising crossing a first parent corn plant with a second parent corn plant and harvesting the resultant first generation corn seed, wherein the first or second parent corn plant is an inbred corn plant of the invention.

According to another aspect, the invention provides a method of producing hybrid corn seeds comprising the steps of: (a) planting seeds of a first inbred corn line according to the invention and seeds of a second inbred corn line having a different genotype; (b) cultivating corn plants resulting from said planting until time of flowering; (c) emasculating flowers of corn plants of one of the corn inbred lines; (d) allowing pollination of the other inbred line to occur, and (e) harvesting the hybrid seed produced thereby.

According to another aspect of the invention, the invention provides a method of selecting corn plants and seeds comprising the nucleic acid molecules of event 5307 on chromosome 5. In one embodiment of the invention, polymorphic markers are used to select or track the sequences specific to the 5307 corn event. The invention provides a method of selecting sequences specific to the 5307 corn event comprising the steps of: (a) detecting a polymorphic marker sequence; (b) designing an assay for the purposes of detecting the marker; (c) running the assay on corn nucleic acid sequences from many corn lines, and (d) selecting corn lines based upon the sequences with nucleotides specific to corn event 5307.

According to another aspect of the invention, the invention provides a site on chromosome 5 for targeted integration of a heterologous nucleic acid. The invention provides a method of selecting sequences specific to the 5307 corn event for targeted integration comprising the steps of: (a) designing homologous sequences based on the insertion site or vector sequence; (b) using these homologous sequences at a target locus; (c) using zinc finger nucleases to create a break in the target locus, and (d) inserting a heterologous donor molecule within nucleotides specific to corn event 5307 or the vector sequence of pSYN12274. An example of this technique is demonstrated in Shukla et al. (Nature vol. 459, 21 May 2009).

The foregoing and other aspects of the invention will become more apparent from the following detailed description.

DESCRIPTION OF THE SEQUENCES IN THE SEQUENCE LISTING

SEQ ID NO: 1 is the 5' genome-insert junction.
SEQ ID NO: 2 is the 3' insert-genome junction.
SEQ ID NO: 3 is the 5' genome+insert sequence.
SEQ ID NO: 4 is the 3' insert+genome sequence.
SEQ ID NO: 5 is the 5' genome+insert sequence.
SEQ ID NO: 6 is the 3' corn genome flanking sequence.
SEQ ID NO: 7 is the event 5307 full length insert.
SEQ ID Nos: 8-14 are 5' flanking sequence primers useful in the invention.
SEQ ID Nos: 15-68 are 5307 transgene insert primers useful in the invention.
SEQ ID Nos: 69-72 are 3' flanking sequence primers useful in the invention.
SEQ ID Nos: 73-75 are FR8a TAQMAN primers and probe.
SEQ ID Nos: 76-78 are PMI TAQMAN primers and probe.
SEQ ID Nos: 79-81 are ZmAdh TAQMAN primers and probe.
SEQ ID Nos: 82-90 are 5307 event specific primers and probes useful in the invention.
SEQ ID Nos: 91-102 are corn genomic primers and probes useful in the invention.
SEQ ID NO: 103 is the AC202955 Chromosome 5 Sequence, where N is any base "A", "T", "G" or "C".
SEQ ID NO: 104 is the umc1475 marker region.
SEQ ID Nos: 105-106 are umc1475 primers.
SEQ ID NO: 107 is the uaz190 marker region.
SEQ ID NOs: 108-109 are uaz190 primers
SEQ ID NO: 110 is the reverse complement of SEQ ID NO: 103, AC202955 Chromosome 5 Sequence, where N is any base "A", "T", "G" or "C".
SEQ ID NO: 111 is the 5' corn genome flanking sequence.

DEFINITIONS

Figure 1:
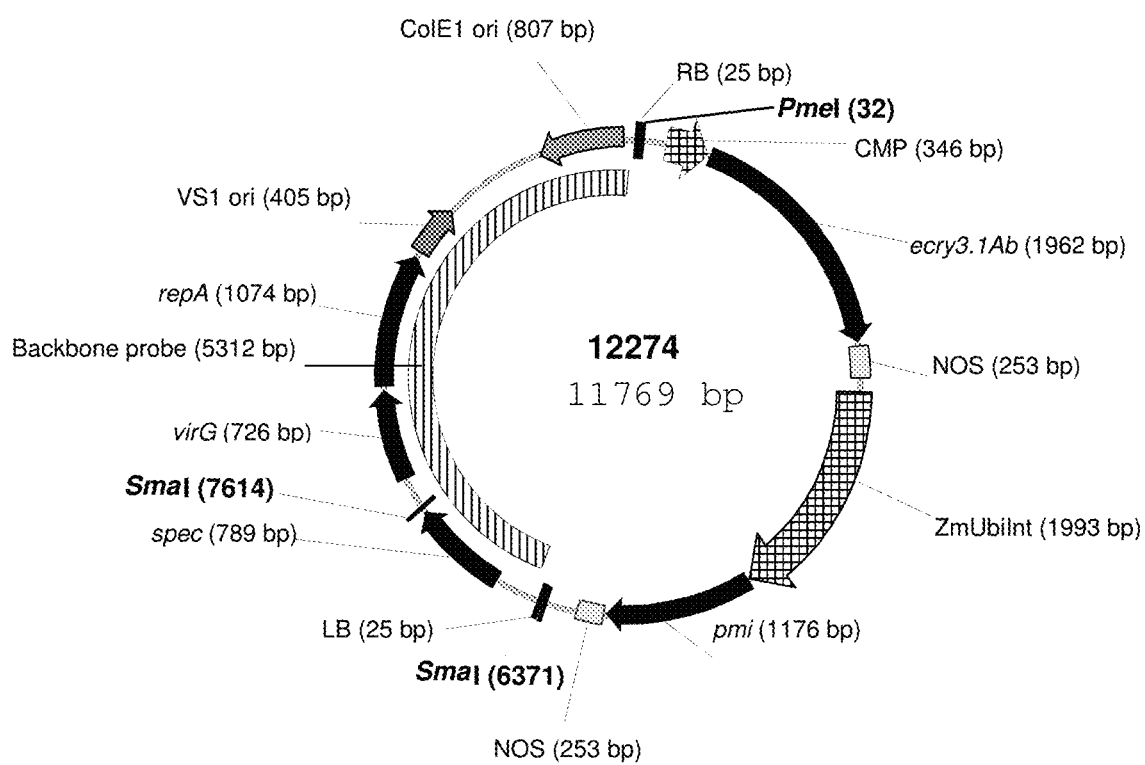
FIG. 1 illustrates a plant expression vector designated pSYN12274. The plasmid map identifies the SmaI and PmeI restriction sites used for Southern analysis.
Figure 2:
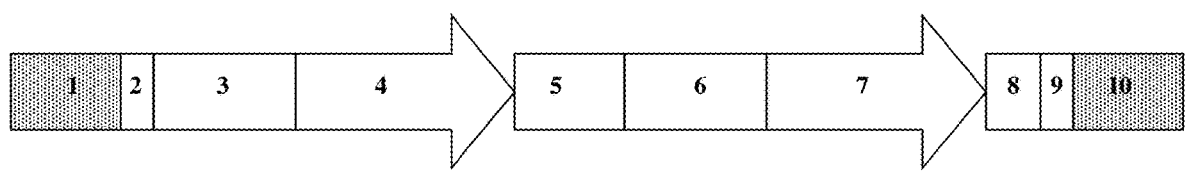
FIG. 2 is a graphical map illustrating the organization of the elements comprising the heterologous nucleic acid sequences inserted into the genome of corn to create event 5307 and sets forth the relative positions at which the inserted nucleic acid sequences are linked to corn genomic DNA sequences which flank the ends of the inserted heterologous DNA sequences. 1=5'flanking plant genome (SEQ ID NO: 5); 2=right border region; 3=CMP promoter; 4=FR8a gene; 5=NOS terminator; 6=ZmUbINT promoter; 7=PMI gene; 8=NOS terminator; 9=left border region (sections 2 through 9 are contained within SEQ ID NO: 7); and 10=3' flanking plant genome (SEQ ID NO: 6).

The following definitions and methods are provided to better define the invention and to guide those of ordinary skill in the art in the practice of the invention. Unless otherwise noted, terms used herein are to be understood according to conventional usage by those of ordinary skill in the relevant art. Definitions of common terms in molecular biology may also be found in Rieger et al., Glossary of Genetics: Classical and Molecular, 5$^{th}$ edition, Springer-Verlag: New York, 1994.

As used herein, the term "amplified" means the construction of multiple copies of a nucleic acid molecule or multiple copies complementary to the nucleic acid molecule using at least one of the nucleic acid molecules as a template. Amplification systems include the polymerase chain reaction (PCR) system, ligase chain reaction (LCR) system, nucleic acid sequence based amplification (NASBA, Cangene, Mississauga, Ontario), Q-Beta Replicase systems, transcription-based amplification system (TAS), and strand displacement amplification (SDA). See, e.g., *Diagnostic Molecular Microbiology: Principles and Applications*, D. H. Persing et al., Ed., American Society for Microbiology, Washington, D.C. (1993). The product of amplification is termed an amplicon.

A "biological sample" is a plant, plant material or products comprising plant material. The term "plant" is intended to encompass corn (*Zea mays*) plant tissues, at any stage of maturity, as well as cells, tissues, organs taken from or derived from any such plant, including without limitation, any seeds, leaves, stems, flowers, roots, single cells, gametes, cell cultures, tissue cultures or protoplasts. "Plant material", as used herein refers to material which is obtained or derived from a plant. Products comprising plant material relate to food, feed or other products which are produced using plant material or can be contaminated by plant material. It is understood that, in the context of the invention, such biological sample are tested for the presence of nucleic acids specific to corn event 5307, implying the presence of nucleic acids in the samples. Thus, the methods referred to herein for identifying corn event 5307 in biological samples, relate to the identification in biological samples of nucleic acids which from an event 5307 corn plant and are diagnostic for event 5307.

A "coding sequence" is a nucleic acid sequence that is transcribed into RNA such as mRNA, rRNA, tRNA, snRNA, sense RNA or antisense RNA. Preferably the RNA is then translated in an organism to produce a protein.

"Detection kit" as used herein refers to a kit used to detect the presence or absence of DNA from event 5307 cornplants in a sample comprising nucleic acid probes and primers of the invention, which hybridize specifically under high stringency conditions to a target DNA sequence, and other materials necessary to enable nucleic acid hybridization or amplification methods.

As used herein the term transgenic "event" refers to a recombinant plant produced by transformation and regeneration of a single plant cell with heterologous DNA, for example, an expression cassette that includes a gene of interest. The term "event" refers to the original transformant and/or progeny of the transformant that include the heterologous DNA. The term "event" also refers to progeny produced by a sexual outcross between the transformant and another corn line. Even after repeated backcrossing to a recurrent parent, the inserted DNA and the flanking DNA from the transformed parent is present in the progeny of the cross at the same chromosomal location. Normally, transformation of plant tissue produces multiple events, each of which represent insertion of a DNA construct into a different location in the genome of a plant cell. Based on the expression of the transgene or other desirable characteristics, a particular event is selected. Thus, "event 5307", "5307 event" or "5307" as used herein, means the original 5307 transformant and/or progeny of the 5307 transformant, including any plant derived therefrom.

"Expression cassette" as used herein means a nucleic acid molecule capable of directing expression of a particular nucleotide sequence in an appropriate host cell, comprising a promoter operably linked to the nucleotide sequence of interest which is operably linked to termination signals. It also typically comprises sequences required for proper translation of the nucleotide sequence. The expression cassette may also comprise sequences not necessary in the direct expression of a nucleotide sequence of interest but which are present due to convenient restriction sites for removal of the cassette from an expression vector. The expression cassette comprising the nucleotide sequence of interest may be chimeric, meaning that at least one of its components is heterologous with respect to at least one of its other components. The expression cassette may also be one that is naturally occurring but has been obtained in a recombinant form useful for heterologous expression. Typically, however, the expression cassette is heterologous with respect to the host, i.e., the particular nucleic acid sequence of the expression cassette does not occur naturally in the host cell and must have been introduced into the host cell or an ancestor of the host cell by a transformation process known in the art. The expression of the nucleotide sequence in the expression cassette may be under the control of a constitutive promoter or of an inducible promoter that initiates transcription only when the host cell is exposed to some particular external stimulus. In the case of a multicellular organism, such as a plant, the promoter can also be specific to a particular tissue, or organ, or stage of development. An expression cassette, or fragment thereof, can also be referred to as "inserted sequence" or "insertion sequence" when transformed into a plant.

A "gene" is a defined region that is located within a genome and that, besides the aforementioned coding nucleic acid sequence, comprises other, primarily regulatory, nucleic acid sequences responsible for the control of the expression, that is to say the transcription and translation, of the coding portion. A gene may also comprise other 5' and 3' untranslated sequences and termination sequences. Further elements that may be present are, for example, introns.

"Gene of interest" refers to any gene which, when transferred to a plant, confers upon the plant a desired characteristic such as antibiotic resistance, virus resistance, insect resistance, disease resistance, or resistance to other pests, herbicide tolerance, improved nutritional value, improved performance in an industrial process or altered reproductive capability. The "gene of interest" may also be one that is transferred to plants for the production of commercially valuable enzymes or metabolites in the plant.

"Genotype" as used herein is the genetic material inherited from parent corn plants not all of which is necessarily expressed in the descendant corn plants. The 5307 genotype refers to the heterologous genetic material transformed into the genome of a plant as well as the genetic material flanking the inserted sequence.

A "heterologous" nucleic acid sequence is a nucleic acid sequence not naturally associated with a host cell into which it is introduced, including non-naturally occurring multiple copies of a naturally occurring nucleic acid sequence.

A "homologous" nucleic acid sequence is a nucleic acid sequence naturally associated with a host cell into which it is introduced.

The term "isolated" when used in relation to a nucleic acid refers to a nucleic acid sequence that is identified and separated from at least one contaminant nucleic acid with which it is ordinarily associated in its natural source. An isolated nucleic acid is present in a form or setting that is different from that in which it is found in nature. In contrast, a non-isolated nucleic acids such as DNA and RNA found in the state they exist in nature. An isolated nucleic acid may be in a transgenic plant and still be considered "isolated".

"Operably-linked" refers to the association of nucleic acid sequences on a single nucleic acid fragment so that the function of one affects the function of the other. For example, a promoter is operably-linked with a coding sequence or functional RNA when it is capable of affecting the expression of that coding sequence or functional RNA (i.e., that the coding sequence or functional RNA is under the transcriptional control of the promoter). Coding sequences in sense or antisense orientation can be operably-linked to regulatory sequences.

"Primers" as used herein are isolated nucleic acids that are annealed to a complimentary target DNA strand by nucleic acid hybridization to form a hybrid between the primer and the target DNA strand, then extended along the target DNA strand by a polymerase, such as DNA polymerase. Primer pairs or sets can be used for amplification of a nucleic acid molecule, for example, by the polymerase chain reaction (PCR) or other conventional nucleic-acid amplification methods.

A "probe" is an isolated nucleic acid to which is attached a conventional detectable label or reporter molecule, such as a radioactive isotope, ligand, chemiluminescent agent, or enzyme. Such a probe is complimentary to a strand of a target nucleic acid, in the case of the invention, to a strand of genomic DNA from corn event, M5307. The genomic DNA of event 5307 can be from a corn plant or from a sample that includes DNA from the event. Probes according to the invention include not only deoxyribonucleic or ribonucleic acids but also polyamides and other probe materials that bind specifically to a target DNA sequence and can be used to detect the presence of that target DNA sequence.

Primers and probes are generally between 10 and 15 nucleotides or more in length, Primers and probes can also be at least 20 nucleotides or more in length, or at least 25 nucleotides or more, or at least 30 nucleotides or more in length. Such primers and probes hybridize specifically to a target sequence under high stringency hybridization conditions. Primers and probes according to the invention may have complete sequence complementarity with the target sequence, although probes differing from the target sequence and which retain the ability to hybridize to target sequences may be designed by conventional methods.

"Stringent conditions" or "stringent hybridization conditions" include reference to conditions under which a probe will hybridize to its target sequence, to a detectably greater degree than to other sequences. Stringent conditions are target-sequence-dependent and will differ depending on the structure of the polynucleotide. By controlling the stringency of the hybridization and/or wash conditions, target sequences can be identified which are 100% complementary to the probe (homologous probing). Alternatively, stringency conditions can be adjusted to allow some mismatching in sequences so that lower degrees of similarity are detected (heterologous probing). Longer sequences hybridize specifically at higher temperatures. An extensive guide to the hybridization of nucleic acids is found in Tijssen (1993) *Laboratory Techniques in Biochemistry and Molecular Biology—Hybridization with Nucleic Acid Probes*, Part I, Chapter 2 "Overview of principles of hybridization and the strategy of nucleic acid probe assays", Elsevier: New York; and *Current Protocols in Molecular Biology*, Chapter 2, Ausubel et al., Eds., Greene Publishing and Wiley-Interscience: New York (1995), and also Sambrook et al. (2001) *Molecular Cloning: A Laboratory Manual* ($5^{th}$ Ed. Cols Spring Harbor Laboratory, Cold Spring Harbor, N.Y.).

Specificity is typically the function of post-hybridization washes, the critical factors being the ionic strength and temperature of the final wash solution. Generally, high stringency hybridization and wash conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Typically, under high stringency conditions a probe will hybridize to its target subsequence, but to no other sequences.

An example of high stringency hybridization conditions for hybridization of complementary nucleic acids which have more than 100 complementary residues on a filter in a Southern or northern blot is 50% formamide with 1 mg of heparin at 42° C., with the hybridization being carried out overnight. An example of very high stringency wash conditions is 0.15M NaCl at 72° C. for about 15 minutes. An example of high stringency wash conditions is a 0.2×SSC wash at 65° C. for 15 minutes (see, Sambrook, infra, for a description of SSC buffer).

Exemplary hybridization conditions for the invention include hybridization in 7% SDS, 0.25 M $NaPO_4$ pH 7.2 at 67° C. overnight, followed by two washings in 5% SDS, 0.20 M $NaPO_4$ pH7.2 at 65° C. for 30 minutes each wash, and two washings in 1% SDS, 0.20 M $NaPO_4$ pH7.2 at 65° C. for 30 minutes each wash. An exemplary medium stringency wash for a duplex of, e.g., more than 100 nucleotides, is 1×SSC at 45° C. for 15 minutes. An exemplary low stringency wash for a duplex of, e.g., more than 100 nucleotides, is 4-6×SSC at 40° C. for 15 minutes.

For probes of about 10 to 50 nucleotides, high stringency conditions typically involve salt concentrations of less than about 1.0 M Na ion, typically about 0.01 to 1.0 M Na ion concentration (or other salts) at pH 7.0 to 8.3, and the temperature is typically at least about 30° C. High stringency conditions can also be achieved with the addition of destabilizing agents such as formamide. In general, a signal to noise ratio of 2× (or higher) than that observed for an unrelated probe in the particular hybridization assay indicates detection of a specific hybridization. Nucleic acids that do not hybridize to each other under high stringency conditions are still substantially identical if the proteins that they encode are substantially identical. This occurs, e.g., when a copy of a nucleic acid is created using the maximum codon degeneracy permitted by the genetic code.

The following are exemplary sets of hybridization/wash conditions that may be used to hybridize nucleotide sequences that are substantially identical to reference nucleotide sequences of the invention: a reference nucleotide sequence preferably hybridizes to the reference nucleotide sequence in 7% sodium dodecyl sulfate (SDS), 0.5 M $NaPO_4$, 1 mM EDTA at 50° C. with washing in 2×SSC, 0.1% SDS at 50° C., more desirably in 7% sodium dodecyl sulfate (SDS), 0.5 M $NaPO_4$, 1 mM EDTA at 50° C. with washing in 1×SSC, 0.1% SDS at 50° C., more desirably still in 7% sodium dodecyl sulfate (SDS), 0.5 M $NaPO_4$, 1 mM EDTA at 50° C. with washing in 0.5×SSC, 0.1% SDS at 50° C., preferably in 7% sodium dodecyl sulfate (SDS), 0.5 M $NaPO_4$, 1 mM EDTA at 50° C. with washing in 0.1×SSC, 0.1% SDS at 50° C., more preferably in 7% sodium dodecyl sulfate (SDS), 0.5 M $NaPO_4$, 1 mM EDTA at 50° C. with washing in 0.1×SSC, 0.1% SDS at 65° C. The sequences of the invention may be detected using all the above conditions. For the purposes of defining the invention, the high stringency conditions are used.

"Transformation" is a process for introducing heterologous nucleic acid into a host cell or organism. In particular, "transformation" means the stable integration of a DNA molecule into the genome of an organism of interest.

"Transformed/transgenic/recombinant" refer to a host organism such as a bacterium or a plant into which a heterologous nucleic acid molecule has been introduced. The nucleic acid molecule can be stably integrated into the genome of the host or the nucleic acid molecule can also be as an extrachromosomal molecule. Such an extrachromosomal molecule can be auto-replicating. Transformed cells, tissues, or plants are understood to encompass not only the end product of a transformation process, but also transgenic progeny thereof. A "non-transformed", "non-transgenic", or "non-recombinant" host refers to a wild-type organism, e.g., a bacterium or plant, which does not contain the heterologous nucleic acid molecule. As used herein, "transgenic" refers to a plant, plant cell, or multitude of structured or unstructured plant cells having integrated, via well known techniques of genetic manipulation and gene insertion, a nucleic acid representing a gene of interest into the plant genome, and typically into a chromosome of a cell nucleus, mitochondria or other organelle containing chromosomes, at a locus different to, or in a number of copies greater than, that normally present in the native plant or plant cell. Transgenic plants result from the manipulation and insertion of such nucleic acid sequences, as opposed to naturally occurring mutations, to produce a non-naturally occurring plant or a plant with a non-naturally occurring genotype. Techniques for transformation of plants and plant cells are well known in the art and may comprise for example electroporation, microinjection, *Agrobacterium*-mediated transformation, and ballistic transformation.

The nomenclature for DNA bases and amino acids as set forth in 37 C.F.R. § 1.822 is used herein.

DETAILED DESCRIPTION

This invention relates to a genetically improved line of corn that produces the insect control protein, FR8a, and a phosphomannose isomerase enzyme (PMI) that allows the plant to utilize mannose as a carbon source. The invention is particularly drawn to a transgenic corn event designated event 5307 comprising a novel genotype, as well as to compositions and methods for detecting nucleic acids from this event in a biological sample. The invention is further drawn to corn plants comprising the event 5307 genotype, to transgenic seed from the corn plants, and to methods for producing a corn plant comprising the event 5307 genotype by crossing a corn inbred comprising the event 5307 genotype with itself or another corn line. Corn plants comprising the event 5307 genotype of the invention are useful in controlling coleopteran insect pests including *Diabrotica virgifera virgifera*, the western corn rootworm, *D. virgifera zeae*, the Mexican corn rootworm, and *D. longicornis barberi*, the northern corn rootworm. Corn plants comprising the event 5307 genotype of the invention are also able to utilize mannose as a carbon source.

In one embodiment, the invention encompasses a transgenic corn seed of an event 5307 corn plant. An example of said seed being deposited as ATCC Accession No: PTA-9561. The transgenic seed of event 5307 comprises SEQ ID NO: 1, SEQ ID NO: 2, SEQ ID NO: 3, SEQ ID NO: 4, SEQ ID NO: 5, or SEQ ID NO: 6, and complements thereof. These sequences define a point of insertion of a heterologous DNA sequence inserted into the corn plant genome of corn event 5307. In another embodiment, the invention encompasses a preferably isolated nucleic acid molecule comprising SEQ ID NO: 1, SEQ ID NO: 2, SEQ ID NO: 3 or SEQ ID NO: 4. In another embodiment, the invention encompasses a preferably isolated nucleic acid molecule, wherein the nucleic acid molecule is comprised in a corn seed deposited as ATCC Accession No. PTA-9561

In one embodiment, the invention encompasses a nucleic acid molecule, preferably isolated, comprising at least 10 or more (for example 15, 20, 25, or 50) contiguous nucleotides of a heterologous DNA sequence inserted into the corn plant genome of corn event 5307 and at least 10 or more (for example 15, 20, 25, or 50) contiguous nucleotides of a corn plant genome DNA flanking the point of insertion of a heterologous DNA sequence inserted into the corn plant genome of corn event 5307. Also included are nucleotide sequences that comprise 10 or more nucleotides of contiguous insert sequence from event 5307 and at lease one nucleotide of flanking DNA from event 5307 adjacent to the insert sequence. Such nucleotide sequences are diagnostic for event 5307. Nucleic acid amplification of genomic DNA from the 5307 event produces an amplicon comprising such diagnostic nucleotide sequences.

In another embodiment, the invention encompasses a nucleic acid molecule, preferably isolated, comprising a nucleotide sequence which comprises at least one junction sequence of event 5307 selected from the group consisting of SEQ ID NO: 1, SEQ ID NO: 2, SEQ ID NO: 3, SEQ ID NO: 4, and complements thereof, wherein a junction sequence spans the junction between a heterologous expression cassette inserted into the corn genome and DNA from the corn genome flanking the insertion site and is diagnostic for the event.

In another embodiment, the invention encompasses a preferably isolated nucleic acid linking a heterologous DNA molecule to the corn plant genome in corn event 5307 comprising a sequence of from about 11 to about 20 contiguous nucleotides selected from the group consisting of SEQ ID NO: 1, SEQ ID NO: 2, and the complements thereof.

In another embodiment, the invention encompasses an nucleic acid molecule, preferably isolated, comprising a nucleotide sequence selected from the group consisting of SEQ ID NO: 1, SEQ ID NO: 2, SEQ ID NO: 3, SEQ ID NO: 4, and complements thereof.

In one embodiment of the invention, an amplicon comprising a nucleotide sequence selected from the group consisting of SEQ ID NO: 1, SEQ ID NO: 2, SEQ ID NO: 3, SEQ ID NO: 4, and the complements thereof is provided.

In another embodiment, the invention encompasses flanking sequence primers for detecting event 5307. Such flanking sequence primers comprise an isolated nucleic acid sequence comprising at least 10-15 contiguous nucleotides from nucleotides 1-1348 of SEQ ID NO: 5 (arbitrarily designated herein as the 5' flanking sequence), or the complements thereof, also disclosed as SEQ ID NO: 111. In one aspect of this embodiment the flanking sequence primers are selected from the group consisting of SEQ ID NO: 8 through SEQ ID NO: 14, and complements thereof. The flanking sequences can be extended to include chromosome 5 sequences, with specific emphasis on nucleotide comprised with SEQ ID NO: 103, useful in detecting sequences associated with the 5307 corn event. In the context of SEQ ID NO: 103, an "N" is defined as any base "A", "T", "G", or "C". SEQ ID NO: 110 is the reverse complement of this sequence. In the context of SEQ ID NO: 110, an "N" is defined as any base "A", "T", "G", or "C".

In another embodiment, the invention encompasses flanking sequence primers that comprise at least 10-15 contiguous nucleotides from nucleotides 1-1093 of SEQ ID NO: 6 (arbitrarily designated herein as the 3' flanking sequence), or the complements thereof. In one aspect of this embodiment the flanking sequence primers are selected from the group consisting of SEQ ID NO: 69 through SEQ ID NO: 72, and complements thereof.

In still another embodiment, the invention encompasses a pair of polynucleotide primers comprising a first polynucleotide primer and a second polynucleotide primer which function together in the presence of a corn event 5307 DNA template in a sample to produce an amplicon diagnostic for the corn event 5307, wherein the first primer sequence is or is complementary to a corn plant genome flanking the point of insertion of a heterologous DNA sequence inserted into the corn plant genome of corn event 5307, and the second polynucleotide primer sequence is or is complementary to the heterologous DNA sequence inserted into the corn plant genome of the corn event 5307.

In one aspect of this embodiment the first polynucleotide primer comprises at least 10 contiguous nucleotides from position 1-1348 of SEQ ID NO: 5 or complements thereof. In a further aspect of this embodiment, the first polynucleotide primer comprises the nucleotide sequence set forth in SEQ ID NO: 8 through SEQ ID NO: 14, or the complements thereof. In another aspect of this embodiment the first polynucleotide primer least 10 contiguous nucleotides from position 1-1093 of SEQ ID NO: 6 or complements thereof. In another aspect of this embodiment, the first polynucleotide primer comprises the nucleotide sequence set forth in SEQ ID NO: 69 through SEQ ID NO: 72, or the complements thereof. In yet another aspect of this embodiment, the second polynucleotide primer comprises at least 10 contiguous nucleotides of SEQ ID NO: 7, or the complements thereof. In still a further aspect of this embodiment, the second polynucleotide primer comprises the nucleotide sequence set forth in SEQ ID NO: 15 to SEQ ID NO: 68, or the complements thereof.

In another aspect of this embodiment, the first polynucleotide primer, which is set forth in SEQ ID NO: 8, and the second polynucleotide primer which is set forth in SEQ ID NO: 41, function together in the presence of a corn event 5307 DNA template in a sample to produce an amplicon diagnostic for the corn events 5307 as described in Example 4. In another aspect of this embodiment, the first polynucleotide primer, which is set forth in SEQ ID NO: 69, and the second polynucleotide primer which is set forth in SEQ ID NO: 72, function together in the presence of a corn event 5307 DNA template in a sample to produce an amplicon diagnostic for the corn event 5307 as described in Example 4.

It is well within the skill in the art to obtain additional sequence further out into the genome sequence flanking either end of the inserted heterologous DNA sequences for use as a primer sequence that can be used in such primer pairs for amplifying the sequences that are diagnostic for the 5307 event. For the purposes of this disclosure, the phrase "further out into the genome sequence flanking either end of the inserted heterologous DNA sequences" refers specifically to a sequential movement away from the ends of the inserted heterologous DNA sequences, the points at which the inserted DNA sequences are adjacent to native genomic DNA sequence, and out into the genomic DNA of the particular chromosome into which the heterologous DNA sequences were inserted. Preferably, a primer sequence corresponding to or complementary to a part of the insert sequence should prime the transcriptional extension of a nascent strand of DNA or RNA toward the nearest flanking sequence junction. Consequently, a primer sequence corresponding to or complementary to a part of the genomic flanking sequence should prime the transcriptional extension of a nascent strand of DNA or RNA toward the nearest flanking sequence junction. A primer sequence can be, or can be complementary to, a heterologous DNA sequence inserted into the chromosome of the plant, or a genomic flanking sequence. One skilled in the art would readily recognize the benefit of whether a primer sequence would need to be, or would need to be complementary to, the sequence as set forth within the inserted heterologous DNA sequence or as set forth in SEQ ID NO: 3 or SEQ ID NO: 4 depending upon the nature of the product desired to be obtained through the use of the nested set of primers intended for use in amplifying a particular flanking sequence containing the junction between the genomic DNA sequence and the inserted heterologous DNA sequence. Further more, one skilled in the art would be able to design primers for a multitude of native corn genes for the purposes of designing a positive control. One such example is the corn Adh1 gene, where examples of suitable primers for producing an amplicon by nucleic acid amplification are set forth as SEQ ID NO: 79 and SEQ ID NO: 80.

In another embodiment, the invention encompasses a method of detecting the presence of DNA corresponding to the event 5307 in a biological sample, wherein the method comprises: (a) contacting the sample comprising DNA with a probe that hybridizes under high stringency conditions with genomic DNA from corn event 5307 and does not hybridize under high stringency conditions with DNA of a control corn plant; (b) subjecting the sample and probe to high stringency hybridization conditions; and (c) detecting hybridization of the probe to the DNA. In one aspect of this embodiment the amplicon comprises a nucleotide sequence selected from the group consisting of SEQ ID NO: 1, SEQ ID NO: 2, SEQ ID NO: 3, SEQ ID NO: 4, and complements thereof.

In another embodiment, the invention encompasses a method of detecting the presence of a DNA corresponding to the 5307 event in a biological sample, wherein the method comprises: (a) contacting the sample comprising DNA with a probe that hybridizes under high stringency conditions with genomic DNA from corn event 5307 and does not hybridize under high stringency conditions with DNA of a control corn plant; (b) subjecting the sample and probe to high stringency hybridization conditions; and (c) detecting hybridization of the probe to the DNA. Detection can be by any means well known in the art including but not limited to fluorescent, chemiluminescent, radiological, immunological, or otherwise. In the case in which hybridization is intended to be used as a means for amplification of a particular sequence to produce an amplicon which is diagnostic for the 5307 corn event, the production and detection by any means well known in the art of the amplicon is intended to be indicative of the intended hybridization to the target sequence where one probe or primer is utilized, or sequences where two or more probes or primers are utilized. The term "biological sample" is intended to comprise a sample that contains or is suspected of containing a nucleic acid comprising from between five and ten nucleotides either side of the point at which one or the other of the two terminal ends of the inserted heterologous DNA sequence contacts the genomic DNA sequence within the chromosome into which the heterologous DNA sequence was inserted, herein also known as the junction sequences. In addition, the junction sequence comprises as little as two nucleotides: those being the first nucleotide within the flanking genomic DNA adjacent to and covalently linked to the first nucleotide within the inserted heterologous DNA sequence.

In yet another embodiment, the invention encompasses a kit for detecting the presence of event 5307 nucleic acids in a biological sample, wherein the kit comprises at least one nucleic acid molecule of sufficient length of contiguous nucleotides homologous or complementary to a nucleotide sequence selected from the group consisting of SEQ ID NO: 1, SEQ ID NO: 2, SEQ ID NO: 3, and SEQ ID NO: 4, that functions as a DNA primer or probe specific for event 5307, and other materials necessary to enable nucleic acid hybridization or amplification. A variety of detection methods can be used including TAQMAN (Perkin Elmer), thermal amplification, ligase chain reaction, southern hybridization, ELISA methods, and colorimetric and fluorescent detection methods. In particular the invention provides for kits for detecting the presence of the target sequence, i.e., at least one of the junctions of the insert DNA with the genomic DNA of the corn plant in event 5307, in a sample containing genomic nucleic acid from event 5307. The kit is comprised of at least one polynucleotide capable of binding to the target site or substantially adjacent to the target site and at least one means for detecting the binding of the polynucleotide to the target site. The detecting means can be fluorescent, chemiluminescent, colorimetric, or isotopic and can be coupled at least with immunological methods for detecting the binding. A kit is also envisioned which can detect the presence of the target site in a sample, i.e., at least one of the junctions of the insert DNA with the genomic DNA of the corn plant in event 5307, taking advantage of two or more polynucleotide sequences which together are capable of binding to nucleotide sequences adjacent to or within about 100 base pairs, or within about 200 base pairs, or within about 500 base pairs or within about 1000 base pairs of the target sequence and which can be extended toward each other to form an amplicon which contains at least the target site In another embodiment, the invention encompasses a method for detecting event 5307 protein in a biological sample, the method comprising: (a) extracting protein from a sample of corn event 5307 tissue; (b) assaying the extracted protein using an immunological method comprising antibody specific for the insecticidal or selectable marker protein produced by the 5307 event; and (c) detecting the binding of said antibody to the insecticidal or selectable marker protein.

Another embodiment of the invention encompasses a corn plant, or parts thereof, comprising the genotype of the transgenic event 5307, wherein the genotype comprises the nucleotide sequence set forth in SEQ ID NO: 1, SEQ ID NO: 2, SEQ ID NO: 3, SEQ ID NO: 4, or the complements thereof. In one aspect of this embodiment, the corn plant is from the inbred corn lines CG5NA58, CG5NA58A, CG3ND97, CG5NA01, CG5NF22, CG4NU15, CG00685, CG00526, CG00716, NP904, NP948, NP934, NP982, NP991, NP993, NP2010, NP2013, NP2015, NP2017, NP2029, NP2031, NP2034, NP2045, NP2052, NP2138, NP2151, NP2166, NP2161, NP2171, NP2174, NP2208, NP2213, NP2222, NP2275, NP2276, NP2316, BCTT609, AF031, H8431, 894, BUTT201, R327H, 2044BT, and 2070BT. One skilled in the art will recognize however, that the event 5307 genotype can be introgressed into any plant variety that can be bred with corn, including wild maize species, and thus the preferred inbred lines of this embodiment are not meant to be limiting.

In another embodiment, the invention encompasses a corn plant comprising at least a first and a second DNA sequence linked together to form a contiguous nucleotide sequence, wherein the first DNA sequence is within a junction sequence and comprises at least about 10-15 contiguous nucleotides selected from the group consisting of nucleotides SEQ ID NO: 5, SEQ ID NO: 6, and complements thereof, wherein the second DNA sequence is within the heterologous insert DNA sequence selected from the group consisting of SEQ ID NO: 15 through SEQ ID NO: 68, and complements thereof; and wherein the first and the second DNA sequences are useful as nucleotide primers or probes for detecting the presence of corn event 5307 nucleic acid sequences in a biological sample. In one aspect of this embodiment, the nucleotide primers are used in a DNA amplification method to amplify a target DNA sequence from template DNA extracted from the corn plant and the corn plant is identifiable from other corn plants by the production of an amplicon corresponding to a DNA sequence comprising SEQ ID NO: 1 or SEQ ID NO: 2

Corn plants of the invention can be further characterized in that digesting the plant's genomic DNA with the restriction endonucleases SmaI and PmeI results in a single hybridizing band using a full length probe under high stringency conditions. Exemplified herein is a full length probe comprising a nucleotide sequence set forth in SEQ ID NO: 7.

In one embodiment, the invention provides a corn plant, wherein the event 5307 genotype confers upon the corn plant resistance to insects or the ability to utilize mannose. In one aspect of this embodiment, the genotype conferring resistance to insects upon the corn plant comprises a FR8a gene. In another aspect of this embodiment, the genotype conferring upon the corn plant the ability to utilize mannose comprises a PMI gene.

In one embodiment, the invention provides a biological sample derived from a event 5307 corn plant, tissue, or seed, wherein the sample comprises a nucleotide sequence which is or is complementary to a sequence selected from the group consisting of SEQ ID NO: 1, SEQ ID NO: 2, SEQ ID NO: 3 and SEQ ID NO: 4, and wherein the sequence is detectable in the sample using a nucleic acid amplification or nucleic acid hybridization method. Thus, the genetic sequence functions a means of detection. In one aspect of this embodiment, the sample is selected from corn flour, corn meal, corn syrup, corn oil, corn starch, and cereals manufactured in whole or in part to contain corn products.

In another embodiment, the invention provides an extract derived from a event 5307 corn plant, tissue, or seed comprising a nucleotide sequence which is or is complementary to a nucleotide sequence selected from the group consisting of SEQ ID NO: 1, SEQ ID NO: 2, SEQ ID NO: 3 and SEQ ID NO: 4. An example of such seed is deposited at the ATCC under Accession No. PTA-9561. In one aspect of this embodiment, the sequence is detected in the extract using a nucleic acid amplification or nucleic acid hybridization method. In another aspect of this embodiment, the sample is selected from corn flour, corn syrup, corn oil, cornstarch, and cereals manufactured in whole or in part to contain corn products.

In yet another embodiment, the invention provides a method for producing a corn plant resistant to at least corn rootworm infestation comprising: (a) sexually crossing a first parent corn plant with a second parent corn plant, wherein said first or second parent corn plant comprises corn event 5307 DNA, thereby producing a plurality of first generation progeny plants; (b) selecting a first generation progeny plant that is resistant to at least corn rootworm infestation; (c) selfing the first generation progeny plant, thereby producing a plurality of second generation progeny plants; and (d) selecting from the second generation progeny plants, a plant that is at least resistant to corn rootworm infestation; wherein the second generation progeny plants comprise a nucleotide sequence selected from the group consisting of SEQ ID NO: 1, SEQ ID NO: 2, SEQ ID NO:3 and SEQ ID NO: 4.

In another embodiment, the invention provides a method of producing hybrid corn seeds comprising: (a) planting seeds of a first inbred corn line comprising a nucleotide sequence selected from the group consisting of SEQ ID NO: 1, SEQ ID NO: 2, SEQ ID NO: 3, and SEQ ID NO: 4, and seeds of a second inbred line having a different genotype; (b) cultivating corn plants resulting from said planting until time of flowering; (c) emasculating said flowers of plants of one of the corn inbred lines; (d) sexually crossing the two different inbred lines with each other; and (e) harvesting the hybrid seed produced thereby. In one aspect of this embodiment, the first inbred corn line provides the female parents. In another aspect of this embodiment, the first inbred corn line provides the male parents. The invention also encompasses the hybrid seed produced by the embodied method and hybrid plants grown from the seed.

In another embodiment, the invention provides a method of selecting markers associated with corn event 5307 comprising: (a) screening corn event 5307 chromosome 5 sequences, (b) comparing these with a non-transgenic NP2222 sequences, (c) comparing the sequences for the purpose of detecting sequence variations, (d) using these sequence variations as a means to develop markers associated with corn event 5307, (e) using the markers to screen lines, and (f) detecting marker confirming the presence of corn event 5307 sequences on chromosome 5.

One skilled in the art will recognize that the transgenic genotype of the invention can be introgressed by breeding into other corn lines comprising different transgenic genotypes. For example, a corn inbred comprising the transgenic genotype of the invention can be crossed with a corn inbred comprising the transgenic genotype of the lepidopteran resistant Bt11 event, which is known in the art, thus producing corn seed that comprises both the transgenic genotype of the invention and the Bt11 transgenic genotype. Examples of other transgenic events which can be crossed with an inbred of the invention include, the glyphosate herbicide tolerant events GA21 and NK603, the glyphosate tolerant/lepidopteran insect resistant MON802 event, the lepidopteran insect resistant event DBT418, the lepidopteran insect resistant event DAS-06275-8, the lepidopteran insect resistant event MIR162, the male sterile event MS3, the phosphinothricin tolerant event B16, the lepidopteran insect resistant event MON 80100, the phosphinothricin herbicide tolerant events T14 and T25, the lepidopteran insect resistant event 176, the coleopteran insect resistant event MIR604 and the coleopteran insect resistant event MON863, all of which are known in the art. It will be further recognized that other combinations can be made with the transgenic genotype of the invention and thus these examples should not be viewed as limiting.

One skilled in the art will also recognize that transgenic corn seed comprising the transgenic genotype of the invention can be treated with various seed-treatment chemicals, including insecticides, to augment or synergize the insecticidal activity of the FR8a protein. For example, the transgenic corn seed of the invention can be treated with the commercial insecticide Cruiser®. Such a combination may be used to increase the spectrum of activity and to increase the efficacy of the expressed protein and chemical.

Breeding

The transgenic genotype of the invention can be introgressed in any corn inbred or hybrid using art recognized breeding techniques. The goal of plant breeding is to combine in a single variety or hybrid various desirable traits. For field crops, these traits may include resistance to insects and diseases, tolerance to herbicides, tolerance to heat and drought, reducing the time to crop maturity, greater yield, and better agronomic quality. With mechanical harvesting of many crops, uniformity of plant characteristics such as germination and stand establishment, growth rate, maturity, and plant and ear height, is important.

Field crops are bred through techniques that take advantage of the plant's method of pollination. A plant is self-pollinated if pollen from one flower is transferred to the same or another flower of the same plant. A plant is cross-pollinated if the pollen comes from a flower on a different plant.

Plants that have been self-pollinated and selected for type for many generations become homozygous at almost all gene loci and produce a uniform population of true breeding progeny. A cross between two different homozygous lines produces a uniform population of hybrid plants that may be heterozygous for many gene loci. A cross of two plants each heterozygous at a number of gene loci will produce a population of hybrid plants that differ genetically and will not be uniform.

Corn can be bred by both self-pollination and cross-pollination techniques. Corn has separate male and female flowers on the same plant, located on the tassel and the ear, respectively. Natural pollination occurs in corn when wind blows pollen from the tassels to the silks that protrude from the tops of the ears.

A reliable method of controlling male fertility in plants offers the opportunity for improved plant breeding. This is especially true for development of corn hybrids, which relies upon some sort of male sterility system. There are several options for controlling male fertility available to breeders, such as: manual or mechanical emasculation (or detasseling), cytoplasmic male sterility, genetic male sterility, gametocides and the like.

Hybrid corn seed is typically produced by a male sterility system incorporating manual or mechanical detasseling. Alternate strips of two corn inbreds are planted in a field, and the pollen-bearing tassels are removed from one of the inbreds (female). Providing that there is sufficient isolation from sources of foreign corn pollen, the ears of the detasseled inbred will be fertilized only from the other inbred (male), and the resulting seed is therefore hybrid and will form hybrid plants.

The laborious, and occasionally unreliable, detasseling process can be avoided by using one of many methods of conferring genetic male sterility in the art, each with its own benefits and drawbacks. These methods use a variety of approaches such as delivering into the plant a gene encoding a cytotoxic substance associated with a male tissue specific promoter or an antisense system in which a gene critical to fertility is identified and an antisense to that gene is inserted in the plant (see: Fabinjanski, et al. EPO 89/3010153.8 publication no. 329,308 and PCT application PCT/CA90/00037 published as WO 90/08828).

Development of Corn Inbred Lines

The use of male sterile inbreds is but one factor in the production of corn hybrids. Plant breeding techniques known in the art and used in a corn plant breeding program include, but are not limited to, recurrent selection, backcrossing, pedigree breeding, restriction length polymorphism enhanced selection, marker assisted selection and transformation. The development of corn hybrids in a corn plant breeding program requires, in general, the development of homozygous inbred lines, the crossing of these lines, and the evaluation of the crosses. Pedigree breeding and recurrent selection breeding methods are used to develop inbred lines from breeding populations. Corn plant breeding programs combine the genetic backgrounds from two or more inbred lines or various other germplasm sources into breeding pools from which new inbred lines are developed by selfing and selection of desired phenotypes. The new inbreds are crossed with other inbred lines and the hybrids from these crosses are evaluated to determine which of those have commercial potential. Plant breeding and hybrid development, as practiced in a corn plant-breeding program, are expensive and time-consuming processes.

Pedigree breeding starts with the crossing of two genotypes, each of which may have one or more desirable characteristics that is lacking in the other or which complements the other. If the two original parents do not provide all the desired characteristics, other sources can be included in the breeding population. In the pedigree method, superior plants are selfed and selected in successive generations. In the succeeding generations the heterozygous condition gives way to homogeneous lines as a result of self-pollination and selection. Typically in the pedigree method of breeding five or more generations of selfing and selection is practiced: $F_1 \rightarrow F_2$; $F_2 \rightarrow F_3$; $F_3 \rightarrow F_4$; $F_4 \rightarrow F_5$; etc.

Recurrent selection breeding, backcrossing for example, can be used to improve an inbred line and a hybrid that is made using those inbreds. Backcrossing can be used to transfer a specific desirable trait from one inbred or source to an inbred that lacks that trait. This can be accomplished, for example, by first crossing a superior inbred (recurrent parent) to a donor inbred (non-recurrent parent), that carries the appropriate gene(s) for the trait in question. The progeny of this cross is then mated back to the superior recurrent parent followed by selection in the resultant progeny for the desired trait to be transferred from the non-recurrent parent. After five or more backcross generations with selection for the desired trait, the progeny will be homozygous for loci controlling the characteristic being transferred, but will be like the superior parent for essentially all other genes. The last backcross generation is then selfed to give pure breeding progeny for the gene(s) being transferred. A hybrid developed from inbreds containing the transferred gene(s) is essentially the same as a hybrid developed from the same inbreds without the transferred gene(s).

Elite inbred lines, that is, pure breeding, homozygous inbred lines, can also be used as starting materials for breeding or source populations from which to develop other inbred lines. These inbred lines derived from elite inbred lines can be developed using the pedigree breeding and recurrent selection breeding methods described earlier. As an example, when backcross breeding is used to create these derived lines in a corn plant-breeding program, elite inbreds can be used as a parental line or starting material or source population and can serve as either the donor or recurrent parent.

Development of Corn Hybrids

A single cross corn hybrid results from the cross of two inbred lines, each of which has a genotype that complements the genotype of the other. The hybrid progeny of the first generation is designated $F_1$. In the development of commercial hybrids in a corn plant-breeding program, only the $F_1$ hybrid plants are sought. Preferred $F_1$ hybrids are more vigorous than their inbred parents. This hybrid vigor, or heterosis, can be manifested in many polygenic traits, including increased vegetative growth and increased yield.

The development of a corn hybrid in a corn plant breeding program involves three steps: (1) the selection of plants from various germplasm pools for initial breeding crosses; (2) the selfing of the selected plants from the breeding crosses for several generations to produce a series of inbred lines, which, although different from each other, breed true and are highly uniform; and (3) crossing the selected inbred lines with different inbred lines to produce the hybrid progeny ($F_1$). During the inbreeding process in corn, the vigor of the lines decreases. Vigor is restored when two different inbred lines are crossed to produce the hybrid progeny ($F_1$). An important consequence of the homozygosity and homogeneity of the inbred lines is that the hybrid between a defined pair of inbreds will always be the same. Once the inbreds that give a superior hybrid have been identified, the hybrid seed can be reproduced indefinitely as long as the homogeneity of the inbred parents is maintained. Much of the hybrid vigor exhibited by $F_1$ hybrids is lost in the next generation ($F_2$). Consequently, seed from hybrids is not used for planting stock.

Hybrid seed production requires elimination or inactivation of pollen produced by the female parent. Incomplete removal or inactivation of the pollen provides the potential for self-pollination. This inadvertently self-pollinated seed may be unintentionally harvested and packaged with hybrid seed.

Once the seed is planted, it is possible to identify and select these self-pollinated plants. These self-pollinated plants will be genetically equivalent to the female inbred line used to produce the hybrid.

As is readily apparent to one skilled in the art, the foregoing are only some of the various ways by which the inbred of the invention can be obtained by those looking to introgress the transgenic genotype of the invention into other corn lines. Other means are available, and the above examples are illustrative only.

EXAMPLES

The invention will be further described by reference to the following detailed examples. These examples are provided for purposes of illustration only, and are not intended to be limiting unless otherwise specified. Standard recombinant DNA and molecular cloning techniques used here are well known in the art and are described by Ausubel (ed.), Current Protocols in Molecular Biology, John Wiley and Sons, Inc. (1994); J. Sambrook, et al., *Molecular Cloning: A Laboratory Manual, 3d Ed.*, Cold Spring Harbor, N.Y.: Cold Spring Harbor Laboratory Press (2001); and by T. J. Silhavy, M. L. Berman, and L. W. Enquist, Experiments with Gene Fusions, Cold Spring Harbor Laboratory, Cold Spring Harbor, N.Y. (1984).

Example 1. Transformation and Selection of the 5307 Event

The 5307 event was produced by *Agrobacterium*-mediated transformation of the inbred corn (*Zea mays*) line NP2222. Immature embryos were transformed essentially as described in Negrotto et al. (Plant Cell Reports 19: 798-803, 2000), incorporated herein by reference, using a DNA fragment from plasmid pSYN12274 (FIG. 1). pSYN12274 contains a nucleotide sequence comprising tandem expression cassettes. The first expression cassette is comprised of a CMP promoter sequence (U.S. Pat. No. 7,166,770) operably linked to a FR8a coding sequence further operably linked to a nopaline synthase 3' end transcription termination and polyadenylation sequence. The second expression cassette is comprised of a maize ubiquitin promoter (ZmUbilnt) (Christensen et al. 1992 PMB 18: 675) operably linked to a PMI coding sequence further operably linked to a nopaline synthase 3' end transcription termination and polyadenylation sequence.

Immature embryos were excised from 8-12 day old ears and rinsed with fresh medium in preparation for transformation. Embryos were mixed with the suspension of *Agrobacterium* cells harboring the transformation vector pSYN12274, vortexed for 30 seconds, and allowed to incubate for an additional 5 minutes. Excess *Agrobacterium* solution was aspirated and embryos were then moved to plates containing a non-selective culture medium. Embryos were co-cultured with the remaining *Agrobacterium* at 22° C. for 2-3 days in the dark. Embryos were transferred to culture medium supplemented with ticarcillin (100 mg/ml) and silver nitrate (1.6 mg/1) and incubated in the dark for 10 days. Embryos producing embryogenic callus were transferred to cell culture medium containing mannose.

Regenerated plantlets were tested by TAQMAN® PCR analysis (see Example 2) for the presence of both the PMI and FR8a genes, as well as for the absence of the antibiotic resistance spectinomycin (spec) gene. Plants positive for both transgenes, and negative for the spec gene, were transferred to the greenhouse for further propagation. Positive events were identified and screened using insect bioassays against corn rootworm. Insecticidal events were characterized for copy number by TAQMAN analysis. Event 5307 was chosen for further analysis based on having a single copy of the transgenes, good protein expression as identified by ELISA, and better insecticidal activity against corn rootworm when compared to other events made with the same construct.

The $T_0$ 5307 event was backcrossed to inbred corn line NP2460, creating the $T_1$ population. The $T_1$ plants were self-pollinated to create the $T_2$ generation, and this process was repeated to create a $T_3$ generation. Progeny testing of the $T_3$ plants was employed to identify homozygous (converted) families. The event 5307-converted NP2460 inbred was crossed to other elite inbred lines to create hybrids used in further studies.

Example 2. Event 5307 Detection by TAQMAN PCR

TAQMAN analysis was essentially carried out as described in Ingham et al. (Biotechniques, 31:132-140, 2001) herein incorporated by reference. Briefly, genomic DNA was isolated from leaves of transgenic and non-transgenic corn plants using the Puregene® Genomic DNA Extraction kit (Gentra Systems, Minneapolis, Minn.) essentially according to the manufacturer's instruction, except all steps were conducted in 1.2 ml 96-well plates. The dried DNA pellet was resuspended in TE buffer (10 Mm Tris-HCl, pH 8.0, 1 mM EDTA).

TAQMAN PCR reactions were carried out in 96-well plates. For the endogenous corn gene control, primers and probes were designed specific to the *Zea mays* alcohol dehydrogenase (Adh) gene (Genbank accession no. AF044295). It will be recognized by the skilled person that other corn genes can be used as endogenous controls. Reactions were multiplexed to simultaneously amplify FR8a and Adh or PMI and Adh. For each sample, a master mixture was generated by combining 20 µL extracted genomic DNA with 35 µL 2×TAQMAN Universal PCR Master Mix (Applied Biosystems) supplemented with primers to a final concentration of 900 nM each, probes to a final concentration of 100 nM each, and water to a 70 µL final volume. This mixture was distributed into three replicates of 20 µL each in 96-well amplification plates and sealed with optically clear heat seal film (Marsh Bio Products). PCR was run in the ABI Prism 7700 instrument using the following amplification parameters: 2 min at 50° C. and 10 min at 95° C., followed by 35 cycles of 15 s at 95° C. and 1 min at 60° C.

Results of the TAQMAN analysis demonstrated that event 5307 had one copy of the FR8a gene and one copy of the PMI gene.

Examples of suitable primer/probe sequence combinations which were used are:

| Primer Name | Primer Sequence | SEQ ID NO: |
|---|---|---|
| FR8a-forward | 5'-TACGAGAGCTGGGTGAACTTCA-3' | SEQ ID NO: 73 |
| FR8a-reverse | 5'-CGATCAGGTCCAGCACGG-3' | SEQ ID NO: 74 |
| FR8a-probe | 5'-CCGCTACCGCCGCGAGATGA-3' (5' label = FAM, 3' label = TAMRA) | SEQ ID NO: 75 |
| PMI-forward | 5'-CCGGGTGAATCAGCGTTT-3' | SEQ ID NO: 76 |
| PMI-reverse | 5'-GCCGTGGCCTTTGACAGT-3' | SEQ ID NO: 77 |
| PMI-probe | 5'-TGCCGCCAACGAATCACCGG-3' (5' label = FAM, 3' label = TAMRA) | SEQ ID NO: 78 |

-continued

| Primer Name | Primer Sequence | SEQ ID NO: |
|---|---|---|
| ZmADH-267 forward | 5'-GAACGTGTGTTGGGTTTGCAT-3' | SEQ ID NO: 79 |
| ZmADH-337 reverse | 5'-TCCAGCAATCCTTGCACCTT-3' | SEQ ID NO: 80 |
| ZmADH-316 probe | 5'-TGCAGCCTAACCATGCGCAGGGTA-3' (5' label= TET, 3' label = TAMRA) | SEQ ID NO: 81 |

The PM1271, MIC5307a and MIC5307b TAQMAN assays are designed as an event specific assay, which covers the 3' junction sequence.

Examples of suitable primer/probe sequence combinations which were used are:

| Primer Name | Primer Sequence | SEQ ID NO: |
|---|---|---|
| PM1277-forward | 5'-GCCGTATCCGCAATGTGTTA-3' | SEQ ID NO: 82 |
| PM1277-reverse | 5'-GGCCCAGGGAAGAGGGTATAT-3' | SEQ ID NO: 83 |
| PM1277-probe | 5'-AAGTTGTCTAAGCGTCAAT-3' (5' label= TET, 3' label = TAMRA) | SEQ ID NO: 84 |
| MICS 307a-forward | 5'-TGTCTAAGCGTCAATTTGTTTACACC-3' | SEQ ID NO: 82 |
| MIC5307a-reverse | 5'-TTTGCCAGTGGGCCCA-3' | SEQ ID NO: 83 |
| MIC5307a-probe | 5'-ACAATATACCCTCTTCCCTGGGCCAGG-3' (5' label= TET, 3' label = TAMRA) | SEQ ID NO: 84 |
| MIC5307b-forward | 5'-GCCGTATCCGCAATGTGTTA-3' | SEQ ID NO: 82 |
| MICS 307b-reverse | 5'-AAGTTGTCTAAGCGTCAAT-3' | SEQ ID NO: 83 |
| MIC5307b-probe | 5'-GGCCCAGGGAAGAGGGTATAT-3' (5' label= TET, 3' label = TAMRA) | SEQ ID NO: 84 |

Example 3. Event 5307 Detection by Southern Blot

Genomic DNA used for southern analysis was isolated from pooled leaf tissue of ten plants representing the backcross six (BC6) generation of event 5307 using essentially the method of Thomas et al. (Theor. Appl. Genet. 86:173-180, 1993), incorporated herein by reference. All plants used for DNA isolation were individually analyzed using TAQMAN PCR (as described in Example 2) to confirm the presence of a single copy of the FR8a gene and the PMI gene. For the negative segregant controls, DNA was isolated from pooled leaf tissue of five plants representing the BC4 generation of event 5307. These negative segregant plants were individually analyzed using TAQMAN PCR and the assays were negative for the presence of the FR8a gene and the PMI gene, but were, as expected, positive for the assay internal control, the endogenous maize Adh gene.

Southern analysis was carried out using conventional molecular biology techniques. Genomic DNA (7.5 jag) was doubly digested with SmaI and PmeI restriction enzymes, which have single recognition sites within the event 5307 T-DNA insert from plasmid pSYN12274 (FIG. 1). This approach allows for determination of the number of copies of the elements, corresponding to the specific probe used for each Southern, which have been incorporated into event 5307. This results in one hybridization band per copy of the element present in event 5307. This results in one hybridization band per copy of the element present in event 5307. Following agarose gel electrophoresis and alkaline transfer to a Nytran® membrane, hybridizations were carried out using element-specific full-length PCR-generated probes. The full length probe used in the Southern blots comprises the nucleotide sequences set forth in SEQ ID NO: 7. The probe was labeled with $^{32}$P via random priming using the Rediprime™ II system (Amersham Biosciences, Cat. No. RPN1633).

The following high stringency hybridization conditions were used: 1-2 million cpm/ml are added to PerfectHyb (Sigma) supplemented with 100 µg/ml Calf Thymus DNA (Invitrogen) pre-warmed to 65° C. Pre-hybridization takes place in the same solution as above, at the same temp overnight or for at least one hour. Hybridization was carried out at 65° C. for 3 hours followed by washing 2× in 2×SSC, 0.1% SDS for 20 minutes at 65° C. and 2× in 0.1×SSC, 0.1% SDS for 20 minutes at 65° C.

Included on each Southern were three control samples: (1) DNA from a negative (non-transformed) segregant used to identify any endogenous Zea mays sequences that may cross-hybridize with the element-specific probe; (2) DNA from a negative segregant into which is introduced an amount of SmaI-PmeI digested pSYN12274 that is equal to one copy number based on probe length, to demonstrate the sensitivity of the experiment in detecting a single gene copy within the Zea mays genome; and (3) SmaI-PmeI digested pSYN12274 plasmid that is equal to one copy number based on probe length, as a positive control for hybridization as well as to demonstrate the sensitivity of the experiment.

The hybridization data provide confirmatory evidence to support the TAQMAN PCR analysis that event 5307 contains a single copy of the FR8a and PMI genes, and that 5307 event does not contain any of the vector backbone sequences present in pSYN12274. As expected for both the FR8a and PMI probes, the SmaI-PmeI digest resulted in a single hybridization band of the correct size, demonstrating that a single copy of each gene is present in the 5307 event. Additionally, for the backbone probe lack of hybridization demonstrates the absence of any pSYN12274 vector backbone sequences being incorporated into event 5307 during the transformation process.

Example 4. T-DNA Insert Sequencing

The nucleotide sequence of the entire transgene DNA insert present in event 5307 was determined to demonstrate overall integrity of the insert, contiguousness of the functional elements and to detect any individual basepair changes. The event 5307 insert was PCR amplified from DNA derived from the BC5 generation as two individual overlapping fragments. Each fragment was amplified using one polynucleotide primer homologous to plant genomic sequences flanking the event 5307 insert and one polynucleotide primer homologous to the FR8a gene. To generate the 5' fragment, a first polynucleotide primer homologous to the 5' flanking sequence, SEQ ID NO: 8 through SEQ ID NO: 15, was combined with a second polynucleotide primer homologous to the inserted DNA the FR8a gene, SEQ ID NO: 33 through SEQ ID NO: 41, the Ubiquitin promoter, SEQ ID NO: 42 through SEQ ID NO: 53 or the PMI gene, SEQ ID NO: 54 through SEQ ID NO: 60. To generate the 3' fragment, a first polynucleotide primer homologous to the 3' flanking sequence, SEQ ID NO: 69 through SEQ ID NO: 72, was combined with a second polynucleotide primer homologous to the inserted DNA within the FR8a gene, SEQ ID NO: 9 through SEQ ID NO: 17, the Ubiquitin promoter, SEQ ID NO: 18 through SEQ ID NO: 26 or the PMI gene, SEQ ID NO: 27 through SEQ ID NO: 32.

PCR amplification was carried out using the Expand High Fidelity PCR system (Roche, Cat. No. 1732650) and the following amplification parameters: 2 min at 94° C. for 1 cycle, followed by 10 cycles of 15 s at 94° C., 30 s at 55-65° C. and 5 min at 68° C., followed by 20 cycles of 15 s 94° C., 30 s at 55-65° C., and 5 min+5 s/cyc of 72° C., followed by 1 cycle of 7 min at 72° C.

The amplicon resulting from the PCR amplification using SEQ ID NO: 8 and SEQ ID NO: 41 comprised the 5' junction sequence (SEQ ID NO: 1). The amplicon resulting from the PCR amplification using SEQ ID NO: 69 and SEQ ID NO: 72 comprised the 3' junction sequence (SEQ ID NO: 2). Each sequencing fragment was individually cloned into the pCR®-XL-TOPO vector (Invitrogen, Cat. No. K4700-20) and three separate clones for each fragment were identified and sequenced. Sequencing was carried out using the ABI3730XL analyzer using ABI BigDye® 1.1 or Big Dye 3.1 dGTP (for GC rich templates) chemistry. The sequence analysis was done using the Phred, Phrap, and Consed package from the University of Washington and was carried out to an error rate of less than 1 in 10,000 bases (Ewing and Green, 1998). The final consensus sequence was determined by combining the sequence data from the six individual clones (three for each sequencing fragment) to generate one consensus sequence of the event 5307 insert. To further validate any individual basepair discrepancies between the event 5307 insert and the pSYN12274 plasmid, small (approximately 300-500 bp) PCR products specific to any regions where a basepair discrepancy was seen in the initial consensus sequence were amplified using the same methodology above. For all putative basepair discrepancies in the event 5307 insert, direct PCR product sequencing resulted in single clear peaks at all basepairs in question, indicating these discrepancies are likely present in the event 5307 insert. Alignment was performed using the ClustalW program with the following parameters: scoring matrix blosum55, gap opening penalty 15, gap extension penalty 6.66 (Thompson et al, 1994, Nucleic Acids Research, 22, 4673-4680).

The consensus sequence data for the event 5307 T-DNA insert demonstrates that the overall integrity of the insert and contiguousness of the functional elements within the insert as intended in pSYN12274 have been maintained.

Example 5. Analysis of Flanking DNA Sequence

Corn genome DNA sequence flanking the heterologous DNA inserted into the corn plant genome of event 5307 was obtained using OmniPlex™ Technology essentially as described in Kamberov et al (Proceedings of SPIE, *Tools for Molecular Analysis and High-Throughput Screening*, 4626: 1-12, 2002), incorporated herein by reference.

The 5' and 3' flanking sequences and junction sequences were confirmed using standard PCR procedures. The 5' flanking and junction sequences were confirmed using a first polynucleotide primer set forth in SEQ ID NO: 8 through SEQ ID NO: 14 combined with a second polynucleotide primer set forth in SEQ ID NO: 33 through SEQ ID NO: 41. The 3' flanking and junction sequences were confirmed using a first polynucleotide primer set forth in SEQ ID NO: 69 through SEQ ID NO: 72 combined with a second polynucleotide primer set forth in SEQ ID NO: 27 through SEQ ID NO: 32. It will be recognized by the skilled person that other primer sequences can be used to confirm the flanking and junction sequences.

The event 5307 insert was found to be flanked on the right border (5' flanking sequence) by the corn genomic sequence shown in SEQ ID NO: 5 and flanked on the left border (3' flanking sequence) by the corn genomic sequence shown in SEQ ID NO: 6. The 5' junction sequence is set forth in SEQ ID NO: 1. The 3' junction sequence is set forth in SEQ ID NO: 2. The integration site of the pSYN12274 vector insertion is comprised within SEQ ID NO: 103 or its reverse complement SEQ ID NO: 110, depending on the orientation of the nucleic acid used.

Example 6. Detection of Event 5307 Protein Via ELISA

To characterize the range of expression of FR8a (the active insecticidal principle) and phosphomannose isomerase (PMI) (the selectable marker) proteins in event 5307 plants, the concentrations of FR8a protein and PMI were determined by ELISA in several plant tissues. The hybrids were hemizygous for the transgenes in event 5307, whereas the inbred was homozygous for the transgenes.

Whole plants and individual parts (except pollen) were reduced to a fine powder by processing using either a coffee grinder, blender, Grindomix™ grinder (Brinkmann Instruments; Westbury, N.Y., USA), mortar with a pestle or mill, or a combination of these devices. All processing was done in the presence of either dry ice or liquid nitrogen. Samples were mixed well to ensure homogeneity. The entire plant tissue sample, or a representative sub-sample, was retained for analysis, allowing sufficient sample size for archival storage of reserve plant tissue samples. The percent dry weight of each sample was determined and the processed samples were stored at ca. −80° C. until lyophilization.

Fresh tissue (except pollen and silage) and whole-plant samples were extracted. For each sample analyzed, a 1.0 g aliquot of the powdered fresh material was weighed into a 15-ml polypropylene tube, suspended in 3 ml extraction buffer [50 mM CAPS, 0.1 M NaCl, 2 mM EDTA, 1 mM dithiothreitol, 1 mM 4-(1-aminoethyl)benzenesulfonyl fluoride HCl, 1 mM leupeptin, pH 10], and extracted using an Autogizer® homogenizer (Tomtek; Hamden, Conn., USA). After centrifugation for 15 min at 10,000×g at 4° C., the supernatant was used for FR8a and PMI analysis by ELISA. After treatment with iodoacetamide as described by Hill and Straka (1988), total protein in the extracts was quantitated using the BCA™ Protein Assay Reagent (Pierce; Rockford, Ill., USA).

Pollen extracts were prepared by suspending pollen 1:30 (w/v) in extraction buffer. After 30 min on ice, the pollen suspensions were disrupted by three passages through a French pressure cell at ca. 15,000 psi, followed by centrifugation at 14,000×g for 5 min at 4° C. Cry3A055 and PMI analyses by ELISA were performed on the supernatants as described below. Total protein was quantitated as described above.

Silage extracts were prepared by suspending silage 1:25 (w/v) in 2× extraction buffer. After 30 min on ice, the silage suspensions were extracted using a Brinkmann Polytron® Homogenizer (Brinkmann; Westbury, N.Y., USA). After centrifugation for 15 min at 10,000×g at 4° C., the supernatant was used for FR8a and PMI analysis by ELISA. Total protein was quantitated as described above.

FR8a Quantification

The extracts prepared as described above were quantitatively analyzed for FR8a by ELISA (Tijssen, 1985) using immuno-affinity purified monoclonal, anti-mCry3A antibody and immuno-affinity purified polyclonal anti-Cry1Ab antibody. The lower limit of quantification of the double-sandwich ELISA was estimated based on the lowest concentration of pure reference protein lying on the linear portion of the standard curve, the maximum volume of a control extract that could be analyzed without background interference, and the corresponding weight of the sample that the aliquot represented.

Quantifiable levels of FR8a protein were detected in all event 5307-derived plant tissues. In most cases, results are presented as means of the five replicate tissue samples. Control sample levels were below the limit of quantification for all tissues.

Across all growth stages, mean FR8a levels measured in leaves, roots and pollen ranged from ca. 18-29 µg/g fresh wt. (77-113 µg/g dry wt.), ca. 1.8-4.1 µg/g fresh wt. (22-41 µg/g dry wt.) and ca. <LOD–0.15 µg/g fresh wt. (<LOD–0.15 µg/g dry wt.) respectively. [limit of detection (LOD)=0.08 µg/g fresh wt., 0.08 µg/g dry wt.].

The levels of FR8a were generally similar among the inbred and hybrid genotypes for each tissue type at each time point PMI Quantification The extracts prepared as described above were quantitatively analyzed for PMI by ELISA (Tjissen, 1985) using Protein A-purified polyclonal rabbit and immunoaffinity-purified polyclonal goat antibodies specific for PMI. The lower limit of quantification of the double-sandwich ELISA was estimated based on the lowest concentration of pure reference protein lying on the linear portion of the standard curve, the maximum volume of a control extract that could be analyzed without background interference, and the corresponding weight of the sample that the aliquot represented.

PMI protein was detected in most of the event 5307-derived plant tissues analyzed. In most cases, results are presented as means of the five replicate tissue samples. Control sample levels were below the limit of quantification for all stages and tissues.

Across all plant stages, mean PMI levels measured in leaves, roots and pollen ranged from ca. 0.4 to ca. 0.6 µg/g fresh wt. (1.5-2.3 µg/g dry wt.), ca. 0.1-0.2 µg/g fresh wt. (0.9-1.5 µg/g dry wt.) and ca. 16.7-30.6 µg/g fresh wt. (17.1-31.1 µg/g dry wt.) respectively. [limit of detection (LOD)=0.08 µg/g fresh wt., 0.08 µg/g dry wt.].

The levels of PMI were generally similar among the inbred and hybrid genotypes for each tissue type at each time point.

Example 7. Field Efficacy of Event 5307

Western and Northern Corn Rootworm

Event 5307 plants were tested for efficacy against western and northern corn rootworm at 12 locations in the United States. Event 5307 was tested with and without the addition of the insecticidal seed treatment Crusier®. Control groups consisted of seed treated with two different rates of Cruiser® and an untreated check. Treatments consisted of four replications of two 17.5-20 foot rows spaced 30" on center designed in a randomized complete block. Ten plants per treatment were chosen at random and evaluated for efficacy using a 0-3 scale wherein 0=No feeding damage (lowest rating that can be given); 1=One node (circle of roots), or the equivalent of an entire node, eaten back within approximately two inches of the stalk (soil line on the $7^{th}$ node); 2=Two complete nodes eaten; 3=Three or more nodes eaten (highest rating that can be given). Damage in between complete nodes eaten was noted as the percentage of the node missing, i.e. 1.50=1½ nodes eaten, 0.25=¼ of one node eaten.

Event 5307 efficacy was compared with commercial granular insecticide standards applied in-furrow. The experimental design was as described above. Results in Table 2 demonstrate that the efficacy of event 5307 was comparable to the commercial standards in protecting plants against corn rootworm feeding damage.

TABLE 2

Comparison of efficacy of event 5307 with commercial insecticides applied in-furrow.

| Treatment | Root Damage Rating (0-3 CRW Scale) |
| --- | --- |
| 5307 | 0.06 |
| Force ® 3G | 0.23 |
| MIR604 | 0.13 |
| Untreated Check | 2.05 |

Mexican Corn Rootworm

Event 5307 plants were evaluated for resistance to the Mexican corn rootworm at two locations in Texas. Experimental design was essentially the same as described above.

A clear rate response was evident. Results shown in Table 3 demonstrate that the efficacy of event 5307 was comparable to the commercial standards in protecting plants against Mexican corn rootworm feeding damage.

TABLE 3

Efficacy of event 5307 compared with commercial insecticides applied in-furrow against Mexican corn rootworm.

| Treatment | Root Damage Rating (0-3 CRW Scale) |
| --- | --- |
| Event 5307 | 0.025 |
| Force ® 3G | 0.084 |
| MIR604 with Cruiser ® | 0.104 |
| Untreated Check | 0.710 |

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the invention.

Example 8. Use of Event 5307 Insertion Site for Targeted Integration in Maize The event 5307 flanking sequences disclosed in SEQ ID NO: 5 and SEQ ID NO: 6 were used to search maize genome databases. Identical matches to both flanking sequences where found on a BAC clone, ZMMBBc0077H14, of chromosome 5 (NCBI Accession No. AC202955). More specifically, the event 5307 insert lies between a 5' marker, designated herein as the public molecular marker umc1475 (SEQ ID No: 104), and a 3' marker, designated herein as the public molecular marker uaz190 (SEQ ID No: 107). Using this information, it was determined that the heterologous DNA inserted into event 5307 displaced 38 nucleotides of maize genomic DNA, which lies between the 5' flanking sequence (upstream of the deleted sequence) and the 3' flanking sequence (down stream of the deleted sequence). Primers useful for identifying molecular marker uaz190 are set forth as SEQ ID NO: 108 and 109. Primers useful for identifying molecular marker umc1475 are set forth as SEQ ID NO: 105 and 106. Further markers were developed for the purposes of fine mapping the insertion site. These markers are designated as SM1108C, SM0584B, SM0377D and SM0501D. Primers and probes useful for detecting these markers are as follows: SM1108C, SEQ ID NO: 91 through SEQ ID NO: 93; SM0584B, SEQ ID NO: 94 through SEQ ID: 96; SM0377D, SEQ ID NO: 97 through SEQ ID NO: 99; and SM0501D, SEQ ID NO: 100 through SEQ ID NO: 102.

Consistent agronomic performance of the transgene of event 5307 over several generations under field conditions suggests that these identified regions around the event 5307 insertion site provide good genomic locations for the targeted integration of other transgenic genes of interest. Such targeted integration overcomes the problems with so-called "positions effects," and the risk of creating a mutation in the genome upon integration of the transgene into the host. Further advantages of such targeted integration include, but are not limited to, reducing the large number of transformation events that must be screened and tested before obtaining a transgenic plant that exhibits the desired level of transgene expression without also exhibiting abnormalities resulting from the inadvertent insertion of the transgene into an important locus in the host genome. Moreover, such targeted integration allows for stacking transgenes rendering the breeding of elite plant lines with both genes more efficient.

Using the above disclosed teaching, the skilled person is able to use methods know in the art to target transgenes to the same insertion site as that in event 5307 or to a site in close proximity to the insertion site in 5307. One such method is disclosed in US Patent Application Publication No. 20060253918, herein incorporated by reference in its entirety. Briefly, up to 20 Kb of the genomic sequence flanking 5' to the insertion site (SEQ ID NO: 5) and up to 20 Kb of the genomic sequence flanking 3' to the insertion site (SEQ ID NO: 6) are used to flank the gene or genes of interest that are intended to be inserted into a genomic location on Chromosome 5 via homologous recombination. These sequences can be further flanked by T-DNA border repeats such as the left border (LB) and right border (RB) repeat sequences and other booster sequences for enhancing T-DNA delivery efficiency. The gene or genes of interest can be placed exactly as in the event 5307 insertion site or can be placed anywhere within the 20 Kb regions around the event 5307 insertion sites to confer consistent level of transgene expression without detrimental effects on the plant. The DNA vectors containing the gene or genes of interest and flanking sequences can be delivered into plant cells via one of the several methods known to those skilled in the art, including but not limited to *Agrobacterium*-mediated transformation. The insertion of the DNA vector into the event 5307 target site can be further enhanced by one of the several methods, including but not limited to the co-expression or up-regulation of recombination enhancing genes or down-regulation of endogenous recombination suppression genes. Furthermore, it is known in the art that cleavage of specific sequences in the genome can be used to increase homologous recombination frequency, therefore insertion into the event 5307 insertion site and its flanking regions can be enhanced by expression of natural or designed sequence-specific endonucleases for cleaving these sequences.

An example of this technique is demonstrated in Shukla et al. (Nature vol. 459, 21 May 2009). This method uses zinc finger nucleases for the purposes of targeting heterologous sequences to a specific locus based upon the use of homologous sequences within the target plant. One skilled in the art could use the event 5307 insert between a 5' marker, designated herein as the public molecular marker umc1475 (SEQ ID No: 104), and a 3' marker, designated herein as the public molecular marker uaz190 (SEQ ID No: 107) to create a locus for targeted insertion.

Example 9. Use of Event 5307 Insertion Site and Flanking Sequences for Stabilization of Gene Expression The genomic sequences flanking the event 5307 insertion site may also be used to stabilize expression of other gene(s) of interest when inserted as a transgene in other genomic locations in maize and other crops. Specifically, up to 20 Kb of the genomic sequence flanking 5' to the insertion site (SEQ ID NO: 5) and up to 20 Kb of the genomic sequence flanking 3' to the insertion site (SEQ OD NO: 6) are used to flank the gene or genes of interest that are intended to be inserted into the genome of plants. These sequences can be further flanked by T-DNA border repeats such as the left border (LB) and right border (RB) repeat sequences and other booster sequences for enhancing T-DNA delivery efficiency. The gene or genes of interest can be placed exactly as in the event 5307 insertion site or can be placed anywhere within the 20 Kb regions around the event 5307 insertion sites to confer consistent level of transgene expression. The DNA vectors containing the gene or genes of interest and event 5307 insertion site flanking sequence can be delivered into plant cells via one of the several methods known to those skilled in the art, including but not limited to protoplast transformation, biolistic bombardment and *Agrobacterium*-mediated transformation. The delivered DNA can be integrated randomly into a plant genome or can also be present as part of the independently segregating genetic units such as artificial chromosome or mini-chromosome. The DNA vectors containing the gene(s) of interest and the event 5307 insertion site flanking sequences can be delivered into plant cells. Thus, by surrounding a gene or genes of interest with the genomic sequence flanking the event 5307 insertion site, the expression of such genes are stabilized in a transgenic host plant such as a dicot plant or a monocot plant like corn.

DEPOSIT

Applicants have made a deposit of corn seed of event 5307 disclosed above on 15 Oct. 2008 in accordance with the Budapest Treaty at the American Type Culture Collection (ATCC), 10801 University Boulevard, Manassas, Va. 20110-2209 under ATCC Accession No. PTA-9561. The deposit will be maintained in the depositary for a period of 30 years, or 5 years after the last request, or the effective life of the patent, whichever is longer, and will be replaced as necessary during that period. Applicants impose no restrictions on the availability of the deposited material from the ATCC; however, applicants have no authority to waive any restrictions imposed by law on the transfer of biological material or its transportation in commerce.

All publications and published patent documents cited in this specification are incorporated herein by reference to the same extent as if each individual publication or patent document was specifically and individually indicated to be incorporated by reference.

What is claimed is:

1. A method of producing corn seed, the method comprising:
   (a) sexually crossing a first inbred corn plant with a second inbred corn plant, wherein the first corn plant or the second corn plant comprises corn event 5307 DNA, and wherein representative seed comprising the corn event 5307 DNA has been deposited at the American Type Culture Collection under the accession number PTA-9561; and
   (b) harvesting the resultant first generation corn seed.

2. A method of producing hybrid corn seeds, the method comprising:
   a) planting seeds of a first inbred corn plant comprising event 5307 DNA and seeds of a second inbred corn plant having a genotype different from the first inbred corn plant, wherein representative seed comprising the corn event 5307 DNA has been deposited at the American Type Culture Collection under the accession number PTA-9561;
   b) cultivating corn plants resulting from said planting until the production of flowers;
   c) emasculating said flowers produced at the time of flowering of either the first or the second inbred corn line;
   d) sexually crossing the non-emasculated inbred plant with pollen of the emasculated inbred plant to produce hybrid corn seeds; and
   e) harvesting the hybrid corn seeds.

3. Hybrid corn seed produced by the method of claim 2.

4. Hybrid corn plants produced by growing hybrid corn seed of claim 3.

5. A method for producing a corn plant resistant to a coleopteran insect pest comprising:
   (a) sexually crossing a first parent corn plant with a second parent corn plant, wherein said first or second parent corn plant comprises corn event 5307 DNA, thereby producing a plurality of first generation progeny plants, and wherein representative seed comprising the corn event 5307 DNA has been deposited at the American Type Culture Collection under the accession number PTA-9561;
   (b) selecting a first generation progeny plant that is resistant to a coleopteran insect pest infestation;
   (c) selfing the first generation progeny plant, thereby producing a plurality of second generation progeny plants; and
   (d) selecting from the second generation progeny plants, a plant that is resistant to a coleopteran insect pest;
   wherein the selected second generation progeny plant comprises a nucleotide sequence selected from the group consisting of SEQ ID NO: 1, SEQ ID NO: 2, SEQ ID NO: 3 and SEQ ID NO: 4.

6. The method according to claim 5, wherein the coleopteran insect pest comprises a corn rootworm.

7. The method according to claim 5, wherein the coleopteran insect pest comprises western corn rootworm.

* * * * *

SEQUENCE LISTING

```
<160> NUMBER OF SEQ ID NOS: 111

<210> SEQ ID NO 1
<211> LENGTH: 20
<212> TYPE: DNA
<213> ORGANISM: Artificial
<220> FEATURE:
<223> OTHER INFORMATION: 5' genome-insert juction

<400> SEQUENCE: 1
caactcacga actgatagtt                                                       20

<210> SEQ ID NO 2
<211> LENGTH: 20
<212> TYPE: DNA
<213> ORGANISM: Artificial
<220> FEATURE:
<223> OTHER INFORMATION: 3' insert-genome junction

<400> SEQUENCE: 2
ccacaatata ccctcttccc                                                       20

<210> SEQ ID NO 3
<211> LENGTH: 200
<212> TYPE: DNA
<213> ORGANISM: Artificial
<220> FEATURE:
<223> OTHER INFORMATION: 5' genome + insert sequence

<400> SEQUENCE: 3
gtcgactcaa acggctagtt ctgacagcta gccgttggac agatggcata ccggacagtc           60
cgatacgctg tccggtgtgc ctctaaaatt caactcacga actgatagtt taaactgaag          120
gcgggaaacg acaatctgat catgagcgga gaattaaggg agtcacgtta tgaccccgc           180 cgatgacgcg ggacaagccg                                                      200

<210> SEQ ID NO 4
<211> LENGTH: 200
<212> TYPE: DNA
<213> ORGANISM: Artificial
<220> FEATURE:
<223> OTHER INFORMATION: 3' insert + genome sequence

<400> SEQUENCE: 4
gccctgcagg aaatttaccg gtgcccgggc ggccagcatg gccgtatccg caatgtgtta           60
ttaagttgtc taagcgtcaa tttgtttaca ccacaatata ccctcttccc tgggccaggc          120
tgggcccact ggcaaagggt gcaccggaca gtccggtgcc ccaaagccag aaaccctagc          180
ttctgttttg tgctgttttt                                                      200
```

<210> SEQ ID NO 5
<211> LENGTH: 1548
<212> TYPE: DNA
<213> ORGANISM: Artificial
<220> FEATURE:
<223> OTHER INFORMATION: 5' genome + insert sequence

<400> SEQUENCE: 5

| | | | | | |
|---|---|---|---|---|---|
| tacaagaata | ttgagacgtg | agtacatagc | attggcattt | tcattagcaa | gcatttcaaa | 60 |
| agaatttaat | tttctcatag | caatgtgata | tctctcctca | cgctcaattc | tagttccttc | 120 |
| atgtagagca | catatgtcca | tccacaaatc | atgacaattt | ttatggtttc | taactctatt | 180 |
| aaacacatct | ttgcaaaggc | ctctaaaaag | ggtgttttg | gccttagcat | tccatttctc | 240 |
| atagttcaac | tcttcaccta | caagatttgt | gggatctcta | ggttcgggga | atctttgtgt | 300 |
| ggcggctttg | tagacaccaa | tgtctatagc | ctctaaatat | gcttccatac | gaattttcca | 360 |
| atatggaaaa | tcgtcaccat | aaaaaacggg | agaaggtcca | tccccaccgg | acatcgttac | 420 |
| tctagcggtt | aagctaatct | aagagcaaca | aggctcttat | accaattgaa | aggatcacga | 480 |
| tgcccaagag | gggggttga | attgggcttt | tctaaaaatc | aacactaact | aaaatctaag | 540 |
| caagagccca | acttcacccc | gacaactagc | actaagagaa | taatactaga | aatacaacaa | 600 |
| tgctaagata | atacttcaaa | tacttgctaa | acaaatacac | aatgtaaaat | acttgaatta | 660 |
| agtgcggaat | gtaaagcaag | gtttagaaga | ctcctccaat | ttttctagag | gtatcaaaga | 720 |
| gtcggcactc | tccctagtc | ctcgttggag | cacctgcgta | agggtatcgc | tctcccttgg | 780 |
| tcatcgcaag | aaccaagtgc | tcacaacgag | atgatccttt | gccactccgg | cgcggtggat | 840 |
| ccctcacgac | cgcttacaaa | cttgagtcgg | gtcaccaaca | agatctccac | ggtgatcacc | 900 |
| gagctcccaa | cgccaccaag | ccgtctaggt | gatgccgatc | accaagagta | ataagccata | 960 |
| gactttcact | tgaccaagag | aagcctaatg | catgcggtgt | gtgctctagg | tggctctcgc | 1020 |
| tagcgttaat | gaggtccaaa | tgcgggatta | agattctcaa | gtcacctcac | taggctttgt | 1080 |
| ggtgcttgca | atgctctacc | aatgtgtagg | agtaaatgtg | ggcagcaaga | ccatcaatat | 1140 |
| ggtaggtgga | tggggtataa | atagccctca | cccaccaact | agccattacc | aggaatctgc | 1200 |
| tgcgcatggg | cgcaccggac | agtccggtgt | gccaccggtg | cgccaacggt | cgactcaaac | 1260 |
| ggctagttct | gacagctagc | cgttggacag | atggcatacc | ggacagtccg | atacgctgtc | 1320 |
| cggtgtgcct | ctaaaattca | actcacgaac | tgatagttta | aactgaaggc | gggaaacgac | 1380 |
| aatctgatca | tgagcggaga | attaagggag | tcacgttatg | accccgccg | atgacgcggg | 1440 |
| acaagccgtt | ttacgtttgg | aactgacaga | accgcaacgc | tgcaggaatt | ggccgcagct | 1500 |
| gccatttaaa | tcaattgggc | gcgccgaatt | cgagctcggt | acaagctt | | 1548 |

<210> SEQ ID NO 6
<211> LENGTH: 1093
<212> TYPE: DNA
<213> ORGANISM: Zea mays

<400> SEQUENCE: 6

| | | | | | |
|---|---|---|---|---|---|
| ccctcttccc | tgggccaggc | tgggcccact | ggcaaagggt | gcaccggaca | gtccggtgcc | 60 |
| ccaaagccag | aaaccctagc | ttctgttttg | tgctgttttt | tcaatttggt | ttttgttcta | 120 |
| acttgtgagt | atgttctaga | gttacaccta | gcactatatg | tgagtgtgaa | tatgcaccaa | 180 |
| cactacacta | gaactctttt | ggtcaaacta | cttatcgaca | acccctcttt | atagtacggc | 240 |
| taaaacaaaa | taaaagacct | aactatatca | cgagtgtccg | caactccttg | acactcggaa | 300 |

```
tacgaagacc ttcactttt tgtttcgtcgc tttagccgtt gcttcaagtt tttatctccg    360
ggattgtttt caccattgta gtacatctac ctgtaatgcg acctaactta ccatttgcct    420
ctgcaaaaca catgttagtc acatataaaa ttacgttgtc attaatcact aaaaccaacc    480
aggggcctag atgctttcta gtttaaatcc ccaacaagtc aaaattcttt ctattttttt    540
ttgcaagttc caattgacat ctgaaaggtt gtaaggtaca cgtttggctc tcattgataa    600
cgggggaaag atacagtgca aaccaccata taatgaccca cttctaatcg aatggacctg    660
taacgacgaa atacctgtg agaactatgg ttcactcatg ttaattcatt gaaattgttg    720
tagtgaattg acatggttgg gagcctgctt agagagtata gattgtcact ttttttttgga   780
ccgcaactta ttttaaaag atattgcgat cgcttgttta gtagctgttt caggccccaa    840
tgcagtttct atcgtgatcc atttaagtca ctcaacattc tcatacttct cattttgcat    900
taattcattc caatctccac tactataaaa tactagcttc gatggtcgtc atacgccatg    960
cacgaagcat gtagatcaat ccgcatacca gtgggcatct atagataggc tgtgaaaacc   1020
acccaaatcc ctactagtgg acattttatc tatagatgga ccgtgagaaa ccacacaagt   1080
ctaacacgac agg                                                       1093

<210> SEQ ID NO 7
<211> LENGTH: 6206
<212> TYPE: DNA
<213> ORGANISM: Artificial
<220> FEATURE:
<223> OTHER INFORMATION: Vector insert

<400> SEQUENCE: 7
ctggcagaca aagtggcaga catactgtcc cacaaatgaa gatggaatct gtaaagaaa     60
acgcgtgaaa taatgcgtct gacaaaggtt aggtcggctg cctttaatca ataccaaagt   120
ggtccctacc acgatggaaa aactgtgcag tcggtttggc tttttctgac gaacaaataa   180
gattcgtggc cgacaggtgg gggtccacca tgtgaaggca tcttcagact ccaataatgg   240
agcaatgacg taagggctta cgaaataagt aagggtagtt tgggaaatgt ccactcaccc   300
gtcagtctat aaatacttag cccctccctc attgttaagg gagcaaggat ccaccatgac   360
tagtaacggc cgccagtgtg ctggtattcg cccttatgac ggccgacaac aacaccgagg   420
cctggacagc agcaccacca aggacgtgat ccagaagggc atcagcgtgg tgggcgacct   480
gctgggcgtg gtgggcttcc ccttcggcgg cgccctggtg agcttctaca ccaacttcct   540
gaacaccatc tggcccagcg aggacccctg gaaggccttc atggagcagg tggaggccct   600
gatggaccag aagatcgccg actacgccaa gaacaaggca ctggccgagc tacagggcct   660
ccagaacaac gtgagggact atgtgagcgc cctgagcagc tggcagaaga ccccgctgc    720
accgttccgc aaccccaca gccagggccg catccgcgag ctgttcagcc aggccgagag   780
ccacttccgc aacagcatgc ccagcttcgc catcagcggc tacgaggtgc tgttcctgac   840
cacctacgcc caggccgcca acacccacct gttcctgctg aaggacgccc aaatctacgg   900
agaggagtgg ggctacgaga aggaggacat cgccgagttc tacaagcgcc agctgaagct   960
gacccaggag tacaccgacc actgcgtgaa gtggtacaac gtgggtctag acaagctccg  1020
cggcagcagc tacgagagct gggtgaactt caaccgctac cgccgcgaga tgaccctgac  1080
cgtgctggac ctgatcgccc tgttcccct gtacgacgtg cgcctgtacc caaggaggt   1140
gaagaccgag ctgaccgcgc acgtgctgac cgaccccatc gtgggcgtga caacctgcg   1200
cggctacggc accaccttca gcaacatcga gaactacatc cgcaagcccc acctgttcga  1260
```

```
ctacctgcac cgcatccagt tccacacgcg tttccagccc ggctactacg gcaacgacag   1320
cttcaactac tggagcggca actacgtgag cacccgcccc agcatcggca gcaacgacat   1380
catcaccagc cccttctacg gcaacaagag cagcgagccc gtgcagaacc ttgagttcaa   1440
cggcgagaag gtgtaccgcg ccgtggctaa caccaacctg gccgtgtggc cctctgcagt   1500
gtacagcggc gtgaccaagg tggagttcag ccagtacaac gaccagaccg acgaggccag   1560
cacccagacc tacgacagca gcgcaacgt gggcgccgtg agctgggaca gcatcgacca   1620 gctgccccc gagaccaccg acgagcccct ggagaagggc tacagccacc agctgaacta   1680
cgtgatgtgc ttcctgatgc agggcagccg cggcaccatc cccgtgctga cctggaccca   1740
caagagcgtc gacttcttca acatgatcga cagcaagaag atcacccagc tgcccctgac   1800
caagagcacc aacctgggca gcggcaccag cgtggtgaag ggccccggct tcaccggcgg   1860
cgacatcctg cgccgcacca gccccggcca gatcagcacc ctgcgcgtga acatcaccgc   1920
ccccctgagc cagcgctacc gcgtccgcat ccgctacgcc agcaccacca acctgcagtt   1980
ccacaccagc atcgacggcc gccccatcaa ccagggcaac ttcagcgcca ccatgagcag   2040
cggcagcaac ctgcagagcg gcagcttccg caccgtgggc ttcaccaccc ccttcaactt   2100
cagcaacggc agcagcgtgt tcaccctgag cgcccacgtg ttcaacagcg gcaacgaggt   2160
gtacatcgac cgcatcgagt tcgtgcccgc cgaggtgacc ttcgaggccg agtacgacct   2220
ggagagggct cagaaggccg tgaacgagct gttcaccagc agcaaccaga tcggcctgaa   2280
gaccgacgtg accgactacc acatcgatca ggtgtaggag ctgagctcta gatccccgaa   2340
tttccccgat cgttcaaaca tttggcaata agtttcttaa agattgaatc ctgttgccgg   2400
tcttgcgatg attatcatat aatttctgtt gaattacgtt aagcatgtaa taattaacat   2460
gtaatgcatg acgttattta tgagatgggt ttttatgatt agagtcccgc aattatacat   2520
ttaatacgcg atagaaaaca aaatatagcg cgcaaactag gataaattat cgcgcgcggt   2580
gtcatctatg ttactagatc gggaattggg taccagcttg catgcctgca gtgcagcgtg   2640
acccggtcgt gcccctctct agagataatg agcattgcat gtctaagtta taaaaaatta   2700
ccacatattt ttttttgtcac acttgtttga agtgcagttt atctatcttt atacatatat   2760
ttaaacttta ctctacgaat aatataatct atagtactac aataatatca gtgttttaga   2820
gaatcatata aatgaacagt tagacatggt ctaaaggaca attgagtatt ttgacaacag   2880
gactctacag ttttatcttt ttagtgtgca tgtgttctcc ttttttttg caaatagctt   2940 cacctatata tacttcatc cattttatta gtacatccat ttagggttta gggttaatgg   3000
tttttataga ctaattttttt tagtacatct attttattct attttagcct ctaaattaag   3060
aaaactaaaa ctctattta gttttttat taataattt agatataaaa tagaataaaa   3120
taaagtgact aaaaattaaa caaatacccct ttaagaaatt aaaaaaacta aggaaacatt   3180
tttcttgttt cgagtagata tgccagcct gttaaacgcc gtcgacgagt ctaacgaca   3240 ccaaccagcg aaccagcagc gtcgcgtcgg gccaagcgaa gcagacggca cggcatctct   3300
gtcgctgcct ctggacccct ctcgagagtt ccgctccacc gttggacttg ctccgctgtc   3360
ggcatccaga aattgcgtgg cggagcggca gacgtgagcc ggcacggcag gcggcctcct   3420
cctcctctca cggcaccggc agctacgggg gattcctttc ccaccgctcc ttcgctttcc   3480
cttcctcgcc cgccgtaata aatagacacc cctccacac cctcttccc caacctcgtg   3540 ttgttcggag cgcacacaca cacaaccaga tctcccccaa atccaccgt cggcacctcc   3600
```

```
gcttcaaggt acgccgctcg tcctccccccc ccccccctct ctaccttctc tagatcggcg    3660
ttccggtcca tggttagggc ccggtagttc tacttctgtt catgtttgtg ttagatccgt    3720
gtttgtgtta gatccgtgct gctagcgttc gtacacggat gcgacctgta cgtcagacac    3780
gttctgattg ctaacttgcc agtgtttctc tttggggaat cctgggatgg ctctagccgt    3840
tccgcagacg ggatcgattt catgattttt tttgtttcgt tgcatagggt ttggtttgcc    3900
cttttccttt atttcaatat atgccgtgca cttgttgtc gggtcatctt ttcatgcttt     3960
tttttgtctt ggttgtgatg atgtggtctg gttgggcggt cgttctagat cggagtagaa    4020
ttctgtttca aactacctgg tggatttatt aattttggat ctgtatgtgt gtgccataca    4080
tattcatagt tacgaattga agatgatgga tggaaatatc gatctaggat aggtatacat    4140
gttgatgcgg gttttactga tgcatataca gagatgcttt ttgttcgctt ggttgtgatg    4200
atgtggtgtg gttgggcggt cgttcattcg ttctagatcg gagtagaata ctgtttcaaa    4260
ctacctggtg tatttattaa ttttggaact gtatgtgtgt gtcatacatc ttcatagtta    4320
cgagtttaag atggatggaa atatcgatct aggataggta tacatgttga tgtgggtttt    4380
actgatgcat atacatgatg gcatatgcag catctattca tatgctctaa ccttgagtac    4440
ctatctatta taataaacaa gtatgttttta taattatttt gatcttgata tacttggatg    4500
atggcatatg cagcagctat atgtggattt ttttagcccct gccttcatac gctatttatt    4560
tgcttggtac tgtttcttttt gtcgatgctc accctgttgt ttggtgttac ttctgcaggg    4620
atccccgatc atgcaaaaac tcattaactc agtgcaaaac tatgcctggg gcagcaaaac    4680
ggcgttgact gaactttatg gtatggaaaa tccgtccagc cagccgatgg ccgagctgtg    4740
gatgggcgca catccgaaaa gcagttcacg agtgcagaat gccgccggag atatcgtttc    4800
actgcgtgat gtgattgaga gtgataaatc gactctgctc ggagaggccg ttgccaaacg    4860
ctttggcgaa ctgccttcc tgttcaaagt attatgcgca gcacagccac tctccattca    4920
ggttcatcca aacaaacaca attctgaaat cggttttgcc aaagaaaatg ccgcaggtat    4980
cccgatggat gccgccgagc gtaactataa agatcctaac cacaagccgg agctggtttt    5040
tgcgctgacg cctttccttg cgatgaacgc gtttcgtgaa ttttccgaga ttgtctccct    5100
actccagccg gtcgcaggtg cacatccggc gattgctcac ttttttacaac agcctgatgc    5160 cgaacgttta agcgaactgt tcgccagcct gttgaatatg cagggtgaag aaaaatcccg    5220
cgcgctggcg attttaaaat cggccctcga tagccagcag ggtgaaccgt ggcaaacgat    5280
tcgtttaatt tctgaatttt acccggaaga cagcggtctg ttctcccgc tattgctgaa    5340 tgtggtgaaa ttgaaccctg cgaagcgat gttcctgttc gctgaaacac cgcacgctta    5400
cctgcaaggc gtggcgctgg aagtgatggc aaactccgat aacgtgctgc gtgcgggtct    5460
gacgcctaaa tacattgata ttccggaact ggttgccaat gtgaaattcg aagccaaacc    5520
ggctaaccag ttgttgaccc agccggtgaa acaaggtgca gaactggact tcccgattcc    5580
agtggatgat tttgccttct cgctgcatga ccttagtgat aaagaaacca ccattagcca    5640
gcagagtgcc gccattttgt tctgcgtcga aggcgatgca acgttgtgga aggttctca    5700 gcagttacag cttaaaccgg tgaatcagc gtttattgcc gccaacgaat caccggtgac    5760
tgtcaaaggc cacggccgtt agcgcgtgt ttacaacaag ctgtaagagc ttactgaaaa    5820
aattaacatc tcttgctaag ctgggagctc gatccgtcga cctgcagatc gttcaaacat    5880
ttggcaataa agtttcttaa gattgaatcc tgttgccggt cttgcgatga ttatcatata    5940
atttctgttg aattacgtta agcatgtaat aattaacatg taatgcatga cgttatttat    6000
```

```
gagatgggtt tttatgatta gagtcccgca attatacatt taatacgcga tagaaaacaa    6060
aatatagcgc gcaaactagg ataaattatc gcgcgcggtg tcatctatgt tactagatct    6120
gctagccctg caggaaattt accggtgccc gggcggccag catggccgta tccgcaatgt    6180
gttattaagt tgtctaagcg tcaatt                                         6206
```

<210> SEQ ID NO 8
<211> LENGTH: 28
<212> TYPE: DNA
<213> ORGANISM: Artificial
<220> FEATURE:
<223> OTHER INFORMATION: Primer

<400> SEQUENCE: 8
cacgaccgct tacaaacttg agttgggt                                       28

<210> SEQ ID NO 9
<211> LENGTH: 21
<212> TYPE: DNA
<213> ORGANISM: Artificial
<220> FEATURE:
<223> OTHER INFORMATION: Primer

<400> SEQUENCE: 9
ctcccaacgc caccaagccg t                                              21

<210> SEQ ID NO 10
<211> LENGTH: 25
<212> TYPE: DNA
<213> ORGANISM: Artificial
<220> FEATURE:
<223> OTHER INFORMATION: Primer

<400> SEQUENCE: 10
cctcactagg ctttgtggtg cttgc                                          25

<210> SEQ ID NO 11
<211> LENGTH: 24
<212> TYPE: DNA
<213> ORGANISM: Artificial
<220> FEATURE:
<223> OTHER INFORMATION: Primer

<400> SEQUENCE: 11
gagtaaatgt gggcagcaag acca                                           24

<210> SEQ ID NO 12
<211> LENGTH: 24
<212> TYPE: DNA
<213> ORGANISM: Artificial
<220> FEATURE:
<223> OTHER INFORMATION: Primer

<400> SEQUENCE: 12
cccaccaact agccattacc agga                                           24

<210> SEQ ID NO 13
<211> LENGTH: 23
<212> TYPE: DNA
<213> ORGANISM: Artificial
<220> FEATURE:
<223> OTHER INFORMATION: Primer

<400> SEQUENCE: 13
aaacggctag ttctgacagc tag        23

<210> SEQ ID NO 14
<211> LENGTH: 21
<212> TYPE: DNA
<213> ORGANISM: Artificial
<220> FEATURE:
<223> OTHER INFORMATION: Primer

<400> SEQUENCE: 14
atacgctgtc cggtgtgcct c        21

<210> SEQ ID NO 15
<211> LENGTH: 18
<212> TYPE: DNA
<213> ORGANISM: Artificial
<220> FEATURE:
<223> OTHER INFORMATION: Primer

<400> SEQUENCE: 15
ggtagtttgg gaaatgtc        18

<210> SEQ ID NO 16
<211> LENGTH: 18
<212> TYPE: DNA
<213> ORGANISM: Artificial
<220> FEATURE:
<223> OTHER INFORMATION: Primer

<400> SEQUENCE: 16
atacttagcc cctccctc        18

<210> SEQ ID NO 17
<211> LENGTH: 17
<212> TYPE: DNA
<213> ORGANISM: Artificial
<220> FEATURE:
<223> OTHER INFORMATION: Primer

<400> SEQUENCE: 17
atgactagta acggccg        17

<210> SEQ ID NO 18
<211> LENGTH: 18
<212> TYPE: DNA
<213> ORGANISM: Artificial
<220> FEATURE:
<223> OTHER INFORMATION: Primer

<400> SEQUENCE: 18
gccgacaaca acaccgag        18

<210> SEQ ID NO 19
<211> LENGTH: 17
<212> TYPE: DNA
<213> ORGANISM: Artificial
<220> FEATURE:
<223> OTHER INFORMATION: Primer

<400> SEQUENCE: 19
ctacgccaag aacaagg        17

<210> SEQ ID NO 20
<211> LENGTH: 17
<212> TYPE: DNA
<213> ORGANISM: Artificial

```
<220> FEATURE:
<223> OTHER INFORMATION: Primer

<400> SEQUENCE: 20
gagaggagtg gggctac                                                   17

<210> SEQ ID NO 21
<211> LENGTH: 17
<212> TYPE: DNA
<213> ORGANISM: Artificial
<220> FEATURE:
<223> OTHER INFORMATION: Primer

<400> SEQUENCE: 21
ccaccttcag caacatc                                                   17

<210> SEQ ID NO 22
<211> LENGTH: 18
<212> TYPE: DNA
<213> ORGANISM: Artificial
<220> FEATURE:
<223> OTHER INFORMATION: Primer

<400> SEQUENCE: 22
agttcagcca gtacaacg                                                  18

<210> SEQ ID NO 23
<211> LENGTH: 17
<212> TYPE: DNA
<213> ORGANISM: Artificial
<220> FEATURE:
<223> OTHER INFORMATION: Primer

<400> SEQUENCE: 23
agaagatcac ccagctg                                                   17

<210> SEQ ID NO 24
<211> LENGTH: 17
<212> TYPE: DNA
<213> ORGANISM: Artificial
<220> FEATURE:
<223> OTHER INFORMATION: Primer

<400> SEQUENCE: 24
ccttcaactt cagcaac                                                   17

<210> SEQ ID NO 25
<211> LENGTH: 17
<212> TYPE: DNA
<213> ORGANISM: Artificial
<220> FEATURE:
<223> OTHER INFORMATION: Primer

<400> SEQUENCE: 25
aggtgtagga gctgagc                                                   17

<210> SEQ ID NO 26
<211> LENGTH: 18
<212> TYPE: DNA
<213> ORGANISM: Artificial
<220> FEATURE:
<223> OTHER INFORMATION: Primer

<400> SEQUENCE: 26
tctagatccc cgaatttc                                                  18
```

-continued

```
<210> SEQ ID NO 27
<211> LENGTH: 19
<212> TYPE: DNA
<213> ORGANISM: Artificial
<220> FEATURE:
<223> OTHER INFORMATION: Primer

<400> SEQUENCE: 27
cccctctcta gagataatg                                                    19

<210> SEQ ID NO 28
<211> LENGTH: 18
<212> TYPE: DNA
<213> ORGANISM: Artificial
<220> FEATURE:
<223> OTHER INFORMATION: Primer

<400> SEQUENCE: 28
tttgcaaata gcttcacc                                                     18

<210> SEQ ID NO 29
<211> LENGTH: 17
<212> TYPE: DNA
<213> ORGANISM: Artificial
<220> FEATURE:
<223> OTHER INFORMATION: Primer

<400> SEQUENCE: 29
atgccagcct gttaaac                                                      17

<210> SEQ ID NO 30
<211> LENGTH: 17
<212> TYPE: DNA
<213> ORGANISM: Artificial
<220> FEATURE:
<223> OTHER INFORMATION: Primer

<400> SEQUENCE: 30
cctcctcctc ctctcac                                                      17

<210> SEQ ID NO 31
<211> LENGTH: 20
<212> TYPE: DNA
<213> ORGANISM: Artificial
<220> FEATURE:
<223> OTHER INFORMATION: Primer

<400> SEQUENCE: 31
tctgttcatg tttgtgttag                                                   20

<210> SEQ ID NO 32
<211> LENGTH: 18
<212> TYPE: DNA
<213> ORGANISM: Artificial
<220> FEATURE:
<223> OTHER INFORMATION: Primer

<400> SEQUENCE: 32
gatgatgtgg tctggttg                                                     18

<210> SEQ ID NO 33
<211> LENGTH: 20
<212> TYPE: DNA
<213> ORGANISM: Artificial
<220> FEATURE:
<223> OTHER INFORMATION: Primer
```

```
<400> SEQUENCE: 33
tgtttcaaac tacctggtgt                                            20

<210> SEQ ID NO 34
<211> LENGTH: 17
<212> TYPE: DNA
<213> ORGANISM: Artificial
<220> FEATURE:
<223> OTHER INFORMATION: Primer

<400> SEQUENCE: 34
tagccctgcc ttcatac                                               17

<210> SEQ ID NO 35
<211> LENGTH: 20
<212> TYPE: DNA
<213> ORGANISM: Artificial
<220> FEATURE:
<223> OTHER INFORMATION: Primer

<400> SEQUENCE: 35
tcattaactc agtgcaaaac                                            20

<210> SEQ ID NO 36
<211> LENGTH: 18
<212> TYPE: DNA
<213> ORGANISM: Artificial
<220> FEATURE:
<223> OTHER INFORMATION: Primer

<400> SEQUENCE: 36
tccgaaaagc agttcacg                                              18

<210> SEQ ID NO 37
<211> LENGTH: 20
<212> TYPE: DNA
<213> ORGANISM: Artificial
<220> FEATURE:
<223> OTHER INFORMATION: Primer

<400> SEQUENCE: 37
aaacacaatt ctgaaatcgg                                            20

<210> SEQ ID NO 38
<211> LENGTH: 17
<212> TYPE: DNA
<213> ORGANISM: Artificial
<220> FEATURE:
<223> OTHER INFORMATION: Primer

<400> SEQUENCE: 38
aatcggccct cgatagc                                               17

<210> SEQ ID NO 39
<211> LENGTH: 20
<212> TYPE: DNA
<213> ORGANISM: Artificial
<220> FEATURE:
<223> OTHER INFORMATION: Primer

<400> SEQUENCE: 39
tggttgccaa tgtgaaattc                                            20

<210> SEQ ID NO 40
```

```
<211> LENGTH: 19
<212> TYPE: DNA
<213> ORGANISM: Artificial
<220> FEATURE:
<223> OTHER INFORMATION: Primer

<400> SEQUENCE: 40
aacgaatcac cggtgactg                                                19

<210> SEQ ID NO 41
<211> LENGTH: 17
<212> TYPE: DNA
<213> ORGANISM: Artificial
<220> FEATURE:
<223> OTHER INFORMATION: Primer

<400> SEQUENCE: 41
gtcataaggg cgaatac                                                  17

<210> SEQ ID NO 42
<211> LENGTH: 19
<212> TYPE: DNA
<213> ORGANISM: Artificial
<220> FEATURE:
<223> OTHER INFORMATION: Primer

<400> SEQUENCE: 42
acgctgatgc ccttctgga                                                19

<210> SEQ ID NO 43
<211> LENGTH: 17
<212> TYPE: DNA
<213> ORGANISM: Artificial
<220> FEATURE:
<223> OTHER INFORMATION: Primer

<400> SEQUENCE: 43
ccttgttctt ggcgtag                                                  17

<210> SEQ ID NO 44
<211> LENGTH: 17
<212> TYPE: DNA
<213> ORGANISM: Artificial
<220> FEATURE:
<223> OTHER INFORMATION: Primer

<400> SEQUENCE: 44
tagaactcgg cgatgtc                                                  17

<210> SEQ ID NO 45
<211> LENGTH: 17
<212> TYPE: DNA
<213> ORGANISM: Artificial
<220> FEATURE:
<223> OTHER INFORMATION: Primer

<400> SEQUENCE: 45
gatgttgctg aaggtgg                                                  17

<210> SEQ ID NO 46
<211> LENGTH: 17
<212> TYPE: DNA
<213> ORGANISM: Artificial
<220> FEATURE:
<223> OTHER INFORMATION: Primer

<400> SEQUENCE: 46
```

-continued ctgtacactg cagaggg                                                                    17

<210> SEQ ID NO 47
<211> LENGTH: 17
<212> TYPE: DNA
<213> ORGANISM: Artificial
<220> FEATURE:
<223> OTHER INFORMATION: Primer

<400> SEQUENCE: 47
gctgggtgat cttcttg                                                                    17

<210> SEQ ID NO 48
<211> LENGTH: 17
<212> TYPE: DNA
<213> ORGANISM: Artificial
<220> FEATURE:
<223> OTHER INFORMATION: Primer

<400> SEQUENCE: 48
ttgctgaagt tgaaggg                                                                    17

<210> SEQ ID NO 49
<211> LENGTH: 17
<212> TYPE: DNA
<213> ORGANISM: Artificial
<220> FEATURE:
<223> OTHER INFORMATION: Primer

<400> SEQUENCE: 49
gtcacgtcgg tcttcag                                                                    17

<210> SEQ ID NO 50
<211> LENGTH: 20
<212> TYPE: DNA
<213> ORGANISM: Artificial
<220> FEATURE:
<223> OTHER INFORMATION: Primer

<400> SEQUENCE: 50
gccaaatgtt tgaacgatcg                                                                 20

<210> SEQ ID NO 51
<211> LENGTH: 21
<212> TYPE: DNA
<213> ORGANISM: Artificial
<220> FEATURE:
<223> OTHER INFORMATION: Primer

<400> SEQUENCE: 51
caatgctcat tatctctaga g                                                               21

<210> SEQ ID NO 52
<211> LENGTH: 20
<212> TYPE: DNA
<213> ORGANISM: Artificial
<220> FEATURE:
<223> OTHER INFORMATION: Primer

<400> SEQUENCE: 52
gtgacaaaaa aaatatgtgg                                                                 20

<210> SEQ ID NO 53
<211> LENGTH: 18
<212> TYPE: DNA

```
<213> ORGANISM: Artificial
<220> FEATURE:
<223> OTHER INFORMATION: Primer

<400> SEQUENCE: 53
ctgcacttca aacaagtg                                                 18

<210> SEQ ID NO 54
<211> LENGTH: 22
<212> TYPE: DNA
<213> ORGANISM: Artificial
<220> FEATURE:
<223> OTHER INFORMATION: Primer

<400> SEQUENCE: 54
tgaagtatta tataggtgaa gc                                            22

<210> SEQ ID NO 55
<211> LENGTH: 19
<212> TYPE: DNA
<213> ORGANISM: Artificial
<220> FEATURE:
<223> OTHER INFORMATION: Primer

<400> SEQUENCE: 55
acaggctggc attatctac                                                19

<210> SEQ ID NO 56
<211> LENGTH: 17
<212> TYPE: DNA
<213> ORGANISM: Artificial
<220> FEATURE:
<223> OTHER INFORMATION: Primer

<400> SEQUENCE: 56
gttagactcg tcgacgg                                                  17

<210> SEQ ID NO 57
<211> LENGTH: 17
<212> TYPE: DNA
<213> ORGANISM: Artificial
<220> FEATURE:
<223> OTHER INFORMATION: Primer

<400> SEQUENCE: 57
ctatttatta cggcggg                                                  17

<210> SEQ ID NO 58
<211> LENGTH: 17
<212> TYPE: DNA
<213> ORGANISM: Artificial
<220> FEATURE:
<223> OTHER INFORMATION: Primer

<400> SEQUENCE: 58
gacgtacagg tcgcatc                                                  17

<210> SEQ ID NO 59
<211> LENGTH: 20
<212> TYPE: DNA
<213> ORGANISM: Artificial
<220> FEATURE:
<223> OTHER INFORMATION: Primer

<400> SEQUENCE: 59
ggtagtttga aacagaattc                                               20
```

<210> SEQ ID NO 60
<211> LENGTH: 23
<212> TYPE: DNA
<213> ORGANISM: Artificial
<220> FEATURE:
<223> OTHER INFORMATION: Primer

<400> SEQUENCE: 60
gtaactatga agatgtatga cac                                       23

<210> SEQ ID NO 61
<211> LENGTH: 17
<212> TYPE: DNA
<213> ORGANISM: Artificial
<220> FEATURE:
<223> OTHER INFORMATION: Primer

<400> SEQUENCE: 61
acaacagggt gagcatc                                              17

<210> SEQ ID NO 62
<211> LENGTH: 17
<212> TYPE: DNA
<213> ORGANISM: Artificial
<220> FEATURE:
<223> OTHER INFORMATION: Primer

<400> SEQUENCE: 62
agtcaacgcc gttttgc                                              17

<210> SEQ ID NO 63
<211> LENGTH: 17
<212> TYPE: DNA
<213> ORGANISM: Artificial
<220> FEATURE:
<223> OTHER INFORMATION: Primer

<400> SEQUENCE: 63
aggaaaggca gttcgcc                                              17

<210> SEQ ID NO 64
<211> LENGTH: 17
<212> TYPE: DNA
<213> ORGANISM: Artificial
<220> FEATURE:
<223> OTHER INFORMATION: Primer

<400> SEQUENCE: 64
aggctggcga acagttc                                              17

<210> SEQ ID NO 65
<211> LENGTH: 20
<212> TYPE: DNA
<213> ORGANISM: Artificial
<220> FEATURE:
<223> OTHER INFORMATION: Primer

<400> SEQUENCE: 65
gcaaccagtt ccggaatatc                                           20

<210> SEQ ID NO 66
<211> LENGTH: 19
<212> TYPE: DNA
<213> ORGANISM: Artificial
<220> FEATURE:

<223> OTHER INFORMATION: Primer

<400> SEQUENCE: 66
agcttgttgt aaacacgcg                                                    19

<210> SEQ ID NO 67
<211> LENGTH: 18
<212> TYPE: DNA
<213> ORGANISM: Artificial
<220> FEATURE:
<223> OTHER INFORMATION: Primer

<400> SEQUENCE: 67
ccagcttagc aagagatg                                                     18

<210> SEQ ID NO 68
<211> LENGTH: 17
<212> TYPE: DNA
<213> ORGANISM: Artificial
<220> FEATURE:
<223> OTHER INFORMATION: Primer

<400> SEQUENCE: 68
taacacattg cggatac                                                      17

<210> SEQ ID NO 69
<211> LENGTH: 21
<212> TYPE: DNA
<213> ORGANISM: Artificial
<220> FEATURE:
<223> OTHER INFORMATION: Primer

<400> SEQUENCE: 69
gcctggccca gggaagaggg t                                                 21

<210> SEQ ID NO 70
<211> LENGTH: 25
<212> TYPE: DNA
<213> ORGANISM: Artificial
<220> FEATURE:
<223> OTHER INFORMATION: Primer

<400> SEQUENCE: 70
cagcacaaaa cagaagctag ggttt                                             25

<210> SEQ ID NO 71
<211> LENGTH: 26
<212> TYPE: DNA
<213> ORGANISM: Artificial
<220> FEATURE:
<223> OTHER INFORMATION: Primer

<400> SEQUENCE: 71
ccgagtgtca aggagttgcg gacact                                            26

<210> SEQ ID NO 72
<211> LENGTH: 26
<212> TYPE: DNA
<213> ORGANISM: Artificial
<220> FEATURE:
<223> OTHER INFORMATION: Primer

<400> SEQUENCE: 72
cttgaagcaa cggctaaagc gacgaa                                            26

```
<210> SEQ ID NO 73
<211> LENGTH: 22
<212> TYPE: DNA
<213> ORGANISM: Artificial
<220> FEATURE:
<223> OTHER INFORMATION: Primer

<400> SEQUENCE: 73
tacgagagct gggtgaactt ca                                              22

<210> SEQ ID NO 74
<211> LENGTH: 18
<212> TYPE: DNA
<213> ORGANISM: Artificial
<220> FEATURE:
<223> OTHER INFORMATION: Primer

<400> SEQUENCE: 74
cgatcaggtc cagcacgg                                                   18

<210> SEQ ID NO 75
<211> LENGTH: 20
<212> TYPE: DNA
<213> ORGANISM: Artificial
<220> FEATURE:
<223> OTHER INFORMATION: Probe

<400> SEQUENCE: 75
ccgctaccgc cgcgagatga                                                 20

<210> SEQ ID NO 76
<211> LENGTH: 18
<212> TYPE: DNA
<213> ORGANISM: Artificial
<220> FEATURE:
<223> OTHER INFORMATION: Primer

<400> SEQUENCE: 76
ccgggtgaat cagcgttt                                                   18

<210> SEQ ID NO 77
<211> LENGTH: 18
<212> TYPE: DNA
<213> ORGANISM: Artificial
<220> FEATURE:
<223> OTHER INFORMATION: Primer

<400> SEQUENCE: 77
gccgtggcct ttgacagt                                                   18

<210> SEQ ID NO 78
<211> LENGTH: 20
<212> TYPE: DNA
<213> ORGANISM: Artificial
<220> FEATURE:
<223> OTHER INFORMATION: Probe

<400> SEQUENCE: 78
tgccgccaac gaatcaccgg                                                 20

<210> SEQ ID NO 79
<211> LENGTH: 21
<212> TYPE: DNA
<213> ORGANISM: Artificial
<220> FEATURE:
<223> OTHER INFORMATION: Primer
```

<400> SEQUENCE: 79
gaacgtgtgt tgggtttgca t                                              21

<210> SEQ ID NO 80
<211> LENGTH: 24
<212> TYPE: DNA
<213> ORGANISM: Artificial
<220> FEATURE:
<223> OTHER INFORMATION: Primer

<400> SEQUENCE: 80
tgcagcctaa ccatgcgcag ggta                                           24

<210> SEQ ID NO 81
<211> LENGTH: 20
<212> TYPE: DNA
<213> ORGANISM: Artificial
<220> FEATURE:
<223> OTHER INFORMATION: Probe

<400> SEQUENCE: 81
tccagcaatc cttgcacctt                                                20

<210> SEQ ID NO 82
<211> LENGTH: 20
<212> TYPE: DNA
<213> ORGANISM: Artificial
<220> FEATURE:
<223> OTHER INFORMATION: Primer

<400> SEQUENCE: 82
gccgtatccg caatgtgtta                                                20

<210> SEQ ID NO 83
<211> LENGTH: 21
<212> TYPE: DNA
<213> ORGANISM: Artificial
<220> FEATURE:
<223> OTHER INFORMATION: Primer

<400> SEQUENCE: 83
ggcccaggga agagggtata t                                              21

<210> SEQ ID NO 84
<211> LENGTH: 19
<212> TYPE: DNA
<213> ORGANISM: Artificial
<220> FEATURE:
<223> OTHER INFORMATION: Probe

<400> SEQUENCE: 84
aagttgtcta agcgtcaat                                                 19

<210> SEQ ID NO 85
<211> LENGTH: 26
<212> TYPE: DNA
<213> ORGANISM: Artificial
<220> FEATURE:
<223> OTHER INFORMATION: Primer

<400> SEQUENCE: 85
tgtctaagcg tcaatttgtt tacacc                                         26

<210> SEQ ID NO 86
<211> LENGTH: 16

-continued

```
<212> TYPE: DNA
<213> ORGANISM: Artificial
<220> FEATURE:
<223> OTHER INFORMATION: Primer

<400> SEQUENCE: 86
tttgccagtg ggccca                                              16

<210> SEQ ID NO 87
<211> LENGTH: 27
<212> TYPE: DNA
<213> ORGANISM: Artificial
<220> FEATURE:
<223> OTHER INFORMATION: Probe

<400> SEQUENCE: 87
acaatatacc ctcttccctg ggccagg                                  27

<210> SEQ ID NO 88
<211> LENGTH: 20
<212> TYPE: DNA
<213> ORGANISM: Artificial
<220> FEATURE:
<223> OTHER INFORMATION: Primer

<400> SEQUENCE: 88
gccgtatccg caatgtgtta                                          20

<210> SEQ ID NO 89
<211> LENGTH: 19
<212> TYPE: DNA
<213> ORGANISM: Artificial
<220> FEATURE:
<223> OTHER INFORMATION: Primer

<400> SEQUENCE: 89
aagttgtcta agcgtcaat                                           19

<210> SEQ ID NO 90
<211> LENGTH: 21
<212> TYPE: DNA
<213> ORGANISM: Artificial
<220> FEATURE:
<223> OTHER INFORMATION: Probe

<400> SEQUENCE: 90
ggcccaggga agagggtata t                                        21

<210> SEQ ID NO 91
<211> LENGTH: 25
<212> TYPE: DNA
<213> ORGANISM: Artificial
<220> FEATURE:
<223> OTHER INFORMATION: Primer

<400> SEQUENCE: 91
ccccacgatt aaatgtcaaa ctgat                                    25

<210> SEQ ID NO 92
<211> LENGTH: 25
<212> TYPE: DNA
<213> ORGANISM: Artificial
<220> FEATURE:
<223> OTHER INFORMATION: Primer

<400> SEQUENCE: 92
```
gctcagcctt gttttgtac attca                                           25

<210> SEQ ID NO 93
<211> LENGTH: 20
<212> TYPE: DNA
<213> ORGANISM: Artificial
<220> FEATURE:
<223> OTHER INFORMATION: Probe

<400> SEQUENCE: 93
aattttcata gcttttgtg                                                 20

<210> SEQ ID NO 94
<211> LENGTH: 27
<212> TYPE: DNA
<213> ORGANISM: Artificial
<220> FEATURE:
<223> OTHER INFORMATION: Primer

<400> SEQUENCE: 94
cgctcttaag tctgctgttt gtttact                                        27

<210> SEQ ID NO 95
<211> LENGTH: 24
<212> TYPE: DNA
<213> ORGANISM: Artificial
<220> FEATURE:
<223> OTHER INFORMATION: Primer

<400> SEQUENCE: 95
cacacgccac ttcttgtctt ctat                                           24

<210> SEQ ID NO 96
<211> LENGTH: 13
<212> TYPE: DNA
<213> ORGANISM: Artificial
<220> FEATURE:
<223> OTHER INFORMATION: Probe

<400> SEQUENCE: 96
cgcgagctca tgc                                                       13

<210> SEQ ID NO 97
<211> LENGTH: 25
<212> TYPE: DNA
<213> ORGANISM: Artificial
<220> FEATURE:
<223> OTHER INFORMATION: Primer

<400> SEQUENCE: 97
gctgcagctc acttgaaggt ataat                                          25

<210> SEQ ID NO 98
<211> LENGTH: 20
<212> TYPE: DNA
<213> ORGANISM: Artificial
<220> FEATURE:
<223> OTHER INFORMATION: Primer

<400> SEQUENCE: 98
ggcaccaccc tgtaaaagca                                                20

<210> SEQ ID NO 99
<211> LENGTH: 17
<212> TYPE: DNA
<213> ORGANISM: Artificial

```
<220> FEATURE:
<223> OTHER INFORMATION: Probe

<400> SEQUENCE: 99
aaccattaga tgcttcc                                                    17

<210> SEQ ID NO 100
<211> LENGTH: 16
<212> TYPE: DNA
<213> ORGANISM: Artificial
<220> FEATURE:
<223> OTHER INFORMATION: Primer

<400> SEQUENCE: 100
ccgtcgacga ggcgaa                                                     16

<210> SEQ ID NO 101
<211> LENGTH: 16
<212> TYPE: DNA
<213> ORGANISM: Artificial
<220> FEATURE:
<223> OTHER INFORMATION: Primer

<400> SEQUENCE: 101
gcggcgagct gttcag                                                     16

<210> SEQ ID NO 102
<211> LENGTH: 16
<212> TYPE: DNA
<213> ORGANISM: Artificial
<220> FEATURE:
<223> OTHER INFORMATION: Probe

<400> SEQUENCE: 102
tctgagcttc ggatac                                                     16

<210> SEQ ID NO 103
<211> LENGTH: 161748
<212> TYPE: DNA
<213> ORGANISM: Zea mays
<220> FEATURE:
<221> NAME/KEY: misc_feature
<222> LOCATION: (2151)..(2250)
<223> OTHER INFORMATION: n is a, c, g, or t
<220> FEATURE:
<221> NAME/KEY: misc_feature
<222> LOCATION: (6108)..(6207)
<223> OTHER INFORMATION: n is a, c, g, or t
<220> FEATURE:
<221> NAME/KEY: misc_feature
<222> LOCATION: (9770)..(9869)
<223> OTHER INFORMATION: n is a, c, g, or t
<220> FEATURE:
<221> NAME/KEY: misc_feature
<222> LOCATION: (18125)..(18224)
<223> OTHER INFORMATION: n is a, c, g, or t
<220> FEATURE:
<221> NAME/KEY: misc_feature
<222> LOCATION: (33520)..(33619)
<223> OTHER INFORMATION: n is a, c, g, or t
<220> FEATURE:
<221> NAME/KEY: misc_feature
<222> LOCATION: (44173)..(44272)
<223> OTHER INFORMATION: n is a, c, g, or t
<220> FEATURE:
<221> NAME/KEY: misc_feature
<222> LOCATION: (67063)..(67162)
<223> OTHER INFORMATION: n is a, c, g, or t
<220> FEATURE:
<221> NAME/KEY: misc_feature
<222> LOCATION: (91565)..(91664)
```

```
<223> OTHER INFORMATION: n is a, c, g, or t
<220> FEATURE:
<221> NAME/KEY: misc_feature
<222> LOCATION: (136173)..(136272)
<223> OTHER INFORMATION: n is a, c, g, or t
<220> FEATURE:
<221> NAME/KEY: misc_feature
<222> LOCATION: (148532)..(148631)
<223> OTHER INFORMATION: n is a, c, g, or t
<220> FEATURE:
<221> NAME/KEY: misc_feature
<222> LOCATION: (154026)..(154125)
<223> OTHER INFORMATION: n is a, c, g, or t
<220> FEATURE:
<221> NAME/KEY: misc_feature
<222> LOCATION: (158039)..(158138)
<223> OTHER INFORMATION: n is a, c, g, or t

<400> SEQUENCE: 103
cccggccgct gatgaatcag cttgattcgt tctgttatca cgggtggtca ctcaacgagc      60
aggtccaaag gaaaggtact caggaaaata gcctgagtct cctaaagtgc cataagaaca     120
tcatcgtaat cataataaca acatcatatc ataaatattc gcatcatgtt tgttgattaa     180
agtggagcaa tagcttgaag cttaccataa taacccaaaa ggtaaacaag gacaagataa     240
atacagacta gtcaaacctt aggtttcaat taagtaaagg gggacagtga attatgaagt     300
aagtaggaca taataggtca gaggacactt gccttcacca ggttgttgcc caggaagatc     360
ttcggcaaca cactcaggaa ccatagactg cttgttgtct acgcaaagcg atcatgcatt     420
caacacattt cgataatgat aaagaaacaa taccaaaaa atatacaatc aagtgaacac     480
taattcaaaa gaaagtaaca aactcaagcg aagcctaggg tctagggtgg accaatacac     540
ataggttt gtggttctct aagtattact tatctcaata gattacataa cttaatttca     600
tttatcttaa tgagacaaaa gaattatacc agggataggt tcatatatta catattatta     660
acccacaaag ttaaacatct aactaccatt atggttttcc ttttatcctt cttattaata     720
aataagccat cagttacact aacctatagt ctaggcataa aattagcaca tgcagacagt     780
aaaaggttat aatttaaaca ggtagagaat aaccttacaa acattttgca atttgaatca     840
ctcaatttgg agttcatatg caaaagatat gaaataaaca agttttggaa ttcaaaatac     900
aaaactaggt ctaattatgt gataacctaa aagattaggg gcctttctgc aaaagtacag     960
gggcatgcgt gcgaaaacca gggacgatgg gttgattctc agaaagccga gggcctttt     1020
aacaaaacta ccacgcaaag gggtatcagc tgatctcgac tgcatgatca cagatcaacg    1080
gccaggatta gatttgagcg cgagcacgag cacgagctaa caggtgggcc aggatagtca    1140
gcgacctagg ggcgaggcgg actgtctggc cgggcctagc tgcagggcgc gggtgaggtg    1200
gcggatccga gtggccagat ctccatcgga cagctgggat cagatcgagt ttaattgaag    1260
ccaggtcgtt agatctcaga tggatgcctg aaatctgatg gcaagctcgg gcggggttgc    1320
taggctgctc atggcgccgc cgcccaattt cgcggcgtgg cgcggccatg gtgagggtct    1380
gggcgctggg aaaaggctca ggcgagctca gggtgacacg gcgggctcag ccatgggcac    1440
gacaccggcg tagaggcacc agagagcacg gtccgaggca aagcagcccc acggcggcgc    1500
agcttaactc tggcgagcga ttgcatggac aacaggcag taaatgggaa attaagggca    1560
tgggtgggtt ggttacgtcg agagatgact ctagagcgct tgagcaacgg cgaggacacc    1620
gcgagggccc tggtggacgg tggcggagac tcgctgcat ggtgataggt ccggtgagcg     1680
aaccaaggga aatagagggg ctggggaaaa ccagagggtg tctcgtgttg ctggcgagga    1740
ggcgaagatc agtagggcaa tggacgcgac aggaactcga cgacggccac ggaacggacg    1800
```

```
gtggactacg gcagtgctcc acggctgtgc gctcggtgcg agagagaggt gcgaggggt    1860 cggctgtggg acgctactga gcgaggggag tgagcgagtg agtgtgggct ccaaaaaagt    1920
caggcgcgtg gggggagtgg ccgaaaaaca cgcgacatgt gtgcatccac ggcggggtgc    1980
gcgagcgggt ggttagggaa aggggaggtg gctgacaggt ggggtccgct tgccagcgag    2040
ggtgaatacg cgaacgagcg gttctgcgct gacaggccga cccaccgagg caaaaaggag    2100
cgggcgtgtt gcgtgaaaga aaccggcacc gacaaaccgg cctccgcgcg nnnnnnnnnn    2160
nnnnnnnnnn nnnnnnnnnn nnnnnnnnnn nnnnnnnnnn nnnnnnnnnn nnnnnnnnnn    2220
nnnnnnnnnn nnnnnnnnnn nnnnnnnnnn ctgcgggtac cacgttctac aaggtttgat    2280
gatagtgagg aaggaagaat tctggcact gaagcaaggg ccctgtctg tcagtgagta     2340 catggacaaa ttcctgcaac tatctcacaa tgcacccgag gatgtcaaca ttgatgctaa    2400
gaggtactac aggtttccga gagggttggt tgacccctgc actactagtt gatgaaccac    2460
acattcccta ccttccaaca tctgattgat agggcaataa tgactgagag gaagcgccag    2520
gagatggaag accaaaagcg caagattggt ggaccctagg ccaggagcag cagtcgtctc    2580
ccgtttctgg caatccaccc tagcagttca agtagatcca ccctcaggga taccaacacc    2640
agaaccaatg ttcgcaccag tagcaattcc agaggcagtt ccctcaacag cagcatgtca    2700
cacccgggtt ttaggggtcc aaaacccagg cgcgaaattc accaagtgct gggatcgagt    2760
ctcacacata tgatgactca tggtatagaa acaaatgtca catctttact atataataga    2820
agttctgcac aaaataacta aataattaca tcatacgatg acgacgatcc atcaaccca     2880 agtttactgt gagacgacgg cctagacctc tcatgaactc atcgcgacat ccttcatgct    2940
cctcatcttg cggtacctgt tcttgaccag ggggatttga gtacagcaag ggtgagctca    3000
catacgttca tcgctcaaca agttgtgggg aataatgtgt atgaactcac caaaggtggg    3060
agctcatgtg aagtgtaagg cttaccaaag gagatgggta agatgagca tgacttttaa     3120 agttggtcaa aattttatta gcagttacta agtataagta gataccgacc caaataaata    3180
agagattaaa ttaataacaa cacccacaat gcaatgcata tgacaattta agtttagttc    3240
cataatttac tcatgtgagg gtccgagctg ctcatgaccg tgagcacggc tgatataaca    3300
gttttacagt ctgcacaggt tgcacatctt tacccacaag tcatgttacc tatttgccaa    3360
gggatcgcga cttctcattc atctctaccg agaagacaag gtaggttacc actacgaggc    3420
ctttacaaac ttccactagc ttccgaaaac ccgctacggt ttctaagaag gaaaatatag    3480
gaatccctcg tccaaaaagc catcgcagca tgatcgactc gagaacctcc ctatacgcat    3540
gctcctctac cgcccttgcc cctttcgggt aaggtagtct tccactagct ttcttaatta    3600
gtcagccaag ggcgtcccat accacccttg tggtagcact gttttcctgg gtggttgctc    3660
catgttccaa ttaacatagc aatcttatca tgaacaataa ttaaaataac aaaagaattg    3720
taacatgatc ataatgtaac attaatttcc caaaaccagg tagagcaata gcaatactac    3780
ccaatagtgc ttttgtttgc aaggtagggg ataaacaata ctaggaaaac ctattgggtc    3840
ccatcaaatt aacctgagca tgtcacagtg attaatagga acattattag gtaaagaaaa    3900
gtgatcaagg gcacaacttg gctgagactc aagattccta ggtaccagct tggtcttcaa    3960
gattctcgta acctcgctgc taatcatagc aatacaaaca acatggtat aggcaaaatt     4020 aacatcacac caaacataaa gaacaaactg cataataatg atctacgcac cacaacgaga    4080
tcctaggttc gagaaccact aaattcggag ttacggttaa caagatgtgg ttttcggaag    4140
```

```
acctatgtga ttaaatatga gactaggtct ttatgttgat tttataaatt atgtgataaa    4200
gatattaaag aaataacttt aatctacatc atactagagt agacataata ttttagttac    4260
cttataatca tagacaaact aactttgatt agtaggaata atctactaag catatattaa    4320
atgaatattt atttttttgga aacatgctat ttgctaaaat aattttacag aagcgtaggc    4380
aaaattatta cgaagctaac gcaacatgaa tacattaaat cagagttaaa atgaaagaga    4440
tatgtattta ttaagttta ggatttaatt ctataattat taaatatttc tggattgggg     4500
acactattct ataaaagatc aggggggctcc atataatatt taggacttat ccgcaatgat   4560
ttctacctat acccgactg cgggctgatt tgcaagaagt ctggggtctc ttttataagt    4620
tagtcacggt gaagggtac acgtgactaa ttccttggat catcagccaa gcgcccagag    4680
tagaagattt gcccgccgaa ccggtacgca tcctagatcg tcggatctac gataaacggc    4740
ccacgcttaa aataatagag atcgatcctc atatgcaaga tccagatcag acgacccgga   4800
tcgattcgga tgaaacgtta cgtgtgatct aatcacagcc gatacctccc agatccacgg   4860
ttcacgcgag gcccagccat gccctgatcg tgatcgctca cccatgatct aacggctgct   4920
gcatttcctt ccacctcacg acggaaagca gagcactggt gcgggcacgc gcgggccatg   4980
ccccaccaca ccaccagtga tatcccgccc ggctccccat ttcctagtat cgagcgtggg   5040
tacgtgaatc acggagagga ggaggctcca agtatgctag ggctgttctt accaaggatc    5100
acggtgtttc aagtgttgac cccaccacg agttgctccg tggcgccgcg ggtcaccagc    5160
gaagcatgca ctggtcgttg ttctcgcacg aggtgccttc tagaatcctg cacgcgtccc   5220
acggatgacc caacccgacg ccgagaccgc aataccggcg tgcccgggaa ccccgtcgg    5280
tggcaattca ccccctgtgt tctccttctc ccttacgacg atggtgatgg cgccttctct    5340
cccgatcggc agaccgagcg tagcccacga tgctgaagga aggaaactaa gagctgcacc   5400
catggccgag gttggagcgt ccgttatata tggccagggg tacggctagc agtgggcggg    5460
tgcaccatgg cacgaaggtc gttgcacagt ttacaggagg cgagcttgca gcggacgagc   5520
aggatcgcca tggggaggat agacttgacg gccatggccc acatgccaga cgcggctgca   5580
ggcgcgagag tgggcaggag cgggctgcgc cggagcaggg aaatagagtt gggcccgcta    5640
acgaaggaaa gaaactgggc cgagaagcca gagatccggc ccatagcgca gaaagcttcc   5700
cctttttctt tattctttaa tgattttctg ttttatcttc cctttcatat ttcttttccct   5760
tattttaaac tctaatctaa atgctcaatc caaaactccg gcatgatatg caataattac   5820
atatatctgt ttagttttgt ttattttatc caaatatttt aagtatgcaa tgcacacaca   5880
tagagtaaaa attacttctt tgaatgtata gtccatttaa aattatgttc ataattttta   5940
agatagagga ttttttttgtg tgtatagtat ttattaaggt ttttttaagct taattctttt   6000
ggagaatatc tctaatcatg ttattcaaca agggttggtt taaattatat gagggtcttt    6060
tatttaatct ctcattataa aagacttcta tttaaatctt ggaattcnnn nnnnnnnnn    6120
nnnnnnnnnn nnnnnnnnnn nnnnnnnnnn nnnnnnnnnn nnnnnnnnnn nnnnnnnnnn   6180
nnnnnnnnnn nnnnnnnnnn nnnnnnnnggg ggttttttctt tatctcgtgc gtggttatcc   6240
atctaatcac gtgggagttt gttggctatc tcttaggaaa aggtccagac ctcctcccct   6300
ataaatataa aggggtacgg ccgattgaga accccgaac acattccaat cgaaccaatt    6360
accttatttta cttttcctgc cctaggagta gatgtagcat agttctagtt gtagtcttcc   6420
acatatccac ctccaccct attcaactct acgtcgtcta gatccgtctt gggtggcctg    6480
ccgatcccaa gacgacccta ggatctcacc cctcccgggg ggcaagatct agttgtccat   6540
```

```
ccaagacttc ttcctcgatt tgatctctta attcctaggc gactccacgt cgtctgggga    6600
cgccccgggt gacctgtcga cccggagcac cttaagatct ttcccccag gggacgagat     6660
ctagattcca gcaaggagta ggaagacgac cctgtcgcca ggtcgcggac cgtccggccc    6720
agagctgcgg accgtccggt gtgacgcagg aagacaccg ctcctgcgcc caggtcgcgg     6780
accgtccggc ccaaggctgc ggaccgtccg gcccaaggct gcggaccgtc cgcgcctgac    6840
cagagggcac cgccacggtt cttgttgagt gtttggcgct ccaaaaaggc gtcaacatac    6900
tttttggcga ctccgctggg gaagaagttg cagatctaca aaatcaggct tacatggccg    6960
attctaaaga tctcaacagt gcttctccaa acagcaacac aaggctgact aatttatcgg    7020
ccgctgagca taaaaaatta gaagatgaca tgaagaaaat agacgaggag gcccaccgac    7080
aaaaggatca ggtgctcaag gtggcggaca agtggtaccct ctcgcacttc aaggtagact   7140
gccaccagaa gaccgtccaa gagagggaga taaacgccga gtatatgtta gccgtgctgc    7200
aacagctccc cacaataggt gatgccaggt cagccgatga tattccatct attaaaattt    7260
cttttgataa tcggattaaa agtatcacgg aggatataga gaggatgaca catgcattag    7320
gaaaaactca catgcctaat ttttttatcac ataaattagg cgatgaaaca attgcgccaa   7380
acacatcggc ggcaaatggg tttccccagc catattctgg tatgccgatg gactcatatc    7440
taggacgacc gtcatcacca tctttgctaa atggtgagtc aaccctgggc acagccggac    7500
cgtccgcaca caattgcgga ccgtccggcc ctctgtcgga ccgtccggca ccctacgccg    7560
gacagtctgg agttacacag agcccaccac aagggtcaca ggtgttgcct gacgtgaccg    7620
gactgtccga ggatagtacc ggaccgtccg atccacccgc agaccgtccg actgtgcaag    7680
tcggaccgtc cggggcacca gaagtcacct gtgatccacc tagtgcggaa ggccgacata    7740
aatataatcg gccacccaag ccccaagaac taaaaaagtc acatgtccct gagcttgttt    7800
ggcccactaa ggccaaacct tctgttcgct cttacccgca ctcgaaacaa aaggaaaagg    7860
ttaagttcac atttaatatt actaaatgtg ataaatatt tgatgagttg cttaaacatg     7920
gtaatattaa attgtcacat gtaattcctc cggttgaaca attaaaaggg cgtgtttatt    7980
gcaaatggca tggctccttt ctccataaca ccaatgattg tgccgtcttc cgtcggcaaa    8040
tacaatcggc tataaacgaa ggccggttga ggtttcaaaa agaggtgaaa attgacaggc    8100
cacctgttcc tgtcaccaca ttagagccca tgagcaaaaa ggccataatt cggccttgtg    8160
cggccgataa aagtaaaaat aaaaatatcg tcattggtga tcctcgcaca ccaaatatgt    8220
cacgcagaat ggttactctg aaggctccgg acaaaagaaa gaccggaggc accgggggggc   8280
aagcacgatc ggacacccga tcacggtcgc ctgtcatgcg tacgccggac gatccgggta    8340
ctaaggccga acagtccgag acaggcgcgg acagtccggc tatgatggcc ggacggtccg    8400
cagatggtca gaagcagcaa cctcagacca tcggaccaca acgttccaac acaagtgtta    8460
ggaaacaaaa cactactaag acgtctggac gactcagtag agtcggccct acttttggtc    8520
agttgcttgc caaatatatg aagaaggccg ttccacacaa ccggccaata aaacaaacaa    8580
agtcaatagg gcgatctgtg cgaaagcaaa agccgactaa acggacccaa agggtagcac    8640
aaccaatatc gccttatcat cctcctccag ggatagcatg gtgcgtccca ttctatccat    8700
cgccgatgtg ttgtcctact catgtgtggg gtggtacggc gatgaatttg tattactggc    8760
ccaatccgtt tgcttatttg ggctgggggg caccacaagt ttttgcctat tgacaggttg    8820
atcagataga catggctgaa gaggatgcga tccgaaacgg cctctgtgca ttaaagtccc    8880
```

| | |
|---|---|
| atcaagtatt tatattatct gatcgcaaga gccgatgact tgcatcgagc tgagtcctta | 8940 |
| cttcggaaaa aaaaacctca tgaggtcaat tgtttccgaa gttttcgcta atgcttttgg | 9000 |
| ttcgccatgc tccaccaaaa ggcaggggg catatgttgg acaccaaaat gagcggacgg | 9060 |
| tccggcccat gggcccggac ggtccgcgtg tcccgagatt agattaactc ggatgtttat | 9120 |
| ccttatctcg tgcgtggtta tccatctaat cacgtgggag tttgttggct atctcttagg | 9180 |
| aaaaggtcca gacctcctcc cctataaata taagggta cggccgattg agaaccccg | 9240 |
| aacacattcc aatcgaacca attaccttat ttactttcc tgccctagga gtagatgtag | 9300 |
| catagttcta gttgtagtct tccacatatc cacctccacc cctattcaac tctacgtcgt | 9360 |
| ctagatccgt cttgggtggc ctgccgatcc caagacgacc ctaggatctc accctccgg | 9420 |
| ggggcaagat ctagttgtcc atccaagact tcttcctcga tttgatctct taattcctag | 9480 |
| gcgactccac gtcgtctggg gacgccccgg gtgacctgtc gacccggagc accttaagat | 9540 |
| ctttccccca ggggacgaga tctagattcc agcaaggagt aggaagacga ccctgtcgcc | 9600 |
| aggtcgcgga cgtccggccc agagctgcgg acgtccggtg tgacgcaggg aagacaccgc | 9660 |
| tcctcgccca ggtcgcggac cgtccgaccc aaggctcgga cgtccgccca aggctgggac | 9720 |
| cgtccgcgcc tgaccagagc acgccacggt ctgtgaggtt gcaagatgcn nnnnnnnnn | 9780 |
| nnnnnnnnnn nnnnnnnnnn nnnnnnnnnn nnnnnnnnnn nnnnnnnnnn nnnnnnnnnn | 9840 |
| nnnnnnnnnn nnnnnnnnnn nnnnnnnnnt aatctataca gacgatctga gattcgtctc | 9900 |
| attttgagcc cgtctcaaga atcccttta tgtctcttgg gttagagatt tttcctgtaa | 9960 |
| aaagaatacc caagtgaagc gagaataatc atccacaata actagacagt acttactccc | 10020 |
| gccgatactt atgtaagcga tcgggccgaa taaatccatg tggaggagct ccagtggcct | 10080 |
| gtcacttgtc attatgttct tgtgtggatg atgagtgcca acttgcttcc cggcttggca | 10140 |
| tgcgctacaa atcctgtctt tctcaaaatg aacatttgtt aatcctaaaa tgtgttctcc | 10200 |
| ctttagaagc ttatgaagat tcttcatccc aacatgggct agtcggcggt gccagagcca | 10260 |
| acccatgtta gtcttggcaa ttaagcatgt gtcgagttca gctctatcaa aatctactaa | 10320 |
| gtatagctga ccctctaaca cacccttaaa tgctattgaa tcgtcacttc ttctaaagac | 10380 |
| agtgacacct acatcagtaa aaagacagtt gtagcccatt tgacacaatt gggaaacaga | 10440 |
| aagcaagttg taatctaatg aatcaacaag aaaaacattg gaaatagtat ggtcaggtga | 10500 |
| tatagcaatt ttacccaatc cttttgaccaa acctcgattt ccatccccga atgtgatagc | 10560 |
| tcgttgggga tcttggtttt tctcatatga ggagaacatc cttttctccc cggtcatgtg | 10620 |
| ggtttgtgca cccgctgtcg agtatccaac ttgagcccc ggatgcataa acctacaaaa | 10680 |
| acaaatttag ttcttgactt taggtaccca aatggttttg ggtcctttgg cattagacac | 10740 |
| aataactttg ggtacccaaa cacaagtctt tgaccccttg tgcttgcccc caacatattt | 10800 |
| ggcaactact tgccggatt tgtttgtaag cacataagaa gcatcaaaag ttttaaatga | 10860 |
| aatagcatga tcatttgatg caataggagt tttctttcta ggcaacttgg cacgggttgg | 10920 |
| ttgcctagag ctagatgtct caccccttata cataaaagca tgattagggc cagagtgaga | 10980 |
| cttcctagaa tgaattttcc taattttgct ctcgggataa ccgcagggt acaaaatgta | 11040 |
| accctcgtta tcctgaggca tgggagcctt gcccttaaca aagttagaca gttttttaag | 11100 |
| agggcatta agtttgacat tgtctcccct ttggaagcca atgccatcct taatgtcagg | 11160 |
| gcgtctccca ttataaagca tgctacgagc aaatttaaat ttctcattct ctaggttgtg | 11220 |
| ctcggcaatt ttagcatcta attttgctat atgatcattt tgttgtttaa ttaaagccat | 11280 |

```
atgatcaaga atagcattaa catcaacatc tctacatcta gtacaaatag atacatgctc    11340
atcaatagat gtagagggtt tgcaagaatt aagttcaaca atcttagcat gaagaatatc    11400
attcttatct ctaagatcgg aaattgtaac tttgcaaaca tcaaaatctt tagccttagc    11460
aatcaaattt tcattctcta atctaaggct agcaagagaa atgtttaatt cttcaatcct    11520
agcaagcaac tcatcattat tatctctagg attgggaatt gaaacattac aaatatgaga    11580
atcaacctta gcatttaaac tagcattttc atttctaagg ttgtcaatca tctcacggca    11640
agtgcttagc tcactagaca attttcaca tttctcaact tctagagcat aagcctttct    11700
aaccttaaca tgtttcttgt tttctttaat tagacaatcc tcttgggaat ccaaaaggtc    11760
atccttttca tgaatagcac tgactaattc atttaatttt tccttttgag ctatgttaag    11820
gttggcaaag aggatacgca aattttcctc ctcatcacta gcattatcat cactagacga    11880
ttcatattta gtggaggagt tggatttaac cttcttcttt ttgccgtcct ttgccatgag    11940
gcacttgtgg ccgacgttgg ggaagagaag tcccttggtg acggcgatgt tggcggcatc    12000
ctcgtcgtcg gaggagtcgc ttgagctctc gtcggagtcc catttgcgac aaacatgggc    12060
atcgccgccc ttcttcttgt aatacctctt ctttctcctt cttctcccct tcttgtcgtc    12120
gcctcggtca ctgtcactag atattggaca tttagcaata aaatgaccgg gcttaccaca    12180
tttgtagcaa accttcttgg agcgggactt gtagtctttc cccctccttt gtttgaggat    12240
ttggcggaag ctcttaatga cgagcgccat ctcctcattg tcaagcttgg aggcgtctat    12300
tggttgtcga cttggtgtag actcctcctt cttctcctcc gttgccttga atgcaacggg    12360
ttgggcttcg gatgagtcgc caagctcgtt gattttcctc gagccttcta tcatgcactc    12420
aaaacttaca aaatgcccga taacttcctc gggggtcatt ttagtatatc taggattacc    12480
acgaatcaat tgaacttgag tgggattaag aaaaatgaga gatcttaaaa taacatttac    12540
cacttcgtga tcgtcccact tcttgctccc gaggttgcgc acttggttca ccaaagtctt    12600
gagccggttg tacatgtgtt gtggctcctc tcctttgtga agccggaacc gaccgagctc    12660 ccctcgatc gtttcccgct tggtgatctt ggtgagctcg tctccctcgt gcgcggtttt    12720
gagtacatcc caaatctcct tggcgctctt caacccttgt actttgttat actcctctct    12780
acttagagag gcgaggagta ttgttgttgc ttgagagttg aagtgctcga tttgggccac    12840
ctcatcctca tcatagtcct catcccctac ggatggtacc tgcgcgccaa actcaacaac    12900
atcccatatg cttttgtgga gcgaggttag atgaaatcgc attaaatcgc tccacctagc    12960
gtaatcttca ccatcaaaag ttggtggttt gcctaatggg acggaaagta aaggtgtatg    13020
tttggaaatg cgagggtagc gtaggggat cttactatac ttcttgcgct cttggcgctt    13080
agaagtgacg gagggcgcat cggagtcgga ggtcgatgtt gatgaagtgt cggtctcgta    13140
gtagaccacc ttcctcatcc ttttgtgctt gtcgcctttc cgatgcggct tgtgggaaga    13200
agatttttcc ttcttctctt tgtggtgaga agaagatttc ttctccttcc ctttgttgga    13260
ggagctcttc ttcttctccc tccttttggt gcgagactct tccgatgaag tgctcccgtg    13320
gcttgtagtg ggccttcgc cggtctccat ctccttcttg gcgtgatctc ccgacatcac    13380
ttcgagcggt taggctctaa tgaagcaccg ggctccgata ccaattgata gtcgcctaga    13440 gggggggtgaa tagggcgaaa ctgaaatttg caaatataaa cacaactaca agccggggtt    13500
agcgttagta ataaggaatg agtccgcaag agagggcgca aaacaaatcc caagcgaatg    13560
agcaagtgag acacggagat tgttttacc gaggttcggt tcttgcaaac ctactccccg    13620
```

```
ttgaggaggc cacaaaggcc gggtctcttt caacccttcc ctctctcaaa cgatccacgg    13680
atcgagtgag cttctcttct caaatcaaag ccgggaacaa aacttcccg caagggccac     13740 cacacaattg gtgcctcttg ccttgattac aatggagttt tgatctcaag aacaagtgag    13800
aaagaaaaga agcaatccaa gcgcaagagc tcaaatgaac acgacaaatc actctcacta    13860
gtcactaggg ctttgtgatg aattggagag gatttgatct ctttgtatgt gtctagaatt    13920
gaatgcctag ctcttgtagt agttgggaag tggaaaactt ggatgctatg aatggtgggg    13980
tggttggggt atttatagcc ccaaccacca aacttgaccg ttggctggag gcgtctgctc    14040
gatggcgcac cggacagtcc ggtgcacacc ggacagtccg gtgcccctgc cacgtcatca    14100
ctgccgttgg attctagccg ttgaagcttc cgacttgtgg gcccgcctgg gtgtccggtg    14160
cacaccggac atgtactgtt tgatgtccgg tgcaccggta tgggcgtgcc tggcgtctgc    14220
gcgcgctgcg cgcgcattaa atgcaccgca gggagccgtt ggcgccgcag ggagccgttg    14280
ctccgctggc acaccggaca gtccggtgca caccggacag tccggtgaat tttagcggag    14340
cggctgccgc gcgaacccga ggctagcgag ttcctgaggc cgacctccct tggcgcaccg    14400
gacactgtcc ggtgtacacc ggacagtccg gtgaattata gccgagtcgc cttagaaatt    14460
cccgaaggtg gcgagtttga gtctgagtcc cctggtgcac cggacaggta ctgttcactg    14520
tccggtggca caccggacag tccggtgcgc cagaccaggg gtgccttcgg ttgccccttt    14580
gctcttttgt tgaatccaaa acttggtctt tttattggct gagtgtgaac cttttactcc    14640
tgtatacact atacacttgg gcaaacaagt tagtccaaaa gatttgtgtt gggcaattca    14700
accaccaaaa ttatttagga actaggtgta agcctaattc cctttcaatc tccccctttt    14760
tggtgattga tgccaacaca aaccaaagca aatatagaag tgcataattg aactagtttg    14820
cataatgtaa gtgtaaaggt tgcttggaat tgagccaata taactactta caagatatgc    14880
atggaatgtt tctttcttta tttagcattt tggaccacgt ttgcaccaca tgttttgttt    14940
ttgcaaattc ttttgtaagt ccatttcaaa gatcttttgc aaatagtcaa aggtgaatga    15000
ataagatttt tgcaaagcat tttcaagatt ttgaagtttt ctcccccctgt ttcaaatgct    15060 tttccttga ctaaacaaaa ctccccctaa attaaatcct cctcttagtg ttcaagaggg      15120
ttttgatata tcattttga aatactactt tctcccccctt ttgaacacga taggatgcca     15180
attgataaat atttcttgga aaacactaag ttttttgaaat tggtggtggt gcggtccttt    15240
tgctttgggc tccttctcc ccctttttgg catgaatcgc caaaaacgga atcattagag     15300
ccctcgaagt aatttcttct cctttggtca taagtaaatg agttaagatt ataccaaaga    15360
cgaagtcctt ttctttgatg ctcatttctc ccccaaagaa tagagagatg gttggagtga    15420
tggcgaagga tgagttacgg agtggaagcc tttgtcttcg ccgaagactc caattccctt    15480
ccaatatacc tatgacttgg tttgaaatag acttgaaaac acattagtca tagcatataa    15540
aagagatatg atcaagggta ttcaaatgag ctatgtgtgc aagctagcaa aagaaatttc    15600
tagaatcaag aatattgagc tcatgcctaa gtctggtaaa agattgttca tcaagtggct    15660
tggtaaagat atcggctaat tgatctttag tattaatgta agaaatctcg atatccccct    15720
tttgttggtg atccctaaga aaatgatacc gaatggctat gtgcttagtg cggctatgct    15780
cgacgggatt gtcggccatt ttgattgcac tctcattatc acatagcaaa gggactttgg    15840
ttaatttgta accatagtcc cgcagggttt gcctcatcca gagcaattgc gcgcaacaat    15900
gtcctgcggc aatgtactcg gcttcggcgg tggaaagagc gaccgagttt tgcttctttg    15960
aagcccaaga caccaaggat cttcccaaga actggcaagt ccccgatgtg ctcttcctat    16020
```

```
taattttgca ccccgcccaa tcggcatccg aataaccaat caaatcaaac gtggatcccc   16080
gagggtacca aagcccaaac ttaggtgtat aagccaaata tctcaagatt cgttttacgg   16140
ccgtaaggtg ggattcctta gggtcggatt ggaatcttgc acacatgcaa acggagagca   16200
taatgtccgg tcgagatgca cataaataaa gcaatgaacc aatcatcgac cggtataccT   16260
tttgatccac ggacttacct cccgtgtcga ggtcgagatg cccattggtt cccatgggtg   16320
ttttgatggg cttggcatcc ttcattccaa acttgcttag gatgtcttga gtgtactttg   16380
tttggctaat gaaagtgccc tcttggagtt gctttacttg aaatcttaag aaatacttca   16440 actccccat catagacatc tcgaatttct gtgtcataat cctactaaac tcttcacatg   16500
tagactcgtt agtagaccca aatataatat catcaacata aatttggcat acaaacaagt   16560
cattttcaag agtttagta aagagtgtag gatcggcctt gccgactttg aagctattag   16620
aaataaggaa atctcttagg cattcatacc atgctcttgg ggcttgcttg agcccataaa   16680
gcgccttaga gagcctatag acatggttag ggtactcact gtcttcaaag ccgggaggtt   16740
gctcaacata gacctcttcc ttgattggtc cattgaggaa ggcactttC acgtccattt   16800 gataaagctt aaagccatgg taagtagcat atgccaataa aatgcgaatt gactcaagcc   16860
tagctacggg tgcataggtt tcaccgaaat ccaaaccttc gacttgggag tatcccttgg   16920
ccacaagtcg agctttgttc cttgtcacca caccatgctc atcttgcttg ttgcggaaga   16980
cccatttggt tcctacaaca ttttggttag gacgtggaac caaatgccat acctcattcc   17040
ttgtgaagtt gttgagctcc tcttgcattg ccaccaccca atccgaatct tgtagtgctt   17100
cctctaccct gtgtggctca atagaggaaa caaacgagta atgttcacaa aaatgtgcaa   17160
tacgagatct agttgttacc cccttatgaa tgtcgccgag gatggtgtcg acggggtgat   17220
ctcgttgtat tgcttggtgg actcttgggt gtggcgccct tggttcttgc tcatcctcct   17280
tttcttgatt atttgcatct ccccccttgat cattgccatc atcttgaggt ggctcatttg   17340
attgatcttc ttcttcatcg acttgagctt cttcctcatc ttgagttggt ggagatgctt   17400
gcatggagga ggatggttga tcttgtgcat ttggaggctc ttcggattcc ttaggacaca   17460
catccccaat ggacatgttc cttaatgcga tgcatggagc ctcttcatca cctatctcat   17520
caagatcaac ttgctctact tgagagccgt tagtttcatc aaacacaacg tcacatgaga   17580
cttcaactag tccagtggac ttgttaaaga ccctatatgc ccttgtgttt gagtcataac   17640
caagtaaaaa accttctaca gttttaggag caaatttaga ttttctacct cttttaacaa   17700
gaataaagca tttgctacca aaaactctaa agtatgaaat gttgggcttt ttaccggtta   17760
ggagttcata tgatgtcttc ttgaggattc ggtgtagata caatcggttg atggcgtagc   17820
aggcggtgtt gaccgcctcg gcccaaaacc gatccgaagt tttgtactca tcgagcatgg   17880
tccttgccat gtccaataga gttcgattct tcctctccac tacaccattt tgttgagggg   17940
tgtagggaga agagaactca tgcttgattc cctcttcctc aagaaagctt tcaatttgag   18000
agttcttgaa ctccgttccg ttgtcgcttc ttattttctt gaccttaag ccgaactcat   18060 tttgagcccg tctcaagaat cccttaatg tctcttgggt ttgaggacga attttctaag   18120
aattnnnnnn nnnnnnnnnn nnnnnnnnnn nnnnnnnnnn nnnnnnnnnn nnnnnnnnnn   18180
nnnnnnnnnn nnnnnnnnnn nnnnnnnnnn nnnnnnnnnn nnnntttca actctgagaa   18240 tcagcttgat tcgttcttct ggcatggctt ctactggcca actgctctct aggagggagc   18300
cgagttggtg aagtcctgcg aagcatgtca gtttcatgca aagcagacac acacacacac   18360
```

-continued

```
cagctcaggc tctgcaaatg attccaccct cttggccatt cgccgtatgg ggggtggata   18420
tcctgggacc atttcctagg gctgtcggcg ggtaccgttt tctctttgtc gccatctaca   18480
aattcataaa gtggtcggag gccaccccta tggtcagtat cacccaaggt gctgctgttg   18540
ccttcctcaa ttcgattgta tgcagatttg gggtcccaag ccatatcatt acggacaatg   18600
ggacccagtt caaaagtcga ctcttccaag agtattgcga gggcattggc acccagctct   18660
gctttacatc tgtgtctcat cccaggagca acgaccaggc tgagagggca acacagaaaa   18720
tccttagggg actcaaggca cacacctacg actgcttaaa aaagcatggt gccaattggg   18780
ccaatgagct tccgtccgta ctatggggga accggaccac acccagccga gctaccgggg   18840
agaccccgtt cttcttggtc tacggggccg aagcctgcct tctcccggaa atcattatgg   18900
gctccccatg agtccagtct ttcgatgagt ctatgcagga atagctacga cgtgaggaca   18960
tggacttcat cgacgaacgc agatggcaag cggtgatccg aaatgcacgg tacaaccaag   19020
cgctcaggcg ctaccaccaa cggtttgtgc atagtaggga gctcagggtc ggggacctag   19080
tcctaaggcg agtactgaac cgagaagggc tccacaaact ctcccccagt tgggaaggac   19140
ccttcaaggt gacagaaata tgccgaccat ggtgtgtccg ccttgccaca acagaaggag   19200
tgcctcttcc caatccctgg aatatagagc atctctgtaa gttctatcca taatagcaaa   19260
actgggggt tgagttttct tcctttgtaa ctaggttacg catatgtgta tgtcaattcg   19320
gtgaggcccg ccctcgtaag cccatctgtt ggtctacacc catgtatatc gagttataag   19380
gaaaggattt accccctaga tgtgattttg tgatggtttt attctacttc ggtttacatg   19440
cattatttt tatctaaccc acccatatag tttcccaccc ttgttggtat gatgacatcc   19500
gaattgagta gacaggcttg cagttcaaga cccctttact gctacagggg gtccggcaaa   19560
ctgcggacca gttctagaga atgggcgcta gcctcctgga ggggtccgga gttgtgtagc   19620
cgcttagcat ggttccgtac cctaagcctg catgctccac cactctataa cgggtgccct   19680
agtatttgga actgtgatcc tatgggtcca ggcatacggc ttggcttccc aggctaaatc   19740
ctgcaggtcc tgttgcataa atcaaggat ggcagatacc agacgatgga tcctatggtg   19800
tgctcctaac actttaaagc cgaagctgtg tacaagtcca ggtcccagtc cagtagtagg   19860
tagtctcaaa ctgtagagac tacctcctag gggccggacc accaattta tctttggtat   19920
actggtatcc agcctcgaca cgtcgagcct acctcccagg gggccaagta ccaaggggaa   19980
gttgatgaca ctacacataa caaggacaaa taacatacaa ataagtttaa gttccaatgc   20040
tacctcatta gcggttctta taatatctta caaaatcaaa agttattaca accgcttccc   20100
agtggaaccc ttgctttgtc tctataggtc gtcagcagga tcgtgctgga agcgctcggc   20160
caccagctcc acggcgtctt gtacactctc ccaggcggcg tcttctatgg cggctaccgg   20220
accagcgatc actagcgcca aggatatggt ggggtcgtga ctccggaagc atgttaggac   20280
ttattcaacc actgcccgac agagcttgct gccctctgcc tctaggcggg ccccgaggat   20340
ctgatccagg cgacggaggc gatcggcggt agagtccagc accgggagcg catcagagat   20400
cgacgctggt agctccgaca ttgggatggg gctcatccct agtggcacta gtgccgtgct   20460
tgcctcgccg gccacgcgca caatacactg gacctcgacg cggtgctccg cttggagatc   20520
ttcaagggcc ttcctggtgg cctccatcgc ttggggaccc ggtgccgcct gcgctgcatt   20580
gaactagcgg atctgctcct ccagcttcct ctctttctcc tctgcctcga gcttgtgctt   20640
ggccagcaac tcgcctcgcc gggtgagcat ttcttccctg aagctgagat ccgtctcttg   20700
cctggcgagg tccgtctccc accggtccaa ggactgctcc ttcgccttaa gatttcctc   20760
```

```
ggcgagggtg gcattgctag ccttgccctc gagctcctgc taccactttt gcagcctctc   20820
cacgaccctg acctgctggg cccgctgggc ttccagagtc tggtccaggg cactcagctt   20880
ggcctggtac tctgttgtga gggtctcccg ctgggtcacg acctcctcct tcctggtcac   20940
cttcttctcc ctccgggacg cctccagctc cctggcgcac accctctgga ggtccctctt   21000
gtactcctta tggtcctgct cgagttggga ccgctcggag atgaattgtt gggacgccgt   21060
tctggtgcgc tcctccagtt gggtgcgcca gtcacttagg cgctggtgct cagcctcaag   21120
cgcctcccac tcccgcaaga ttgctgcccc agtgtcacta aggacctagt gggcacgaga   21180
cattatgcga gggaggggga ctggcgccgc ttcttgctcg gcacccgacc ggagtcgccg   21240
cccaaacacc acctccatct cctccggagc aggcgggggg ttggagctgg acatgcctac   21300
tgcgtcaccc ccagtgtcga gagcgggcgc ggatccccca gctgggacct ccttcgccac   21360
tgcgacgccg cctgacgctg ccaccggacc cccggctggg gcatgagaag ccgctggtgc   21420
tgtcttggca gcagctgggg gtgggccgcc ggcaccactc tcagcaggtt cctgctgttg   21480
agagccagac ccgtcggtgg gcctggtatc tggtggagga ggcatgacct tgggagcggc   21540
gaaggaagaa gccctagcga acagatgatg ggttaaaact ggtcggcatg atgattagac   21600
tcatggaaaa ggggctacgc ttacttgggg ccctagactt tctagtgacc ctggaagcgg   21660
ggcgatcacc gctcctgctg ttgctatcgc tgttgctgtt gctgttgctg ctgctggtgc   21720
ccctgggggt gaggactgac gcgcctctgc gcgccgtggg cctgggagct agcttcctcg   21780
gccccacctg cagccctctg acgcttctgg gggggctcc gaaatgagcg acccatcagc   21840
gcgacatggc ctgcgttgcc tctcctcctc cgacccctc ggagctacct ggggcggagg   21900
cactgctcgc agcccctttg cctttgtcca aggggctagg ggccacggcg gggttggtgc   21960
tgggagccgc accagtgggc tgggaacctc caatcggtgc attagaaatc tggatcccac   22020 ggaggggtc ccggccaccg gtctagcgaa ccgccatgcc gctctcgtcg agggtcggca   22080
acgtggccaa gatcaccatc ctcaggcctg gatcgtcgca gagcgcaggg atgttctggg   22140
ggagtatcag ggactcaggg acaaaagttt ccccaataat ccctcccatc aggactgcta   22200
gctcgtccca ggacagaacg gtgcccggcc tgcgttggat cctatcgatg tcgtttgggc   22260
cggtgaacca acagcacata cgcggtctcc tctgcagcgg cgcgatccgg tgcttcagga   22320
gatcgccgac cacgtgcatt gatggcaggc cgcccgtagc caagcccttg attctgtcca   22380
atacaggcag gaactctagc aagagggacg gcttagtcct ccactgcttg cggtcgagcg   22440
ctggcccatc gctcggcagg acgaggcggt cgttggcctc ggcgctggca atcacccaat   22500
cgttgcgcca gtttttccac ctcgcaccgc caaaggtggg gatgtatacg acggctggat   22560
ctggcctcgt ctggaagtag taggcaccga tgtggtccct agtcttcccg aacttgacca   22620
gcacgaagaa gcagcggaag agggaagtac aggggccac acctacgaac atctcacaga   22680
ggtggacgaa gatggctgcc tggaggacgg agtggggtgt gaggtgttga agctgaagcc   22740
caaactcctc cagcagcagc aagaagaagg gcgagaatcg gcaacgccaa cccgtagaag   22800
atgtaggagg tgaacagcac gaactccccg gcggtgagat cgccatgagg gacggcgccg   22860
gcgcggaact tccggcgagc cctggcgcgc tccatccaag caggccgcgc accaggttga   22920
gcgcctcctt agactgaaag cagtcaggat gaccaagcga ggccatggcg tgtgcggcgg   22980
cgcgagcgtg gaacagagga gcacgaaggc aaagggtgc aggcgattgg gagagaatgc   23040
gaaaaggtaa ctgctgcacg cggggtgaat ccttttttcaa ggaaacctga gtccttgttc   23100
```

| | |
|---|---|
| agggaaaccc ttccgtgcgc ccttgaattg ccacaggaaa tctcgcccga tgcgcacata | 23160 |
| ggacccaggc agcccactct atgacacggt ggcccgggtc acaagtcat acagattgtg | 23220 |
| tgctggattt cgagtgcgga aagagcgaat cgccatgcga actgccgcgc acgatagcgc | 23280 |
| acctcctcgg ggccgctgca gaagacaaaa ggttatgcag cggcaacgag cgtcccacg | 23340 |
| cgtggcccga cgaaaccacc aggcatgggg ccatgggtca gtcagctgca gagacagata | 23400 |
| tggcagttga cgtgactgaa ggcggattga cagcgggcgt gtctgcagac cgctaaaac | 23460 |
| ggcatgccaa tcaccgatca ggtcacgttg aagcaaagta caagctttgg ccccacatgc | 23520 |
| aggctcgcat cctcccctaa ggtgggtccg ggggccactt tcggcaccct gaaacaaggg | 23580 |
| tacccccttac tactgtataa atacgcagta cccacgcgac tatctttagt cgcgtggtaa | 23640 |
| aagagctgta tgtgggacca aaccatgact cgccctagcc tcgggcgact actctaggcc | 23700 |
| agcaacagca cctgacccca ccacatgggc gggtccgggg ccgccatgtg tccagagaaa | 23760 |
| gtgatgtact ccaaggcatc aatagtgagt ccggacccccc ataggagagt gccgaaccca | 23820 |
| tgccagaccc ctgtatatac ggtccaggcc tccaagtttg gtcatgcgtt actctgtcag | 23880 |
| cattagttat ttacataatc tatttcttcc attatgctcc taggcccgca tgtcgaggct | 23940 |
| cagcatcctt gtatgtgcct cctgtgcacc cccagtgtca cctaggggttt ctcttaaaaa | 24000 |
| gccaaaccaa ggaccattat tttatgtgaa ccaaagtaag catgagcatc aaaataactt | 24060 |
| aagtaagaaa gaattcacca agtatatgct taaaagtgtc atgatcaaga caattgagtc | 24120 |
| tcttaaagga taagaatgtg caaccctaat taagaaccct aagtgaaccc catgaacaaa | 24180 |
| attcaagaaa ataagcaaaa gggaatgaaa agtttaaaat tttgagttga gccaattata | 24240 |
| taagttaaag tatatttgat aagcaacaag atagattgag aaagcttagc caaaataatt | 24300 |
| caagaaaacc cccaaatcaa gcttcttttg ttgggactca ttgggaattc tgaatttcag | 24360 |
| aattctgaaa ttcagaccttt gagccaaaga tcagggatgt tcaccttgat ccctaactcg | 24420 |
| aatcctaatg gccccattga caaaattgtg tctaactaac ccctctgtct tgtgccagaa | 24480 |
| gatggcattg ggacgcgagc cctagacacg acaaaacttg ggatttgcct cgggtttggg | 24540 |
| cagggagaca gaccagattt cctggctcca tatctctgca accagtaggc aaaatcctat | 24600 |
| gacctccaca caagaatggt agcttgtagg gaggagaaga ggttttgtgc actgaccaag | 24660 |
| gcgagagcag gctcggatga gcgaccacac gcgccagagc ttgggcagaa cgcacgggca | 24720 |
| cacgtgttcg accctggtcg gcacgccaga gctcgcccaa cccgcgcgcg cgctcgcccc | 24780 |
| ggcgtccggt caagtccgcc gcgcgcccac gccctcggcc gtgcccgccc gcgcctataa | 24840 |
| agcctccccg ggcgcacctc tcttcgcccc gcactcaccc tcaccggcca gccactgttc | 24900 |
| cttagctccg gcgagctcat ttccgcccgc cattgccgcc agaactacgg ccgccgtggc | 24960 |
| cagcccactc cagccaccct ccagcccaac cagtgctcgg ctagctccgc cagtagcccg | 25020 |
| tgaagcttgc caagccctcg gacccgaccg gaacttcacc gggaggcccg aagaatcaac | 25080 |
| ctcaccggac ttcggtcttc cgccgccgcg cgtggaccaa gctatccagt gagtctcccg | 25140 |
| cccgattcct ttcgctcatg tcttctctgg catcccgtgg acctccatga cctatttgat | 25200 |
| tgaactatct cgccgcgacc aggccggtct cctcgccgcc gacgagcatc cccgcctgcg | 25260 |
| cgcgtggacc gaccgactcc ggccatctcc gacggtgttc cgcacaccgt tgtgatcccc | 25320 |
| gcgacctccc cttcaccctc ggccacttca ccggaacagt ctccgccgcg gtaagcccct | 25380 |
| ccgccctttt cttcgccgcg gctactgttt aaggtagaag aaggacctcg ggttaggttc | 25440 |
| tgtagaaccc gaggggtttt tcgtaatgtc agcgactcat gagaatagta acctaaggac | 25500 |

```
tgaattgcga ggaaaactta gaaaaccgcc agggacccca gtgcaaagtg gatttccatt    25560
taatcaattt tgttatttct ttttaaaatg accagagaac ttagaaaatc cataacttga    25620
tgaaatctta atgaaaagct gtcaaaccaa ttttgctagc tctggaattt tatgacctat    25680
catttaaaaa tagtgaacca tatgctttct gttctaaatt ttagagttta aaattaaaaa    25740
cagaaacccc ctaaaccttg tttaattaag gaaaattagt ttttcttttg tgctgagctt    25800
aagaaaattt gtagatgctt ataccttaat tagacactgt ttaaaaatag taggagccct    25860
agcattagag attatgatgt agttattcat ttaaagccat tttgtccaaa acttagagaa    25920
aatcagaaag gccttagaga ttaatgaaca gtgattagta atattttcc tagattactt     25980 atgcagcaga gaacctagga aaaatgcaga gaccattaat ttggaccagt ttctaattaa    26040
gatgctttaa ttagcattat gtagactgaa aatcaattat tagaattgca aaactataac    26100
caaagtggtt aacaaaaatc cagtgaactt ataaccacca gagccccact acaaaaatac    26160
agagcacccc agcctaactt tttaagtagg gaaaataaat acagaatgat aataaggcat    26220
tttcccacta aatcatgagc aaccccaaat aatgtgataa tgggcaacca aaattttgct    26280
aagtccatga tgagataaac caccagagaa aaatacaaac ccatgaaaaa gaagtgaacc    26340
catgcctttt gctagtaatt tgtgaggaag gccatttagc tcaaataatg caaaccaccc    26400
cttcccttag gcaaaaggaa gccaaactcc agaatgattg ctcttgcaca aaatactagc    26460
taagaaaaat aagaactctg ttgtttgatg tttttcaagt atagtggtag tagaaagcac    26520
ccctttggct agaaacctta agaaaatctt agggaaagaa ttaaagggta ttaatgacta    26580
gaaatttgta tcaagtcatg ttataacacc taaaagccag caaaaataag ttttttgagaa   26640 ttacccacta ttaaataata gttgtagttc aaagtacccc ttctgcccta aaatttggta    26700
attttgtcca gagaaaacca ttcactttct gaaccccaaa ttttgagaca gagaaccata    26760
caccagtaac aagccactgt aattttttgca gaattttttgg aattttataa aagcaacttg    26820
tagttcaaac ctactccaaa acattaaaga gaataaaaga aaagagaaga agaaataaac     26880
ctcatcccaa taagactaac ccaatttacc aagtatacca ctaaagggtt ttacataagt    26940
aaagttaact ggttttaaat caaaagatca tacatcttta aagttataaa ttctaaagca    27000
catatcatat catgcatata tcttacgcat tgcattcatt agattgtaat cttgccgacg    27060
gagagtacgt gctcatccct gagcaaggac ctatccaaga ggaggaccag gagcaggctt    27120
cagaggctgc tattgaggat ctccccgcag ccccagcaat tgaaggcaag ccccggtttt    27180
atgcataacc atgttattat atgctacttt actacactta atgcttgtag gattgcaatg    27240
tgcacttaag tgtaggagtt gcttgaaacc tctagttgca tgaacttagg attcctttt     27300 gagatgaata ctagtatgct aggtcgagta gctgcttgct aatcaggatc tcggtagaag    27360
tcgagtgatt tttctagcac tcgcgcgagg tcaggaattg attgtattca tcttgataat    27420
ggggtatatg ttagtccgtg gacttgggtc caggaggat gccatgtcca tgagacggga    27480
aaaatgaatt aaggattaat gtgtggatac ctgagtcaag cttttgaacg tactaagcac    27540
atgccgggaa aaatggtaac cggtaaacct agtacctgag tgaagccggg cgcggacttt    27600
atccctcatg cgacctgaga cagggtctcc catgctagct atggtgggta caagtgcggc    27660
cactgcatga cggcagtcgg ggtcagtgga gcattgtatg ccaaggcggt gaggcctgga    27720
cgcgaacggg gaatcgatgg ggacggttgt catgtgtggg gtcggagtac cctgacatgc    27780
cgtgtgttta ggtttacctt gcaaggttta aaaactcgat tcgaatcgtc tgcttctcgc    27840
```

```
agctaatgag actgcttgat tccttgtact gcatcgagta agaagtgaaa tgtggattat   27900
atgagataac ttgttgactg aactaattga ttgttaccat gtatgcttag aaggagcaaa   27960
tctagctaag ttaatgatgg tagaatttga aaagctaaaa gttgatttta gaaacagcta   28020
gtgcttttgg caaaccaaac ccctcagcca aacagctgca tagtctagag gtagaggagt   28080
agactcctca caccggttaa gtctagctga gtattagtat actcagcctt gcttgtggca   28140
ccatttttgc aggtaccatg caggatgtag ttgatggtgt gacttggcct accaccctgc   28200
caccggggttg gacggtcgag tgggatgttg ctccggcagg agaggagcat gaggagtagt   28260
gggctaggcc ttgcccattt cctcattacc gacgacatcg attatccgct gcactttaat   28320
ttatgaactt tattcgctac tcaaaaactc cgatttatgt aataactcag tacttaattt   28380
gaggtttcct gttttattgt atttcttctg tgactcacct tcgagtgaga ttgtgggatt   28440
tgatcctggt taagtggctt catcagacta gatctgaggg actgacgggt tattccgatt   28500
taagtgtgtt acggccctg aggcgtgact taggcactta agctggaata attcgggcgg    28560
ttctgccaca gctggtatca gagcaaattc caccacagaa aagggcaata aaccatgaat   28620
accaattttc aaaatctaaa acctgcctag aagctactac ggatcgtcag gactagaccg   28680
ctagacctag gacgaaaggc cttaggcata gagggagaaa taggtggcta actaattagg   28740
ccctgtgggc caatacttat attttaggat gccctaaaaa ggcaccctat ttccttttg    28800
agaggcaacg tttctttccg catgcatgca ttataaaaca taaagaggaa ttaaaattga   28860
gctaacccc ttttcttcga aatcatccgg gctctctttt tcttttttcct tccaccataa   28920
tcttatctt tgattcccttt ccgcagatga attcacccac ccccgccagt ggaggagact   28980
ctcgtttcag ttctgacttc ctttctcgcg atggcttccc ttccattttg tgggaagtgc   29040
ttaattccgc cggttaccct acgccccctt tgtacacggt gcagttgtat gaggagcatc   29100
gggtacctcg ttgtcgggtc tggctaactt tggaggctca tcccctttcag ccggggttggc  29160
gttctcttga ctctgagacg attggactca ggacggacga caccgttgag gcagcagcca   29220
tgaagactct gacgacttt tgtggctacc atcccctgga gatggtgatg caccccttgg    29280
gactcttccc cgctgagaag aaggatgatc ccatgtggtg taaccgcgtg agccatgtga   29340
aggatgtgtg ggcaatgtat cctgacttgg ttgggagggt cactgttcag tgcatgagtg   29400
cgctgtaccg ccttcaggcc cttcagagcg atgctatgac acttcttgcc aataccgctc   29460
aggcagccaa gctcacctc gacagtcggg aagattttgt ggtcgaccta tccacagagt   29520
tggtggaaaa ggatctgcag gtggagaggc tgaaccagcg tattaccacc ctggagcagc   29580
aagtggagat ccgagataac actattgatg tcttggagaa ccagcttcac gacgtgcaga   29640
gggaactcga ggaagcaaat gaccacttgg acatgcacca cctggagatg gaggccaatg   29700
aagcaggaag cgagggagaa gaggctcccg aggagctagg accagcccct ggtgccaatg   29760
ggactacctc cgcgataccct ccttcacccg tatccagtgt cgcttccacc gctcagggtt   29820
aagcagtcgc tttgacattt ttaggcggat agaaacctat gcgagcttag tggtatcaca   29880
ttttggacta ggcttgtggg taccttcccc tgattaatgt aaccctgtaa acttttgata   29940
tctgtgggat ccttgtcacc atgttatctt cattcgaacc taatattatg attatggcat   30000
tttccttcca tatgagatga tatcttgtcg ttcggaaatg tgaattggga taacaatggc   30060
gacaatctct gttttcagat ggcagcgagg cagcgtcgcg ggcaaaatga gcaagctccc   30120
ccgccacctc ctccagctcc cacagtgcag gagctgatgg cccagcagaa tgagattctg   30180
cgacagctct tgcagcgcca gccccaccct cagcatcctg gtggaggcca gcatcagcga   30240
```

```
cctccggcta tggcaacata ccaggagttt ctgagcacgc agccgccctt gttcaccaag    30300
gcagaggatc cattggacgc cgacgtgtgg cttcgcgtcg tcgagtccaa gtttcccctc    30360
ctcacaggag actgccctga tgaggccaag gctcgcttcg ccgcacagca gcttcgcggc    30420
cctgctcgga cttggtggga tcacttccgt gctatgctcc ccggtgatcg tgaagtatct    30480
tgggaggaat tcaagactgc cttcagaggg caccacattc cagctggcat tcttgatcgg    30540
aagttgaacg aattcctggc cctcaatcaa ggaacccgca cggtactgca gtatgcgcaa    30600
gccttcaacg acttatgcca gtatgcaggg tatcatgctg attctgatga aagaagagg    30660 gatcgcttcc gcagggtct caataccaag ctgcggaac gactcaacac tgtccgggcc    30720
gatagcttca atgagttggt caacatggcc atctctcagg aggattgcat tgttgctcac    30780
cgggcagaga agaagagaaa ggcaccaatg gcagcaccat ccgctcaggc tcagaggttc    30840
cggattgttt ctcacaatca gagcaggggt tttcagcagc aggcaggcag atgggtgatc    30900
aggccacctc agcagcagca gcagccggca cccaaccgct atccagctcc cgccccaaga    30960
aacaatcagc ctccgcagca gcagcagttc cgccagggca tgggaacaa gtgtttcact    31020 tgtggcaatg tgggccacta tgccaagaat tgtcccagga accagcagag gcagatgcca    31080
gcaccaaatc aagacaaggg aagaaagcag aaggtacaag tcaggcaagg gaagctcaac    31140
ttcactgctc tagaggaagt gccagaagga gctcccatca tgaccggtac cttttcagtt    31200
tataatcaac ctgctttaat tctgtttgat tctggtgcat ctcatagttt cattagccaa    31260
aagttcagtg ctaattgcaa acttccattc tctcactcaa aagggtcatt catgatagtc    31320
acacctgggg gtaaaattgc aactaatcaa ttaaaccaaa gtgtgcctat tcaactggga    31380
agccacatta tcaaaaccac tcttcttgtg ttgggattgg aaaatgtgga cattattcta    31440
ggagcaaatt ggatgacctt gcaccaagtt gtgctcgacg tagccagtcg taccgtggaa    31500
gttaattctc ccttctgcgg gaatttcact ttgattctgc ctagtcaggg ttcttctcag    31560
tcatgtgctt tctctatgac ggaattaccc ctgaagaaga tcccagtggt ctgtgagtat    31620
gcagatgtct ttcctgatga attgccaaga atgccactgg accgggatat tgagttcgcc    31680
atcgagttgc aaccgggaac ggccccaatt tccaagaggc cctaccgaat gccacccgct    31740
gagttggcag agttgaagaa gcagttgcaa gagttgctgg ataagggatt tattcgccca    31800
agcacttcgc cttgggctg tccagcactg tttgtgaaga agaaggatga agcttgagg    31860 ttgtgtatag attaccgccc tcttaatgcg gtaactatca agaacaagta tcctttgcct    31920
cgtattgatg ttctctttga ccagttggtc ggggccaagg tgttttccaa gatagaccttt    31980 cgctctggct accatcagat caaaatacga gcaagtgata ttccgaagac ggcattctca    32040
accagatatg ggctatatga attcttggtg atgtcattcg ggctgacgaa tgcaccagca    32100
tatttcatgt atctgatgaa ttctgttttc atgccagaat tggacaagtt cgtggtggtt    32160
ttcatcgatg atattctggt gtactcaagg aacgaagaag aacatgccgg gcatttgcat    32220
gtagtacttc aacgtctgcg agatcaccac ctttatgcca agttatccaa atgtgatttt    32280
tggctaaagg aaatcaaatt cttgggtcac actatctctc aggctggaat agctgttgat    32340
cctgataaag tgcaagaggt gatgaactgg aggccaccaa cgactgttcg ccagattcgg    32400
agttttctgg gattggctgg ttattaccga agatttattc cggacttctc tcgaattgcg    32460
aagcctatta ctgagttgct gaagaaagaa gtcaaatttg tgtggagtca gaagtgcgaa    32520
gatgccttcc atgcattaag gcagcatctg accacagcac cagtattggc gcaacccgac    32580
```

```
agcagcaagc cttttgatgt atattgtgat gcctctggca ccgggctagg ttgtgtcttg  32640
atgcaagaca accgagtcat tgcttatgcc tcaagagcac tcaggcctca tgagcaaaat  32700
tatcctactc atgaccttga gttagcagca gtggttcatg cattgaagat gtggaggcac  32760
tatctaatgg gaacccactg caacatcttc actgatcata agagccttaa gtacattttt  32820
actcaggctg atctcaacat gaggcagaga agatggctag agctgatcaa ggattatgac  32880
ctggaggtac attatcaccc agggaaagct aatgtggtag cagatgcctt gagtcggaag  32940
ttgcagtgca actgtattct gatggattct cgtgttaaca ccttgtgtga tgagttgagc  33000
aagatgcaaa ttgaagtgat tccttctggt tctttgtctc acattgctgt tgagccagcc  33060
ttgcaagacc agattatcat ggcccagctc agtgacaagg gagtgcaaat tatcaagaag  33120
aatctccatc agaaggttga gaagtataat tgtttccgcc aggatgagaa gggtgtgtta  33180
tggttcaaaa gcagattggt aattcctaag gaccaggatc tcaagaagaa aattttggat  33240
gaggctcatc tctccaaatt ctctatgcat ccgggaagca ccagatgta ccatgatttg  33300 aagcataaca atccccaccc ttttcctata agtctcaccc ttcgcttcac cctgggagga  33360
ctctggcccg aatctcggga cgagattcct ttaagggggg aaggctgtga caccctagtg  33420
tcacctacgg tttctcttaa aaatgccaaa ccaagaacca ttattttatg tgaaccaaag  33480
taagcatgag gatcaaatta acttaggaat aaagaattcn nnnnnnnnnn nnnnnnnnnn  33540
nnnnnnnnnn nnnnnnnnnn nnnnnnnnnn nnnnnnnnnn nnnnnnnnnn nnnnnnnnnn  33600
nnnnnnnnnn nnnnnnnnng ggtgctaatc atgaaccagt ccagagcaac actatccgat  33660
ggccattgcg tccggtcgca cgagagacgc gtgcggaacg tcccgtagga gcggccaacc  33720
ccccattttg cagctagcag ccgtccagta gggacagccg ccgagctccc cgacatgtct  33780
ccttcgggac cgggcttcta tttcaagctg cgggacggtg cggtcaatcc atgtggacac  33840
catgcgagtt cgcgcttcac tatctgggct ggggacccac ctccatcaat ggtctgcatg  33900
acgcaggata ttccatcagc catggtgcag tggaatccgt tccagaggat ggcctctgca  33960
ccaaacgctc gccaaggtaa cagaagcaat ccaggcccat cgggcgtgat ctcccatcga  34020
tccgtatcga tcctttgaca tgaaaaggca atcacgggct cacgcttttc ggagtgtaat  34080
tcaggctccc gggtgcagct ttttgcgcgc ttgcggcagg gggcatctgg tggacatcaa  34140
atgatatggg cttgcttggt ccagggaacc ggcagcacct gctgtcccga gatcagttgt  34200
gatgctatgt catccgtcga tagtcggagc ttatccagct cggatcaggt gatacgcttc  34260
cctttcggag aggtttgagt ttcagacctg gtgctcagtt atgataaaaa gggtcggcag  34320
tgagagaaac cccgaaaact tgtcaatcga accaattacc ttatttactt ttcctgccct  34380
aggagtagat gtagcatagt tctagttgta gtcttccaca tatccacctc caccgctatt  34440
cgactctacg tcgtctagat ccgtcttggg tggcctgccg atcccaagac gaccctagga  34500
tctcacccct cccgggggc aagatctagt tgtccatcca agacttcttc ctcgatttga  34560
tctcttaatt cctaggcgac tccacgtcgt ctggggacgc cccgggtgac ctgtcgaccc  34620
ggagcacctt aagatctttc cccccagggg acagatcta gattccagca aggagtagga  34680
agacgaccct gtcgccaggt cgcggaccgt ccggcccaga gctgcggacc gtccggtgtg  34740
acgcagggaa gacaccgctc ctgcgcccag gtcgcggacc gtccgaccca aggctgcgga  34800
ccgtccggcc caaggctgcg gaccgtccgc gcctgaccag agggcaccgc cacggttctt  34860
gttgagtgtt tggcgctcca aaaaggcgtc aacagtagcc gtcacatcat ctattgtgtg  34920
gctatgctta agtgtgcctt gatataattt agaataagtc gagtctctag aacgcggcaa  34980
```

```
tttttaaaag taaacagaag ctgaatttat tgattgctgt tttgggctgc acgcactgtt    35040
ttagttgtgc tgtttgtttg ataaaccaaa tcatgttttc tgtagaaaag tcatatagaa    35100
gagttgtaga tgacatgatt atcttgcttg tactaaaatt tgacagccat aaacctgatt    35160
gtttaggagt tgtgcttttc acaagcccag cacctgaatc tgtcaaattt ctgaacatat    35220
ttcagaaatt gcaatggttg cttaagttaa tgttgaaatt agttattggt ggtcacaaga    35280
aagttgtaga taactttatt atcgtacttg tgttaaaatt tgacaggcat aagtctaatt    35340
gtttaggagt tatgtttttt acaaattcag taactgaatc tgtccacttt ctgtacagat    35400
ttcagaagct gcattgtttg cttaagttaa tgttagaatc agcccttgta gattataaga    35460
aaagttgtag aggcttttct tatcttgctt gtgttaaaat ttcataacta taggcctgac    35520
ggtttaagag ttatgaattt tacaaactgg ttgctgtgtt ctgtccaccg tcagaacaga    35580
tttcgaaaac tgtaatattt gatttagtta aacctggaat cacttcttgg tgattatgaa    35640
agttgtgtag tacttttgct aagattttca aaaagtctta gatcactctt tttggtggtc    35700
tgaagattaa gttacatgtg tttgaagtgt gaagactgaa tctgtccagt tttggacagc    35760
acagccttca tagtatattt taaccttgat acatgctaaa ccagcctggg atgtttataa    35820
ataatttgta gaacatttaa ttagctttcc agaaagtcta ggatcaattt gtttggatgt    35880
ctgaatcttc agttatgaat ttttaaaatc acaagtctga atctgtccaa atctggacag    35940
agctgttgtg attgcacttt ttgaccttgc taagtgttta atcatgctgt gatgaaaata    36000
ccaaaattgt agagcacttt ctaaactttc cagaaagttt tagtttgcta ttttttggatt   36060 aatatttgaa aagttattat taaaacaagt aactgctgtg ctgctgtcca aaaaatctgc    36120
acgtgctcaa atgaatattt agttcaccat tttggctaaa aacgcttagt tagcacttaa    36180
cggacataga cttgtgatgg ctaaacttag gttaacatgt gttccatgat taatgtgctt    36240
gcttgctata gttgattgtg atagaggagt ccatcgacat tgatgcatcg gtcctttatt    36300
aaacttgtgt ttgtgatgct tttgtgtgat caatagaaga actaatgaaa agccgtagca    36360
actaaataaa tgcttgtaca tatgatatcg tgttgcgttg gttaattgta ggtagtgatc    36420
attgtctttc cagtggtagt gtttacgtgt gcccaatgac acataaataa ctagtgtttg    36480
cgtatagttg ttgcagtgtc ttactaatta atgtttagtt cgccactgtg tcttggtata    36540
tcttatgtta cttttattat attcatacat atgcatcttg cacctcatat aggaccgaga    36600
gatgatgatc gagccagtga tgtggtgcca accacaagat gccgttgatg gacgacctaa    36660
agaatggact taaccagtgg atgctcgcca agcgagtacc tcccccagca aacactacct    36720
aagtgttaaa ttaaaggcaa gccccggttt tatgcataac tgttatatat atgctatttt    36780
actgcactta atgtttgtag gcttgtacca tgcacttaag tgtaggagtt gaatgaaacc    36840
ctagttgcat gaactcagga ttcccttttga gatggatact agtatgctag gttgagtagc    36900
tgctttgcta attagggatc tcggtagaag tcgagtgatt tttctagcac tcgcgcgagg    36960
tcaggaattg gttgtatcca ctttgataac ataatggtga tggtctgtgg acacgggtcc    37020
atggggacgc gtggtctacg agatgaaatt ggaataagga ttaacgtgcg gatacctgtg    37080
tcaagcgttt gaacgtacta aacacatgcc gagaaatatg gtaaatcggt aagcctagta    37140
cctgagtgaa cctgcccgca gattgccctc ctcaggcgac ctgagacgtg gtctcccatt    37200
ccggttatgg tgggtacaag tgcggtcact gcacgacggc agtcgggtc agtgaggcat    37260 tgtacgccaa ggcggtgagc ccctttctgt tgccagggaa tcgatgggga cggttgatgt    37320
```

```
gtgtggggac ggagtgcccc tacatgtcgt gtgtttaggt ttaccttgca aggtttaaaa    37380
acttgattcg aatcgtctgc ttctcgcagc taatgagact tcttgatcca ttgtactgca    37440
ttgagtaata agtggaaatg aggtgattgg caaaagatgt tgtttgataa aaattcttga    37500
tatcatgtat gattagctag gtacacatct agtcaaaaag gatcatacta aaacttgaaa    37560
agctaaaact tgattttaga ctcagctagt gcttttggca aaccaaaccc ctcagccaaa    37620
cagctgcatg tctagaggta gagaagtaga ctcctcacac cgggtaagtc tagttgagta    37680
atgtatactc agccttgctt gtggcataat ttttgcagat attcattagg atgattggtt    37740
gatggtgtga cttggcctcc atccctacca ccgggataga tggtcgagtg ggttactgct    37800
tccgcaagag aggaccagga ggagtagagt ggccaggctt cgccatgtta ctcggttctt    37860
ctccgttagt tatttctgct gcattaaaat ttatggttat tatttctgaa actccgataa    37920
tgtaatcact aatgatactt attaaatttg tggtattatg ttttattgta tttctctgtg    37980
tctcaccttc gagtgagcta gtggtattcg atcctggata agtggcttta tcggactaga    38040
tccgagggac tgacggttta ttcctattta agtgtggtct agcctctaag gcgggacttg    38100
ggcacttaag tttgaataat tcgggcggtt ccgccacagc tggtatcgga gcgaatacca    38160
tcacagagaa gtcaataagt catgattacc aaccttttct aaaagtaaaa cttgctagaa    38220
accaatgttg gatagatgtc aggacgataa ggatagactt aggacgtgaa gccttaggaa    38280
atagatgggt agctaggtgg ctatttatat aggccataaa ggctactact actattaata    38340
aggatgctgt agaagcaacc gaaaaagtag ttaggtctga aagacgact agaatgagca    38400 tgcatcatga ttgtcgcatt ataattgtct tttgtgcacc aacatgcttc tctcaccttt    38460
attcaaataa taaaaaaaat tgtgaataat gtgctgtatt gctaggaact gcaaaaaaaa    38520
tgtcttatct tgtgtgtcat gatagtcttt actaggttat gttatgtgct tctcttgtct    38580
tgctatctag gtagtattgt aattgttcaa cccttttgc aaaacatttt gttgcttgtt    38640
ctgttcataa aaagactcct ccaaacaacc ttgagtttag caagtgaacc cgcttttaaa    38700
aaaatgcttg tgttggcgtt ttctagccct tgtgggtttt acccttgaag ttacacctgc    38760
acagcttgta gattcccata gcttgactcc tagatcgacc aaagcttcct tgtgcactgg    38820
ttacgtcaaa aaaaatttgt tgtttggtgt ctagttgcgc aaaccctatc aaggccatgt    38880
ttctttccat aaaattccttg cccctaaaac ttcatagcat tcctgttgat catccagctg    38940
atcttgttgc ctacctctcc tttcgcatgg atctagtgat cttttccctt gtgaatcatg    39000
ttgtgacctt atcatccgaa tctctgatct ttcatgattc tgccctatta tcttgttatc    39060
tactataacc cgttctcaag tatcgaatgt tgatctacct aagtctctca attctggtca    39120
ttctcatact cgttctctga ggatcatgac gatgtttatc aactttatct ctaaacagtg    39180
tatccatttg gttcaaggga tgttgttgtc atcttgtggt tctctcatgt ctctacaagt    39240
tcatcaacat gatctctgga gtgcttcctt ctcatatcaa atctcgtact aatcgctggc    39300
ctgctaatcc ccgtgatgat cataaaataa ctctatgagt tgaagaaaat tctcatgtga    39360
tgatcttttg ccaataatct ctgcttcaac tctgatcaca ttcttatttt ctgagccata    39420
ctctcatggg ctccaactat cagtgctatg tgaatttctt attggttgcg tttggtaatg    39480
atgtcatgac taacgactga tggtgccgcg acgaaaccga gagcctacta tggtgcacac    39540
atggttgagc tgctcggcac gcgctagtat cgcggttaat agtcgtgatc cattacgaga    39600
ctatactgat gtgctatttt tttgtggaca ctctcagaat gatcgctgca ttttgtctcg    39660
atatgtcgcg atattctaac caaatctgtc tccagtatct tgtcagatac cctctcatga    39720
```

```
atttgcatct atcttcagtc tgggagttac atgcttctcc acccataaat atcctcattc   39780
gaatctcggg acgagattct ttttaagggg ggaaggctgt gacacccccag gtgtcagttt  39840
cgtgttacgt cgcgagattt atcctaatct cggatgctca gtaaaaattt ctatttctcg   39900
ctcgcgtatg tccctgatta tccagattat tcattcacgt ttcaccgaat tcggagttac   39960
tcagtctcac agaaggccaa ttttggagcc tgttaaaact tttatcgtcg gcacaaatgc   40020
gaactcaaaa atcattctcg aattataaac ctcatctgaa gctcattaaa tcaaactctc   40080
gacgactgtt atttgatctg tgtccgaatc caatttctcg atgttcgatc gatgtccaac   40140
tattttaatc cgagtccata ctcacaaacg aaataatcaa tatgtcgtcc tctaatcaaa   40200
tcttactcga ctcagcttag catctctgta tccaatccga tttcaaaatc aacatcggca   40260
acgatttta tatatcacga ttcgctttct ccgactaaaa atccaaaacc gatcaaatct    40320
caggacgatt tattttcgat ttacgcgtag ggaattattt tcaagcgaaa tctaaacaga   40380
ctctcggccg agtaatcgc gcaaccttcc gttcgtccga actcttttcg ctctgtttct    40440
cagtagcgac gaattccgca ggaacatttt tagtccggaa aatatttagc gcgacccaat   40500
ttagtgtttt gggccaaatc cagtccagcc cattcggccc ataagaaacc ctaccctaat   40560
ttctcctcta taaatatggg cttccctccc ttgcattctg aaaatttttcc atttccaccc  40620
cagccgccaa caccccttctc ttcctcctct accatttttcc agccgtgggc tccttcaagc 40680
acgtagagct ggagctcctt ccccagcgcg caggggcttc catggccggg cgttccttcc   40740
ctccagcgcg ccgaagctct tcccgtggcg tcctctgcct ttcttcttcc ctgcttcaca   40800
gcagcaaggc caccagcagg ctccctgctc cccgcgcccc cagccatggc atccttcact   40860
cccctactgt ttttctccca gggcgcagca gcaaatccca tgcagcggct ccatggccga   40920
gcgccctgcc cggtgctcca gccggcctcc tctgccccctg ccattttcca caggagccga  40980
gctcctacct gcagcaggcg cccctgctc tttcctatcc gcgaccaggg agcttcagct    41040
ggcgtgaaac ttcacttgcg cacggcggcc agcaccctct ccttgggctc caacagcttg   41100
gatgccgaac cccttttcttc cttccccctgg ccgagctcga gcttcccatg gcgccattcc  41160
tccctctctc tgttgtacat agcgccaagc agcaactcca ttttccctgc ccgcgcccaa   41220
ggtcggcgac cagcctcccc ttccctgttc ttgctgtggc cgagccacca cttccccagc   41280
cgtagccctc tcccccctcca ttgtttcagc gcctgaaaca aacacctggc cgccatccac  41340
acttgtgctc gatgaaatgt gcagcagccc cgacggctcc gcgcgctgac ggcttgctgt   41400
tttgttgcgc agtgagcagc acgccgtgat gccgccgtgt gttcgctgtt tttgcgcagc   41460
cccaaacgtc gtcgtcgttc accccggtga gaccgcgacg ctccttgttc gattccgcat   41520
cgatgttatt ttcctatgat taattatgta tgtgtgttgc tttgttttat ttttgtggag   41580
gagagaaccc cgtgtttttgc gaggagaaag caagtcgctt aacgctcgtc ggatgtttgg   41640
agcgatgcac gaatcggaat caccgtcatt cttgcaaaca tcgttgggt ttgtttatgg     41700
tgagccgatg catgtcgctc tcgatcgact cgattaatca ttttgtatgg atgtgtgtaa   41760
aatgttcgat tatgcgcatt ggtaggatca tgtttgcgat tggagaacaa gaggttaatt   41820
gatgtgcgcg atttgtagtt gtctaattat gttttggtcg atgatgtgca tgtggttata   41880
tgtgtgtaaa agtataattt tataaatgga cgcgtgtagg gaagaaaatg aaatacaaaa   41940
gaactcgagt attttttattt tgataggaaa atatgcgatg cgttgtttga tgcgaaaact  42000
aagttacaaa atgtggattt tgttttggaa aatgcatcga tgtgtttatg tgaaaagtgt   42060
```

```
atttgtttta agcaatgtga tgggattcgt aattttagag gggatatatt tattgatgtg    42120
acgagtagtt tagagaatgc tagtttgcgt agaggatgta tcgttaagac atgagtgtcg    42180
gagtccattt atactagtgg tcgcgccaca tggattgaag tgtctcgagt gcacgccata    42240
atatggttgt atgcgagaca gggttatgcg tacgatgagt ttagtaaaaa ttccatcggt    42300
gtcagttgtg ttaagttgaa gtttatttgt gcgtataaag tagtaaggta tttaatgctt    42360
acgactctta atcgatggta gaaattgtct tgacttaaat agagaggtgg tgacatgcca    42420
gagtagtcat cgctttctct atatttatag gtcaagtcat gacgatgcgt attatgcgtt    42480
cgttaaaatt atgtttcgta tatagtgtat gattgtgctc acgatttcga gtagacactt    42540
caaataagtc aagtagcttt gtaatgcaag atgtgtgatg aagttagttt gttttaggat    42600
atgtgttgaa atgctccatt cctgtgatag acatgtaggg ttatttcaaa acgggtcgat    42660
gtgtgtgatg atgatattca tgatttaagt agatgtcctg aaattatgtg gcgaagctta    42720
ggttaagttg caagcgatgt ggaaatgttt tcgtaaagat atatgtggaa tgtgaacgag    42780
tcattcaatg tattcggtat gtcgtgtagt ggtggtatga aaaatgagtt aggaatcgat    42840
cggctaaatg ccaagttcgg ttagagttat tttgatagtt gggattgtgg ggtgaagtga    42900
tggcatgact acgtagctgt tggacaccaa aatgagcgga cggtccggcc catgggcccg    42960
gacggtccgc gtgtcccgag attagattaa ctcggatgtt tatccttatc tcgtgcgtgg    43020
ttatccatct aatcacgtgg gagtttgttg gctatctctt aggaaaaggt ccagacctcc    43080
tcccctataa atataaaggg gtacggccga ttgagaaccc ccgaacacat tccaatcgaa    43140
ccaattacct tatttacttt tcctgcccta ggagtagatg tagcatagtt ctagttgtag    43200
tcttccacat atccacctcc accccctattc gactctacgt cgtctagatc cgtcttgggt    43260
ggcctgccga tcccaagacg accctaggat ctcaccccct ccggggggca agatctagtt    43320
gtccatccaa gacttcttcc tcgatttgat ctcttaattc ctaggcgact ccacgtcgtc    43380
tggggacgcc ccgggtgacc tgtcgacccg gagcaccttta agatctttcc ccccagggga    43440
cgagatctag attccagcaa ggagtaggaa gacgaccctg tcgccaggtc gcggaccgtc    43500
cggcccagag ctgcggaccg tccggtgtga cgcagggaag acaccactcc tgcgcccagg    43560
tcgcggaccg tccggcccaa ggctgcggat cgtccggccc aaggctgcag accgtccgcg    43620
cctgaccaga gggcaccgcc acggttcttg ttgagtgttt ggcgctccaa aaaggcgtca    43680
acatactttt tggcgactcc gctggggaag aagttgcaga tctacaaaat caggcttaca    43740
tggccgattc taaagatctc aacagtgctt ctccaaacag caacacaagg ctgactaatt    43800
tatcggccgc tgagcataaa aaattagaag atgacatgaa gaaaatagac gaggaggccc    43860
accgacaaaa ggatcaggtg ctcaaggtgg cggacaagtg gtacctctcg cacttcaagg    43920
tagactgcca ccagaagacc gtccaagaga gggagataaa cgccgagtat atgttagccg    43980
tgctgcaaca gctcccccaca ataggtgatg ccaggtcagc cgatgatatt ccatctatta    44040
aaatttcttt tgataatcgg attaaaagta tcacggagga tatagagagg atgacacatg    44100
catttgttaa aactcacatg cctaattttt taaaacataa attaggcgat gagaacgatt    44160
actctagatt tcnnnnnnnn nnnnnnnnnn nnnnnnnnnn nnnnnnnnnn nnnnnnnnnn    44220
nnnnnnnnnn nnnnnnnnnn nnnnnnnnnn nnnnnnnnnn nnnnnnnnnn nngctgagca    44280
atattgccaa gagcggtagg accggtcgtc caaagagaat aaagtttatg actatgttca    44340
gaaataaaga aaggatcata taaacaagcg cgattaattc acgataggag tcctcatttg    44400
ttgcagagca tgggggcagt agacacgatg agggacgccg agtgataaga aaaaggaga    44460
```

```
taagccgctc aaattcgcca ccccaatcgg tttgcatagc aatgattttt ctattgagca    44520
agcgctcaac aaggctttga aattctttga agaactgaaa cacctcagac ttatggcgaa    44580
gaagatagat ccaagtaaat ttactataat catcaatgaa gctgacataa tacctttat    44640 tacaaaaaga atcaatggcg ggtccccaga catcgaaaaa caccagatct aaaggagcag    44700
cagactgact ggtcgactta ggataaggca actgatgggc cttagcacga aggcaggcat    44760
cacaaacata ctccgaggaa tctaagcctg aacacactaa attattattt ctaatgacac    44820
gagcgacaat atcacgcgat ggatgaccta atctgcaatg ccaacgctca taggatggct    44880
ttattgcggc aaggtcgtgc ttctgggtag gtgtgcaaga gatgtcaatg ggtagaggcc    44940
acccctacat ggtccgcgca ccagcacttg cctcgtggcc tgatccttaa tcaagaaaaa    45000
gaacggatgg aactcaataa aggtgttatt atcaagattg aaacgatgaa tggaaacaag    45060 attttatgg gtatgaggga cacgaaggac atgatttagg tgcagagggc ggaaggaagt    45120
gggcaaaaca gaataaccaa tgtgagtaat ctccatacct gcaccattag ccgcccgaat    45180
ctgatcattg ccattgtaac gatcatgctg ttagcttttc cagctcgtcg gtgatgtgat    45240
cagtcacacc gaagtcaagg taccagtttg atcagcagc agtggaggat gatgccatgg    45300
ccgcaacccg atcatcagga gtgaattctt cataaaagcg gtaccaacag atattagctc    45360
tgtgaccgac tttaaggtag acctagcagc gtggacaaga ctggccaccg gattgatctg    45420
tcggtggacc ggaactgcgc ctgaagtagt tgttgttgct gtagttgccg cgcgaagacg    45480
acgaaggata gccatggcca tttccgcgcg agcgtccgcg accgtgattt tggagaacca    45540
tcatgccagg agccaccacg gccacgagta gccgtattgg ctgatccatg agcagcgtac    45600
ctgccgccgg actgcttcgc aagccgaagc tcatagctga gcatctgcga gtataacttg    45660
gcagaggaga ttggctcgac gcaagtgacg atggacgaca caagcgggtt gtagatttct    45720
tcatcaaggt cggtgaggac ataggcgacg aactcctcat cgcccagagg ttggccggac    45780
gccgacatct catcggcata actcttcatc ttggattaga atccggccat tgtggtcgtg    45840
cctttcttcg tggtggcgag cgcaatgcgc gtgttgacag aacgcgcacg tgtgcaagat    45900
ccgtacatag ccgcgaggga gctccagacg tcggccgagg tcgtggctgt cgtgacaccc    45960
atcaagacct cacgcatcag agaggagagg atatatccca gcagcgcttg atcgtgagtc    46020
acccagttga tgtactcggg attgggcgtc tccatatagg cgtcgttagt catcacagag    46080
acagtcttaa ccagcatctt ttctttgccg atgagcagac cgtagagctg tgcagattgg    46140
atgggcggta ggatttgggc actccatagg cggtagttgg ttttggtgag ttttttcggtg    46200 accgggatcg agaaggagga ggggatggtg gtggaatttg agaatctact cgccatgatg    46260
gatgtgttgt agaggacctg gctatggtac catgtagatt ggaatggttg atgtggcaga    46320 accgccgga ttattccagt ttaagtgccc aagtcacgcc ttaaaggccg caatgcactt    46380
aaatcggaat aagccatcag tccctcagat ctagtctaat aaagccactt atccaggatc    46440
aaataccaca agctcactcg aaggtgagtc acagaagaaa tacaataaaa caggaaaacc    46500
tcaaattaaa gtactggagt tattacataa atcagagttt ttcaagtagc tgagaaaagt    46560
tcacaaaata aactgcagcg ataatcgat gtcgtcaaaa gcgaggaata gggcaaggcc    46620
tggcccacta cttctcctgc tcctctcctg ccggagcagc atcccactcg accgtccaac    46680
ccggtgacag ggttgtaggc caagttacac cgtcaaccat atcctagagc gtacctgcaa    46740
aaattatgcc acaagcaagg ctaagtatac taatactcag ctagacttac ccggtgtgag    46800
```

```
gaatctactc ttctacctct agaccatgta gctgtttggt tgaggggttt ggtttgccaa    46860
aagcactagt tgtatctaag gtcaacttta tcttttccat ttctagtatc attattgtag    46920
ctaagtttgc tctttctaag catacatggt aacaatcatt taatacaatc aacaagttat    46980
ctcatgtaat cctcatttca cttcttactc aatgtagtac aagggtcaa gcagtctcat     47040 tagctgcgag aagcagacga ttcaaatcga gtattaacct tgcaaggtaa acctaaacac    47100
acgacatgtc agggcactcc gtccccatcg attcccttt cgcggccagg gctcaccgcc     47160
ttggcataca atgctccact gacccgggct gccgccgtgc agtgaccgca cttgtaccca    47220
ccaaagctag cataggagac ccagtctcag gacgagtgag gagaaaagtc cgcgcccagc    47280
ttcaatcagg tactaggttt accggttacc atatttcccg acatgtgttt agtacgttca    47340
aacgcttgac tcaggtatcc acacattaat ccttaattca ttttcctgtc tcatggacaa    47400
ggcatccacc ctggatccaa gaccatagac catcatagat cccattatca agatgaatac    47460
aatcaattcc tgacctcgcg cgattgctag aaaaatcact cgacttctac cgagatccta    47520
attagtaaag cagctactcg acctagcata ctagtatcca tctcaaaaag gaatcctgag    47580
ttcatgcaac taagggtttc aagcaactcc tacacttaag tgcacattac aagcctacaa    47640
acactaagtg tagtaaagta gcatatataa attggttatg cataaaaccg gggcttgcct    47700
ccaaatgatg gggctgcggg gagatcctcg atggcagtct cgggagcttg ctcctggtct    47760
tcctcgtgga cagctccttg ctcagggatg agcacgtact ctccatcagc gaggttcaa     47820 tctaatgaat gcaatgagta agatatatgc atggcatgat atttaattta gcaattaaaa    47880
tttgatggag gatgatcaat ttaatagggt agacctcatt ctcactactg agattttg      47940 gtggtacact caccaactta gggtcaagtt gattactgaa tggttaaccc attttagtg     48000 ttctactgat tttcttcttt atatcttatg gatattttaa caagattctt agctgccatg    48060
ttggggtaat acttattaat ctttctaatt cctcccttct ttattccttt tatgcttta     48120 aggtgggttt gaactacaag atagcttaat aaatttccag aaattctgca acattacag     48180 tagcttctta ctggtgtata attttctgtc tcaaaatttg gggcttaaaa agtgaggggt    48240
tctctctgta caaaattagc aagtgttagg gcaaagggga tgttttgaac tacaactctc    48300
ttttaacagt gggttattct ttaagactta ttttttgctgg catttagatg ttataacatg   48360
attttgtaca aattttcagc cactaatatt tattagttat tttattatga ttttctaaag    48420
tttctagcca aaggggtgct ttctactacc actatacttg aaaaatatca acaacagat     48480 ttccaatttt tcctatcttc ttctttgcgc aagagcaatc attctaaaat ttggtaacct    48540
ttttcttaag ggaagggtgg taggaatttc ttgaattaaa tggcctttttt catgaagtag   48600 gggcaatggg tattactttg tagttttgaat aggttttgca ttttgctctg gtgatctatt   48660
ccattaataa tctagtaaaa atttattcgc ccattgttgc acactttttg gcttgcttat    48720
gatttaattg gaatatggct caatatcaag tttatttgt tcaacccact taaaatgatg     48780
ggctaggtat ttatcatttt tgtagtggtg tcctagtggt tacaagtcta ctgaattttt    48840
cttaccaatt ttgaaattgt tctcatattt ctaataattg cccttctagc tttattagtg    48900
cctaataaaa catttcacct tgaatttgct ctggactagt gttccttta ttttttctag     48960 gttcttcatt acttaagtgg gctaggaaaa atatttgcat ccactgttca ttattttcta    49020
gtacctttct tattttccta agttttggac aattatggct tttaatagat aaccctgttt    49080
aaatcttcaa tactagggtg ctcaatattt ttaaacagtg tctaagtggg gtttgaactt    49140
ctacaaattt tcttaagttc agcacagaag cataactaat tttcttcatt ttaataaggt    49200
```

```
ttggtcagtt tctttaatta attctaaact ccaaaattta aaacagaaag cacagggttc   49260 aatatttta tgtgatagtt cataatattt tgaatctagt aaaattggtt tgactaaatt    49320
tggttgaata tttctcaaga tacaaatttc ctaagtcctt tactgaattt aaaaagaata   49380
aacagaaatg gataaaggaa aaagggtttt gcactgggt ccctggcgaa aggttttaag    49440
tgtattacag acaggtcctt ggttcactat ttatctgagt ctatgactct gcagaaaacc   49500
cctagggttt tgcgaaatcg aacccgcgat ccttcccta atggaatagt gaccgcagtg    49560
gaagaaaagg gcggaggggc ttaccggcgg cgaggttgct ccggtgaggg gtcgggtgag   49620
gtccggggtc tctggcgatc acgtcgaggt gcggatcgtc ggcggtggtg gtcggagtag   49680
gttggtccac gtgcacaggc ggggagctcg tcggcggcga gggatccggc ctgctcacgg   49740
cgcgatagtc caattgaaca ggttagggag cttcaccaga ggtcaaggaa gacatgcgcg   49800
cgaggaattt gagaatgaat caccggattg ctcggtctac gcgcggctgc gggtgaccga   49860
agtccagcga ggtcgatcct gggtctctgg tgaaactctg ttgggtccga ggacttggaa   49920
agcttcacgg gccactggcg aagctaaccg agtgactggt gcagcttgga agtggctgga   49980
gggagctggc cgcggtggcc gaggctcggg cggtgatggc gggcggggga gagctcgcgg   50040
agttggagtt cttgctcgag gcgtgaggcg gagtgaaggg cagaccattg tgcatccagg   50100
gtacttatag gcgccctcag gcatggctga gtgcaggcgc ggggggacaga agccgaccgt   50160 gcatggcgcg cgatcagagg gcagccagtg cgcggccaag cgcttgagca cgcgatcgaa   50220
cacgtggaag tgtgattctg cccgagttca aacgcctgtt ggccgaccaa aacgtgcata   50280
tcttgccaag gatcctgtgt agcgtctctt caccgtgcca aggtcttcct gtcgtgtgtg   50340
agtcccgagt gaagatatgg cctaggtgag aagatatgat ggcctgaaga tagctctgtt   50400
agcactgtcc aaaccgagac aaaacttatg tcaagtcgtg tcaaacgatt cgggtttgat   50460
ctcaaacttc tccaaagtgt tcctagggta ttttggcgcc actttgatat ttggactttg   50520
tggattcgag ttttggaaaa cagggaacac atctgaactt tgggaaaggg tttgaaattc   50580
agttttctga atttctgaat ttccccatag ggcattggtt catggctga tttgggattt    50640 tggaaaattc aaatggcaaa actttcttac tatattttgt tggttattta gtgcactaaa   50700
actttgttat ttggttctta ccaaaatttt gtattttccc aagtctttc ccaaattccc    50760 tttatgtgct taaatggtcc acttaggatt aattagggtt tgagagttct tcttaccttg   50820
aggtgcatgg catgattaag gagaatttct taagatgaaa aagactcact taaaccttgt   50880
tcttaatttt tttatgttca ttcctctttt tggttcacat gtgataatgg ttggagtcaa   50940
ctctaggaaa aaccctacgt gacactgggg tgtcacagtt gaagcgttct accacactag   51000
gtggccaagg attgcatgtt tatataggca caaggctggg tgcaacaact tatacaataa   51060
ggtaaccgaa tcaatctatt gttggagttt ctatctatgc acagcctaga atatatcctt   51120
tctatctata ggagattgat tcggttggct aaagattaca tgcacaagaa acttctagaa   51180
tatcgtaact tcatctaaca gttacaactc atgaacacaa tataatattc tgctatagaa   51240
atcatgattg tgtaattgtt tgttgcaata tgttatattt gatttatggt tgatctgttt   51300
tatatcagct aggggttga gctagattat ggaaatgtca ccagcaggat cacaatcaac    51360
actgatcatg gtctctcaag ttacaacaag caatatgcaa gggactcttc aaaaaagtga   51420
tgccttaact accagcttca gaggctagcc atgcttcgag aataccaaca acaaaatgtt   51480
gatgaaaatc actgaaccaa cagtgacacc acaaagcagg aatgccagga ccacttctaa   51540
```

| | |
|---|---|
| ggtatattct aactcacatt tgacagtaat ttgtgaaatc actcaaacaa cagaatacag | 51600 |
| ttcgcatgtt tgactaccaa tttgatttt tgtacactca tattttattc ttaaatctgt | 51660 |
| ggaagatgat atgaatctgc acatcatgag tgcagtttct gcaagttgct ttgcgaggtc | 51720 |
| aacagaaaca cagaaaactg atggtgatgc ccttatacct aaggtaaatt tttcttctaa | 51780 |
| ctgaagcctc ttttcgcctt ggaactcatt cctttagcta atactaagag atgatggaaa | 51840 |
| ttctctcatt ccaatgtcac cagcagtatg atgctaattt ctgtcaaatg ttcttgccat | 51900 |
| attaatctta gcatttcatt gaatttacat agtacttgaa aataaaataa catgagacac | 51960 |
| catgtctaaa atataatggt aatctatgtg cttgatcgcg ggttgctaca gatctttgat | 52020 |
| gctagtgtga acctggggtg gttctataac cgggacacag aagagtggta taaaaaaggt | 52080 |
| aacctttgta acgcaaaaat ctacttattt gtttccataa tacatatgag atcttatcct | 52140 |
| attgttgatt gcaatctact gataggactt acccacccct cccctgccaa aaagggcaa | 52200 |
| agaaactctt ccaagattgt gactttgaag atgttgatgg tgatgcctct gccaaagatg | 52260 |
| aggctgagct agggtactca gcctatctat ttctcaattt catcatattt ataattgtca | 52320 |
| atgcaattgg agatgataaa aatgctctat tttacataaa aacactgatc ttgatttgga | 52380 |
| ttgtttgcta aattgtctct ttatttgatg gtcttggcta tacttgtctc tggtagattt | 52440 |
| ttgcatcaca gggtgagcga tgcttagcca ccaagaaaga aaaaaatacc actacctctc | 52500 |
| tggtttcctt ttgtattgga tatttatgtc tcttgtcttt gttttgctc caaagtctta | 52560 |
| tacattatcg ttgactgcat tttagtcctt ctcccaaaaa ttcacttgtt agtggcgagg | 52620 |
| atatcataat aattgttggg gacttgttct caaatgctat gagttaagaa caaggcaaca | 52680 |
| caaaatgtta aatgttaatg tccttcgtcc ttcgaagcat tatttcccct aggagataac | 52740 |
| gatcttcgga cgaaggttat gaaggacata ccttcataag tatgacatgt ataaacaaag | 52800 |
| gatgaagctt atgaaacata ggaagacaac ataaacaatt atataacatc ttaacataaa | 52860 |
| tatttattat taaataatca taagaacata agaataatat caaattacat ttataccttg | 52920 |
| agcttgatag aaggcaaaga taaagtaag atgcgaaagc gtgaacagta cgagggtact | 52980 |
| gttcacctat ttataggcac agggcgcagc ctgtgtaaat ttacattcat gtcctctaca | 53040 |
| aatgattaca atcataacat agattatcat gggcccaatt cgtcatttca tctttaagtc | 53100 |
| ggtgcatctg gaaatacgct acgaagctct ctgattggta gcttcggcat cattcctgtt | 53160 |
| ctggccttcc gaaggtgttt tttctcacag gaccttcggc gacgaaacag accccaaca | 53220 |
| gtagccctt cacggtgcca gatcattttt tgtaacgagc tcgacccgtg aaaaattctt | 53280 |
| ttaggcttcg gaatgccgaa ggtccgaaaa acaccttccc tgagctcgtt gtcgagaaac | 53340 |
| gatttaagta ttcctagtgc gaggtggtcc caccatagga cgggtacgca cgatctggtg | 53400 |
| attctccttc tcgcgccatg cggtccaccg ttcagtgaat gcgagcgact gttcggcggg | 53460 |
| tgcaggtggc ttgatgattc accttccac ctgtagcact atataaacag acgggtaggt | 53520 |
| gtgaagttac cacagcattc attactatcg tattgttgtg ctgctgaaaa atttgaccat | 53580 |
| agccgaagct tattcttcgt attctcaatt agagcatcgt cttgttcttt agcttcgtca | 53640 |
| aaagagggag cttcggcaaa atcaaaaagt aatcaacttt gtcaaaaccg cgagaaattc | 53700 |
| agcatcaaat ggccagggtg cgttcaactg ctagagtcac acgcgacggg gaggaggccg | 53760 |
| aagctgccga gaccgcccca atctccgaag taatgagaca atcaggcttg gttgtgctag | 53820 |
| agggtgtttc tgacgaaggt gcacgtgctg ccgaaaccga gcaggctgac attgaagaag | 53880 |
| gtgaggctga tgaagaggag atagattatt tcgtcatgcc atctaaaccc agccacttgg | 53940 |

```
aatttggaaa gtctaccgtc tctgaggccg atatgcccat gatgacgaag ctaggctact   54000
tcggggaagc cgagaagaag ctaattcgtt ttggcggaga ataaatcact ccgaagctag   54060
aaaatgatga ggtggtagtt ttcagaagtt tctttaaagc aggactgagg tttcctctgc   54120
atgggatgat tgtggatgtt ttggaaaatt tcgaaattta ttttcatcag ctgactccta   54180
acgctatcgt taggcttagc gtctttatct gggctcttcg aagccaagga gtggagccgc   54240
ttgccgaagc cttctaccgg gtgcacgaac ttcactatca gacgaaggct agagaagatg   54300
gactgcacga gaacttcggc tgctataatt ttgcctaccg caaagacatg aagacaccgt   54360
tggttagcta ccgcaccaaa tggacaaccg gttggaaaac tgaatggttt tatgttaagg   54420
ttgatgagaa gaaggagaag ctagtttaga gcccactggg cctaaccttc gggttaacta   54480
ggccccagtg tcgcatgacg ctgggatcat catgcccaga tgttgtgggt gaatttagag   54540
ttgtgtccga gcatatcgga actagggatt tggttcagga atacttagcc aatagagtat   54600
tcccaacgtt aaaggaatgg agtatgccga agcttaaagg agagaagaaa aagaatgaac   54660
ttgttcgact gccctatcat tttaagttca agaaacactt caaagaaccc tgccaagaat   54720
ggttggatac gatcgaagtt atgtgcaatg aaatattggg caattatacg aagaaagaag   54780
atcaattgat gacggcagcc ttcggcaccc gaccgaaacg aaggctaaac cgagtaatga   54840
acactctgaa atttgaatac ccagactatg aacggttaag taaaggtgcc gaagggccaa   54900
aacaaaaaag agctgtcagt gttatgcaaa gacaagctgc cagaatgata aagaagatg    54960 aaaatttagc aaaaaagaaa aaaatccag ccctgagccg aagtggccg tttcgaagaa     55020 aagaaaagct acagctccga agccaaaagc tgatttagaa gaagttccct caacaccttc   55080
tgccactgac gcagaagaaa ttttaaaggt aatgaccgaa tctctaccta ataagctaag   55140
cccgctggga ccggaactga tgaagctttt acagaagaag aagaaggaac cttcggttgc   55200
cgagaagccc gctgaaccaa aaaagcgaag gattattact atcattgagg ctattgaaga   55260
aacaccatcg tcgcctcag tgctaaaaac agcagcagcc aaagctgctc cagccgaagc   55320
ttctacttcc gaagttgcag cagccgaagc cacaaatttg gaaaacacgc ttactgacat   55380
tgatgaaata attttgaata tggctgagga agaaactgct gcagctgctg aggaaacccc   55440
ggctacagtg cctgaaaagg agaaggagct tgccgaagat gcttcggaag aaagaaatat   55500
caactttcaa aacataattg acaagagtt gtctaaggct aaaaaagaag agctgaggga   55560
ctttgctata tcttgcgggt accagccagg ggcactgctc ttcggtggta tagacgaaga   55620
gagcttaggt tgccttttgag accggactgg ggagaaagtt gtcaggactt tatcgaaaag   55680
tgttggtttt ccgaaactcg aagccgatct cagcagatac cgacgacagc atatcgtcgg   55740
tagcctattt tattctaact ttaaggtaaa attcttccct taacttttta ttgttttgat   55800
atgaagatgt tttctgatga aggttatttt gtcagagcct actactaagc aaaaccttga   55860
ggatgcaaca agacctcgag gacaagaaaa acgaagttat aattgagggc ttagagaaca   55920
agattaaaga tcatgaagct gccctagaaa agaaagactt cataattcaa acaatggaag   55980
gttcactggc agaagctcaa gccgagatcg ccagactgaa tagtgaactt tccatgaagt   56040
caaaaagcat tgagcaagag aagaaagatt tcgaacaaa actcgaagct gaagttgaaa   56100
aaagttcaaa tctgcagaaa tcactcaaag atcttcaaga agcatggtct tgtacttgtt   56160
tggtgacttg tgcccgcttg atttctgctg agagccgagg caagggctga gcgcttggtc   56220
acgtacccga gcccccctga caagggggtt gcccatgccg tagtggttga cacagtactg   56280
```

```
agtatggcaa aaagtcccta agtaatatgt cagctctgca gtatatggtg acgttgggcg    56340
cctttccgtt gtggatattg aggctagagt cgggctcggg cgaggcagaa gtccgcccga    56400
ggtcacgacc gagcccgctc cagtattcgc ggggagcagg taaacgaggc cgggctcagg    56460
cgaggcgaag tttgtcccga ggccgaggtc gccttcagcg aggcagagtt cacgtccgag    56520
agccatcctg cactcttgtc gtattgtacg tcccatcagg ggttgacaga tggcatgtgg    56580
gaatagtggt cgcatgcgtc atcgtagttg gtgaagcttg acaggaccgc ggtcttgttg    56640
ctcctgttca cctgcaactc tacgtggggt aggtatgcat attgaatgct cctgccccct    56700
gcagactttg gttgagtctt gcattggggt tgtcttcctt acccgagatg tgctcgggcg    56760
aggcaaagac ttttgttctg ggagatggag cctcggccgg gacgagaatt ctccctagag    56820
cacaccatgt ccgagggcag gcttgagcga agcggaccta tggtgacccc tgagcggggc    56880
ctcgggcgaa gcgcggttta tgatcctttg atctcgggga atgtgtcttg aaggtggtct    56940
aagggttaag tgtgttttag gggcataatc tgggtacccc taattatgat acccgacaag    57000
tggtattgat tagaaatggc tcaacaaaag ataatggatg gttgaacaaa atgtgaatgg    57060
ctgacatcag ttttatagtg tatgtgtgta tatatgtgtg cacacataca atatctctcc    57120
tttatataac ataaacagac ataagttata gtggtagaag acgctcgctt gtatcgaaag    57180
agcatggttt gaatccccac gtcctatttt ttgtgtggtt attccacgcg cctggctggc    57240
tggttcgtga ctaggtcgga cccatgcaac tggctagccc aaatttcccc aattatttca    57300
taaccaacct ctcatttgtt ctcctttatc tttatgttat taggatcaat catttgtagt    57360
tatcaaggtg aatcacttgt acttttatca aggtcaatca ttatagttac taggatcagt    57420
cgtgtattta tcagggtcat tcattgtaat tattagggtc atttattttt ttaccagggc    57480
cagtcattgt atttatcag gatcagtcat tgtacttctt ctattagggt ctacattta    57540 tcaaggtcag ttattgtagt tatcaggatc aatcattata ttttaatcag tgtcagtcaa    57600
tgtatttatt aaggtcaatc attgtattat taggatcagt cattgtattt atatcagagt    57660
cactcattat agttatcaag gtcggtcatt gtattttttt attagggtca gtcattgtat    57720
ttagcaggat attttatca gggttagtta ttgtattatt aggttcaatc attgtatttt    57780
atcagggtca ctcattatag ctatcaagat aagtcattgt attttttatt agagccagtc    57840
atcgtattta ttaggaccaa tcattgtatt tattagggtc ggacattgcg attaaataaa    57900
aaattgaaaa agatatagca tgagtgtcta gttttgttcg aaaatctcat aaacacgaat    57960
ataacaaaaa aagggatttt ggttttttat gcctatatat gcgggttgca tgactgcata    58020
cacgcatact cgctgagcgt ggtgccaaat agtatccact gcgtgccctg cgctctaacc    58080
ggatgctcta tccatcacac ctcaataacc cattgagcat ccctccccccc acacgcctgt    58140 gctccaatca gatgcttgtt tgactaatag caaggagatt ctccaatatc atgctaagaa    58200
tagctaggat ttccagaaga agatgtcatt cgtttgatga gaaataaaaa ggaatatcga    58260
gaattcgcgt ggctaaagct gaagcaacta ctttcgaagt aacagaaaga aaagcaacga    58320
ttggagtggg ggagtcagag tcaaaaagag aattcctcgc ttctttctct catgcaaaac    58380
cgtgcatgag actttcatct cgcacggctt ctaagtgata aagaaagaa gtccaatcgt    58440 gataaaaata attacatcaa tttaatagaa aggaatgact taaaaacata ttatgagtct    58500
ctggatgaat aaactattgg atgacttaaa atatttgtaa gaaagtcttg taacaactgt    58560
tgacaatatg aaatatttta aataagtcat aaaatgacta aatgacatgt gatgactaga    58620
attgtaacag aatgacttaa tttaacataa tatgtactga atgacctaac gagtgaatga    58680
```

```
ctgagaaaaa aatagaatgt tttaaataat catcaaaatg tcttaaatga ttaagaaata   58740
cttgattatc ttataaaata actagtacaa cacatgtgcg ctgcgacgac atacaatcat   58800
atttgatacc aataaaaaaa taatatcaaa tatcaaagtg aacatatggt ccatatatca   58860
gatactaaac tgataaaaac aaatattacg cttttatctt agctaaaata tcaggaaagg   58920
tatgagttga aagaagcctg actacttttt taaagcttgc tcgatggctt gtcctccttt   58980
aggtagtgag gtggttctat gtgggagcgc tgcgctgcgt ttggcttccc tgtcgtgtta   59040
gacttgtgtg gtttctcacg gtccatctat agataaaatg tccactagta gggatttggg   59100
tggttttcac agcctatcta tagatgccca ctggtatgcg gattgatcta catgcttcgt   59160
gcatggcgta tgacgaccat cgaagctagt attttatagt agtggagatt ggaatgaatt   59220
aatgcaaaat gagaagtatg agaatgttga gtgacttaaa tggatcacga tagaaactgc   59280
attggggcct gaaacagcta ctaaacaagc gatcgcaata tcttttaaaa ataagttgcg   59340
gtccaaaaaa aagtgacaat ctatactctc taagcaggct cccaaccatg tcaattcact   59400
acaacaattt caatgaatta acatgagtga accatagttc tcacagggta tttcgtcgtt   59460
acaggtccat tcgattagaa gtgggtcatt atatggtggt ttgcactgta tctttccccc   59520
gttatcaatg agagccaaac gtgtacctta caacctttca gatgtcaatt ggaacttgca   59580
aaaaaaaata gaaagaattt tgacttgttg gggatttaaa ctagaaagca tctaggcccc   59640
tggttggttt tagtgattaa tgcaacgta attttatatg tgactaacat gtgttttgca   59700
gaggcaaatg gtaagttagg tcgcattaca ggtagatgta ctacaatggt gaaaacaatc   59760
ccggagataa aaacttgaag caacggctaa agcgacgaaa caaaaagtga aggtcttcgt   59820
attccgagtg tcaaggagtt gcggacactc gtgatatagt taggtctttt attttgtttt   59880
agccgtacta taaagagggg ttgtcgataa gtagtttgac caaaagagtt ctagtgtagt   59940
gttggtgcat attcacactc acatatagtg ctaggtgtaa ctctagaaca tactcacaag   60000
ttagaacaaa aaccaaattg aaaaaacagc acaaaacaga agctagggtt tctggctttg   60060
gggcaccgga ctgtccggtg caccctttgc cagtgggccc agcctggccc agggaagagg   60120
gttccctgcg cgcagaaacc cgagagcgcg ctgttcgtga gttgaatttt agaggcacac   60180
cggacagcgt atcggactgt ccggtatgcc atctgtccaa cggctagctg tcagaactag   60240
ccgtttgagt cgaccgttgg cgcaccggtg gcacaccgga ctgtccggtg cgcccatgcg   60300
cagcagattc ctggtaatgg ctagttggtg ggtgagggct atttataccc catccaccta   60360
ccatattgat ggtcttgctg cccacatttta ctcctacaca ttggtagagc attgcaagca   60420
ccacaaagcc tagtgaggtg acttgagaat cttaatcccg catttggacc tcattaacgc   60480
tagcgagagc cacctagagc acacaccgca tgcattaggc ttctcttggt caagtgaaag   60540
tctatggctt attactcttg gtgatcggca tcacctagac ggcttggtgg cgttgggagc   60600
tcggtgatca ccgtggagat cttgttggtg acccgactca agtttgtaag cggtcgtgag   60660
ggatccaccg cgccggagtg gcaaaggatc atctcgttgt gagcacttgg ttcttgcgat   60720
gaccaaggga gagcgatacc cttacgcagg tgctccaacg aggactaggg gagagtgccg   60780
actctttgat acctctagaa aaattggagg agtcttctaa accttgcttt acattccgca   60840
cttaattcaa gtattttaca ttgtgtattt gtttagcaag tatttgaagt attatcttag   60900
cattgttgta tttctagtat tattctctta gtgctagttg tcggggtgaa gttgggctct   60960
tgcttagatt ttagttagtg ttgattttta gaaaagccca attcaccccc ccctcttggg   61020
```

```
catcgtgatc ctttcaattg gtataagagc cttgttgctc ttagattagc ttaaccgcta   61080
gagtaacgat gtccggtggg gatggacctt ctcccgtttt ttatggtgac gattttccat   61140
attggaaaat tcgtatggaa gcatatttag aggctataga cattggtgtc tacaaagccg   61200
ccacacaaag attccccgaa cctagagatc ccacaaatct tgtaggtgaa gagttgaact   61260
atgagaaatg gaatgctaag gccaaaaaca cccttttag aggcctttgc aaagatgtgt   61320
ttaatagagt tagaaaccat aaaaattgtc atgatttgtg gatggacata tgtgctctac   61380
atgaaggaac tagaattgag cgtgaggaga gatatcacat tgctatgaga aaattaaatt   61440
cttttgaaat gcttgctaat gaaaatgcca atgctatgta ctcacgtctc aatattcttg   61500
tagaggaagt aaatggcttg gggcttacac aaatttcaca accggatgtt gtgaggaaga   61560
ttctcagtgt cctcccaatt gataaatatg gacacattgt cactgtgctg catcagatgg   61620
atctttcagt tgtcactcct acacaaattt tgggaaagat caatgcacat gagatgtaca   61680
tgcacatcaa tgacaaggat gagtcatctt acaagagaaa ggatttggct ctcaaagaaa   61740
atcaagaaag agaaggaaaa gctaaagtac aagttgagga ggaatcctca agtgacgatg   61800
atcttaatgc taacattgcc ttgatggtga ggaagaccac caagatatta agaagctca   61860 acagagaagg catcaaattt gactcaagaa agaagaaatt cttttccagc aaaagaaagc   61920
ccatttctta aatggattgc tacaactgtg gagagcttgg tcatcttgct catcaatgta   61980
acaagtccaa gaagaacaag ttcaagggca agaaagaaga tgacagtgat gatgagaaaa   62040
atgaaaagag attcttcaag aggaaggatg gaaagcataa gaggttccac aaaaagaaaa   62100
atgtaaaggc atacattgtt ggtgattggc tcactgacat tgagtcgtca agtggatctt   62160
cttcaagtga agaagaaaat gatgaaaaag ttaccgccat cgctggggac ttctcttcac   62220
caccaccatc tccatcatcg acttctcacc tatgcctcat ggctagaggt gaacgaaaag   62280
tacaaaatga taatgatatt attgatgata gtgatagtga tagtgatgaa gaatttgctt   62340
caccttccta tgatgaacta gttgacttgc ttaatgaata cactcaactc attaggaagt   62400
caaaagctaa atgtgataag ttgaaagatg aaaatgaatt tttaaatgct aaatatgaca   62460
tagttatgaa agctagtaat gaaatgaaag aagaaacaa aactatgtca tccactgtaa   62520
atgagcttac atcctcccta aaagatgcta aggataaatg tgacaagtta aatgaagcta   62580
atagggagtt gaaagataga ctagtaaaaa ataaggaaga ctatactaag attaaatttg   62640
atcatgataa tcttcttgtt gaaaatgaac ttttatcttg caatacacat gaggctatta   62700
accctgttgt taatattgat gtagcaacct catgtgatga tttgagtcaa ggtgatcaaa   62760
ctagtctaca tgatgaattg actgaaaag ttgaagtctt gacattagac aaccaaaaat   62820
tgaagagata cttgactgat gcaactacta gaggaaaggt tgccattgag aacaatgact   62880
tcaacaatga gttggcagtg gataaagaaa ggcttaaaat gaggtcaaga aacttaagcg   62940
tgaaaatgaa catcttgcaa caagtgtgca aagttcaac aagggccaat acctctaaaa   63000
tgaattgctc atgaacactg tcatgaaaaa caacaagagt ggtattggat ataactcctt   63060
tgtgcaaaag aaagctacaa ctcaatacaa gccaaatcag actcataagc atatcaaatg   63120
ctttgagtgt ggaaaagaag gtcattttc ccacaactgc aaagccaaac caccaactcc   63180
cctgccaaag cactcaagac catttgcctt caatgctcat tatgttttaa gaagtagcaa   63240
atggaaaagt cgaagttaca ttcctaggtc caccaagcaa gagtagacct agacaaattt   63300
gggttgcaaa gtccttgatt gagaaagtca ctggtcctat gcaatatagg gccctcaaaa   63360
cttaggcttg atttgtctgt ggatgtaggt gaactacaag accggtggga gccattgggt   63420
```

```
tattgatagt ggatgcacat aacatatgat aggcaaccca cggatgttca cctcacttga    63480
tgataatgtt gatggacaag acaaaatcac atttggggac aattcaaagg gaaaagttca    63540
aggacttggc aaggtggcaa tttcaaatga tctatcaatt tcaaatgttc tcttggttgc    63600
acctttaaga ttcaacttat tatcagtggg tcaactctgt gttcttggac ttcaatgctt    63660
attcactcca acagaggtta ttgtatcaaa aatggatgat gaataaatgg tgctcaaagg    63720
atttagatac aacaatctct acttagtgga tttcacctct gaagatgcag acttaagaac    63780
ttgcctcttt accaaagcat ctcttggatg actatggcat agaaggcttg cacatgttgg    63840
aatgagcaca ctgaagaaag tattaaagaa ggacatggtt agaggactaa aggatgttat    63900
atttgaaaag acaagccctt gtagtgctta tcaagctgga aagcaagttg ctaacacaca    63960
tcctacaaaa gctttcatgt caacatcaag gccactggaa ctacttcaca tggatctatt    64020
tggaccaaca acttatgcaa gtgctggtgg caacctctac tgtctggtga tagttgatga    64080
tttctcaaga tacacttggg tgtttttctc catgataaat ctgaagttgc atctatattc    64140
aagaagtttg ccaagaaagc tcaaaatgaa tttgattaca agatcaagaa gattagaagt    64200
gataatggaa aagaatttga caacaccaac attcatgaat actgtgatga gattgggatc    64260
aagcatgaag tatcagcaac atatacacct caacaaaatg gagttgttga aaggaaaaat    64320
aggaccttga tcacacttgc aaggacaatg attgatgagt ataacacacc ggagaggttt    64380
tgggccgaag ctatcaacac tgcatgttat gcatcaaaca ggctatttcc tcactggcta    64440
cttgcgaaga ctctctatga actgctaaat gggaaaaagc cagacgtctc attcttttgg    64500
gtgtttggat gcaaatgcta catttacaag aaacgccatc acctagggaa gtttcaaaga    64560
cgttgtgata ttggttttct tctgggttat tcattaaagt ccaaagcata tcgagtattc    64620
aatcatgcca ctggcgtggt agaataaaca tatgatgtgg agtttgatga gactaatggc    64680
tcccaaggag cacttgaaaa tcttgatgat gtaggtgatg agccacttaa ggaagccatg    64740
aagaacatgc caattggagc tatcaaacca aaagaagatg aagaagaggt gcaaaacatt    64800
aataggcctt cttcatcaag tgtaccacaa gatgatgaaa aagatgagag gcatgcaaat    64860
gaagatacat ttgtctctca tgaacaagca aggatacaag ccgaagatgt tgatgctcca    64920
ggatcttctt cctaagtggt tgataggaga aactcatcac tgcttcaagc acacccacaa    64980
gatcaaatca ttggaagtcc ttcacaaggg gttattactc gatcacataa acatgcttct    65040
tttattgaac atcactcctt tgtttcttgt gttgagccta ctgtatagat gaggcgctac    65100
aggatccgga ctgggtgaat gccatgcatg aacaactaaa caacttcacc cgtaaccaag    65160
tttggaccct ggagaagcct ccacagatg caaggatcat tggaacaaag tggttattca    65220
gaaacaaaca agatgatcaa ggcgtgattg tgaggaacaa ggcaagactt gttgcaaagg    65280
gcttctctca agttgaaggt ttagattttg gagagacctt tgcaccggtt gctcgacttg    65340
aagccatctg tatcctactc gcatatgcat catgctatga taaaaagctt tatcaaatgg    65400
atgtaaaaag tgcattttta aatggcttca taaatgaact tgtatatgtt gagcaaccac    65460
ccgggtttga agaccctaga tatcctaacc atgcttatag gttgtccaag gcgctatatg    65520
ggttaaagca agctccaagg gcttggtatg agcgtcttcg cgacttcctc atcaaaaagg    65580
gcttcaagat caagaccgtc gacacaactc tattcacaaa gaaacataac ggtgatattt    65640
tcatttgtca agtatatgtt gatgacataa tctttggctc gataaatcgc tatcattgca    65700
aggaatttgg tgagttgatg tcgaaggagt tcgagatgtc aatgattggt gagctgatgt    65760
```

```
atttcctcgg ctttcaagtg aagcaaatga aagatggtaa cttcctctca caagagaagt   65820
ataccaaaga cttgttgaaa aggttcaaca tggagatcac ttgttgaaaa gatggtaact   65880
ctctaccgtt ctatgattgg tagtttattg tatcttattg catctaggcc cgatatcatg   65940
tttagtgtat gcatgtgtgc tagatttcaa tcaaatccta agaaagctca tatttgcgct   66000
cttaaaagaa ttcttaggta tctcaagcac accccaagtg ttggcctttg gtatcccaaa   66060
ggagctactt tgatttaat tggctattcc gattcggatt atgccggttg caaaattgat    66120
agaaaaagta cttctagggg tgtaatttgc ttgggagatc actactatta tggacatcca   66180
aaaagaaaaa tagtgttgcc ttgtcaaccg ccgaagcgga atacattgcc gctggtgctt   66240
gttgcacaca gattttatat atgaaacaaa ctcttctaga ctatggtgta gttctagaaa   66300
aggtaccttt gttgtgtgac aatgagagtg ctgttaaaat tgctaataat cttgtacaac   66360
actctcgcac caagcacatt gatattcgtc atcacttcct tagagatcat attgctaaag   66420
gagacattat tttagaagaa gtgaggtcgg aagatcaatt agaggatatt ttcactaagc   66480
ctcttgataa aacccgcttt tgcatgttga gaaatgaatt aaacatactt gatctcagaa   66540 atttttattta aagatctcaa aatagtgttg tcaagcctgc attgcatatt taaatttctt   66600
gtattgcatc tagggcttgt ctaacctagt taagataacc gccaacaaag cgagtgaaaa   66660
aagcttaact cgggctcaaa cttgacaagt cttagcttta agcttttagt acttaaattc   66720
ttatttacta tgccattgtt ggttcttgag atatgcatgt agtactacac ttagggggg    66780 agtattcaaa actcaaatta ttcatgaaaa cccctagttc aaagctaaaa tgcaaatctc   66840
accatttgac tatttctct aaaaattgac tagcctatgg caaatatttt ttgaaaatta    66900
tgggaaaata tatgaggggg ccaataccta tcccaatagg tgttctttttg tatgattata  66960 agttgggatt tggtttggtt aaaatttaga tcgaaaaatt tgaaaatttt caaaatcacc   67020
tctgcctagg ctcaccggaa agtccggtgc actgtgcact gtnnnnnnnn nnnnnnnnnn   67080
nnnnnnnnnn nnnnnnnnnn nnnnnnnnnn nnnnnnnnnn nnnnnnnnnn nnnnnnnnnn   67140
nnnnnnnnnn nnnnnnnnnn nnagctactc gacctagcat actagtatcc atctcaaagg   67200
gaatcctgag ttcatgcaac tagggtttca ttcaactcct acacttaagt gcacggtaca   67260
agcctacaaa cattaagtgc agtaaaatag catatatata atggttatgc ataaaaccgg   67320
ggcttgcctt taatttaaca cttaggtagt gtttgctggg ggaggtactc gcttggtgag   67380
catccactgg ttaagtccat tcttcaggtc gtccatcaac ggcatcttgt ggttggcacc   67440
acatcactgg ctcgatcatc atctctcggt cctatatgag gtgcaagatg catatgtatg   67500
aatataataa aagtaacata agatatacca agacacagtg gcgaactaaa cattaattag   67560
taagacactg caacaactat acgcaaacac tagttattta tgtgtcattg ggcacacgta   67620
aacactacca ctggaaagac aatgatcact acctacaatt aaccaacgca acacgatatc   67680
atatgtacaa gcatttattt agttgctacg gcttttcatt aattcttata ttgatcacac   67740
aaaaacatca caaacacaag tttaataaaa ggaccgatgc atcaatgtcg atggactcct   67800
ctatcacaat caactacagc aagcaaacac attaattatg gaacacatgt taacctaagt   67860
ttagccatca caagtctatg tccgttaagt gcttactaaa gcgttttag ccaaaatggt    67920 gaactaaata ttcatttgag cacgtgcaga tttttaggac agcagcacag cagctacttg   67980
ttttaatcat aacttttaaa atattaatcc aaaaatagca aactaaaact ttctggaaag   68040
tttagaaagt gctctacaat tttggtattt tcatcacagc atgattaaac acttagcaag   68100
gtcaaaaagt gcaatcacag cagctctgtc cagatttgga cagattcaga cttgtgattt   68160
```

```
taaaaattca taactgaaga ttcagacatc caaacaaatt gatcctagac tttctggaaa   68220
gctaattaaa tgttctacaa attatttata aacatcccag ctggtttag catgtatcaa    68280 ggttaaaata tactatgaag gctgtgctgt ccaaaactgg acagattcag tcttcacact   68340
tcaaacacat gtaacttaat cttcagacca ccaaaaagag tgatctaaga cttttgaaa    68400 agcttagcaa aagtactaca caactttat aatcaccaag aagtgattcc aggtttaact    68460
aaatcaaata ttacagtttt cgaaatctgt tctgacggtg gacagaacac agcaaccagt   68520
ttgtaaaatt cataactctt aaaccgtcag gcctatagtt atgaaatttt aacacaagca   68580
agacaagaaa agcctctaca actttcttat aattgacaag ggctgattct aacattaact   68640
taagcaaaca atgcagcttt tgaaatctgt acagaaagtg gacagattca gttactgaat   68700
ttgtaaaaaa cataactcct aaacaatcag acttatgcct gtcaaatttt aacacaagta   68760
cgataataaa gttatctaca actttttgt gaccaccaat aactaatttc aacattaact    68820 taagcaaatca ttgcaatttc tgaaatatgt tcagaaattt gacagattca ggtgctgggc  68880
ttgtgaaaag cacaactcct aaacaatcag gtttatggct gtcaaatttt agtacaagca   68940
agataatcat gtcatctaca actcttctat atgactttc tatagaaaac atgattggt     69000 ttatcaaaca aacagcacaa ctaaaacagt gcgtgcagcc caaaacagca atcaataaat   69060
tcagcttcta tttactttta aaaattgccg cgttctagag actcgactta ttctaaatta   69120
tatcaaggca cgcttaagca tagccacgca atagatgacg tgacggctac gtagtcatgc   69180
catcacttca ccccacaatc ccaactatca aaataactgt cggagaccat aattagggg    69240 accctcaaga ctcctaattc tcagctggta acccccacca gcataaagct gcaaaggcct   69300
gataggtgcg attaagtcag ggatcagtcc attcgagcga ctcgatcacg cctcgcccga   69360
gcctagcctc ggacaagggc agccgacccc agaggatttc cgtctcgccc gaggccccc    69420 tctaacggcg gacacatctt cggctcgccc gaggccctgc cttcgctaag aagcaaccct   69480
gactaaatcg ccgcaccgac cgaccaagtc gcaggagcat ttaacgcaaa ggtggcctga   69540 caccttatc ctgacgcgcg ccctccggca gagccgaagt gaccgccgtc acttcgccgc    69600
tccactgacc ggtctgacag aaggacacgc ccgcctgcgc cacttcgact gcagtgccac   69660
ttgacagagt gatattgaca ggaagccagg ccctgccaaa ggcgccatag gaagctccgc   69720
ccgacccagg gctcggactc gggctcagcc ccggaagacg gcgaactccg ctccgcccga   69780
cccagggctc ggactcgggc tcagccccgg aagacggcga actccgctcc gcccgaccca   69840
gggctcggac tcgggctaag acccggaaga cggcgaactc cgctctgccc gacccaggc   69900 tcggactcgg gctaagaccc ggaagacggc gaactccgct ccgcccgacc cagggctcgg   69960
actcgggcta agaccggaa gacgacgaac tccgcttcgc ccgaccccag ggctcggct    70020 cgagctcagc cccagaagac gacgaattcc gcttcacccg agcccagggc tcggacaccg   70080
ccctggactt tgccgacga ccttccgcct tggcccgacc cagtgggctt cggactcgac    70140
cctcggccat ggaagatcca ctccacctcg gcttcggagg agcctccacg taccccagac    70200
ctagggcgca ggccagccac gtcaacagga agcgccatca ttaccctacc ccgagctgac   70260
tcggaccgta gagaacaaga ccggtgtccc atctggctgt ctccaccaga taggcaatga   70320
tggcgccccg catgccctgt gacgacggca gctctcagct ctcttacgga agcaggagga   70380
cgtcggcaag gacacaaccg ctccgacagc tgtccctccg ccaggctccg ccgctcctcc   70440
gacggccacg acatcacact agctgggttc caagatctct ccggctgcca cattggcatg   70500
```

```
tactcagggc actagctctc cctcgctaga cacgtagcac tctgctacac ccccattgta   70560
cacatggatc ctctccttgc gtctataaaa ggaaggacca gggccctctt agagagggtt   70620
ggccgcgcgg gacgaggacg ggacaggcgc tctcttgggg ccgctcgctt ccctcacccg   70680
cgtggacact tgtaacccccc tactgcaagc gcaccgacc tgggcgcggg acgaacacga   70740
aggccgcgtg attcccacct ctctcacgcc ggtctccggc cgcctcgctc ctttcccccc   70800
ttcacgcttg cccacgcgct cgacccatct gggctgggc acgcggcact cactcgtcgg    70860
cctgagggac cccccggtct cgaaacgcct acagttggcg cgccaggtag gggcctgctg   70920
cgtgttgacg aacagcttcc cgtcgagctc cagatgggca gtctccaaca acctctccaa   70980
cccgggacgg tgctccgttt cgggagtctt gagttcatgt ccctcgacgg cagctacgac   71040
atgatactcc ttccaccgcc gcgcgacaac gacgatggcg gccgacagcc cgcccgccgg   71100
cggcggaatc gacgacgtct tccccgcgtg gcggaagaac aacattcgag ctcgcccgt    71160 cctctccccc gccaacggag gaggaggcgg ggcaacaaag gccaagcagg aggccgcgcc   71220
tcgtcggctg tcgagcgagt cgacgtccct agcaccccaa cgggggcgc gttgggcgtc    71280 gacctcgcgt ttgagacaaa ggcgagcgcc gtctccccgc gacacgccaa tcccgagcaa   71340
gtggacgacg ccagcgcgct tgcgaaaagc ttgcaggaca tcgccctcgt acctgaggcg   71400
acgatgcggt cagtcctcga cgtgacttca tcgccgctcg acgaccaaaa ggtaccaacc   71460
gattcccatc ctacgtcatt tgtactcagc ctcaacccgt ctagcaatct tgctttggcg   71520 ggcgccttg tagaggcgag tacaaaccct ctggggtttc gcttgcggtc gccttgggac     71580
cggctgacgg acgtctcgac ctacgggccc tctgggtccg aggaagatga cgaccccaac   71640
atctgttggg atttctctgg atttggcaac cctagtgcca gcggaacttc atgaccgcat   71700
gtgactactg cctctccgac tgttccgacg gtagccgcag cctcgacgac gaggactgcg   71760
gcccaagccg cgaatgtttc cacgtcgatc taggggtcc ctccgaaggc aatcatctcg     71820
gcatgccgga ggacggtgct cccctgggc cggtgcctcg cgctgacatc ccgcgggagc    71880
tagttgtggt ccctgttccg gcgggggtt acgacccaca gctcgagcaa gtccgcgggg    71940
cgcaggccag gatcgacgag ggagcaggag cgcttgagcc gatccgccgg gacgtcgggc   72000
aggcatgggc gggccaaccc ccggccggag aaatacgtca cctgccccag ggtctccagc   72060
accgcgtcgc cgatgtcgtc agggtcaggc caccacctgc atccagtggg gtcggtcaga   72120
acctggtcgc agcagcgatg ctcctccgcg cgatgccgga gccatccacc accgagggtc   72180
ggcgaatcta gggagagctc aaaaatctcc tggaaggcgc cacggtccga cgggccgaga   72240
gcactgcctc ccgaaggcaa ggatacccct cggaacctca tgccgcgact tcccgattca   72300
tgcgggaagc ctcggtctac accgggcgca cgcgcaacac cgcgcctgcg gccccgggcc   72360
acctcggcaa cgagcgccat cactgcgacc gtcgagccca cctcgacgag agggtgcgct   72420
gaggctatca ccccaggcgt gggggacgct acgacagcgg ggaggatcgg agtccctcgc   72480
ccgaaccacc cggtccgcag gccttcagcc gggccatccg gcgggcaccg ttcccgaccc   72540
ggttccgacc cccgactact atcacaaagt actcggggga acgaggccg gatttgtggc    72600 tcgcggacta ccgcctggcc tgccaactgg gtggaacaga cgacgacaac ctcatcatcc   72660
gcaacctccc cctgttcctc tccgacaccg ctcgcgcctg gttggagcac ctgcctccgg   72720
ggcagatctc caactgggat gacctggtcc aagccttcgc cggaaatttc cagggcacgt   72780
atgtgcgccc tgggaattcc tgggacctcc gaagctgctg acagcagccg ggagagtctc   72840 ttcggggacta catccggcga ttctcgaagc agcgcaccga gctgcccaac atcaccgact   72900
```

```
cagatgtcat cggcgcgttc cttgccggca ccacctgccg cgacctggtg agcaagttgg   72960
gtcgcaagac ccccaccagg gcgagcgagc tgatggacat cgccaccaag ttcgcctctg   73020
gccaggaggc ggtcgaggct atcttccgaa aggacaagca gccccagggc cgcccgtcgg   73080
aagatgctcc cgaggcgtct actccgtgcg gcgccaagaa gaaaggcaag aagaagtcgt   73140
aagcgaaacg cgacgccgcc gacgcggacc ttgtcgccgc cgccgagtac aagaaccctc   73200
gaaagccccc cggaggtgcc aacctctttg acaagatgct caaggagccg tgccctatc    73260 atcaggggcc cgtcaagcac cccttgagg agtgcgtcat gcttcggcgc cacttccaca   73320
gggccgggcc acccgcggag ggtggcaggg cccgcgacga cgacaagaag gaagatcacc   73380
aagtaggaga gttccacgag gtccgcgact gcttcatgat ctacggcggg catgtggcga   73440
atgcctcggc tcagcatcgc aagcaagagc gccgggaggc tgctcggtg aaggtggcgg    73500 cgccagccta cctagactgg tccgacaagc ccatcacctt cgaccaagct gatcaccccg   73560
accacgtgcc gagcccgggg aaatacccac tcgtcgtcga ccctgtcatc ggtgacgtca   73620
ggctcaccaa ggtccttatg gacgggggca gcagcctcaa catcatcaac gccgagaccc   73680
tcgggctcct gcgcgtcgat ctgtcctccg tccgagcagg cgctgcgccc ttccacggga   73740
tcattcccgg gaagcgcgtc cagcccctcg gacgactcga cctccctgtc tgtttcggaa   73800
caccctccaa cttcggaagg gagactctga cgttcgaggt ggtcgggttc cgaggaacct   73860
accacgcggt gctggggagg ccatgctacg cgaagttcat ggccgtcccc aactacacct   73920
acctgaagct caagatgccg ggccccaacg gggtcatcac cgtcggcccc acgtacaaac   73980
acgcgttcga atgcgacgtg gagtgcgtgg agtacgccga ggcctcgcc gagtccgagg    74040 ccctcatcgc cgacctggag agcctctcca aagaggtgcc agacgtgaag cgtcatgccg   74100
gcaacttcga gccagtggag acggctaagg ccgtcccct cgacccagt ggcgacgcct    74160 ccaagcagat ccggatcggt tccgggctcg agcccaaata ggaagcagtg ctcgtcgact   74220
ttctccgcgc gaacgccgac gtcttcgcgt ggagtccctc agacatgcct agcataccga   74280
gggatgtcgc cgagcactcg ctggatattc gggccggagc ccgaccggtc aagcagcctc   74340
tgcgccgatt cgacgaggag aagcgcagag cgataggcga ggagatccac aagctaatgg   74400
cagccgggtt catcaaagag gtattccatc ccgaatggct cgccaaccct gtgcttgtga   74460
gaaagaaagg ggggaaatgg cggatgtgtg tagactacac tggtctcaac aaagcatgtc   74520
cgaaggttcc ttaccctctg cctcgcatcg atcaaatcgt ggattccact gctgggtgcg   74580
aaaccctgtc tttcctcgat gcctactcag ggtatcatca aatcaggatg aaagagtccg   74640
accagctcgc gacttctttc atcacgccct tcggcatgta ctgctatgtc accatgccgt   74700
tcggtttgag gaatgcgggt gcgacgtacc agcggtgcat gaaccatgtg ttcggcgaac   74760
acatcggtcg cacggtcgag gcctacgtcg atgacatcat agtcaagaca aggaaagctt   74820
ccgacctcct ctccgacctt gaagtgacat tccgtgtgtct caaggcaaaa ggcgtcaagc   74880
tcaatcccga gaagtgtgtc ttcggggtgc cccggggcat gctcttgggg ttcatcgtct   74940
ccgagcgggg catcgaagcc aacctggaga agatcgcagc catcaccagc atggggccca   75000
tcaaggactt aaaaggtgta cagagggtca tgggatgtct cgcggccctg agccgcttca   75060
tctcacgcct cggcgaaaga ggcctgcctc tgtaccgcct cttaaggaag gccgagtgct   75120
tcacttggac ccctgaggcc gaggaagctc tcgtagacct gaaggcgctc ctcaccaagg   75180
tgcctatctt ggtgccccca gctgatggag aaaaagccct cttggtctac gtcgccgcga   75240
```

```
ccactcaggt ggttagcgcc gcgattgtgg tcgagaggca agaagagggg catgcattgc    75300
ccattcagag gctagtttac ttcgtcagtg aggtactgtc cgaaaccaag atccgctacc    75360
cacaagttca gaagctgctg tatgcagtga tcctgacgag gcggaagttg cgacactact    75420
ttgagtctca cccggtaact gtggtgtcat ccttcccccct gggggagatc atccagtgcc   75480
gagaggcctc gggcaggatt gcgaagtggg cggtggaaat catgggcgag accatctcgt    75540
tcgcgcctcg gaaggccatc aagtcccagg tcttggcgga cttcgtagcc gaatgggtcg    75600
acacccagct accgacggct ccgatccaac cggagctctg gaccatgttt ttcgacgggt    75660
cattgatgaa gacaggagcc ggcgcgggcc tactcttcgt ctcacccctc gggaaacacc    75720
tacgctatgt gctacgcctc catttcccgg cgtcgaacaa tgtggctgag tacgaagctc    75780
tgaccaacgg attgcgaatc gccatcgagc taggggtccg acgcctcgac gctcgcggcg    75840
actcgcagct cgtcatcgac caagtcatga agaactccca ctatcgcgac tcgaagatgg    75900
aggcctattg cgatgaggtt cggcgcctgg aagacaagtt ctacgggctc gagcttaatc    75960
acatcgctcg gcgctacaac gagactgcag acgagctggg aaaaatagcc tcggggcgaa    76020
caacggttcc ccggacgtct tctcccggga tctgcattag ccctccgtca agatcgatga    76080
ccctcccgag cccgaggcgc cctcggacca gcccgaggta cgctcggcac ggcccgaggc    76140
accctcagct caacccgagg taccctcggt ctccgagggc gaggcatcgc gcatcgagga    76200
ggagcgaagt ggggccatgc ctgatcgaaa ttggcagacc ccgtacctgc aatatctccg    76260
ccaaggagag ctaccctcg accgagccga ggctcgacgg atagcgcgac gcgccaagtc    76320
gttcgtcttg ctgggcgatg agcaggagct ctaccaccgc aatccctcgg gcatcctcca    76380
gcgatgcatc tccatcgccg aaggtcagga actcctgcaa gagatacact cgggggcttg    76440
cggccatcac gcagcgcctc gagccctcgt tgggaatgct ttccggcaag gcttctactg    76500
gccaacggcg gtggctgacg ccactagaat tgtccgcacc tgcgaagggt gtcaattcta    76560
tgcaaagtag acccacctgc ccgctcaggc tctgcagaca ataccatca cctggccctt     76620 cgctgtgtgg ggtctggacc tcgtcggccc tttgcagaag gcgcccgggg gctacacgca    76680
cctgctggtc gccatcgaca aattctccaa gtgggtcgag gtccgacctc tgaacagcat    76740
caggtccgag caggcggtga cgttcttcac caacatcatc catcgcttcg ggtcctgaa    76800 ctccatcatc accgacaacg gcacccagtt caccggcaga aaattcttgg acttctgcga    76860
ggatcaccac atccgggtgg actgggccgc cgtagctcat cccatgtcga atgggcaagt    76920
agagtgtgcc agcggcatga ttctacaagg gctcaagcct cggatttaca acgacctcaa    76980
caagttcggc aagcgatgga tgaaggaact ccctcggtg gtctggagcc tgaggacgac     77040
gccgagccgg gccacgggtt ttcacgccgt tcttcctggt ctacggggct gaggccgtct    77100
tgcccactga cctagaatac ggctccccga ggacgagggc ctacgacgat caaagcaacc    77160
aagctagccg agaagactcg ctggaccagc tggaagaggc tcgggacaag gccttactac    77220
actcggcgcg gtatcagcag tccctgcggc gctaccacgc ccgaggggtc cgaccccgag    77280
acctccaggt gggcgacctg gtgcttcggc tgcggcaaga cgcccgaggg aggcacaagc    77340
tcacgccccc ctgggagggg ccattcgtca tcgccaaagt tctgaagccc ggaacgtaca    77400
agctggccaa cagtcaaggc gaggtctacg gcaacgcttg gaacatccaa cagctacgtc    77460
gcttctaccc ttaagatgtt ttcaggtcgt tcatatacct cgcacccacg caaagtttag    77520
tcatcaagga agggtcggcc tcgcctcggc aaagcccgac cctccctcgg gggctaaaag    77580 gggggggaacc ccctctgcgt cgaaatttc ctcgaaaaaa ggtctcttct gccagaatat   77640
```

```
ctttcgtgct ttttgactac ttcgaaaagt ggatcctgaa aacgacggag tacacgtaag    77700
cagtcaaggc ggaccgagcc gagggactcc tacgcctccg ggatacggat acctcactca    77760
tcaccttctg cgataagtaa ctcgcgttcg gataaagtga ttccgcggac cgaacaagtc    77820
ttcatgttcg gaagttcttc tgccgaagca atccttcgag ccttctcgac tgagtcggtg    77880
gcagggcctc atggacgagt gaaagtacgt gtaagcggca aggccgaccg agccgaggga    77940
cttccacgcc tccgggatac ggatacctca ctcatcacct tccgcgagaa gcaactccca    78000
ctcacacaaa catccctgtt accgacaaaa aagtcaagat actcgaaaca agaggaaagg    78060
agacgcagct ttacaacaca gcgagggcgt gtattctggc ctcggcggct gcagaaggca    78120
cacgctacaa gacaatctga ccctacaggc tcgggtcttg acgctggaag ggggcagcaa    78180 cacccctcggc atcgatgaca ccttcagcga ggcccgacct agcctcggac ggcgacgcgg    78240
tccgaggatc tccgctccga aggacgatgt catcaccacg cccgggcaat cgctgccagg    78300
gacttctccg ggaatccggc ccgagcaggc ggctcggccg gttaccccctg gggcctcggc    78360 cgaccatctc ccaagggcgc cagcccgacc tgaggcctcg gctgatcagc cccgacgtcg    78420
gtcccgccaa cggacaaccc ggctaggctc cgaccaacca ggtttcattt tcgagccaac    78480
tccgcctctg ttcacactga tatcgctacc cctggcctcg gctcgtcgaa gagcggccga    78540
ggggtccctt taactaagct agaggagcct cggacagcaa ggccgaccga ccgagggac    78600 tcctacgcct ccgggatacg gatacctcac tcgtcacctt gacacggggc gactcatgct    78660
tggtgaagcg gttcagataa tcaacagacg agtcttagcg ctcaaaaatg aggaaaaaca    78720
cggctccgtg ccggaattac atacatgttc aggccccgaa agccgcaatg aacaaaaaca    78780
ccggcattcg aagtgccatt acaaacggaa ctccggttcc ccctccgca ggtacgaaca    78840 gccccactcg atagggggtgg gcctacggag caacagaaga ctgacgagcg gctcgccgcc    78900
gcccgctctg actacgacga catgcaagca actgcaccgc cacttgcgcc accaccgcgc    78960
ctcctcgatt gcggaaccaa taccgcgact cgaggcgacc cagcgtgcga cccagcagcg    79020
ccagcctgac gcggcggtca acacggccaa aagtgggccg gcagtaatga cggtggcagg    79080
cgcgtgggag cagcggtcac gtcgtcagcc aagctcacgt cccatccggg ggcagcaaga    79140
gaaccccctc tcacggcgtg aagacaacgc gcccgtgatc cgttcctcga acggctcgcg    79200
cacgcgcaac ggctgccccg ccaactactc gcctcgtcgc attaactccg cggctggaca    79260
ggcggcgctt ctggcaggag cagcgggcga cacttcgcct tcgccgaaat aaccgcgcca    79320
aaaaaggtac gccgcgtcgt tcggtttcgt atccttttcc cttttttcctc tttctctatc    79380 tcttgcgaca gggaccggga aaggggggata ccccgaaagg gatccttccc cgtgaaggaa    79440
ccaggctccg agcctcctta ctgatcagag gttcgaaggc tggccccccg aagggttcaa    79500
cagccgcctc agatcgcgtg ggccctacac ccactactgg tcagaggttc gaaggccggc    79560
cccccgaagg gttccacggt cgcctcaggc tactcgggct ccgtgcccat tactgatcag    79620
gggttcgaag gctggccccc gaagggttca cagccgcctc agacgccgag cgagggatga    79680
ccaggggtac gttcgataca taaccaaggc tcgggctgcg ctcctgaggt accctaggac    79740
atttccgaga ccagcgggag cgatcttgta atggaatccc atcggaggga ggcatcgagc    79800
cctcggaccc cgtcgccagg ggaccgggtc cggcagatca cccgcaggta cttttgggcg    79860
tgcctctggg ccctagccg acccctaacg aacggggcac ggacgtccac tcggattacc    79920
tgcttgcagc tcaccggaga caccatgttc ggcgcccatc gagggtaaca tggcgccctc    79980
```

```
cccctagtcc tccttgcgga aaggcgacgc aggggcatat gtaaaaaagc cgagtctgtc   80040
cctgatcgcc ctcttgccct gtgcagaggc tcaggggctg ctctcgcaaa cccggctccg   80100
gccaaaccgt tgacagcgtc aacataccag cccgagaact tgggcccega ccgtacaccc   80160 gggctacgge cagctcgcat gagggaacaa ccagaccagc cgaagcatta cgcaaggcat   80220
taagacctcg aaggagtgaa accactcctc cgaggcctcg ggggctacac ccggcgggtg   80280
cgctcgcgcg cacccaccgg aacaaaatgc aaccgagaaa ggctggtccc ttgcaaaaaa   80340
gtgcgacgaa agcctccaag cgagtgctaa cactcctttc gaggctcggg ggctactgtc   80400
ggggaccata attaggggta ccctcaagac tcctaattct cagctggtaa cccccatcag   80460
cataaagctg caaaggcctg atgggtgcga ttaagtcagg gatcagtcca ttcgagcgac   80520
tcgatcacgc ctcgcccgag cctagcctcg gacaagggca gccgaccccg gaggatttcc   80580
gtctcgcctg aggcccccct ctaacggcgg acacatcttc ggctcgcccg aggccctgcc   80640
ttcgctaaga gcaaccctg actaaatcgc cgcaccgacc gaccaagtcg caggagcatt   80700
taacgcaaac gtgacctgac acctttatcc tgacgcgcgc cctccggcag agccgaagtg   80760
accgccgtca cttcgccgct ccactgaccg gtctgacaga aggacagcgc cgcctgcgcc   80820
acttcgactg cagtgccact tgacagagag atactgacag gaagccaggc cctgccaaag   80880
gcgccatagg aagctccgcc cgacccaggg ctcggactcg ggctcagccc cggaagacgg   80940
cgaactccgc tccgcccgac ccagggctcg gactcgggct cagccccgga agacggcgaa   81000
ctccgctccg cccgacccag ggctcggact cgggctaaga cccggaagac ggcgaactcc   81060
gctccgtccg acccagggct cggactcggg ctaagacccg gaagacggcg aactccgctc   81120
caaccgaccc agggctcgga ctcgggctaa gacccggaag acgacgaact ccgcttcgcc   81180
cgaccccagg gctcgggctc gggctcagcc ccagaagacg acgaactccg cttcgcccga   81240
ccccagggct cggacaccgc cctggcctct gccgacgacc tccgcctcgc ccgacccagg   81300
ggctcggact cgtcctcggc catggaagac agactcgacc tcggcttcgg aggagcctcc   81360
acgtcgccca acctagggcg caggccagcc acgtcaacag gaagcgccat catcccccta   81420
ccccgagctg actcgggccg tagagaacaa gaccggtgtc ccatctggct gtctccacca   81480
gataggcaat gatggcgccc cgcatgccct gtgacgacgg cagctctcag ctctcttacg   81540
gaagcaggag gacgtcagca aggacacaac cgctccgaca gctgtccctc cgccaggctc   81600
cgccgctcct ccgacggcca cgacatcaca ctagctgggt tccaagatct cttcggctgc   81660
cacattggca tgtactcagg gcactagctc tccctcgcta gacacgtagc actctgctac   81720 accccccattg tacacctgga tcctctcctt gcgtctataa aaggaaggac cagggtcctc   81780
ttagagaggg ttggccgcgc gggacgagga cgggacaggc gctctcttgg ggccgctcgc   81840
ttccctcacc cgtgtggacg cttgtaaccc cctactgcaa gcgcacccga cctgggcgcg   81900
ggacgaacac gaaggccgcg ggattccac ctctctcacg ccggtctccg gccgcctcgc   81960 tccttttcccc ccttcgcgct cgcccacgcg ctcgacccat ctgggctggc gcacgcggca   82020
ctcactcgtc gacctgaggg accccccggt ctcgaaacgc cgacaataac tctaaccgaa   82080
cttggcattt agccgatcga ttcctaaccc atttttcata ccaccactac atgacatacc   82140
gaatacattg aatgactcgt tcacattcca catatatctt tacgaaaaca tttccacatc   82200
gcttgcaact taacctaagc ttcgccacat aatttcagga catctactta aatcatgaat   82260
atcatcatca cacacatcga cccgttttga aataaccccta catgtctatc acaggaatgg   82320
agcatttcaa cacatatcct aaaacaaact aacttcatca cacatcttgc attacaaagc   82380
```

```
tacttgactt atttgaagtg tctactcgaa atcgtgagca caatcataca ctatatacga    82440
aacataattt taacgaacgc ataatacgca tcgtcatgac ttgacctata aatatagaga    82500
aagcgatgac tactctggca tgtcaccacc tctctattta agtcaagaca atttctacca    82560
tcgattaaga gtcgtaagca ttaaatacct tactacttta tacgcacaaa taaacttcaa    82620
cttaacacaa ctgacaccga tggaattttt actaaactca tcgtacgcat aaccctgtct    82680
cgcatacaac catattatgg cgtgcactcg agacacttca atccatgtgg cgcgaccact    82740
agtataaatg gactctgaca ctcatgtctt aacgatacat cctctacgca aactagcatt    82800
ctctaaacta ctcgtcacat caataaatat atccectcta aaattatgaa tcccatcaca    82860
ttgcttaaaa caaatacact tttcacataa acacatcgat gcatttccca aaacaaaatc    82920
cacattttgt aacttagttt tcgcatcaaa caacgcatcg catattttcc tatcaaaata    82980
aaaatactcg agttctttc tatttcaatt tcttccctac acgcgtccat ttataaaatt    83040
atacagttac acacatataa ccacatgcac atcatcgacc aaaacataat tagacaacta    83100
caaatcgtgc acatcaatta acctcttgtt ctccaatcgc aaacgtgatc ctaccaatgc    83160
gcataatcga acatttttaca cacatccata caaaatgatt aatcgagtcg atcgagagcg    83220
acatgcatcg gctcaccata aacaaaccca aatgatgttt gcaagaatga cggtgattcc    83280
gattcgtgca tcgctccaaa catccaacga gcgttaagcg acttgctttc tcctcgcaaa    83340
acacggggtt ctctcctcca caaaataaa acaaagcaac acacatacat aattaatcat    83400
aggaaaataa catcgatgcg gaatcaaaca aggagcgtcg cggtctcacc ggggtgaacg    83460
acgacgacgt ttggggctgc gcaaaaacag cgaacacacg gcggcatcac ggcgtgctgc    83520
tcactacgca acaaaacagc aagccggcag cacgcggagc cgtcgggct gctgcacatt    83580 tcatcgagca caagtgtgga tggcggccag gtgtttgttt caggcgctga acaatggag    83640 ggggagaggg ctacgctgg ggaagtggtg gctcggccac ggcaagaaca gggaagggga    83700
ggctggtcac cgaccttggg cgcggccagg gaaaatggag ttgctgcttg gcactatgta    83760
caacagagag agggaggaat ggctccatgg gaagctcgag ctcggccagg gaaggaaga    83820 aagggttcg gcatccaagc tgttggagcc caaggagagg gtgctggccg ccgtgcgcaa    83880
gtgaagtttc acgccagctg aagctccctg gtcgcggaca ggaaagagca gggggcgcct    83940
gctgcaggta ggagctcgac tcctatggaa aatggcaggg gcagaggagg ccggctggag    84000
caccgggcag ggtgctcggc catggagccg ctgcatggat ttgctgctgc gccctgggag    84060
aaaaacagta ggggagtgaa ggatgccatg gctgggggcg cggggagcag ggagcctgct    84120
ggtggccttg ctgccgtgaa gcggggaaga agaaaggcag aggacgctac gagaagagct    84180
tcgacgcgct ggaggaagg aacgccggc catgaagcc cctgcgcgct ggggaaggag    84240
ctccagctct acgtgcttga aggagcccat ggctggaaaa tggtagagga ggaagagaag    84300
ggtgttggcg gctggggtgg aaatggaaaa ttttcagaat gcaaggtagg gaagcccata    84360
tttatagagg agaaattagg gtagggtttc ttatggccca aacgggctgg actggatttg    84420
gcccaaaaca ctaaattggg tcgcgctaaa taatttccgg actaaaaatg ttcctgcgga    84480
attcgtcgct actgagaaac agagcgaaaa gagttcggac gaacgaaagg ttgcgcgatt    84540
aactcagccg agagtctgtt tagattttgc ttgaaaataa ttccctacgc gtaaatcgaa    84600
aataaaccgt cctgagattt gatcggtttt ggattttag tcggagaaag cgaatcgtga    84660
tatataaaaa tcgttgccga tgttgatttt gaaatcggat tggatacaga gatgctaagc    84720
```

```
tgagtcgagt aagatttgat cagaggacga catattgatt atttcgtttg tgagtatgga   84780
ctcggattaa aatagttgga catcgatcga acatcgagaa attggattcg gacacagatc   84840
aaataacagc cgtcgagagt ttgatttatt gagcttcaga tgaggtttat aattcgagaa   84900 tgattttttga gttcgcattt gtgccaagga taaaagttttt aacaggctcc aaaattggcc   84960
ttctatgaga ctgagtaact ccgaattcgg tgaaacatga atgaataatc tggataatca   85020
gggacatacg cgagcgagaa atagaaattt ttactgagca tccgagatta ggataaatct   85080
cgcgacgtaa cacgaaactg acacctgggg tgtcacaact ccagcactgc caccctgctg   85140
gcaggcggat ccgtcgaaga aaagcatcca gtggggctca gtgaagaccg aagcccttgg   85200
ctccgcaggt gtggtgtccg aatcgggatc tggaccccca ggagcgctcg ggaaggggt   85260 ccactccacg atgaagtcag ccaggacctg gctcttgaca gcgtggcggg gctggaactc   85320
cagttggaac tcagcaagct ccgtggccca cttggcgatg ttgcctgtgg cgtttgagtt   85380
gtggagaatg gcccttaacg ggaaggaggt caccaccaca actctgtgtg cctaaaaata   85440
gtggcgcaat ttcctggaca caacaagtat agcatagata agcttgtgcg tctcaaggta   85500
cctggctttt gcctcatgga ggacctcgct gacgtagtag accggcttct ggatggttcg   85560 gaccccctgca ttcagtcccg agtcctcaaa ctcctggcct tctgtcaaca tcgtggtggt   85620
cagaccacca ccttctccta ggggaactttt atgactcccc tagggatgtt gtgtcgtact   85680
ttcgacgacc agcaccatgc tcaccgcctc tgtagccgct gcaatgtact agtataatgg   85740
ctctcctggc tctggagcta ccagtattga tagggacaca tggtgctgct tcaactcttg   85800
aaaggcttgt tctgtctctt tggtccaaga gaatgggtcg gacttccgca atagcttgaa   85860
gaagggtagt gccctctcaa ccagtcttga gatgaagcga ctaagggcgg ccagtgaccc   85920
cgtaagcttc tggacgtctt tgattcaggc cggaggcctc attgtctcta ttgctttgat   85980
cttctctggg tttgcttcaa tgccccggtg tgaaaccagg aatcctagca acttccctgc   86040
agagacacca aagacgcact tgtccgggtt cagcttcatg cgtgttgcct gcagcttgtc   86100
aaagactagg gttaagtctt ccactagggt cgaccctccc ttagtcttga ctacgatgtc   86160
atcgacgtat acctctaccc tgtccctaat caagtcacca aaagtattac tcatcgcccg   86220
tacaaatgtt ggcaaggcgt ttttcagact gtaaggcatt acaacataac agtaaagtcc   86280
atccacagtt acaaaagcgg tatgcttcct atcttgccta gacatctcga tctgatggaa   86340
actagagtaa gcatccagga aggataggag gttgcaccca gaggtagaat ccacgatttg   86400
atctattcgt ggaagtggat atgggtcctt gggacaggcc ttattgaggc tggtgtagtc   86460
gatgcacatc caaagcttcc cgttagcctt ggggacgatg actagattgg ccagccatac   86520
tgggtgatgg acctcttcga tgaaaccagc gtccagcagc ttccggacct ccttacggat   86580
gaaatcctgc cgctcgatgg actgtctttg aggcttctga ctcaccggtt tggcgtcagg   86640
gtggatcttc agatgttgct cgatcacctc cctaggatc ccaggcatct gcgatagttc   86700
ccatgcgaat acattggcat ttgcctggag gaaggcgatg agcgcgattt cctatttctc   86760
ctccagatcg cccgtgatgc gagtggtctg ggaggaatcc ccgttgagcc ggatggtctt   86820
gacagggacg ccgtctgccc cagatggttg caccttaggc accttagcag gcatcttggt   86880
acaggaagtc gaggggtccc tccctcgtc atccgggcga gcagcttctg ccgctagggc   86940
atgcaacttc tcgatagctg caagcgcagc gggacggtcg ccccgcatgg tgaggacccc   87000 agcagggat ggcatcttga ggaccaagta cctgtaatgg gcaatggaca tgaaccggta   87060
cagggccggc ctgccaatga tggcattgaa agggaggtta acctccgcaa catcgaacta   87120
```

| | |
|---|---|
| gacattctta gtgtggaagt tatcctcagt cccgaatgta accaggagtg tgatgctccc | 87180 |
| aaggggatac accggtttag ggcccactcc agagaacgtg cgagagggtc ctagtcggga | 87240 |
| tcctgggatc tgcagctgct tgaacgcagc gtggctgatg acgttgagcc caaccccacc | 87300 |
| atcaatcagc acatgatgca acttcatgtt ggcgatgaca ggggcagtga tgagtggtag | 87360 |
| tataccagcc cctgccatgt tttcggggca gtcgggtgcc ccgaaggaga tagtggtgct | 87420 |
| ccgccaccgc tgatgtgggg ctgccttcgg gaccccgggt gtcgccaaaa ggacctcgcg | 87480 |
| gcgcagggac ttcacgttcc tacgggaggt gagctcccag cttccaccat acattacgta | 87540 |
| cagcttcttg cggcggtcgt tgtcatcacc ggagtcggag tctccagtga ggatatcctt | 87600 |
| gaggacttgc tcgggggcct aattctcgag gtcccattct cccgtggcca ggtcaccttc | 87660 |
| gtcgaccttc tccttgccag gccggcgccg aggcggcgag ccatccctgg aggcatgctc | 87720 |
| gcgccgctca ctgatgcgct tcacgagctt caggatctct cgtcattctg aggcactgtg | 87780 |
| gcgactgttg gggtggacag ggcatgaccc aatgtcactt ccctgttgcc gtggatgctt | 87840 |
| gccgcgctcg tcccggtccc cagccgtagc tacagcaact ggagcaccag actacggcct | 87900 |
| atcgtgacac ggtgcttctt cttttt cttg ccaccaccct gggtggcagc acctgagcca | 87960 |
| cccatttggg tgactctggt ttgcagcgtc gagtgccatg cacggccctc agtagctctg | 88020 |
| gcacatttgt cggccagagt gaagagcgta gtgacggttt ccacgtcatg cgtcgccaat | 88080 |
| ttctccaaca tcttcttatc acgcaccccc ctgttggaaa gcagtgataa tggaggcatc | 88140 |
| ggagatgcga ggtatagtcc cctgtaccct ggtgaagcgg gagatgaaag cccgagagt | 88200 |
| ctcctcgggt tcctgcctca ctgcatggag atgagcctcc acgccatgct actgataagc | 88260 |
| actggcgaag ttcattgtga accgtgcaca gagctcttcc caggagtaga tcgaccccgg | 88320 |
| ggtgaggttc atgagccagg tctgtgccgg cacattcaag gctacatgga aatagcttac | 88380 |
| cattacagca gtgttcccac cagctgccgt aatggcggtg acatagacct acaggaattt | 88440 |
| cgacaggttc gatgtcccat cgtacttctc cggcaggtgt ggccggaaca tgggtggcca | 88500 |
| agtcgccgcg cggagatgat ctgctagtgc ggcgcagccc acgccgacca atgggacacc | 88560 |
| catctggatt cgggcgtccc ttgcagtgaa gtcttggtcg aggttgcgac cctcgaagtt | 88620 |
| ttgccggcgc tcacgcgccc tctccagaga gattcgagca tcctcgcctg cacgcctgtg | 88680 |
| gttgagttct gctcgcaggt cgttagtctg tgccccctca ctgagggtga atgcacagac | 88740 |
| gttgacgcct cgcgctgatg ccggaatgat cgaggcctgg acctggccga gctaggatgg | 88800 |
| gccatgccga ggagacggtc gacatcttca cgccactgcc tcatggcccc cggggaggcc | 88860 |
| gtggaacttg gtgggttacg cagcaactcc ctggctgcag acaatggccc accataggta | 88920 |
| gccctcgacg gagtcctaga ggtctgtgcg ggcgtgtgtt gctgcgcagc gtgcatagca | 88980 |
| gcagcaccag gcacagcgcg gttggagcct cgtggcatgg aagataatgc cccttcctcc | 89040 |
| atcaagaagt cctcgggaga caagccacgg tgctcgacga tctgaaccat cgtgtcgagc | 89100 |
| aagaaaacag gcaaaaacct aaagccaaag cccctacct ggagcaccaa atgtcgaagg | 89160 |
| gaaaatcctc cggccgggtg gcggaatgca cccgccctaa tcctaagatg aggaggggc | 89220 |
| ctaagcggtt gcctgtttgg tgaattcggg atgaacacaa gaggacacga gggattatag | 89280 |
| tggttcaggc cgccggagcg taatacacta cctccactgt gtgtatgttg tattgagtgt | 89340 |
| gtacagcgtg tcccttgtaa cgttgtgtgc cttccctttt atagtttaag ggaggcacat | 89400 |
| acaaggatgc tgagccccga catgtgggcc caggagcata atggaagaaa tacattatgt | 89460 |

```
gaataactaa tgctgacaga gtaacacatg agtaatcagc gggagtcatg atggctgcag    89520
tccatgcagc attgatagac agtaacccct ttcttggaaa catacgagta atggtgagtc    89580
attgccctcg atatggtaac gtgtgagtaa ctgcatggcc cacgtatcgt ggactgagca    89640
tgccgcctgt cagtggaatg acaggcgca catcttctcc gtaatgaatg cgaaggcacg    89700
cgtagcccag aggcatcatg ccaggttcca cccgttggtt tatgccgcgc gcagtatgcc    89760
acgtggcagc atcgggtctc cgcctgagca gggagaagga gtgtatgcgg ataggtccgg    89820
atcccaccag accaggtcta gacacgtgtc ggctccggac ccccacctgg gtcctaatca    89880
aggcccgggt atgttctgtc ctagaaccct gggaccccac tatgggtggc ccagacccat    89940
acggggggtt cggatcccat cctaggggtc cggtttgtac acgtggaggt cctggaccaa    90000
acttggaggc ctggaccgta tatacagggg tctggcactg gtccggcact ctcccatggg    90060
gtccggactc actgttgatg ccttggagta catcactttc tctggacaca tggcggcccc    90120
gaacccgccc atgtggtggg gtcaggtgct gttgctggcc cagagtagtc gcccgaggct    90180
agggcgagtc atggtctggt cccacataca gcttatttac cacgcgacta aagatagtcg    90240
tgtgggtact gcgtctttat acagtagtaa ggggtaccct agttttaggg tgccgacaca    90300
catcttcctc tagaacacca tgaagaaacg cgttctgcac atccagttgg cagaggctcc    90360
aaccctgaga gacagcaaga gacaaaataa ggcggacagt agcaaattta actactaggc    90420
taaaagtgtc atcatagtca atgtcgtagc gctgtttaaa acctttagcc accaatcgag    90480
ctttatgatg gtcaatagac tcatcagctt ttctcttgag tttataaacc cacttgcaat    90540
caatcaaatt tctgtcaggt gcgggaggaa ccaagtgcca tgttttattc cgcataaggg    90600
cagaaaattc taggtccatg gcagcttttc cagtttgggt caaacaatgc aacagacaag    90660
ctggagggtt cttcacaaat tgccaaattt ccatacctga tcgtgccatc tgtaaacttt    90720
ctgggcttca caataccact ctgtagccga gtgcgcctag caggaagcgg aataggacac    90780
gaggctgatg gcgagggcag atggctgtca gtgagagagg gaccagccgc gccagagtcg    90840
gcacgaggca atcccgaagt ggctgctgct attgatgcgg ccgtggtggt gggaagcacc    90900
gcgttgctgg gcgcacctgt agccgcgtcg gaggggtgtg gcgtggagcc tagcaacaga    90960
tcagcaccgg gattgaggcc accagccggg acagaatttg cagcagggat cattggtggc    91020
tgcaaaagct ggttaggcca caaaatcgga gcaagcatgc tggattcagc aggagaatta    91080
gtcacaagat catctgagtt ggcccgagaa ttattaggat cgggtagaag aagcacgtca    91140
gaggtatatc gagcaccgac tgtgggatgg agagcagcaa agggaaaagc gtctcatcaa    91200
aaacaacatc atgtgaaata taaacacggc ccgttgagat gtcaagacac ttgtaaccct    91260
tgtgaaggtt gctatagact agaaaagcac accaaatgga ccgaaactag agtttatggg    91320
tgttgtatgg ccgcaaattt ggctaacatg catagccaaa gacgcgtaga ttagagtaat    91380
ctggggtagc acctaagaga cggtggagcg atgtgtcata atcaagaagc ttagtaggag    91440
ttctattgat aagatgtgtt gaggtgagga acgcttggtc ccaaaacttg agcggtattg    91500
tccattagcg agtaaagaga ggcccatctc aacaatgtgc aacgaatcaa gctgatacat    91560
aagannnnnn nnnnnnnnnn nnnnnnnnnn nnnnnnnnnn nnnnnnnnnn nnnnnnnnnn    91620
nnnnnnnnnn nnnnnnnnnn nnnnnnnnnn nnnnnnnnnn nnnnnnnnnn nnnncaattc tagaagattt    91680
cgtcgatctt gatggtgtcg ttggccttga tgagcgggtc ggggtagcgg atggtgcggt    91740
cgtcgtaggt gtttaggcag gggatgcctt tctggccaaa ctgaacagac cttaccttgc    91800
agagcatgaa ctgcacacaa accaatagaa aagcagtgag aatttcacag gcgtactatg    91860
```

```
aaagggcatg ggaatttcca gcgatgtaaa tggatagata gacagagcaa catctattaa   91920
tagtcctaac gattgtagca catgacattt tcaatgcaag actttcatgc acacaacata   91980
tatggacagt atagcaagga taaggtacat agatctacag aaaaaaaaga acaacctgaa   92040
gcattagaca aatggggaag tacagaagat tgtaggtacc aaagctagaa aatattgttt   92100
tgtcggcgtt tcgaccccgg ggggtccctg gaccgacgag taaattgtcg ctgcgtgtcc   92160
cagcccagat gggtcgacgc gagacagaac acaaaggggg gaaaacagca aaggggaacc   92220
cgcggccttc gtgttgtcct gcgcccaggg cggatgcgct tgcagtaggg ggttacaagc   92280
gttcgtgtgg gagagagaga gagccttgtg cgtcagcccg ttctcccgcg cggccaaccc   92340
tctcgtacga gagccctgga ccttcctttt atagacgtaa ggagagggcc caggtgtaca   92400
atgggggtg tagcaatgtg ctaacatgtc tagcagagag gagacagagc cctaagtaca    92460
tgccgtcgtg gctgtcggag aggttttggc gccctgttca tgtgatgtcg tggccgtcgg   92520
aggagcgttt gagccctgtg gaagtacaac tatcggggct gtcggatcct tgctgacgtc   92580
tccttgcttc cgtaaggggc tgagagccgc cgtcgtcacg gagcacgcgg ggtgccatca   92640
ttacttgttt accggggcga gccagatggg acgccggtct tgttccccat agcctgagct   92700
agctaggggt agggtaatga tggctccccc tgcgacgtgt cggtccgagc ctgaggtcgg   92760
gcgaggcgga ggctcctccg aggtcgaggt tgagcccgag ccctaggatc gggcgaggca   92820
gagtccgtct tccgaggtcg aggctaagtc caagccctgg ggtcgggcga ggcggagtcc   92880
atcgtccgag gtcgaggctg agtccgagcc ctggggtcgg gcgagccgga gtccgtcttt   92940
cgaggtcgag gttgagtccg agccctgggg tcgggcgagg cggagtccgt cgtccgacgt   93000
ccaggttgag cccgagctct ggggtcgggc gaggcggagc ttcccatggc gcccgaggct   93060
ggacttagct gctgtcagcc tcactctgtc gagtggcata gcagtcggag cagggcaggc   93120
gatgctattt tcccgtcagg tcggtcagtg gagcggcgat gtgactgcag tcacttcggc   93180
cctgtcgact gaggagcacg cgtcaggata aggtgtcagt cgatccttgc attaaatgct   93240
cctgcgatac ggttggttgg cgtggcgatc tggccaaggt tccttctccg cgaagcttgg   93300
gcctcgggcg agccgaaggt gcgtccgttg cttgagggga ccctcgggca agacgtgaat   93360
cctcctgggt cggctgcctt tgcctgaggc taggctcggg cgaggcggga tcgtgtccct   93420
tgagtggaca gagccttgac ctgaattgcg cccatcaggc ctttgcagct ttgtgctgat   93480
gggggttacc agctgagatt aggagtcttg ggggtacccc taattatggt ccccgacagt   93540
agccccgag cctcgaaggg agtgttggta ctcacttgga ggcttttgtc gcacttttt    93600
gcaaggggac cggcctttct cggttgcgtt tcgttccggt gggtgcgcgc gagtgcaccc   93660
gccgggtgta gccctgagg cctcggagga gtggtttgac tccttcgagg tcttagcacg    93720
tttcgtgatg cttcggccgg tctggttgtt ccctcatgcg aactggccgt agcccgggtg   93780
catagtcagg ttccaagttc tcgggctggt ttggttgttc cctcatgcga gagcagcccc   93840
cgagcctccg cacagagcga gaggacggcc aaggactgac tcggcttttt tcatacgccc   93900
ctgcgtcgcc tttccgcaag gaggaggggg gggaaagcgc catgttgccc tcagagggcg   93960
tcgaacatgg tgtctccagt gagttgctaa cggttgatcc gagtggacgc ccgtgccccg   94020
ttcgataagg gtcggctagt ggcccagagg cgcgctccaa aagtacctac aggtgatttg   94080
ccggacccgg tcccgtttga tagggtccga gggctcgatg cctccctctg atgggattcc   94140
gttacagaat cgctcctgtt ggtctcggaa atgtcctagg gtacctcggg agcgtagccc   94200
```

```
gagcctcggc catgtatcgg acgtacccag agtcatccct cgctctgcgt gctctgaggc  94260
ggctggcgaa tccttcgggg gccagcctac aaacccctga tcagtagtgg gcgcagagct  94320
cgagtggctt gaggcggctg tcgaaccccc tccgaggggct agccttcgaa cctctgacca  94380
gtagtgggca cggaacccga gtgctctgag gcggctgtcg aacccttccg aggggccagc  94440
cttcgaacct ctgatcagta ggagggcgcg agcccgagt gctctaaggc gactgtcgaa  94500
cccttccgag gggccagcct tcgaacctct gattagtagg agggctcggg gcccgcttcc  94560
ttcgcggaga aggatccctt tcggagtatc ctctttcccg gtccctatag caagagagag  94620
aaagaggaag ggtaaaagga tacgaaatca aacgacgtgg cgcacctttt ttgacgcggt  94680
cattaaggcg gaggtgaagc gtcacctgct tcgcctgcca aaggtgccgc ctgtcctgcc  94740
gcagagttaa tgcgacggga tgagtggttc gcggggcagc cgttgtgcgt gcgctagccg  94800
ttcgaggaac ggaacacggg cgtgtcgtct tcacgccgtg ggaggggggct ctctcgctgt  94860
cccaggaggg gacgtgagcc tacagacgac ttgaccgctg cttccgcccg cctgccgccg  94920
ccattactgc cggcccactt ttggccatat caaccatcgc gccttctccc gcggctgact  94980
gacccgtgat cgatgtgctc ggttggcact gttgggccat gcgcagggtt gcctcgagtc  95040
gcggcaccgg ttccgcagtc gagaaggcgc ggtactagca caagtggcgg tgcagttttct  95100
cgcgcgtagt aaccggcgcg ccggttacat gacgtgtggg cctgggcccc cgtgctggac  95160
gcgtcggagt cgaaagggtg caccccttg gtgcggttgc atgccgcctg catggcggtc  95220
cgcccttttca cccgccggtc tgggcgaaag tggaggagtg cttgtaaccg ctgggcagtt  95280
acgcactctg cgcgcgacgg tttggcttct tctgccctgg gccagcttgc atgacgcgtg  95340
ggacccagcc cccatgtcgt aggggggagga ccttggagcg tgttggtgaa gactcagtcc  95400
gcgacggctg aggacgcaag tggggagagt cgcctttaaa aggagggcga ccccccttgga  95460
tggcaaccat gtcttcacac tcccttcatg catcgcgccc ttccaacttc cgagccccg  95520
gatgggagc gcccgcgttg ctttcgtctt gtcgtcgttg gaggaacgca acttcgcgga  95580
agttggtacc tttcagccat cgctcggctt caaggatttt catcaggcgg cccggctgca  95640
tccctcgct ggtggtcacc caagacggtg accaccagtt tgatggtggg gacgtgggcg  95700
agggccttgt cgcagcagcg tctgcactga ggtcatcgct gctgctgttt ggctgtccgg  95760
agcggaggtc gttgtcgctg ctgccagagc gggcctcggc gagctgtcta gggttttgtt  95820
gctgaaagtt ccccttgacc cgggaacagg atctggatgt cgcctagagg gggggtgaat  95880
aggcgaataa aacttttcac tttaaaactt aaattcttac tctactcgaa gacttagtat  95940
gcagtggagt gagaagactc ttcaagtagg ttgcagcgga atagaagatc ctgtctcaaa  96000
atgtcctgca cttcaaataa agcttatacc acagataagt attgaagtgc agatataaag  96060
gcgagtagaa agagagtcag gatacaatac agaacagagc acacagacgc aaggatttat  96120
cctgaggttc ggccaagcct gaaatgcttg cctagtcctc gttggagtta gccacacctg  96180
ggcttggagt ctatttcaac tccttcctcc gtttgctcag atctgtcagt atgacagata  96240
gagcctttca ctattgagtg gggttacaac agaaccgcgg ctgcttacag acttcttggc  96300
agcaccccgg tagagtaacg atatgctcaa gaccttgctc tagctcttag cagcactact  96360
cctctctcta aggcttatag ttgtgccttc tacacaaact atagagttac acacaagagg  96420
gagagtgaga attgattcca gtggagtcta cacttgttgg ctgcacttct attttgctgg  96480
aggcacctag gggtcccttt tatagacaca aggggcctag gagccgttgg aagcaatcca  96540
ggaaggcaaa tcttgccttc tgtcgggtgg cgcaccggac agtccggtgc acaccggaca  96600
```

```
ctgtccggtg cccgatttct ttccttctac gtcgaagccg accgttggca gtcttggagc   96660
cgttcgcgca ccggacatgt ccggtgcaca ccggacagtc cggtgcctcc atctagccgt   96720
tggctcggcc acgtgtcccg cgcagatcgc gcggccaacc gttggcccgg ccgaccgttg   96780
gctcaccgga tagtccggtg cacaccggac agtccggtga attatagccg tacgtcgccg   96840
gtgaattccc gagagtggcc agttcgccag agttcagcct ggcgcaccgg acactgtccg   96900
gtgcaccacc ggacagtctg gtgtgccaga ctgaactaag tcttggctgt acacagccaa   96960
gcctttcaca cctcttccct tttcttcttc tttctgtttc taacacttag acaagtatat   97020
tagtccccaa aaccaatgta ctaagtctag aaacatacct tctattaatc attacatcta   97080
tagcatttca caagcttgag ctttgatgtt ggactcataa attatcaagt cagcttgact   97140
tgatctagat tgacatcgct tggctccaac atcctgtaaa ggtcacatag aacatctcca   97200
aacataggaa caacccaaac taaagatcaa agtgaactta gctcttttgg gctgcttcca   97260
gttctggttt cgacacttgt tctccttcta gtgaccttga tctcctcctt agagcttgat   97320
cttgagcctt atgacttaca ccacataact atagctgtta cctcattggc tgtaagtcac   97380
gtccttatgt agtgatcctt gatgtgccgt agctgttctc aactcgatca cccttgactt   97440
tgcaagcctt cttcttcacc cttggctttg ggttcctcag cctccttgac cttctcccat   97500
gcatttggta cctcgaagct tttcttgcct ccgtccttgg cttgatcagt tgtcttcgag   97560
ctacgcaccc gagtctcact ttgtgcaatg tccatcttac ttgtgatgtc cattatgtat   97620
ccataatcca gttcttggac catcacattt gttcacttgt gttgaaccct gtaggcttta   97680
ccttaagcac atgttcaaca cttagtatac ttgttagtcc tttaattgag ttgtcatcca   97740
aacaccaaaa ctcacaagag agctttcaat ctcccccttt ttggtgattg gtggcaacac   97800
aattaaagct tacataagaa taagatttga agcacaaatt tgaattctaa gattatagaa   97860
tgctccccct aaataagtgc ttacttcaaa aacctaattt tgaccacaaa cgtcaatttg   97920
cacatactta ggaaaattga aacatttcta caccttagca ctttttagga tgcattatgt   97980
caagaatcaa accatgatgc tataacacac aaatgcacat aatcagagtt aaacaccatt   98040
caaattagtg gatatatcac aggaatatca acctaccact attcaccatt aagataccaa   98100
cttaaactaa gatatcaatt taaagcaatc ttaaagcacc attaaccaca tgactatcta   98160
tttcactata gaagccaaat aattcatcgc agcggaaaca ctggtctagt ccatatgatc   98220
aacacgtata atactgcaag aaacatatga atataaaaca ctagtctagt ccatatgatc   98280
aacacgtata atactgcaag aaacatatga atatcacact tggcaaagct caaactaaca   98340
catcacccat taggataagc tttcctctca ggttgagata agctttaatg cacaacttct   98400 cccccttttga catcaaacac caaaaaccat actcaagcaa gaacatatga tgatgtcaag   98460
ggacagcagg gtgttaaggg gaaaaacgac tatcaaaact cccccttatt tattgaacat   98520
atgtcctatc aacatttagg taagatacat atatgcaaaa agattaatac ttccttttgt   98580
acctttacca tgatgtagtg tacttcccat cttgaaagta gttaatctct cgagagcttc   98640
tccacacttg tgcctgattc tctctcctaa ctttttcttg ttgctaagac accaaactta   98700
gaacaagtta tagtattggg cacaagaaga aacttctatt ctcatgatta tcaaaagatg   98760
tcaattgaag cgaactatta cggctaccaa ttgaaagata ccaattgcaa agttcattta   98820
ttatcatggc tccatgatat ttaagaataa gcatctatta tcaccagata ttatagagca   98880
tgagcaatct aaaaatatgc acttactcac aacttgagat accaatttc ttgacttaca   98940
```

```
gaggtaccca agtcctgatt gctccatttc ttgcttatct tctctttttcc acctagagac   99000 tatacaagat tgctcaagaa acagttagtc tcaaaagaca caagttatgt gtgctccccc    99060
tcaagttgtg catcaagtat ttgaatgact tgcactttgc acattctagc ttccttagaa    99120
ttagagggga tcacaacata ccttggtcaa ggcatactct accactttca tcacccaaag    99180
atgccaattt gaatatcaaa tgaaacgcca cataacacca attgaaggct aaatgaaagg    99240
ttgactaaat acaacaatgc acgcctcagt ggcacctaag ccaattgaat actcacagga    99300
agtctaacat ttacgcaact tgtacatgct tcatatttaa ctatcattgt atataccaat    99360
taaagataaa cacaatcgaa atatctaagc atgttataat taagaaggtt tcttaggtgc    99420 acaaagaaa caacatttta aaggcataaa ttacctaagc caagatatta ccaattgaaa     99480
ggcaagaaca tagctatgat cacaatgaat ggaatttcaa gaatatttaa tgaaattgca    99540
tagctccatt ttccataccht ttgcctttat gagagcccht gttatcgcca atttagggct    99600
ccttttgctt acgcacctca tagctcaaaa gggcacgaca tggatttgaa attcacacag    99660
taccaaacta gggtaatcat gtgaacatgg actaaacaaa atgtcataat tgcacatagc    99720
atgacttaca aaagttacag gtttatccat atacatcaag agagttatcg ttgtggatat    99780
aacaaatgaa atagctaccc atgaatgatt caaaagatat atcctttata gcaccagtca    99840
tgattaagca accatcatta tgatcaattt aacacaggca atcataaagc ataactactc    99900
taaggacagg tagcacaaca agccaactta agagcaatac taaattgcaa ttatgtactt    99960
aaaatacacg ggtaccgtcc tttggagagc aggttgtaga ttctcatcaa gatcctttac   100020
ttgattcacc aataatgatt caggacctat acaccttatt tctcttgaga tgaacatggg   100080
attagtgttt cacaataatt caaccttggg tcaataaaca ctaaacaat taacagctta    100140 agcatagagt tttagataac cgtcttaatc tttcccatgg tctccagtcc atctcgaggc   100200
acctgcatgg tctagttggc acagtttggt atccatctcg ggatgggtac ataatgatca   100260
tgtaaatgtg cctttggtac ccaaattgcc tttgtgctag ttctaggtga tctcgttata   100320
gatctagcac aagtgtatga tttgggtctc ctatgcgaat aagattgaca caaattcact   100380
tgtttaggaa tcttaccttt gtaacatacc ttggatagat gaccttgctc accacacttg   100440
tagcagaagc gtcgctcaac ttgacatgac gcttgttttg tgtcattttc cttggtgagg   100500
gtcactttgg aggatgcata tccttgattc ttcatgaccg gacatgaagt gatcatgtgg   100560
tccttattgt tgcatccaaa acaactcctt gttctttcat ccttgtcttt gtacggacaa   100620
gacgcgatga ggtggcctgt ctccttgcat ttgaagcacc tccttttttcc tcttcccttt   100680 ttgtgcttga atgacatgga gagatgatca gtgcaaacaa catgactaat tgaattttta   100740 ccttttttcct tgttcatgtt gatttcttca tttatagctt tgggaacatt cttcttattg   100800
agcttaacac ttgctgcagt tttttccttttc tcaagcttct tcaccacgcg cccgtggata   100860
tcttgagaga gttgagcaat gtgtcttctc cttagttgtc tttgcttctt gttcccacag   100920 aattttcttttt gtgaccctaa aacttgttgc tcaatcaatg attggctttc ttttgagcaa   100980
caggggttag cacatggtga tatacacttc aaatgcgcac acgtgcgaga atgaggttca   101040
catgaattta agtttgcaat tataacctca tgagcaacat taagcatgat atggtcatca   101100
actaatttat tatgagaatt tgacaacata tcatactttt tacctagagc acgttttctt   101160
aagttcattg tttctacttg actcttaagc atagaatttt ccgttttaag ttgagcaata   101220
ttagataatg catcatgact atttcttgc tcaattaaaa catattcata cctttggacc    101280
aaatcatcat gagagcgcct tagcttctca tgttctttgg tcatcttctc caggctgttg   101340
```

```
ttggttttga tgagggactc ctctagcctg agaagcgtct cgccttgttc cttgttcctt  101400
ctcaacagct taaccaagag tgccttgtcc tctttgttga gatggatgta gaaacggtga  101460
atctcctctt cctccacatc atcggtctca ttttccctgt cattaatgtc agtggaagca  101520
atataggaaa atgtaccttg tgatgatgaa gattcatcct catatttctc cttatcatgg  101580
ctttcgtctc caccgtcatt gttagcaata aaacatttat cactagtgga gaacaaacct  101640
gtcgacgagg tggattcatc gtttggatgc catcgttctt gttcttctcc ctttgaatgg  101700
ttagtatcac aagtaatata gggagtagga gcatcacagt ttgccacaaa atattttct   101760 ttaatcctat tccataaatc atgagcatca acaaatagat cactatcact actcatgatg  101820
gcaaaatagg cacctctaga tagagaatca actaagatgt tgcaagcatg gtgatttaga  101880
gttagacatc ttagttcttc attggatggg ttttactaa tattggaggg aaaaatacta   101940
ctactaaaga cctgtctcaa atcaggatca acactcatga aagcactata aatagagaca  102000
gaccaagact tgtaattaga gccatcgtct aaaagaagtt ccacagttac ctcttgtgac  102060
gacatcgtca tctccggacg gctaagccca cactggagag gcctagctct gataccaatt  102120
gaaagttccc tttgacccgg aacaggatc tggatgtcgc ctagagggg gggggtgaat    102180 aggcgaataa aacttttcac tttaaaactt aaattcttac tctactcgaa gacttagtat  102240
gcagtggagt gagaagactc ttcaagtagg ttgcagccga atagaagatc ctgtctcaaa  102300
atgtcctgca cttcaaataa agcttatacc acagataagt attgaagtgc agatataaag  102360
gcgagtagaa agagagtcag gatacaatac agaacagagc acacagacgc aaggatttat  102420
cccgaggttc ggccaagcct gaaatgcttg cctagtcctc gttggagtta gccacacctg  102480
ggcttggagt ctatttcaac tccttcctcc gtttgctcag atctgtcagt atgacagata  102540
gagcctttca ctattgagtg gggttacaac agaaccgcgg ctgcttacag acttcttggc  102600
agcaccccgg tagagtaacg atatgctcaa gaccttgctc tagctcttag cagcactact  102660
cctctctcta aggcttatag ctgtgccttc tacacaaact atagagttac acacaagagg  102720
gagagtgaga attgattcca gtggagtcta cacttgttgg ctgcacttct attttgctgg  102780
aggcgcctag gggtcccttt tatagacaca aggggcctag aagccgttgg aagcaatcca  102840
ggaaggcaaa tcttgccttc tgtcgggtgg cgcaccggac agtccggtgc acaccggaca  102900
ctgtccggtg cacaccggac actgtccggt gcccgatttc tttccttcta cgtcgaagcc  102960
gaccgttggc agtcttggag ccgttggcgc accggacatg tccggtgcac accggacaat  103020
ccggtgcctc catctagccg ttggctcggc cacgtgtccc gcgcagatcg cgcggccaac  103080
cgttggcccg gccgaccgtt ggctcaccgg acagtccggt gcacaccgga cagtccggtg  103140
aattatagcc atacatcgcc ggtgaattcc cgagagcggc cagttcgcca gagttcagcc  103200
tggcgcaccg gacactgtcc ggtgcaccac cggacagtcc ggtgtgccag actgaactaa  103260
gtcttggctg tacacagcca agcctttcgc acctcttccc ttttcttctt ctttctgttt  103320
ctaacactta gacaagtata ttagtcccca aaaccaatgt actaagtcta gaaacatacc  103380
ttctattaat cattacatct atagcatttc acatgcttga gctttgatgt tggactcata  103440
aattatcaag tcagcttgac ttgatctaga ttgcatcgc ttggctccaa catcctgtaa   103500
aggtcacata gaacatctcc aaacatagga acaacccaaa ctaaagatca aagtgaactt  103560
agctcttttg ggctgcttcc agttctggtt tcgacacttg ttctccttct agtgaccttg  103620
atctcctcct tagagcttga tcttgagcct tatgacttac accacataac tatagctgtt  103680
```

```
acctcattgg ctgtaagtca cgtccttatg tagtgatcct tgatgtgccg tagctgttct    103740
caactcgatc acccttgact ttgcaagcct tcttcttcac ccttggcttt gggttcctca    103800
gcctccttga ccttctcccg tgcatttggt acctcgaagc ttttcttgcc tccgtccttg    103860
gcttgatcag ttgtctccga gctacgcacc cgagtctcac tttgtgcaat gtccatctta    103920
cttgtgatgt ccattatgta tccataatcc agttcttgga ccatcacatt tgttcacttg    103980
tgttgaaccc tgtaggcttt accttaagca cctgttcaac acttagtaca cttgttagtc    104040
ctttaattga gttgtcatcc aaacaccaaa actcacaaga gagctttcag ttccccgca    104100 ggccctccaa tgtgggggt cgttcgtacc tgtgggggcg aaccagagt tctgtttgta    104160 atggcacctt gagtgccggt gtctgttcat tgcggctgtc ggggcctgaa gatgtgtatt    104220
ttggctaaag ccgtattttt tcctcatttc gagcactagg actcgcctgt cggctagctg    104280
aaccgcttaa ccaagtgtga gttgcctcgt gcggaaggtg acgagtgagg tatccgtatc    104340
ccggaggcgt aggagtccct cggatcggtc ggccttgccg cccgaggctt ctcttgctta    104400
gttaaagaaa ccctcggccg ctctgcgatg agccggagct agaggcagcg tgtcagcgg    104460 tgtcagcgtg gacagaggcg gagttggctc aaaaagaagc ttcatcggcc ggagcctggt    104520
cgggccgtcc actggtggga ccgacgccgg agtcgggttg ccgaggccat gagccgggct    104580
gatgtcctcg ggggacagct ggctgaggct acagagcggt cggtcgagtc gtctactcgg    104640
gccgggttcc tggaggacac ctcggcgatg cccaggcgc ggtgctgaca ggttccttcg    104700
agatggagat cctccgaccg tgtcgccgtc cgaggctggg tcggactccg ccgaaggtgg    104760
agtcgacgcc gagggtgctg ctgctccccc actgatgtct gatcctgcag gaacaattta    104820
tctgtagtgt gcgtatgttt tttgcggccg ccgaggccca acataccgt cgtcgtgttg    104880 taaagcggcg tttcttttcc ccttgtttcg agtatcggga cttgttcgtc agtaacagaa    104940
ttgcttatcc gagcaagagt tacttttcac ggaaggtgat gagtgaggta tccgtatccc    105000
gaaggtgtag gagtccctcg gctcggtcgg ccttgccgct tacgtgtact cttactcgtc    105060
cgttggattc tgttatcgat atagtcgaga aggcacaaaa aatcgtttcg gcagaaaagc    105120
tttcgaacgt taagacttgt tcggccagcg ggatcgctta tccgagcgtg agttacttat    105180
cgcagaaggt gatgagtgag gtatccgtat cccggaggcg taggagtccc tcggctcggt    105240
cgtccttgcc tgcttacgtg tactccgtcg ttttcaggat cccactttcg aagtagtcga    105300
aaagcacgaa agatgttctg gcagaaagac tttttcgag gaaattttg acgtagaggg    105360 ggtgcccccc ttctagcccc cgagggaggg tcgggctttg ccgaggcaag gctgacccct    105420
ccttgatggt tagactttgt tggcgtatgt aaacgaggtg tatgaacgac ttgaaaacat    105480
cttaagggta gaagcgacgt agctgtcgga tgttccaagc gttgatgtag acctcgcctt    105540
gactgttggc cagcttgtat gttccgggct tcttagggag gcgtgagctt gtgacaccct    105600
cgggcgtctt gacgtagccg aagcaccaag tcgcccacct ggaggtctcg ggaccgaacc    105660
ccttgggcgt ggtagcgtcg cagggactgc tgataccgcg ccgagtgtag taaggccatg    105720
tcccgagcct cttccagctg gtccagtgag tcttctcggt tggttcgatt gcttcggtcg    105780
tcgtacgccc tcgtccccat agactagaaa aaacagcgtg aagatggccc agtgagtctg    105840
tgggcaagat ggcctcggcc ccatagacta gaaaaaacgg cgtgaagccc gtggctcagc    105900
ttggtgtcgt tctcagactc cagaccaccg aggggagttc cttcatccat cgcctgctga    105960
acttgttgag gtcgttgtag atccgtggct tgagtccttg tagaatcatg tcgttggcac    106020
gctctagctg cccattcgtc atggggtgag ctacggcggc ctagtccacc cggatgtggt    106080
```

```
aatcctcgca gtaggaactt tctaccggtg aactgggtgc cgttgtcggt gatgatggag    106140
ttcgggaccc caaagcgatg gatgatgttg gtgaagaacg ccaccgcctg ttcggacctg    106200
atgctgttta ggggtctgac ctcgatccac ttggagaatt tgtcgatggc gaccagcagg    106260
tgcgtgtagc ccccgggtgc cttctgcaag gggctgacaa ggtccagacc ccacacagca    106320
aacggccagg tgatgggtat tgtttgcaga gcctgagcgg gcaggtgggt ctgctttgca    106380
tagaattgac acccttggca ggtgcgtaca atcctagtgg cgtcggccac cgcggttggc    106440
cagtagaaac cctgtcggaa ggcatttcca acgagggctc gaggtgctgc gtggtgaccg    106500
caagcccccg agtgtatttc ttgtaataac tcctgacctt cggcgatgga tatgcaacgt    106560
tgtaggacgc ctgaggggct gcggtggtag agctccttcc cgtcacccag caagacgaac    106620
gacttggcgc cccacgctag ttgccgagct tcggctctgt cgaggggtag ctctcctcgg    106680
tggagatatt gcaggtacag ggtctgccag tttcgattag gcgtgacccc ataccgctct    106740
tcctcgacgc gcagtgcctc accctcgggg gccgagggtg cctcgggcag ggccaaggct    106800
ttctcgggct cgggcgtgtc gctggtcttg actgagggtt gatgtaggtc tcgggagaag    106860
acgtccgggg gaaccgttgt ccgcgccgag gctatcttag ccagctcatc cgtagtctcg    106920
ttgtatcgtc gggcgatgtg gttgagctcg agcccataga acttgtcctc caggcgccga    106980
acctcatcgc agtaggcttc catcttcggg tcgcgacagt gggagttctt catgacttgt    107040
cgatgacaag ttgcgagtcg ccgcgagcgt cgaggcgtcg gacccctagc tcggtggcaa    107100
ttcgcaaccc gttaaccgag cctcgtactc ggccacgttg ttggacgccg ggaaatggag    107160
gtgcaacacg tagcggaggt gcttcccgag gggcgagatg aagagcaggc ccgcgcccgc    107220
tcctgttttc atcaacgacc cgtcgaaaaa catggtccag agttccagtt ggatcggagc    107280
tgctggaagc tgggtgtcga cccattcagc cacaaagtcc gccaagactt gggacttgat    107340
ggccttccga ggggcgaatg agattgtctc gcccataatc tccactgccc actttgcaat    107400
cctacccgag gcctctcggc actggatgat ctctcccagg gggaaggatg acaccacagt    107460
caccggatga gactcgaagt agtgtcgcaa cttrcgccgc gtcagaatta ccgcgtaaag    107520
tagcttctgg aatttgcggg tagcggattt tggtctcaga cagtacttca ctgatgaagt    107580
agaccggcct ctggacgggc aatgcgtgcc cctcttctcg tctctcgacc atgatcgcgg    107640
cgctgaccac ctgagtggta gcggcgacgt agaccaagag ggcttctccg gcaacagggg    107700
gcaccaagat gggcgcgctt gtgaggagca cctttaggtt cccgagggct tcctcggcct    107760 cggggggtcca agtgaagcgc tcggtcttcc tcaagaggcg gtacagaggt aggcctcttt    107820
cgccgaggcg tgagatgaaa cggctcagag ccgcaaggca tcccatgacc ctctgtactc    107880
ctttcaagtc cttgatgggg cccatgttgg tgatggccgc gattttctcc gggttggcct    107940
cgatgccccg ctcggagacg atgaacccca agagcatgcc tcggggggact ccgaagacac    108000 acttctcggg attgagtttt acgcctttcg ccttgagaca cttgaatgtc gtttcaaggt    108060
cggagaggag gtcggaggct ttcctcgtct tgactatgat gtcatcgacg taagcctcaa    108120
ccgttcgacc aatgtgctct ccgaacacgt ggttcatgca tctttggtat gtcgcacccg    108180
cattcctcaa accgaatggc atagtaacgt agcagtacat gccaaagggt gtgatgaaag    108240
aagtcgcgag ctggtcggac tctttcatcc tgatttggtg ataccctgag taggcatcga    108300
ggaaagacag ggtttcgcac ccagcagtgg aatccatgat ttgatcgatg cgaggcgagg    108360
ggagggaact ttcggacatg ctttgtttag accagtgtag tctacacaca tccgccattt    108420
```

```
ccctccttta tttctcacaa gcacagggtt gacaagccat tcgggatgga atacctcttt   108480
aatgaaccct gcagccatca gcttgtggat ctcctcgcct atggctctgc gcttttcttc   108540
gtcgaatcga tgtagaggct gcttcacggg tcgggctcca gctcggatat ccagcgagtg   108600
ctcggcgaca tccctcggta tgctaggcat gtccgaggga ctccatgcaa aaacctcggc   108660
gttcgcgcgg agaaagtcga cgagcactgc ttcctatttg gggtcgagct cggagccgat   108720
ccggatctgc ttggaggcgt cgttgctggg gccgagaggg acggacttaa tcgtctcagc   108780
tggctcgaag ttgccggcgt ggcgcttcgc atctggcgcc tccttggaga ggctccccag   108840
gtcggcgatg agggcctcgg attcggcgag ggcctcggcg tactccacgc actccacgtc   108900
gcattcgtac gtgtgtcggt acgtggagcc gatggtgatg accccgttgg ggcccgacat   108960
cttgagcttg aggtaggtgt agttggggac ggccatgaac ttggcgtagc atggtctccc   109020
cagcactgcg tggtaggttc ctcggaaccc gaccacctcg aacgtgaggg tttcctttcg   109080
gaagttggag ggagtcccga agcagactga cagattgagt tgcccaaggg gttggacgcg   109140
tttcccgggg atgatcccgt gaaaaggcgt cgcaccggcc cggatcgagg acagatcgat   109200
ctgcaggagc ccgagggtcg cggcgtagat gatgttgagg ctgctgcctc cgtccatgag   109260
gaccttggta agcctgacgt tgccgatgac ggggtcgaca atgagagggt actttcctag   109320
gctcggcacg cggtcggggt ggtcgccctg gtcgaaggtg atgggcttgt cggaccagtc   109380
taggtagact ggcgctgcca cctttactga gcagacctcc cgacgctctt gcttgcggtg   109440
ccgagtcgag gcgttcgcca cttgcccacc atagatcatg aagcagtcgt ggacctcggg   109500
gaactcctct gccttgtgat cctccttctt gtcgttgttg tgggctctgc caccttctcgc   109560 cggtggcccg gccttgtgga agtagcgtcg aagcatgacg cattcctcaa gggtgtgctt   109620
gatgggaccc tgatgatagg ggcacgactc cttgaccatc ctatcgaaca ggttggcgcc   109680
tccgggaggc ttccgagggt ttctgtgctc ggcggcggcg acaatgtctg tgtcggcgac   109740
gtcgcgtttt gcttgtgact tcttcttgcc cttcttcctc gcgccgcgct gagcggacgc   109800
cttggggacg tcttccggct gacgcccctg aggctgcttg tccttccgga agatggcctc   109860
gaccgcctcc tgaccagagg cgaacttggt ggcgatgtcc atcagctcgc tcgccctagt   109920
gggagtcttg cgacccagct tgctcaccag gtcgcgacaa gtggtaccgg tgaggaacgc   109980
gccgatgaca tccgagttgg tgatgttggg cagctcggtg ccctgcttcg aaaatcgccg   110040
gatgtagtcc cagagggatt ctctcggctg ctggcggcac cttcggagat cccaggagtt   110100
cccagggcgc acgtatgtgc cctggaagtt gccgacgaaa gctttgacca ggtcgtccca   110160
gttggagatc tgcacaggag atagatgctc cagccaggct cgggcggcgt cggagaggaa   110220
caggggaagg atgcagatga tgaggttgtc atcgtccgtc ccactcagct ggcaggccag   110280
ccggtagtcc gcgagccaca gttccggctt cgactccccc gagtacttgg tgatggtagt   110340
cggggttcag aaccaggtcg ggaacggtgc ccgttgtatg gccggctga aagcttgcgg   110400 actgggtggt tcgggcgagg ggctccgatc ctccacgctg tcgtagcgtc ccccacgcct   110460
ggggtggtag cctcgacgca ccttctcgtc gaggtgggct tgacggtcgc ggcggtgctc   110520
gttgccgagg cgtcttgggg ccgcaggcgc tgtgtcccgc gtgcgccggg tgtgaccga    110580 ggcttcccgc atgaatcggg aagtcgcagc gcgatgctcc gggggtaccc ctgccttcgg   110640
gaggcagagc tctcggcccg tcggaccgcg acatcctcta ggagattttt gagctctcct   110700
tggatacgcc accctcgt ggtggatggt ttcggcatcg ctcggagtag tatcgctgct   110760
gcagccaggt tctggccgac cccactggaa gccgggggca gcctcgccct ggcatcgtcg   110820
```

```
gtgatgcggt gctggacgtc ctgggccaga tgacgcgctt ctccagccgg tgctcggcct  110880
gcccactcct gcccgatatt ttgccgaagc tgcacaagtt gtcctgcttc ctcgtcgagc  110940
ctggcctgta cctcgcgcat ttgctcaagc cgtgcgtctt gacccccgc agggactggg  111000 accacagcta gctcccgaag gatgtcaacg cgaggcgcag gcctaggggg atcaccatcc  111060
tccggcatac caagatggtt gccttcgtca agaccccta gatcgacgtg gaagcattcg  111120
caccttgggc cacagtcctc gtcgccgagg ctgtggctgc tatcggagca atcggagagg  111180
cagtagtcac atgcggtcat gaagtcccgc atgacactgg ggttatcgag cccggagaaa  111240
tcccaaccag agtcaggctc gtcatcttcc tcggaacccg ggggcccata ggtcgagacg  111300
gccgtcagtc ggtcccaggt tgaccgcata tgatacccccg gagggtttgg acatgccttt  111360
atgaaagcgt ccaccgaagc gggatcgctt ggtgggtcac aactgaatct aaaaggcatg  111420
ggatgggaaa cggacggtac ctcttgatcg acgggtggtg acgaagtcgc gtcagggacg  111480
gactgcaccg ttgtctcagg tacgaggtta acgcccagga agtccttcgc gagcgtgctg  111540
gcgtcatccg tctgcttggg gttggcgtgt tgcgggaaa cgacgcttgt cttcgtctca  111600
gacgcgaggt caacgcccga cgtgtccccc gttggggcgt cggcgccgtc gactcgctcg  111660
acagccgacg aggtgccgcc tcctgattgg ccatgcctac cccgcctcct cctccgtcag  111720
cggggaaggt gacgggacag acccggatat cgctcttccg ccacgtgggg aagacgtcgt  111780
cgattccgcc gccgacgggc gggctgacgg ccgccattgt cgttgtcgcg cggcggagga  111840
aggagtgtca tgtcgtagct gccgtcgagg gacatgaact caagactcct gaaatggagc  111900
accgtcccgg gttggagtgg ttgctggaga ctacccatct ggaacttgac gggaagctgt  111960
tcgtcaccat gcagtaggcc cctacctggc gtgccaactg tcagcgtttc gaccccgggg  112020
ggtccctgga ccgacgagta aactgtcgct gcgtgtccca ttccagatgg gtcggcacga  112080
gacgaaacac aaaggggga aaacagcaaa gggggaaccccg tggccttcgt gttgtcctgt  112140
gcccagggcg gatgcgcttg cagtaggggg ttacaagcgt tcgtgtggga gagagagaga  112200
gagagccttg tgcgtcagcc cgttctcccg cgcggccaac cctctcgtac gagagccctta  112260 gaccttcctt ttatagacgt aaggagaggg cccaggtgta caatgggggg tgtagcaatg  112320
tgctaacgtg tctagcagag aggagccaga gccctaagta catgctgtcg tggctgtcgg  112380 agaggtttg gcgccctgtt catgtgatgt cgtggccgtc ggaggagcgt ttgagccctg  112440
tggaagtaca gctgtcgggg ctgtcggatc cttgctgacg tctccttgct tccataaggg  112500
gctgagagcc gccgtcgtca cggagcacat ggggtgccat cattacttgt ttaccggggc  112560
gagccagatg ggacgtcggt cttgttcccc gtagcctgag ctagctaggg gtagggtaat  112620
gatggctccc cctgcgacgt ggtcggtccg agcccgaggt cgggcgaggc ggaggctcct  112680
ccgaggtcga ggttgagccc gagccctggg atcgggcgag gcggagtccg tcttccgagg  112740
tcgaggctga gtccgagccc tggggtcggg cgaggcggag tccgtcgtcc ggcgtcgagg  112800
ttgagcccga gctctggggt cgggcgaggc ggagcttctc atggcgcccg aggctggact  112860
tagctgctgt cagcctcact ctgtcgagtg gcacagcagt cggagcaggg caggcggcgc  112920
tattttcccg tcaggtcggt cagtggagcg gcgaagtgac tgcggtcact tcggccctat  112980
cgactgagga gcgcgcgtta ggataaggtg tcagtcgatc cttgcattaa atgctcctgc  113040
gatacggttg gttggcgtgg cgatctgtcc aaggttgctt ctccgcgaag cctgggcctc  113100
gggcgagccg aagtgcgtc cgttgcttga ggggaccctc gggcgagacg tgaatcctcc  113160
```

```
tgggtcggct gcctttgccc gaggctgggc tcgggcgagg cgggatcgtg tcccttgagt   113220
ggacggagcc ttgacctgaa tcgcgcccat caggcctttg cagctttgtg ctgatggggg   113280
ttaccagctg agattaggag tcttgggggt acccctaatt atggtccccg acatgtttac   113340
ttacaaaagc tccaccaagc ttgtcgagca tccaatgctt gggcgcattg agcctcttca   113400
agtgcttctt caatcccta gcctggattg caaaataata atgatcaaca aaagcgcaac   113460
agattccagt atggcattca taggtgactc atccagattg cattagctgt aaaagtaac   113520
agcaactaca cactacttga aaacaaaaga ccctttcat acatgtctat ctctattact   113580
tatatatgag cagtgccatc gtcagcacct cctgtatgta tacctaggac gacatcagct   113640
ggcgaggggc acgggacgc acgggcgtct tggacgggct caccctaaaa acacactaga   113700
acgactctgt tatccaaccg cccagaagag ctccttcctc aatgcaaagc gtaagaagat   113760
cagttagagt tttaccttat tggcaaggat cccagtacca caccgctaca gtgagagcgg   113820
cagtagcact ttctgccttg aaaaaaaatt gaggcccagt cttaaaacaa ctcgcagaat   113880
aataaggcat ttgaacagca gaccaaacaa ctagcagaat aaaaaagaag ctacgcaaat   113940
ttgaaggcga aggtatgctt agctgaccat cacgaatccc agtttcagcc catggagcgg   114000
gatttgttgc tcatgtctgc ctttctgtcc ttttagatag ctaatgccaa tagttcatgc   114060
aaaactatta tcaactgttc cattgtacat gtataatact tggaaataaa cacagccagt   114120
agccaccaat acccattcct tatgccaaat ttgtgacatg agatggaaat agtacatcaa   114180
taaccaaacg aggggtgagc atagaaattt aacatccaac atcaaaactt gcaaaacttg   114240
gatgtttgag tccacctctc gagcctaacg gacgtgaaat cgccatgacc tggcagcctt   114300
tgcatcaaaa aataactcca gttctatagt aaatgtaacc atgtgtgcat acgtaccttg   114360
cagttctgtg cggcctagta cttggtcacc tgcacaaggt acttgtaaca cccctggtgt   114420
tactgcaact aaaacttgag catagcatca taaacattgg cattgcatat gtttgacaca   114480
cctagagtgc attcactagg taaaaatttc aaacaagttg tattgttta gtgttttgca   114540
aatagaaccc tagatagga atttaaccct aaatagggat taaggggta agatataacc   114600
caaattgaga aaacctaaaa gctctaggga aatagtcatc aaatattctc aagaataaag   114660
ttgaaccaca tttataccc tcggatacca aaaaccctaa ttggaaccct agaaaaccct   114720
aaatccaaac cctaggggct tatgtgcaaa attcgaccac ttttggacta aagtgcaaaa   114780
accaagttaa ataagtatct taagtcattt gggtcactca tatgtgaatt tacaagccaa   114840
accctaagtt ttggcctcat ttgcaaaaag gaccctattt gaggttttat actaagtctg   114900
aaaacagtgt tatgggctca acttttgagc cttgtaactt ttaaatcata gggtttttgc   114960
cctaggtcac cacattaaaa ttatagccca atcataggag aacaactttg cttaagagtg   115020
tgagcatagt tttaagaaaa tattggagat aattgagcct gaagttggac tgtcagactg   115080
cttgaaatct gaaattcaga ttaacagtgg gatgacatga acttagggct taatttaag   115140
caagattcag tgactttttg tgggagcaca ttgtagcaaa gttatagctg gattgtagct   115200
ctacaacttt gctgtaggtc actggatgag ttgttatttg aaattgagag aaaactgggc   115260
tccaaacttg actgtcaggc tgtctgaata taaatctcca tggtacagtg ctaccaggga   115320
gatcagacca ccagcgcggc agtctctcac cgccgatgac tgatcttcgc tgagattcac   115380
gccgccgccg ttgcgattca cgtcgccggt gaccagataa gatcgctcgg taaaggcatg   115440
cgctggacgg cactccggtg aaccccagt acttcccctc taccgtgcgg cttgagcaga   115500
taagcccgct ggggatcccc gtcgctcggc cttacgccac gtatccgggc acctctgtcg   115560
```

```
catcgccgtg actccccact gttgtctcat cattgccggt gagcccgcca cggcggtgga  115620
cacgaaatcg cgaagccgat gatcttcctt atctccggcc gcccacactg tccactcaaa  115680
ttaagcgcca ccgcccctgg gatctataaa ttgaccctgc agagagcttc acaacatcat  115740
cacccaccca gccaccacgt attgctagca attgttcgcc caagctcgcg aattttgaat  115800 tcgcccaaa tcaattctcc gccacccgaa acccaacctc actgcggcca gccttattct  115860
ggtcagttcg tctccttctc tccctcattt aagctttccc ttaagtctac gatgcttgcc  115920
gacccacaca atcgagctag gagccctttg gtcgccggga acgcgactgt cttgccgcga  115980
tgttcacggc caccgtggcc agagcaagcc attgggccat agatggaatt aggttagggg  116040
aaatgctcgg gctaggtcca atttgatgtc cgccgctcgg gaaccctagc cgttgccccg  116100
ttcggccggt gcaggcactc gccggagttc ggctgggcgt gaacgccgtc gaggacctcc  116160
ctctgcgaag agttagaact acaggggctt ctctgcaatc tgtcagcgac acagtgtaat  116220
agtgatagaa gccagttctg attagccaaa ccccgaggac ctctgtgcaa agtcgccagg  116280
gcgcgagcgc gcgcgcgcgt tttcccctag tactgggccg gctgggctag aatcagccca  116340
acactattca atcttttttcc ttttctttttt ttgtagagct ttggaaattt gttaaaaatt  116400
gtagaaaaat cctaaaattg tgaaaccaat tttcctaggc ttcttatttt ccatagaatt  116460
taataaaaat agttgtatga attttaggtt aactaaggaa ttttaaggta tttaaagtag  116520
tttaaggtag tggttctgga tttttagaaa ataaatggaa tttccaaaaa tgtccaaact  116580
ttttacataa gttctataca ttatttagag gccttgggta gaatttgggt tgatttggac  116640
cttgtttgat acttagaacc taaaaccccc ctgcccttg aactccttta ctgactccgg  116700
aaaccctaag ttctcggagt tccgtgaagg aaagttgtat tcaagactta gataataaat  116760
ctttattatc ttcgcactct catgagcatt acatggcatt cattcttata tatataccta  116820
tatggttata tttagaaaat gaagaagaga ttgaagtgac caaagagaag acaccaccac  116880
ctacggattc tcaggccggc aattgtttct acttcgatat ctgcgggact gagcctgact  116940
cacctactaa cgaaggcaag ccccggtgca tttaccacct ccttgatgct tttaaaatct  117000
ttctcacttg attgctgcat taggtgatag gagttgaatg cttaaacaat tcctgcacta  117060
ccttccttga atttgattac cttccttgat cacccgtttt acaaaaggat tttgatgctt  117120
tgccttgctc tagaaaaaca aaaggatttg ttttacaaaa gatgtttggc aaaagtggga  117180
gggttatttt tgaaaataaa acttgatggt gaatctgtca aaggccttga tggattcaac  117240
atcggaaaag atgtacctct gccaggtacc aaactttggg tttgaaatga ttaagccgag  117300
accgggcggg tgacttgcac gagaaaggag tctcggtgta gtgtctccgt ctgagtcgat  117360
taaggaccgt ctcgatgtag gcctgctgac cggggaccct ttaactggtc acatgcctcg  117420
tcatgggtaa gccttgcctc gggcagacta aggccagaat aagataacac gaaatgggcg  117480
tggagcggtg gcgggagtag cgtgtaccct ccgtggcaag aggctggacg gtggtgtatc  117540
tgtgctctcg gtttgtgtga acctgatctg gtcttaaaaa ccccagtggc gggttgacat  117600
atgcaagggt taagtgctac atatgtcgtg tgattggaga tcctcagctg agtataatcg  117660
attcggatcg ccgtaccttc gcggttatga agacttggtc actgacttac acgtagcatt  117720
ccactaaaga tgatggtttt gttaagaaat tggctagtgc aggacaagtg atttgaacta  117780
gggtagaaag aactctagtt acaggtaatt ctacttaatt tgcaaataa aactggattt  117840 ttaaggatcc actttagtaa gcatttctgc aaaacagagt ctttgattat tgaaaagcct  117900
```

```
taccttgact cccttaacca gcatacccct gagagtcttt tctttagtcg ggtaagactt   117960
gctgagtaat tccatactca gggtttatcc ctccgttgtt tttaggtgag aagcgacaa    118020 atttttattg cttctgctcc aaggtggttc ccaaggaaga aaaacaagag tgaagccgcg   118080
ggaggacttg gtcctccata taggactttt gtttaaaaac tatcgggagg agttttttgcc  118140 tcccttggta ttgtaataat attactctgc actcctagga taactctggt ctgtaataag   118200
taacttgatc ttactttta aataaatgta agttatgtaa tcgcttctgc atttctatat    118260
cttcgatgtt ctgtaatgtc tgcaagacgg gtgaaacgtt cctggaaagg taagaaagaa   118320
gataccgaac ttgtgaagta atttaggaac atctataggg tgtctgatgt ctgttggaca   118380
aggacaactg taggtgggct taattacttg ggaggttccg tcacagctgg tatcggagcg   118440
tagcccttct ttgcagatat tatgaggcat cttcaaaaag attttctaaa agtcttacct   118500
agaaactctc ttcctttctt acctaagtat tctgaagagt ctatcttaaa gaccaggtag   118560
taagagtgca acatatagaa ggtgtgaatc aactaaggtt gattctgtaa ttatacatgc   118620
atcatgctaa gaaccatact aatcaaattt tcccccttag aaaatgccgc cgcgcacaag   118680
gagaacaacg cgcaaacata ctggaccgat tggtgtgccg agtcaccagc tgaccccaag   118740
gcatgataat agtagtagcg gaagcaatga tcctataggg gatcttgaag ctgaagtaag   118800
tcgactccaa gcgaaactcc gccgcagaac gactatctgg gtcatagatg gcgaccgcat   118860
aaatgagttg agaagagata tctgccatct gcgagatcag ctcgcggacc gggatttggc   118920
acttgactgg gttgttcaat cccgttcgct tgcatgggac aaggagcaaa agctcaagc    118980 tcgagtagcc gagctcaact tggctgttga tgaactgcag acatattgca ataccttaca   119040
tgaagagatt catgtattat attcgcaact gcatcccagt gagcctacga atcctggtga   119100
gtcggaagcc ggaccctcgc atgttgcggg acacgcgctt ggtggtgagt tagacctttt   119160 tcagcccccct ccttctatga ggctagtcga cgaatggtct cccacacccg acgacgaggc   119220
cgccaaaagc aacggaaagc aggaataatg gggtagtaga agtagaagta gtgtattgta   119280
taacaggttg ctctaatgta taatatttg tactattgca ataggttg tgctattgta     119340 taataggtaa tgtatcctgt tgtaaaaatt cgagtctgta cattactctt tttggtaatg   119400
taaaatggat ggttttcct tggcatatca tattgttttc caaatgttgt tgccacagat    119460
gccttccaag actcgagcac aggacggagc tagtacctcc tgtgggaggg agtctacccc   119520
aaatccacct cctgttcctc ccacactggc cgaggcgatt gtggccttgg taaatgcaac   119580
cgcggataat acccgttttc ttagagagat ggcgggtcaa caattgcaac aacaaggtgg   119640
gcggggttat caacagggcc cccgtgaaac ctcttacttg gacttctcag agacgcgacc   119700
accgctgttt gtcaaagccg aagacccgtt agaagcagat gaatggcttc gtgtgattga   119760
gcaaaagttt ggactgctgc gatgttcaga aacccagaag cctttattcg cagcccagca   119820
actgcgcgga cctgccagca cttggtgggg taattttgtg ccgttcaac cggccaatca    119880 ttagataact tgggaagaat tcaaggtggc cttccgcgag cactatatac cagaaggtgt   119940
tcttcacatg aagcaagaag agtttatgaa gctgaaacaa ggagggata ctgttaacca    120000 gtatctcaat aagttcaatc atttgtcaca atatgcaatc gatcaagtga acactgattt   120060
gaagaagaag aattgcttta tgagaggatt aaatgatcga ctgcaaagga agatggcaac   120120
ctgcatagat cttacttatg gaagagctgt cagtacagca ctggcagtag aagcgaagta   120180
tgcaggcgct ggtaaatcca agggtttggg aggtgacagg tctagtcagg gcccggtgaa   120240
caggcaacgg ttcgtcatcc ggccttctaa ccagaatcgt tctttcgctc gtccaccctc   120300
```

```
ctttcctttt aagcagccag tctttattcg tcccaataat gcccctacta catcaagtca 120360
gccgggtgcc ccaggcactc gattccctgc tttacccagc tcgtcgactg gatgtttcaa 120420
ttgtggcaaa tctgggcatt ttatcaagga ttgcccttat ccaaagcaga accagtcaaa 120480
taatcagcaa ggatctggga attcatctca agccaaggaa ataatatgg gcaaaaatac 120540 aaagaagacg ggacgcatat attatacgca agtggccact acaccggacg gtgagccggt 120600
aatgatgggt acgtttcttg tggccaatca tcccgcagtt attctctttg attctggtgc 120660
ttcgcataca ttcatcagca agaaatttgt ggagcaacat tgcatctcat gccatgaatc 120720
aaaagagggg tttaaaaatt cactcaccag ggggacaaat atttactaga gaagtggcct 120780
atcaagtgcc cgtaaccttg gccggatggg actttcctac taatatgatc attctgaaag 120840
gccaagatat atatgtcatt ttgggtatga attggttagc cagacataaa gcaactctca 120900
acactgatca gagaattatc aggttgagtc ataaccagga agaaattctt ttgcctatcc 120960
ccattccaac caaagctact ggcagagctt atgaagccat tataccggaa atcaaggata 121020
ttccggtggt atgcgagttt cccaatgtct ttcccgagga tttgcccgga ctgccacctg 121080
aacgggaggt agagtttgta attgagttga aacccggtac ggctccagta tctagaagat 121140
cgtaccgaat gcctcctaat gagttggcag aactgaagat ccaattacaa gatctacttg 121200
agaaaggatt tatccggcca agctcatcgc cgtgggggttg tccagccata ttcgtcaaaa 121260
agaaggatca aactttacaa atgtgtgtgg attatcgacc cctgaatgag gtcaccatca 121320
aaaacaagta ccctcttcca aggattgaca tttttatttga tcaactgact ggagcaaggg 121380
tattttccaa gattgatctc agatcgggct atcaccagat ccgtattcgg cccgaagata 121440
taccaaagac cgccttcact acgcggtatg gattatttga atacctggta atgtctttcg 121500
gattgacaaa tgctcctgcc cacttcacgt atttgatgaa ctcggtattt atgcccgagt 121560
tggacaagtt tgtggtagtc ttcattgacg atatttttgat atattccaag aatgaagagg 121620
agcacgccca acatttacgg atcgtgttaa cgcgcttgag agaacatcag ttatatgcca 121680
agtttagcaa atgcgtgttt tggctggacg aaattcagtt tctgggacat gtattgtctg 121740 ccaggggat tgcggtagat cccagcaaag tcaaggacat tttggagtgg aaaccccga 121800 ccactgttca tcaggtccga agtttccttg gactggctgg atattaccgc cgattcatac 121860
cagatttttc taagcttgtg aagccaatca caagtttatt gaagaatgat attaagttca 121920
attggtcttc aaagtgtgat gaagcttttg aacaattgaa gacattagta accactactc 121980
cggtattggc tcaaccggac atcaccaagc cctttgatgt atattgtgat gcatcaggca 122040
gtggactcgg ttgtgtgcta atgcaagaag gccgagtaat tgcatatgct tcaaggcagt 122100
tgcgccgaca tgaggaacat tatcctactc atgatctgga gttagctgtg gtggttcatg 122160
ccctaaagat ctggcgtcat tatttgctgg gtaatgtctg tcatattat acagaccata 122220 aaagcttgaa atacatcttc acccagtcag aattgaatat gagacagagg cgatggctcg 122280
agctaatcaa ggattatgaa ttagaaatcc attatcaccc aggaaaagca atgtagtgg 122340 cagatgcgct caattgcaag gcttcctgcc attgtttaac agtgaggact tctgacatta 122400
cattatgcca ggagatggag aaattaaacc tgggaatgat tcaacatggg acttcaaatc 122460
atttgaagct ggagtcaatc atcatacgaa gaataattga cgcacaaaaa gatgatgagg 122520
gtatgaagca catacgtgag aagataatgg ctggaacagc caaatgtttc aaagaagatg 122580
atcaaggtgt gatatggttc aataaccgca tagtggtgcc gaagaatgaa gaactccgcc 122640
```

```
agcaaatctt agatgaagca catcttagtc gctattctat tcatctggga agcactaaga   122700
tgtatcatga tctaaagcag cactactggt ggacgaagat gaaaattgaa attgcacgct   122760
atgtggctaa gtgtgacact tgcagacttg tcaaggccat acacatgaag atagctggtc   122820
cattacaacc tttgccgatc ccaacataga aatgggaaga tattagtatg gacttcattg   122880
tgggattacc caggactaca aaagggtatg attctatctg ggttataatt gatcggctta   122940
cgaaaattgc tcactttcta ccggtcaaga cagatcaccc ggttactgtc tatgcccatt   123000
tgtacattgc tcgtattctt agtctgcatg gtgttccgaa gacccatagt gtcggatcgt   123060
ggacctcaat ttgtagccaa gttttgggaa gcacttcaca aatccttggg tactaagttg   123120
ctccatagtt cggcctacca tcctcaaacc agtggacaga ctgagagagt aaaccaaata   123180
cttgaagata tgctgcgggc atgtgttctg gaatttccac aaaaatggga tgaatgtttg   123240
ccgttagcgg aattttcata taataatagc tatcaagaaa gcatcaagat ggcacccttt   123300
gaagctttat atggacgacg atgtcgtact ccgctaaatt ggtctgaacc tggtgaaagg   123360
tacttcttca ggcctgatat ggtgaaagag actgaagaaa gagttcaaag gataattcat   123420
aatttgaaga aagctcaagc tcgtcaaaag agttacgtag acaaacggcg aatgcccctta   123480 tatttccttg aaggatacta tgtctactta aaggtttcac caatgaaggg agtatcgcgt   123540
ttcggagtta aaggaaagct tgcaccataa tatattggtc cttttcttat cctggaaaga   123600
tatgggccag tggcataccg acttcagtta cccgaaacct tgtttgctgt gcataatgtg   123660
tttcacgtgt cccaattgaa gaagtgtctt cgggttcctg atcgaaccgt tgaagtgaca   123720
gatgttgtcc ttgaaccgga cttgacatat tctgagcacc ctattcgagt cttggatcaa   123780
aaggacaggg ttacccggag aaaactctca agttttataa gatacagtgg aaccaacatt   123840
ccgaagatga ggctacatgg gaaactcaag acttttttaga taagaatttc ccaggctttt   123900
tagcttcttg taaattgtaa agcctgtata gctgttgtaa taaggagtg attccaaaac   123960 cacccctgcc ttgtaccaga aataaggaaa taaaagtatg tcgtgtttcc ttttccatta   124020
cttaccctag gacttttaat ctcgggacga gattctttta tgggggaag gatgtaacac   124080 ccctggtgtt actgcaacta aaacttgagc atagcatcat aaacattggc attgcatatg   124140
tttgacacac ctagagtgca ttcactaggt aaaaatttca aacaagttgt attgtttag   124200 tgttttgcaa atagaaccta gatagggaat ttaaccctaa ataggatta aaggggtaag   124260 atataaccca aattgagaaa acctaaaagc tctagggaaa tagtcatgaa atattcccaa   124320
gaataaagtt gaaccacatt tatacctctg ggataccaaa aaccctaatc ggaacctag   124380 aaaccctaa atccaaaccc taggggctta tgtgcaaaat tagtccactt ttggactaaa   124440
gtgcaaaaac caagttaaat aagtatctta agtcatttgg gtcactcata tgtgaattta   124500
caagccaaac cctaagtttt ggcctcattt gcaaaaagga ccctatttga gatttatac   124560 taagtctgaa aaatagtgtt atgggctcaa cttttgagcc ttgtaacttt taaatcatag   124620 ggtttttttcc ctaggtcacc acattaaaat tatagcccaa tcataggaga caaacttttc   124680
ttaagagtgt gagcatagtt gttaagaaaa tactggagat aattgagcct aaagttggac   124740
tgtcagactg cttgaaatct gaaattcaga ttaacagtgg gatgacatga acttagggct   124800 taatttttaag caagatccag tgacttttttg tgggagcaca ttgtagcaaa gttatagctg   124860
gattgtagct ctacaacttt gctgcaggtc actggatgag ttgttatttg aaattgagag   124920
aaaattgggc tccaaacttg actgtcaggc tgtctaaata taactctcca tggtacagtg   124980
ctaccaggga gatcagacag ccagcgcggt agtctctcac cgccgacgac tgatcttcgc   125040
```

```
tgagattcac gtcgccgccg ttgtgattca cgtcgccggt gaccagataa gatcgctcgg  125100
taaaggcatg cgctggacgg cactccggtg aaccccagt acttccctc tgccgtgcgg  125160 cttgagcaga taagcccgcc ggggatcacc gtcgctcggc cttacaccat gtatccgagc  125220
acctctgtcg catcgccgtg actccccact gttgtctcat cattgccggt gagcccgcca  125280
cggcggtgga cacgaaatcg cgaagccgat gatcttcctt atctccggcc gcccacactg  125340
tcggctcaaa ttaagcgcca ccgccctgg gatctataaa ttgaccccgc agagagcttc  125400
acaacatcat cacccaccca gccaccacgt attgctagca attgttcgcc cgagctcacg  125460
aattttgaat tcgccccaaa tcaattctcc gccacccgaa accgaacctc acctcggcca  125520
gccttattcc ggtcagttcg tctccttctc tccctcgttt aagctttccc ttaagtctat  125580
gatgcttgcc gacccacaca atcgagctag gagccctttg gtcgccggga acgcgactgt  125640
cttgccgcga tgttcacggc accgtggcc agagcaagcc attgggccat agatggaatt  125700
aggttagggg aaatgctcgg gctaggtcca atttgatgtc cgccgctcgg gaaccctagt  125760
cgttgccccg ttcggccggt gcaggcactc gccggagttc ggctgggcgt gaacgccgtc  125820
gaggacctcc ctctgcgaag agttagaact gcagggcctt ctctgcaatc tgtcagcgac  125880
acagtgtaat agtgatagaa gccagttcta attagccaaa ccccgaggac ctctgtgcaa  125940
agtcgccagg gcgagggcgc gcgcgcgcgt tttcccctgg tactgggccg gctgggctag  126000
aatcagccca acactattca atcttttcc ttttcttttt ctatagagct ttggaaattt  126060
tttaaaaatt gtagaaaaat cctaaaattg tgaaaccaat tttcctaggc ttcttatttt  126120
ccatagaatt taataaaaat agttatatga attttaggtt aactaaggaa ttttaaggta  126180
tttaaagtag tttaaggtag tggttttgga ttttttagaaa ataaatggaa tttccaaaaa  126240
tgtccaaact ttttacataa gttctatgca ttatttagag gccttgggta gaatttgggt  126300
tgatttggac cttgtttgat acttagaacc taaaacccccc ctgccctttg aactccttta  126360
ctgactccgg aaaccctaag ttctcggagt tccgtgaagg aaagttgtat tcaagactta  126420
gataataaat cttttattatc ttcgcactct catgagcatt acatggcatt cattcttata  126480
tatatatata cctatatggt tatatttaga aaacgaagaa gagattgaag tgaccgaaga  126540
gaagacaccc ccaccttcgg attctcaggc cggcaattgt ttctacttcg atatctgcgg  126600
gaccgagcct aactcaccta ctaacgaagg caagccccgg tgcatttgcc acctccttga  126660
tgcttttaaa atctttctca cttgattgct gcattaggtg ataggagttg aatgcttaaa  126720
caattcctgc attaccttcc ttgaatttga ttaccatcct tgatcacccg ttttacaaaa  126780
ggattttgat gcttagcctt gctctagaaa aacaaaagga tttgttttac aaaagatgtt  126840
tggcaaaagt gggagggttg ttttcaaaaa taaaacttga tggtgaatct gtcaaaggcc  126900
ttgatggatt caacatcgga aaagatgtac ctctgccagg taccaaactt tgggtttgaa  126960
atgattaagc cgagaccggg cgggtgactt gcacgagaaa ggagtctcgg tgtagtgtct  127020
ccgtctgagt cgattaagga ccgtctcgat gtaggcctgc tgatcgggga ccctttaact  127080
ggtcacatgc ctcgtcatgg gtaagccttg cctcgggcag actaaggcca gaataagata  127140
acacaaaatg ggcgtggagc ggtggcggga gtagcgtgta ccctccgtgg caagaggctg  127200
gacggtggtg tatctgtgct ctcggtttgc gtgaacctga tctggtctta agaaccccgg  127260
tggcgggttg acatatgcaa gggttaagtg ctacatatgt cgtgtgattg gagatcctca  127320
gctgagtata atcgattcgg atcgccgtac cttcgcggtt atgaagactt ggtcactgac  127380
```

```
ttacacgtag cattccacta aagatgatgg ttttgttaag aaattggcta gtgcaggaca  127440
agtgattgaa ctagggtaga aagaactcta gttacaggta attctactta atttgacaaa  127500
taaaactgga ttttaagga tccactttag taagcatttc tgcaaaacag agtctttgat  127560
tattgaaaag ccttaccttg actcccttaa ccagcatacc cttgagagtc ttttctttag  127620
tcgggtaaga cttgctgagt aattccatac tcatggttta ttcctccgtt gtttttaggt  127680
gaggaagcga caaattttg ttgcttctgc tccaaggtgg ttcccaagga agaaaaacaa  127740
gagtgaagcc gcgggaagac ttggtcctcc atatagaact tttgtttaaa aaccatcggg  127800
aggagttttt gcctcccttg gtattgtaat aatattactc tgcacttcta ggataactct  127860
ggtctgtaat aagtaacttg atcttacttt ttaaataaat gtaagttatg taatcgcttc  127920
tgcatttcta tatctccgat gttctgtaat gtctgcaaga tgggtgaaac gttcctggaa  127980
aggtaagaaa gaagataccg aacttgtgaa gtgatttagg aacatctata gggtgtctga  128040
tgtctgttgg acaaggacaa ctataggtgg gcctaattac ttgggaggtt ccgtcacagt  128100
actgatggta ctccggtggc gccatttaca tctcaagcaa ttttctcaa agttggattc  128160 ttgatccctg catatcgctg gtcgtgaccc gtgggcacgg cgctcggatc cggcagcagc  128220
agatcgaggc gaggccgcga gggaggagaa gagccatgat gggggcatc agatcatcgc  128280 tcaacgacag cagtatgggc gtcctcttcc tgctggtgct cctgctggat gcgggcgtcg  128340
tcctcctagc cgtgctccta gcagtagagg ctccagtagc aggagaagag caggatgcg  128400 ggcgtcgtcc tcctggccgt gctcctactg ggcggcgtgt cgtgctcctg ctggtgctcg  128460
acgactggag cctgctgctt ggtggtgctc ggcggatgag caggggatcc gatcgggtag  128520
gggatgagga tgagatgact gatcggatca gatgggcagg ggatgaggat gagtggatga  128580
ccgaccggat gagttggttt gctcggaagc tgccggctgg gggatgggga ttagatcatt  128640
agtgtttgtc ggtttgggtg tttgccactt tgggtctttg gcggaatgat gccttagtgg  128700
gcaatgggct ggcgcttggc gcctgggcac aatggacaat ggtgggctgg cgatttgttc  128760
attggtgtcc atgtgtggat cgacagtaat ggactaatgg ttaatttcgg atatccaacg  128820
aattacccgc gggtgaggtt taatatccaa atccatgtct gctttatctc ggatcgggta  128880
cgggtctaac ccgcaggtca aaaaacatat ccatatcctg atccgtcggg tcgaatatcc  128940
gacggatatc actatccacg cattaaattg ccatccctag atgtgagact taaggcatgt  129000
ttgttcgcta cctaagttat cacactttgc ctaactttt cgtctaaggt tagttattca  129060
attcggacga ctaaacttag gcaaagtgtg gcacatttag ccacaaacca aacatgcctt  129120
taaccctctg gtttagatcc cgtttcgttt gagctgaata tacttattaa atgtctaaag  129180
catagcctag agcctgtcat gtcatgaatc atgaaatgac aataaaacat aaacaaaagc  129240
atagcctggg agtttggagc accgcgctgg gggcactgaa gacgacggat cttgcctctc  129300
agcctcggcg atgggcgtcg gacgcaggag atggcattaa ccaccgctat attaataaaa  129360
cgtattgtat atatgtgcaa tacgtatata aagagaaata ttcgtggcat taaccaccgc  129420
ttatcaggtt gcttataccg tacaaagaga cgatattata actataaaca tactgttgat  129480
gagaaaataa aaaataatca tatttcaaac gtataatttt atttgaagaa gattcttatt  129540
taagcaagat ttttaccta tatgatatat agaaaccgta cgaacataca gtcagctaac  129600
tagttcattt taaattccaa aaaatgttta gttcaatcta atcagaattt actattgact  129660
atgttttttc acaatatgtc ctatcaaaaa tatcgtacga gacggtttta tgtttacaag  129720
tttctagtat actcactaac atctaagaca attttgtata gtctagatga ctctaataat  129780
```

```
atctttattt gagatggttt catatacaga agtgtctaat atactaacca aaataaaaga  129840
cacttcttgt aaacttaatg cctcaaaagg tatatttatt tgagacggtt ttcaacatca  129900
aactgtatta aatcaatata agacatttcc aaccatatat ctgcctcaaa aaccttcttc  129960
attaaagacg gatatccaac aaaccgtctt accgtactca gcaccatatg ataaaagacg  130020
cttctataaa atgcactgat atttgtctta agatgtatgt cttaaataag catatttcta  130080
gtagtggatg tccaagacat ccacagagtc attaacttag gtcataatca aaattttgaa  130140
cgaaacgcag tacgataagg ccttcacagg cagctaactg agggtttgcc actaatctag  130200
tctagaactc gtcgaagtcc tgaaactcct gaaagtcctc cacgttgcct tcatcttctc  130260
ctgagcacta gttgcaatgg ggacaacctg gggtttggtg tttttaagca atggtgagta  130320
cacctcaacg tactcaacaa atgtcctgtt tggctaaagt ggactagctg tatgtggggt  130380
taagcttaaa gcagttgctt ttagttggtt aggtatttat taccagtaga gagccatgtt  130440
ttagcaataa ccccaagtta taaacccaaa cattactccc tccaagagga aataccaaga  130500
attcataatc ataatcacca tcattaagca tcatcataaa agtatccaga gtaactctaa  130560
tcaaaggagc tcccaaggct gctcataact gtgagcatgg ctgatatact agcttctaac  130620
actctacaga ggttgcacac tttacccaca agtcgtgatc cctttttgcc tcaggtcgat  130680
caaaccctca aacactacca aggtgagtcg gcaaggtttc actacgtagc tgtaacaccc  130740
tgaattttgg ggtataaaaa tttccttgct ctatactcaa aatctaggtg ttacccttc   130800 ctttattcac ttttcttttc cctttatcaa aacagtagag agttattttg gttctatatt  130860
ggtgtgagct ctagaagtgt catgattgtt gcattcatgc tgctacatag tgtttccaag  130920
tgatgatccg aggtgaggac gagctgacca gtcgggccca cgctagggc acagatgact   130980 gacaagtggg gcccagggggc aagggcaccc acgtgaagcg atatccagcg atctagaccg  131040
ctagatcaag gctaaacggc taggattagg cgtcaggggg gttaacagca ctgcggccgg  131100
cgctgctcca tccgcagcgg tgaagtcgcc aaagacgaga caagcgcgga ccccaggggg  131160
tctggggtcg ctggagttgg ccagaccggt gaggggacc cgacgaactc gatggcaggg   131220
ttctggccat gagaacggga ctggaggtga gtgaatggcg gaggggcgc tctgggcggg   131280 acacttattg tgatatcctg gcccctggga tgggatgtcc tggcccaagg cttaatagaa  131340
ttaatagtgt aatcatacca acaaggtgca tcttcttttt cggaagccta tctcgaaaga  131400
acctccaagt taagcgtgct tggcttggag caatttggga tgggtgaccg accgggaagt  131460
tttctcgggt gcgcatgagt gaggacaaag tgcgcacaaa agactcgtgt tggtctgtgg  131520
ggacaatata tgatcctaga cagctgccag gagtaagtac cgccggtcca gggattagac  131580
ggggtgttac aagtggtatc agagccgaca ctcgcggttt cacggcgtg tgtgggctag   131640 ggggttcggg tatatggcgc atggcacatg tgggcccgga gtggtcacat ggcatggcat  131700
atgacggcac tagacacaca gacgtggcca agaggggagg ttcctggatt ggggttgacc  131760
gacgaggacg tcggtcttct aaggggggtg gattgtgata tcctggcccc tgggatggga  131820
tgtcctggcc caaggcttaa tagaattaat agtgtaatca taccaacaag gtgcatcttc  131880
tttttcggaa gcctatctcg aaagaacctc caagttaagc gtgcttggct tggagcaatt  131940
tgggatgggt gaccgaccgg gaagttttct cgggtgcgca tgagtgagga caaagtgcgc  132000
acaaaagact cgtgttggtc tgtggggaca atatatgatc ctagacagct gccaggagta  132060
agtaccgccg gtccagggat tggacggggt gtgtaacacc ccaggtgttt attttccgct  132120
```

```
caacaacgag ttcggattta agcacgcaat atcagtggat aaaacgaatt ttaaatttta   132180
atcattgtcg cttatcgcta ttttaatatc gcatcggtgt cgtttgtcgc gagtgcgaca   132240 tcgttttat tttttatct gtccgggctc ttcctaaatt ttcgtaatgt tcggaaccta   132300
gctgttccga aaatcggtgc gtccgatgag tatttaaaat ccatcgctcg cgcgaacaca   132360
aattcggaag cccgaactca ctcgaatgat cttatttcga gcaaattaat ttgaacttga   132420
cgactaaaat gttcagggta aaataatctg aatcgcgcat tgtctgagaa agatcgtgcg   132480
cggggatatg atctaatttg ttctttagcc cgcaatgtag gataaccaaa tcaactgtgt   132540
tttggtgacg gataagtttt tatctgattt caattaaatg taacaccgat taaaacattg   132600
taactaaaat catttttaat tttagtcctc ttacatcttt ccaaattcta gtcccaatct   132660
ccagctgata attgtatttt tattcaaatt tttgagtaaa agaaaacgaa ggaagaaaat   132720
atctgcaacc gctcttctct ctgattttat ccaccgcttt tcccttccat atctgaagtc   132780
actagcctgg atattttctc cacgtagttc tcctcttcct cacgtctcct tctctcttat   132840
ccattggacg ctagctcgct ggaaaatctc acgcacgtct ctcctccagc cttacccagc   132900
gaccagcatt tcttccatcc atcagcatcc aaaggcagcc ggctgccggc tgtgctcgtc   132960
ggaccctccg agcacctctg tgcccgacga cctgaccaag ctcgtctcca gcttgcgtcc   133020
atcctgtgct cagtttccat ccactagcac cgtgtctctg gtcctgctcg tcgtggacat   133080
cgtcggctct agttccttgc tcgagctcgc cctttgcgca gaccgcgtct cccctcacct   133140
tgccgcggtc gggctggccg tcgtcgtcag cttgtgtcca tgccgacgaa tttgtcgaac   133200
tgctcactgc atctctttaa tctcgtcgcc tgatttttct gtaccgcgcc cgcaaccccc   133260
tagaaataaa aatcacgccg ccgagcgctc ctatccttat cccgccaccg cccttggtct   133320
cctacaaatc tccagcgcgc aggtttcttc tccacgcacg cccggcagca agccgcagcc   133380
gagcagctcc ttcccatctc ccctctgctc gctggctgaa tccccagccg ctcggctctg   133440
cttttctccc atggcgcggg gttccctgca ggctgctcgc ggtatccatc tcctctgctc   133500
ctgctcgtcc gtccctgagc tcctgtgccg cggcacctct gttcggccac gcctgatcgg   133560
atttcttgtg ccgtggcttc ccctccgagc tcgcccagct ctattccgc gcccatggcc   133620 ggcgctccct gcttggttcc gtcgtcgcg ccgtcgtctt actgctcgcc tttgcgtcgc   133680
gcgcatagcg ttctgttgtt cttgcacgcg cgaagctctt tgctcgtcaa cgcttcagcc   133740
tggatttcgc tttgtcgccc agctcggctc tacatgacta catctcccat gactgtctac   133800
tctagctcgc cgtagttcct gcgcgcgtcg agttttctct actctagctc gccgtagttc   133860
ctgcgcgcgt cgagttttcg tgtggagctc tctgctcacg cgtagctcgc tctttctttg   133920
ttgccgcgcg cacgaatttt atctgctcgt cacagcgtgt cgagttctca caccatcatc   133980
gcttctgtcg caagctcgtt ggtcacagtt gtcttgaccg cgttaactcg cgactgtggt   134040
cgtgttcatc gaattcgcca actctttgtt gccgatttga ctgtcgtcgc ttcgcgtgtt   134100
gtcgagccgt cgttttttcc tgtcttgtgc tcgcacggtt tcctgctcgc cagcgtgccc   134160
tctcggctcg ctcggcttta atttccaatc acgtcgtcga tctcgtcgtt tgccgtcgag   134220
ttgtcaaaca cgtcatctcc ggctcgatcc ccacctcacc agcttacccc agacttcaat   134280
cgaaggtcat cgtcgctcgt gcgtccccaa gaaaacccaa gaatcgggtg aagacgaagt   134340
tagcagcgcg atattcccta agcgctcgac aaattgcgtg gatcgaaaaa tcactgccga   134400
tctcatggat tcgtgtcaac tgttgaaacg gtaagctgat gaattgttta gaatagttcg   134460
atcgttgaat aagttaatgt gttagtgcga ggctcattag ggtgctcgat aaattgcgta   134520
```

```
agtcacgaaa ctctcgtcga cttcgcagtt cttgcgatta tcgagccagg ttcagttata 134580
gcgagttatt tcgctattcc ggtcacttag ctgaattagt ggaccgagta gaattttagt 134640
aggcatatgt gttgataaaa tattttaatc acttataaag atgtagtata atttataagg 134700
caagggatta gttcagaatt taattaatta actgataagt tgtgattagg ctaattatat 134760
ttcttgtgta tagtttgttg ttcgtgatgt ttgcgttagg ttcgagaagc gtaatcattg 134820
cgcgtagtcg catattaata actagtgttt ccgtacaaaa ttgtacaacg cctcgccact 134880
aggtgtttaa tacgctatcg tatagcacta tttagatttg tgctattctt gtttatatgc 134940
attcatgtgc atcgtgcatc tcaattaggt acgataattg atcgcgtgat gcggaagaca 135000
agccaagtcg accccaagcg cgggctaatc cgcaggatga tgctgatgga caaacctgaa 135060
aatggtcgcc aagtggacgt cgtctaacaa cactaaccta gtgttaccca ggcaagcccc 135120
ggtgcatttg ccacctccct tgatgttttt aaaatctttc tcacttgatt gctgcattag 135180
gtgacaggag ttgattgatt aaacaattcc tgcattacct tccttgatct tgattaccct 135240
ccttgaaaac ctgtttttac aaaaaggttt tactatgctt agtattgctt agaaaaacaa 135300
aaggatttgt tttagaaaag atgtttggca aagtgggagg gttgttttca aaataaaac 135360 ttgatggtga atccatcatg gctatgatgg attcaacatc ggaaaagatg tacctctgct 135420
aggtaccaag ttttttggtta aaagattaag ctaaggccgg gcgggtgact tgcacgggaa 135480
aggagtctcg gtgtagtgtc tccgtctgag tcgattaagg accttgtcga tgtaggcttg 135540
atgatcgagg acccttaac tggtcacatg cctcgtcatg ggtaagcctt gcctcgggca 135600
gactaaggcc agaataagat aacacgaaat gggcgtggag cagtggcgag agtagcgtgt 135660
accctccgtg gcaagaggct ggacggtggt gtaactgtgc tctcggtttg cgtgaacctg 135720
atctggtctt aagaaccccg gtggcgggtt gacatatgca agggttaagt gctacatatg 135780
tcgtgtgatt ggagatcctc agctgagtat aatcgattcg gatcgccgta ccttcgtggt 135840
tatgaagact tggtcactgc cctacacgta gcattccact aaagatgatg ggtttttgtt 135900
aagaaattgg ctagtgcagg accagtgatt gaactagggt agaaagaact ctagttacag 135960
gtaattctac ttaacttgac aaataaaact ggattttaag gatccacatt agtaagcatt 136020
tctgcaaaac agagtctttg attattgaaa agccttacct tgactcccat atacccagca 136080 taccctttgag agtctttctct ttagtcgggt aagacttgct gagtaattcc atactcaggg 136140
ttttatccta acgaatcaag ctgatcatca acnnnnnnnn nnnnnnnnnn nnnnnnnnnn 136200
nnnnnnnnnn nnnnnnnnnn nnnnnnnnnn nnnnnnnnnn nnnnnnnnnn nnnnnnnnnn 136260
nnnnnnnnnn nnggtcagcc cagattgctt ctgcgagcgc accggctatt gggtcttcct 136320
gtgttctgct agccgctggt gcagactctg agatgcatct cacatatttg ctgggacttc 136380
tcactcttct gactaccagc ggcagatatg ttgaggagtg ggtccgtgtg ttcaatgcgt 136440
cagtatggat cgacccccgat caccagtgga tgaggttccg ctttgagcga gaggatgtta 136500
cacttcatgc tagctagatt cgccagctgt ttggattcaa tgagtcatcg acttgtcttc 136560
atagcttgtg ctatggtacc tctgatcctc ctcgtcgccc tcacgacgga gttgctccag 136620
ctacagctca catcgcggct ttgttccgac cgcccttctc agatgggtcg cgacgttctc 136680
cggcagattt cactacagta gccaagtact tatatcagct catgagacgg acgcttctgt 136740
cgtggatggg ttatagagag gctaccactc atattcagct ttggctcctc ggtgccctga 136800
tctttcattc agagtttgat gttgttgact tccttatttg tgagatcgag gacacggtat 136860
```

```
tggatggtct tcgtgctcgg cgacagctgc caaatgctca ttatctctgc cacatcttcg    136920
cacagctgat ccgaccacca tagttccagg gcacccttga ggcctcacgc ctcctatttg    136980
gctcctacca tccagcccct gaggatccag taccagtacc tgatccagtg acagacattc    137040
aggcagagga tacaagtttc catcagtttg agacttaggg cgcagcagtt cctgacgatg    137100
atgatgatga tgatgatgat gattttggga ttccgcctct gcctcctgtg cctccacgct    137160
cacatgacca tgaggcccgg agttctcgtg ctgcccctgc tgttcctcct gccattgacc    137220
ctgctctggc tgcgatcctc cagactctta ctcagcagca ggctcatctg gcagcggtgc    137280
aacagcagat gtccgagaga atgctatcga tgttttagac tattcaggac agacaggaca    137340
ctctgcagca gcagcttttg gcagacaagg ctgagaaccg ggccttcatg actcacatac    137400
ttcagcatac cggtgctcag attcctcctg ttcagtctgc accccctcta gatcttcagg    137460
ccgctgttgt gctagcccct caggcaggac cccctctacc ttcatttggt ccttcttcct    137520
ctccgctcct gccggtcacc ctggtttttct cgtcgccggt catcagctcc atcagcgctc    137580
agccgccagt gccaccagct cctgctgtta ccactgctgt tgtggcggtg tctgtgacct    137640
cttcagcttc ggtagctcct gcagcacagc ctccatccga gtcagtacta gctccagctt    137700
ctacggtaga tcctggatcc gaggctgact ctgaccctca gctggcgttt gctcttctgc    137760
cacgatcgtg atcggatgcg ccccagccac ctccttcctc ttctggtctg taggttcagg    137820
tttccttttg gtgtttgacg ccaaaggggg agagatatga gagttgtgag agctaggggg    137880
agttagggag ttagtataga gtcattttga tgtaatatat gtgcttgata ctctctgtac    137940
tagatccact tttgtatgac gattttggct cacaaactct attatatgct ctcgatgctt    138000
atgttgactg tgtgtgtatt gtgttttcac cttatatgtt atcaccagtc tctagttctt    138060
gttcatcgat ttgatttcac tttatatga acaagaaact tacaatgtgt atgcactcac    138120
tcttattatt atgttacaca ctcttttctgt caaaaatttt tgagtataac taaccatctt    138180
ctctattgac agaaatttca aaacaaacta ctctcacaat cttgtaggtt gtcatcaatc    138240
accaaaaagg gggagattga aagcatctag gcccctggtt ggttttagtg attaatgaca    138300
atgtaatttt atatgtgact aacatgtgtt ttgcagaggc aaatggtaag ttaggtcgca    138360
ttacatgtag atgtactaca acggtgaaaa caatctcgga gataagaact tgaagcgacg    138420
gctaaagcga caaacaaaa agtgaaggtc ttcgtattcc gagtgtcaag gagttgcgga    138480
cactcgtgat atagttaggt cttttatttt gttttagtcg tactataaag aggggttgtc    138540
gatgagtagt ttgaccaaga gagttctagt gtagtgttgg tgcatattca cactcacata    138600
tagtgctagg tgccactcta gaacatactc acaagttaga acgaaaaccg aattgaaaaa    138660
acagcacaaa acagaaacta gggtttctgg ctttggggca ccggactgtc cggtgtgcac    138720
cggactgtcc ggtgcaccct ctgccagtgg ggccagcctg gcccaaggaa gagggttccc    138780
tgcgcacaga aacctgagag cgcgttgttc gcgagttgaa ttttagtgga ctgtccggtg    138840
tgccatctgc ccaacggcta gctgtcagaa ctagccattg gagtcgaccg ttggcgcacc    138900
gttggcgcac cggactgtcc ggtgcgccca tgtgcagcag attcctggta atggctagtt    138960
ggtgggtgag ggctatttat accccctcca cccactatat tgatggtctt gctacccaca    139020
tttactccta cacattggta gagcattgca agcaccacaa agcctagtga ggttatttga    139080
gaatcttaat cccgcatttg daccttatta gcgctagcga gagccaccta gagcatacac    139140
cgcatgcatt aggcttctct tggtcaagtg aaagtctatg gcttgttact cttggtgatc    139200
gtcatcacct agacggcttg gtggcgttgg gagctcggtg atcaccgtgg agatcttgtt    139260
```

-continued

```
ggtgacccga ctcaagtttg taagcggtcg tgagggatcc actgcgctgg agtggcaaag   139320
gatcatctcg ttgtgagcac ttggttcttg cgaggaccaa gggggagtga tacccttgcg   139380
agggtgctcc aacgaggact agaggagagt gccgactctt cgatacctcg agaaaaattg   139440
gagtcttcta aaccttgctt tacattccgc acttaattaa aacattttac attgtgtatt   139500
tgtttagcaa gtatttgaaa tattgtctta acattgttgt atttctatta ttattctctt   139560
agtgatagtt atcggggtga agttggactc ttgcttagat tttaattagt gttgattttt   139620
agaaaagtcc aattcaccct cctcttgggc atcgtgatcc tttcaaaact cactcaattc   139680
cgtctaatcc acgtggattc aaaataaaac gaacagaccc taatacatgc gatccgacgc   139740
tacaccggaa ctatcagtgg tcagcttcta ggcttcagca ttatacgtac tatgaaaata   139800
tgaatgcact tcaggtcatc atcaacaacc aaaatggata tagcaaatat tcaggctcat   139860
tatacttgaa aacaatagaa ttacattaaa aaaggccgaa accgtgaggc tggattaaca   139920
agagaaacgg taatggtaca gtaattcatg aagtgaagga ttttacatca ccaccagctg   139980
gtgctgaacc ttcccgttgg atccagctaa ctgcccttgg caggagcatc tacaaccaat   140040
acccaaagtg ggttatctta cttatctaga gccctggtat cgcaagccca atatgcctca   140100
gggtcagggc aggaccaaga aatgtggtga agttcacatt cccaaggcaa ccctacgtct   140160
caatgccacc tcgaagtatc atctagtaaa agcaaagttc aacagaaatg ctgtgccagc   140220
aagttgtctt ggaaccgacg tggtaaaatg agcatcgttt gatcactttg tttttcttct   140280
cgatgcaatc tccgctgccc atgcttttcc caagtctgtc tgaaatttgc ctgcatggga   140340
attaggtgcg gggatatggt tttgttacac aatgactcta atgctaatag cctaggctaa   140400
gtttaccatc cccatattca aattccactc tgcgaatagt gcaatctaag tgcaaaacag   140460
tgttttgggt gggtgaactg ctggacacgg tctaatacaa tgtaaaaatg agatcaaaca   140520
taagcacgtg ataaaagaaa accataaaag gcataggcat gtatcagttc atggtaaaga   140580
aaaccattat aggtggtagt gtccagtttt caattagcaa taatcattca ggcactaata   140640
tgttctgaat tgctgatgaa tgtttatatt atctcaggaa aacatttttta agtgtaagac   140700 caaaaaaatg gcaacatcct tctcagctta aatgaactgt tcaaatttat gtacaggatg   140760
ctcatgaaaa ttgagaagag caagatttat gtactggatt gtcatgaaaa ttgagaagag   140820
caagatttat gtactggata tcatgaaaa ttgagaagag cataacagaa agagaaaat   140880 cacacctgct gttgattgga agaattcttc aaggtcccgt ccttgctctg aaaattttaa   140940
aatacatagg cgtaagtgtg atactgttaa ccccatctat caacaaggag ttcaccaggt   141000
gttaagtgat agtacattga tcatatgtat cacttctcac acccagaagg ccgtggagca   141060
aattaaataa tggtgtaagc acagatgggc agatctaggg cggaggctgc cacatgagtg   141120
gggtcttgag atgggataaa tcgagacaag cctcccctgc aaatgcagag aggctgtttc   141180
gaactggcaa catagtgact tagtgagact gccctcacca ctacaccagg cctacccaat   141240
ataagcacaa atgatgcaaa gaaaagatg tgctgtattt gaaatgtgaa atgtgagctg   141300 atttactat atacatttat ttggttatta caacaagaat atttgatgaa tgcatttaaa   141360
tagttgtggt ttgtacttta tagctactgt gcatgggaaa tgttagttca aatattcaag   141420
caccagtatg aactcacccct tttcatactc cagagcttga agtatcatct caacctggaa   141480
atataacagt gcaacaaagg attacagcat gcaaaggaaa aggaagaagt ggagccatat   141540
gggttagggc cataaatcat aatgattgcc tacattagtt aaatatcctg ccagtttat   141600
```

```
gcattgccta ttgaatgatc acaagaacta ccatctgata gcttcagaca gacgttgcaa 141660
tcatgccacc aacttgatgg attgaaatat gaaactgtac cttgtcaaaa tctttgacaa 141720
ccttcgcttc caaagacgca ttctcctcat actccatcca aagttcacga atttcttgtg 141780
ctgcaagaca acagcatgca gataaaggca agtatttatt atatatacca tgtcaaagat 141840
cacatgaact ctttagtctc gcctgtacag agaacatcct tttatcctgc atgaaaaact 141900
gtttccaaaa ggctgctaag atactttatt tagttctaaa aggttcactt cacatgtaag 141960
ggatgctgga tctctccaat attttttaac gattaatgat atgaataatg agaacacaac 142020
cagaatacta gaattctatg ttgtgaaact cttagggaaa aaatgttgga tgctatgata 142080
gccatttgag cataaataat ttacgatcca taatgcttca aggtagaaaa tcattagaga 142140
tggaataata ttatcaccat caattacaat atcatgttca aattccaaaa ctcatagtca 142200
tcaacatttg ctgaatataa actcttcggt tttggcttct acaaaaacat cccttatctt 142260
ttcaacctcc atttcaaaat gtagggcgta aggattcaaa aaagtcaatg aaactagtca 142320
aaatatttgt atatttattg cacaaagata aatctataga ttcatatttc acatgcattt 142380
tagtgagaca ttgcttttgt agtaattgat aatatattga gttcatatat tgcaagggaa 142440
attattggat aaagcatatc tttgaatgaa attctcaaac actaatacac cttataaaaa 142500
gaaaaagaga agtataaata acagtttctc tggaaataat ctgagtgatt ttaagttacc 142560
aagagtttcc ttgacaccta actaagggat gtgaatactc taagaattat ccaatactta 142620
tttaaactat gtatcaaaaa ataagaacaa aagctgcccg ctggatttct acaaaataat 142680
tgccaggtta tgatctgctt ccctgatgga agtgaaaagt atcggatgga aaaatgacca 142740
tctaagaaat aataataaca gatgaatagc ttttcaaggg taaaataaaa tatgtatatg 142800
acctgcaagt actatagtat tgtattcaca aaattcattg gcatccacat attgttcttt 142860
tttccttgaa actatggtac tatgcacaca taatgggatc attaagtcta gactattgag 142920
taatctagaa agatgatgcc agtgtgcaat agcaccacat tcatttcata tataactaaa 142980
tcatgaaaag acaatttgag gcataagatg cctaattaac tacagcataa aatgctaatg 143040
tatcacaatt gcaagtttca gtattcacct cttgaaccac caccaagcag ctcgcacata 143100
tggtccaatg cttctttctc cctgcggttc ttctcttcct tgggtacatt atcagaaggg 143160
gtgatgtcac caacaattgc tggagtacca aaagaaaaaa caattgaaat gagtcaactg 143220
aacccacatc ctcataggca gttagttcca gaaacaggca agctggctta ggaacagcag 143280
caagagtcca tatgagcgga gggcaaaatc atgtgttcat ttctaagctg agcatgcttc 143340
tgaatgaaaa taggaaaatg tgcacatagt ttaaagtttt acactttggc tagcagaggt 143400
caaagaacca actaattggc acaagtactt gaacacacat cctacattcc tactacaggt 143460
ctccagtcca gtggtctagt taccatctac caacatctca ggtagtaata ggctcgcata 143520
ttcacaaaat tgcatccctc atctcacaca aagcccccaaa acttcagtga agccgtctag 143580
acggaagtct tttgagacca taccttctgc aatgtcgtgc acaatcgcca tcttgacaca 143640
cctgtaattg aagggataaa taaacagtgt atgaaaacgg aaccgtaaga aggctaaata 143700
ctgccgagct agacttgaga gcgaaactgt caggatcacc tgtcgcggtt gacgccgggt 143760
agatcggccg cgacgagcgc catgacgccc atccggtaca tgtggtcggc caccgactcg 143820
ggcgcctgca ccccgcgctt cacccacccc gccctcttgg tcgtctgcaa ttacatccac 143880
aatctcatcc atcgcgtcac atttccatcc atctcaacca agccggcccg tggaaatgcg 143940
aagcgactaa acaggggcgc tcagtcgctc accttgaggc ggtagcagag cgtgaggaag 144000
```

```
tcgatggcgt tggacgccga aggggccggg gcaccggcgt ccaccgatgc ggcgggggtc   144060
ggggaggaag aggaggacat ggcggcggcg aggcggtggg ggagcgcgcg gtgagccggg   144120
gcgaagggga cggggtgctg tgggggcttg gcggcggcga gggtggtggc gcagagggag   144180
gagagggaaa gggctcggct cccaccaccc atcgttatta gctgaggccg gagtaggcgg   144240
aggagcggtg ggcagcgcag ggcaggctcc gcggatggcg gggtggtcgc tcgcggaacc   144300
ggcgcatgcc cgcccgcgag cccgtggccc agcttgcgcg gcgggcggac cgtggatcac   144360
gtggggtact gaggttctcc taatttgggc cccagcgcac ggggatcgat cgcgctagag   144420
ggtcgatcct ttccttttc attttcggct gccgggccca ttcggccaat ccggattccg   144480
gagtctgcaa tgttgcggat agcccatggt tggccaagaa tgcggcccgg cccgtgaggg   144540 gtccacccc acgtggaaat aacaccagcc catcaattta tatgtctttg agtctgaatt   144600
ttaacccagc taaatctgtc gagaacttac agcaagggaa gagattaagc gctgtttgga   144660
tcaaaatatt agactcactt atccaataaa ataggtaaca cagaatttta gatgatatta   144720
tttacagagt tgcgtttaat ataggaataa aatagaggat acaataggggg atcagttgga   144780 gatggcctta tactatcaaa aaatcttatg tgggctaata tcaaacgaga agctctagtc   144840
gtctatataa caaggaaata gttttttgtg cttctgcctc gacaaaaaga gaataagccc   144900
tccattgctg aggagagggt tcaaggtctg aatttggaaa ttgcaccaca gcaagtcctc   144960
ccgccttgcc taattgtctt acatgatagg cttcgtttcc gttcgctgaa taagaagca    145020 cggtatgtcg ttttttgaccg ctctagacaa ttgtttagta gattttgttc aaactagatt   145080
gttttctcgc ggtcagatac atattgtaga gtgatttctt actgtcagat acatattgta   145140
gattgattta tgtatacact agcatgttaa atcctgatga tttgacctgc ttaatatatc   145200
caatctatta cttttactta aaaagccatc gatgtcctac taaccgcggg tcgtacgaat   145260
caccccgatg gcgaggctcg tgcgccagtc gcgtgcacta cacccacc ccaccggtgg     145320 cccacacgtt gcgttcatga atagatcggt catgccggct tctagtcgta cactatgtcg   145380
gcgcccccaa ctctgcgcct tgatgtcaca ctgacccacg cacccatgcc ctgctgctgg   145440
tcacgccatc tcgagctgag atggttcacg ctgcgtcagc ccacgcgcc accccgcact    145500 gggtcgcgct tgctcggcca gctggggcgc agctcgtcgg catatgcttc agccacgcct   145560
cgtcagcacg ccctggaccg gctcccgtgg gtcatgcaat ttatctattt aaatttctat   145620
tattgataat tagcacgcct aattaaccta aagttaattt tgtgtgacgg actatggttg   145680
aagacaacag aattgattcg tggagcttgt cctcaatggc aagaactaac cgacctagac   145740
taacgactgc aagtttcacc tagaggcgat atagctagga aaggagatct tctggtaggg   145800
cccgaatgac acttgcctga aacttcatga gaaagcaaaa attacgatct tcgtcggca    145860 ccacatccat ccaggcctga agatggagta tccagaggtg aaagaccata tgatattgtg   145920
gacagagcta tgtgagtgtt tcagtgtgga aagcatgtg atgctcccgc gggcgcaaca    145980
tgaatgggcc actctcgact tcaatgcagt tgaggcttac aacactgtca tccatcgcat   146040
tgtcgctcag ctacatttct gtggccagat agccatagac ttagagatga tcgagaaaac   146100
tctccaaacc ttctaccct ccaatatggt gctccaacag cagtactgta gcaacaagta    146160
cacaaataat gtgacctcgt caacatgttg cttggtgcta aggctcagaa tgagcttctg   146220
atgcagaact actagaagca tccattcggc acgcggtcat gcataaagca cacgccaact   146280
tctagtctta aaggaagaaa ggtccctcca gagaaagggg tcatgggcac tgtaataatc   146340
```

```
aggggatgag aggggggaatt tttacgaagc caccacaaaa tggcagtaga gtagcaatgg 146400
ctatggcaaa ggcaaaggca aaggcaaaac ctcagaaggg ctatgcaagc tcctcaaagc 146460
atgccagtga aggttgtttc aaagaaacac ttgattggca tgtatcagga gtggaagaaa 146520
cgcatagctc ataggctcac cttatttatt catgcatcta tacacgctat gattatagag 146580
cctatgtaac accctgaatt tgggggtata aaatttcttc tctaatatct accaaattca 146640
ggtgttacca cttttctcat ctccgtagat ttcctatttt cttcctttct aatagagttt 146700
tggttatata tttgggagat gtattttttt tctttactat attcaaacct aggggagaca 146760
tgaattgttg catcatgctg agcttaaact ttgtttttgg ttgatgcaca tgtttgaaat 146820
attcaaattt gaatttgtgg tttcgttgga tttgaattca atagagaaaa taaaaataaa 146880
aggaactaga aattcagaat aaaaagaaaa tagaaaagca gcccagccta cgcacctgcc 146940
ctctctctcc atctgccagg tgggcccgac ctattggtgc cgctcaccct cgcgcgcacg 147000
cccccgctct ccctctgtgc agtgggccca gcccatcagc gctgaatcat ttcctcctca 147060
cacgtgctcg tgcctctact ctgtgggccc gccttgtcag tctcatcttc cccgcaaccg 147120
ctgctgaccc gcacacgcac tcacgccgag gaagccgacc acgttgccta cccacgcccc 147180
cagctcccct ttgagcccccg cctacacccg ctctccctcc ccttcctaat ttcacccact 147240
ctcaacctct ctcgcgctta gccgccgccg ctcaagctcg ccggagaagc gcgccaccgc 147300
gtcgtctgcc cggagctcct agcatcgtgt caagcatccc cgagcacact cctaaggtaa 147360
ggaaccatcc ccgtgcccct cctgccccga ttcttttccc tctacggtga atttgtgttc 147420
gctggagctc tatcgcgctg gtttgccgcg cccgctcggt gtccgaccga ttcagccccg 147480
ccccgtgccc gtgccttggc cctaggcgtc cctcaccccct caccgaagct tgtgctggcc 147540
tcggtgcacc ggattccgcc tcctcacggt cgggattgct caccggagta accccgacct 147600
gtggcagaac ctcccaagtt attaggccca catgcaccta tccttgtccc aaagacctca 147660
gaccccaaaa aacgtgcacc agataactta acaggatctg taagatctac caaaggacat 147720
cggataaacc acttacaacc agaaccgcga gaaaacgaat cccaaatcac acacaccaat 147780
attgttgcag cgaacatctt actaccaaat tttacaggtt acaaaatttt tacattagtt 147840
tatcggagtg attacaaaag tataagtttg aaatatatat gctagctcaa gggatcatcc 147900
tcaataagaa gtatagaagg gttacttaga ctcataagaa ggccgagccc accggcactt 147960
aacaccatca acaacagcac aaagttagaa cctgaaaaac aacaaggaat aaaaccctga 148020
gtatggaatt actcagcaag tcttacccga ctaaagaaaa gactctcaag ggtatgctgg 148080
ttatatggga gtcaaggtaa ggcttttcaa taatcaaaga ctctgttttg cagaaatgct 148140
tactaaagtg gatccttaaa atccagtttt atttgtcaag ttaagtagaa ttacctgtaa 148200
ctagagttct ttctacccta gttcaatcac ttgtcctgca ctagccaatt tcttaacaaa 148260
aacccatcat ctttagtgga atgctacgtg tagggcagtg accaagtctt cataaccacg 148320
aaggtacggc gatccgaatc gattatactt agctgaggat ctccaatcac acgacatatg 148380
tagcacttaa ccccttgcata tgtcaacccg ccaccggggt tcttaagacc agatcaggtt 148440
cacgcaaacc gagagcacag ttacaccacc gtccagcctc ttgccacgga ggtacacgct 148500
actctcgcca ccgctccacg cccatttcgt gnnnnnnnnn nnnnnnnnnn nnnnnnnnnn 148560
nnnnnnnnnn nnnnnnnnnn nnnnnnnnnn nnnnnnnnnn nnnnnnnnnn nnnnnnnnnn 148620
nnnnnnnnnn nttcagggat taaacaatgt cattttgaga aagactggat ttgtagagca 148680
taccagtcgg aagcaagtgg cactcatcat ccacacacga acaaaaagac aacgaccgcc 148740
```

```
cagtgaagat cctcccccaa agcaacagtc aagcatccct gacagaactc ttaacgtaag   148800
taagtacctt caggcccttc ctgccccgat tcttttccct ctacggtgaa tttgtgttcg   148860
ctggagctct atcgcggtgg tttgccgcgc ccgctcggtg tccgaccgat tcagcccgc    148920 cccgtgcccg tgccttggcc ctaggcgtcc ctcacccctc accgaagctt gtgctggcct   148980
cggtgcaccg gattccgcct cctcacggtc gggattgctc accggagtaa ccccgacctg   149040
tggcagaacc tcccaagtta ttaggcccac atgcacctat ccttgtccca aagacctcag   149100
acggctgtgc atgtgcacca gataacttaa caggatgtgt ccgattgccc caaggacatc   149160
ggataaacca atttcaacca gaaccgcgag attaagtctt gaaactcaca cacggataca   149220
aagtggtagc ggaaatatta ttgacaaatt tgacaggtta cacaaatttt tcatacctct   149280
atcggaggga atacaaaatt ctaagtctga aatataaatg ctagctcaag ggatcatcct   149340
caataagaag tatagaaggg ttacttagac tcataagaag gccgagccca ccggcactta   149400
acaccatcaa caacagcaca aagttagaac ctgaaaaaca acaaggaata aaaccctgag   149460
tatggaatta ctcagcaagt cttacccgac taaagaaaag actctcaagg gtatgctggt   149520
tatatgggag tcaaggtaag gcttttcaat aatcaaagac tctgttttgc agaaatgctt   149580
actaaagtgg atccttaaaa tccagtttta tttgtcaagt taagtagaat tacctgtaac   149640
tagagttctt tctaccctag ttcaatcact tgtcctgcac tagccaattt cttaacaaaa   149700
acccatcatc tttagtggaa tgctacgtgt agggcagtga ccaagtcttc ataaccacga   149760
aggtacggcg atccgaatcg attatactta gctgaggatc tccaatcaca cgacatatgt   149820
agcacttaac ccttgcatat gtcaacccgc caccggggtt cttaagacca gatcaggttc   149880
acgcaaaccg agagcacagt tacaccaccg tccagcctct tgccacggag ggtacacgct   149940
actctcgcca ccgctccacg cccatttcgt gttatcttat tctggcctta gtctgcccga   150000
ggcaaggctt acccatgacg aggcatgtga ccagttaaag ggtcctcgat catcaagcct   150060
acatcgacaa ggtccttaat cgactcagac ggagacacta caccgagact cctttcccgt   150120
gcaagtcacc cgcccggtct tagcttaatc ttttaaccca aaaacttggt acctggcaga   150180
ggtacatctt ttccgatgtt gaatccatca tagccatgat ggattcacca tcaagtttta   150240
tttttgaaaa caaccctccc actttgccaa acatcttttc taaaacaaat cctttgttt    150300 ttctaagcaa tactaagcat agtaaaacct ttttgtaaaa acgggttttc aaggagggta   150360
atcaagatca aggaaggtaa tgcaggaatt gtttaatcaa tcaactcctg tcacctaatg   150420
cagcaatcaa gtgagaaaga ttttaaaaac atcaagggag gtggcaaatg caccggggct   150480
tgcctgggta acactaggtt agtgttgtta gacgatgtcc acttggcgac cattttcagg   150540
tttgtccatc agcatcatcc tgcggattag cccgcgcttg gggtcgactt ggcttgtctt   150600
ccgcatcacg cgatcaatta tcgtacctaa ttgagatgca cgatgcacat gaatgcatat   150660
aaacaagaat agcacaaatc taaatagtgc tatacgatag cgtattaaac acctagtggc   150720
gaggcgttgt acaattttgt acagaaacac tagttattaa tatgcgacta cgcacaatga   150780
ttacgcttct cgaacctaac gcaaacatca cgaacaacaa actatacaca agaaatataa   150840
ttagcctaat cacaacttat cagttaatta attaaattct gaactaatcc cttgccttat   150900
aaattatact acatctttat aagtgattaa atatttat caacacatat gcctactaaa    150960
attctactcg gtccactaat tcagctaagt gaccgaaata gcgaaataac tcgctataac   151020
tgaacctggc tcgataatcg caagaactgc gaagtcgacg agagtttcgt gacttacgca   151080
```

```
atttatcgag cacectaatg agcctcgcac taacacatta acttattcaa cgatcgaact   151140
attctaaaca attcattagc ttaccgaact attctaaaca attcatcagc ttaccgtttc   151200
aacagctgac acgaatccgt gagatcggca gtgattttc  gatccacgca atttgtcgag   151260
cgcttaggga atatcgcgct gctaacttcg tcttcacccg attcttgggt tttcttgggg   151320
acgcacgagc gacgatgacc ttcgattgaa gtctggggta agctggtgag gtggggatcg   151380
agccggagat gacgtgtttg acaactcgac ggcaaacgac gagatcgacg acgtgattgg   151440
aaattaaagc cgagcgagcc gagagggcac gctggcgagc aggaaaccgt gcgagcacaa   151500
gacaggaaaa acgacggctc gacaacacgc gaagcgacga cagtcaaatc ggcaacaaag   151560
cgttggcgaa ttcgatgaac acgaccacag tcgcgagtta acgcggtcaa gacaactgtg   151620
accaacgagc ttgcgacaga agtgatgatg gtgtgggaac tcgacacgct gtgacgagca   151680
gataaaattc gtgcgcgcgg caacaaagaa agagcgagct gcgcgtgagc agagagctcc   151740
acacgaaaac tcgacgcgcg caggaactac ggcgagctag agtagagaaa actcgacgcg   151800
cgcaggaact acgcgagct  agagtagaca gtcatgggag atgtagtcat gtagagccga   151860
gctgggcgac aaagcgaaat ccaggctgaa gcgttgacga gcaaagagct tcgcgcgtgc   151920
aagaacaaca gaacgctatg cgcgcgacgc aaaggcgagc agtaagacga cggcgcgaca   151980
gacgaaccga agcagggagc gccggccatg ggcgcggcaa tagagctggg cgagctcgga   152040
ggggaagcca cggcacaaga aatccgatca ggcgcggccg aacagaggtg ccgcggcaca   152100
ggagctcagg gacggacgag caggagcaga ggagatggat accgcgagca gcctgcaggg   152160
aaccccgcgc catgggagaa aagcagagcc gagcggctgg ggattcagcc agcgagcaga   152220
ggggagatgg gaaggagctg ctcggctgcg gcttgctgcc gggcgtgcgt ggagaagaaa   152280
cctgcgcgct ggagatttgt aggagaccaa gggcggtggc gggataagga taggagcgct   152340
cggcggcgtg attttattt  ctaggggttg cgcggcgcgg tacagaaaaa tcaggcgacg   152400
agattaaaga gatgcagtga gcagttcgac aaattcgtcg gcatggacac aagctgacga   152460
cgacggccag cccgaccgcg gcaaggtgag gggagacgcg gtctgcgcaa agggcgagct   152520
cgagcaagga actagagccg acgatgtcca cgacagcag  gaccagagac acggtgctag   152580
tggatggaaa ctgagcacag gatggatgca agctggagac gagcttggtc aggtcgtcgg   152640
gcacagaggt gctcggaggg tccgacgagc acagccggct gccggctgcc tttggatgct   152700
gatggatgga agaaatgctg gtcgctgggt aaggctggag gagagacgtg cgtgagattt   152760
tccagcgagc tagcgtccaa tggataagag agaaggagac gtgaggaaga ggagaactac   152820
gtggagaaaa tatccaggct agtgacttca gatatggaag gggaaagcgg tggataaaat   152880
cagagagaag agcggttgca gatattttct tccttcgttt tcttttactc gaaaatttga   152940
ataaaatac  aattatcagc tggagattgg gactagaatt tggaaagatg taagaggact   153000
aaaattaaaa atgattttag ttacaatgtt ttaatcggtg ttacatttaa ttgaaatcag   153060
ataaaaactt atccgtcacc aaaacacagt tgatttggtt atcctacatt gcgggctaaa   153120
gaacaaatta gatcatattg aaagggaatt aggcttacac ctagttccta ataattttg   153180
gtggttgaat tgcccaacac aaatcttttg gactaacttg tttgcccaag tgtatagtgt   153240
atacaggagt aaaaggttca cactcagcca ataaaaagac caagttttgg attcaacaaa   153300
agagcaaagg ggcaaccgaa ggcacccctg gtctggcgca ccggactgtc cggtgtgcca   153360
ccggacagtg aacagtacct gtccggtgca ccaggggact cagactcaaa ctcgccacct   153420
tcgggaattt ctaaggcgac tcggctataa ttcaccggac tgtccggtgt acaccggaca   153480
```

```
gtgtccggtg cgccaaggga ggtcggcctc aggaactcgc tagcctcggg ttcgcgcggc   153540
agccgctccg ctaaaattca ccggactgtc cggtgtgcac cggactgtcc ggtgtgccag   153600
cggagcaacg gctccctgcg gcgccaacgg ctccctgcgg tgcatttaat gcgcgcgcag   153660
cgcgcgcaga cgccaggcac gcccataccg gtgcaccgga catcaaattc cagatgtccg   153720
cagtccgcta cacactggta ttgtgaagcc cataaaattt accgatggct cgatcccgta   153780
tggaaatttg acaatttgtg aagaaccctc cagcttgtct gttgcattgt ttgacccaaa   153840
ctggaaaagc tgccatggac ctagaatttt ctgcccttat gcggaataaa acatggcact   153900
tggttcctcc cgcacctgac agaaatttga ttgattgcaa gtgggtttat aaactcaaga   153960
gaaaagctga tgagtctatt gaccatcata agctcgatg ggtggctaaa tgttttaaac   154020
agcttnnnnn nnnnnnnnnn nnnnnnnnnn nnnnnnnnnn nnnnnnnnnn nnnnnnnnnn   154080
nnnnnnnnnn nnnnnnnnnn nnnnnnnnnn nnnnnnnnnn nnnnntgaaa ctagagattc   154140
gtcctcagct ggtttaggcg tgagcagaag gattgtcccc tcatataagg accggtttgt   154200
catcttcact acctgtactc tttaatagta caaccactcg agactgtgtg ggcagtcact   154260
caatctgaac tcgtacggtc caaccccagg gttatgaagg ctggggagca ccggaggat   154320 aaggaggggg aaagttttgt ccggtttgga catggtggtg gcctgactcc ttcaggataa   154380
ccattaaggt taggacatgc ggggaaagaa agagagtcgg attcgggtct cattgatcat   154440
gggatcgcag agctggacta gtgggtaaag tgtacacctc tgcgcagagt ttgaaaacct   154500
attcgaatag tctgtgtcca caggaatgga cgagtctggt atggtatggc aattaatgtt   154560 ttgtttttcca aaaaaagag atgcttttga aaagtggttt ttaaaaggtc cggcggttga   154620
gccgtgagct atggtggacg ggaagtccag tagctgtttt tgaaaatgaa accagtggg   154680 aaactgctga gatacctgga tggtttagtc caggggattt tgttataata ctgaaaaact   154740
tcctgctcct tttggagagg atgcactttg caaaatacaa atgttttc aaacaacccc   154800 tgcataaaat attgctgttt ctgcaaatat cctgagctct acatattcca tgcattatat   154860
ctgatttccc cattccgcgg gtgaaggtgg gctgctgagt acgtttgtac tcacccttgc   154920
ttatttgttg tttttcagaa aaaagagatc gggtaagagt tacgactgtt cccaaccttg   154980
cctgtggctg ttggaccgct gaattgcttc actgcgtata tcgggctgct tcagccccac   155040
tctgatgata tgtcccgagt tgtggaccaa ctcttaaagt tgatcgccac ctttataggt   155100
ttgtctcgtt taagcagatc tgaatcatct gatgtataaa tgtgtttact agcctcctgg   155160
gactagtaat tgtatcacat ttgagtccca gaggattggg gacgcttcaa gctgtggcag   155220
aacctcccaa gttattgggc ccacatgcac ctgtccttgt cccaaagacc tcagacggct   155280
gtgcatgtgc accagataac ttaacaggat ctgtccgatt gccccaagga catcggataa   155340
accacttaca accagaaccg caggattaag taacacaaat cacacacacc aatattgttg   155400
cagcggaaat cttactacca aattttacag gttacaaaaa ttttacatta gtttatcgga   155460
gtgattacaa aagtataagt ttgaaatata tatgctagct caagggatca tcctcaataa   155520
gaagtataga agggttactt agacttataa gaaggccgag cccaccggca cttaacacca   155580
tcaacaacag cacaaagtta gaacctgaaa acaacaggga aataaaaccc tgagtatgga   155640
attactcagc aagtcttacc cgactaaaga aaagactctc aagggtatgc tggttatatg   155700
ggagtcaagg taaggctttt caataatcaa agactctgtt ttgcagaaat gcttactaaa   155760
gtggatcctt aaaatccagt tttatttgtc aagttaagta gaattacctg taactagagt   155820
```

```
tctttctacc ctagttcaat cactggtcct gcactagcca atttcttaac aaaaacccat  155880
catctttagt ggaatgctac gtgtagggca atgaccaagt cttcataacc gcgaaggtac  155940
ggcgatccga atcgattata ctcagctgag gatctccaat cacacgacat atgtagcact  156000
taacccttgc atatgtcaac ccgccaccgg ggttcttaag accagatcag gttcacgcaa  156060
accgagagca cagttacacc accgtccagc ctcttgccac ggagggtaca cgctactctc  156120
gccaccgctc cacgcccatt tcgtgttatc ttattctggc cttagtctgc ccgaggcaag  156180
gcttacccat gacgaggcat gtgaccagtt aaagggtcct cgatcatcaa gcctacatcg  156240
acaaggtcct taatcgactc agacggagac actacactga gactcctttc ccgtgcaagt  156300
caccccgcccg gtcttagctt aatctttaa cccaaaaact tggtacctgg cagaggtaca  156360
tcttttccga tgttgaatcc atcatatcca tgatggattc accatcaagt tttatttttg  156420
aaaacaaccc tcccactttg ccaaacatct tttctaaaac aaatcctttt gttttctaa  156480
gcaatactaa gcatagtaaa acctttttgt aaaaacgggt tttcaaggag ggtaatcaag  156540
atcaaggaag gtaatgcagg aattgtttaa tcaatcaact cctgtcacct aatgcagcaa  156600
tcaagtgaga aagatttta aaacatcaag ggaggtggca aatgcaccgg ggcttgcctg  156660
ggtaacacta ggttagtgtt gttagacgac gtccacttgg cgaccatttt caggtttgtc  156720
catcagcatc atcctgcgga ttagcccgcg cttggggtcg acttggcttg tcttccgcat  156780
cacgcgatca attatcgtac ctaattgaga tgcacgatgc acatgaatgc atataaacaa  156840
gaatagcaca aatctaaata gtgctatacg atagcgtatt aaacacctag tggcgaggcg  156900
ttgtacaatt ttgtacggaa acactagtta ttaatatgcg actacgcgct atgattacgc  156960
ttctcgaacc taacgcaaac atcacgaaca acaaactata cacaagaaat ataattagcc  157020
taatcacaac ttatcagtta attaattaaa ttctgaacta atcccttgcc ttataaatta  157080
tactacatct ttataagtga ttaaaatatt ttatcaacac atatgcctac taaaattcta  157140
ctcggtccac taattcagct aagtgaccgg aatagcgaaa taactcgcta taactgaacc  157200
tggctcgata atcgcaagaa ctgcgaagtc gacgagagtt tcgtgactta cgcaatttat  157260
cgagcaccct aatgagcctc gcactaacac attaacttat tcaacgatcg aactattcta  157320
aacaattcat cagcttacta aactattcta aacaattcat cagcttaccg tttcaacagc  157380
tgacacgaat ccgtgagatc ggcagtgatt tttcgatcca cgcaatttgt cgagcgctta  157440
gggaatattg cgctgctaac ttcgtcttca cccgattctt gggttttctt ggggacgcac  157500
gagcgacgat gaccttcgat tgaagtctgg ggtaagctgg tgaggtgggg atcgagccgg  157560
agatgacgtg tttgacaact cgacggcaaa cgacgagatc gacgacgtga ttggaaatta  157620
aagccgagcg agccgagagg gcacgctggc gagcaggaaa ccgtgcgagc acaagacagg  157680
aaaaacgacg actcgacaac acgcgaagcg acgacagtca aatcggcaac aaagcgttgg  157740
cgaattcgat gaacacgacc acagtcgcga gttaacgcgg tcaagacaac tgtgaccaac  157800
gagcttgcga cagaagcgat gatggcgtgg gaactcgaca cgctgtgacg agcagataaa  157860
ttcgtgtgcg cggcacaaga tagagcgagt gctcgtgagc agagagctcc acacgaaact  157920
cgacgcgcgc tgactacgcg agctagagta gagaaactcg acgcgcgcag actacgtgag  157980
ctaagtagac agtcatggag atgtagtcat gtaaagcgag ctggcgacaa cgaatcagnn  158040
nnnnnnnnnn nnnnnnnnnn nnnnnnnnnn nnnnnnnnnn nnnnnnnnnn nnnnnnnnnn  158100
nnnnnnnnnn nnnnnnnnnn nnnnnnnnnn nnnnnnnnat ttattctaac catttcatca  158160
gctttataaa ctattctaaa caattcatca gcttaccgtt tcaacagctg acacgaatcc  158220
```

```
gtgagatcgg gcagtgattt ttcgatccac gcatttgtcg agcgcttagg gaatattgcg   158280
ctgctaactt cgtcttcacc cgattcttgg gttttcttgg ggaacgcacg agcgacgatg   158340
accttcgatt gaagtctggg gtaagctggt gaggtgggga tcgagccgga gatgacgtgt   158400
ttgacaactc gacggcaaac gacgagatcg acgacgtgat tggaaattaa agccgagcga   158460
gccgagaggg cacgctggcg agcaggaaac cgtgcgagca caagacagga aaaacgacga   158520
ctcgacaaca cgcgaagcga cgacagtcaa atcggcaaca aagcgttggc gaattcgatg   158580
aacacgacca cagtcgcgag ttaacgcggt caagacaact gtgaccaacg agcttgcgac   158640
agaagcgatg atggcgtggg aactcgacac gctgtgacga gcagataaaa ttcgtgtgcg   158700
cggcaacaaa gaaagagcga gttgcgcgtg agcagagagc tccacacgaa aactcgacgc   158760
gcgcaggaac tacggcgagc tagagtagag aaaactcgac gcgcgcagga acttcggtga   158820
gctagagtag acagtcatgg gagatgtagt catgtagagc cgagctgggc gacaaagcga   158880
aatccaggct gaagcgttga cgagcaaaga gcttcgcgcg tgcaagaaca acagaacgct   158940
atgcgcgcga cgcaaaggcg agcagtaaga cgacggcgcg acagacggaa ccaagcaggg   159000
agcgccggcc atgggagaaa agcagagccg agcggctggg gattcagcca gcgagcgag   159060 gggagatggg aaggagctgc tcggctgcgg cttgctgccg ggcgtgcgtg gagaagaaac   159120
ctgcgcgctg gagatttgta ggagaccaag ggcggtggcg ggataaggat aggagcgctc   159180
ggcggcgtga tttttatttc taggggttgc gcggcgcggt acagaaaaat caggcgacga   159240
gattaaagag atgcagtgag cagttcgaca aattcgtcgg catggacaca agctgacgac   159300
gacggccagc ccgaccgcgg caaggtgagg ggagacgcgg tctgcgcaaa gggcgagctc   159360
gagcaaggaa ctagagccga cgatgtccac gacgagcagg accagagaca cggtgctagt   159420
ggatggaaac tgagcacagg atggacgcaa gctggagacg agcttggtca ggtcgtcggg   159480
cacagaggtg ctcggagggt ccgacgagca cagccggctg ccggctgcct ttggatgctg   159540
atggatggaa gaaatgctgg tcgctgggta aggctggagg agagacgtgc gtgagatttt   159600
ccagcgagct agcgtccaat ggataagaga gaaggagacg tgaggaagag gagaactacg   159660
tggagaaaat atccaggcta gtgacttcag atatggaagg ggaaagcgat ggataaaatt   159720
agagagaaga gcggttgcag atattttctt ccttcgtttt cttttactcg aaaatttgaa   159780
taaaaataca attatcagct ggagattggg actagaattt ggaaagatgt aagaggacta   159840
aaattaaaaa tgattttagt tacaatgttt taatcggtgt tacatttaat tgaaatcaga   159900
taaaaactta tccgtcacca aaacacagtt gatttggtta tcctacattg cgggctaaag   159960
aacaaattag atcatatccc cgcgcacgat ctttctcaga caatgcgcga ttcggattat   160020
tttaccctga acatttagt cgtcaagttc aaattatttt gctcggaata agatcattcg   160080
agtgagttcg ggcttccgaa ttcgtgttcg cgcgagcgat ggattttaaa tactcatcgg   160140
acgcaccgat tttcggaaca gctaggttcc gaacattacg aaaatttagg aagagcccgg   160200
acagataaaa aaataaaaac gatgtcgcac tcgcgacaaa cgacaccgat gcgatattaa   160260
aatcgcgata agcgacgatg attaaaattt aaaatccgtt ttatccactg atattgcgtg   160320
cttaaatccg aactcgttgt tgagcggaaa ataaacacct ggggtgttac agccctcccc   160380
ccttaaaaga atctcgtccc gagattcaaa acgaaagact tctaagagta gagaagcatg   160440
taacccatgt ccatatcagc gataatcatg agacaattcc aaacaaagtc gagtgtctca   160500
aaatgtcgtt cctctagtgg acataacatg tgtcgcctta ggctaattta gaaatgtcca   160560
```

```
ccaatagaga cgatgtctgc cagaagtaca cataaggttc catgtgtgca gtttactttt    160620
tctgatgaca ctgtaatatc tgagtctgtt gagcgagtgg tagatatgca actttacaca    160680
aacagaatca gatgcaacct cttgggtaaa acacacagaa agagatttac caacaagtgg    160740
tcacggtaag ttcatagcac acgagacgag tgtggatgtc gaataacatc acagttaact    160800
cgtgttagcc agagaatcca agtccaagaa aaatgataaa gacttgaaaa aaattaccag    160860
cagagggatc tgtaaatgct gccttcgcaa ccaatccatt ttatcaagca ctaatcatgg    160920
atctacttga tcacacatgc tggaaaagca cacgtgagac gatcgaggca tgactagagc    160980
gatgtttagg tggttactgg ccgacttaat ctcgattctt gaaagtactt ccttaggatg    161040
gtttggacca tagcgagttt agataactcg atgaaacgat ctctaaactc gaccttcgtt    161100
cacaaagcag ttacaagtta gtaaaaccaa cttgttaaac tacttttgac attgagcaag    161160
tcctctcagt accattggta atccaagggt tgagagttca catttgctaa caggaaatca    161220
tgcacttggg tagaaatcca tttggtcacg ttgttcatcc gtttcttcta tacaagatga    161280
accgacttgg ttagggaata catggattaa ataagagagc gaatgaacaa attcttgcat    161340
ttcagcagca ggggaaacaa atctccattt tgggaactaa ttggttgtct gcaacacta    161400 aaaagctcca aggcttcacc tttacacaaa ggatgtaaag ggaacttgta tgtgtgaagt    161460
caccatcaaa gtcaagagat aagagatcac acatgaaagt ggtatgccct tttgatccac    161520
agagatgata gatgttgctt gatcacttga caaacaacat agaaattgtt tcaagggagg    161580
actccacgga agatcacaca tcagtgtact tccacaatgg atcatgacca cagaccttga    161640
taccagcatc cgatgagtgg cacagtccta tgtgcgcatt cacaggaggc tctcagtttt    161700
cgttgcggca ccataagtca ttaatcatga ccaccactac cgaagctg                  161748
```

<210> SEQ ID NO 104  
<211> LENGTH: 634  
<212> TYPE: DNA  
<213> ORGANISM: Zea mays
<400> SEQUENCE: 104

```
caatccaggg ccaggccagg ccaggccaac caaaccctag gcactgcgcc acgcctagcg     60
cgcgtggtat ccatgggctg accgcgtccc ggtggggagc ccggatccgg agctagggtt    120
ccgtcctagg cggcaccacc atggagtggg acagcgagtc cgacggcgcc ggcagcgtcg    180
acgccggcta tgaggagcag gaggaggagg aggaggagcg gggaggcgag ggtggaggtg    240
gcgacgccgg gggcggcggt gggatgttca cgttcgcgat tgaaggcatg ctgcgctcct    300 ccgggcccctg cgggctagtc gtcaccgacg cgctcgagcc cgattgcccc atcatctacg    360
tcaaccgcgg cttcgaggag gccacgggct accgcgccga ggaggtcctc ggcaggaact    420
gccgatttct gcagtgcaga gggccattcg ctcgaaggag gcaccccta gttgatgctg    480 cactggtttc agagattcga agatgcatag acaatggcat tgagttccgt ggtgatttac    540
taaatttcag aaaagatgga tctccagtga tgaacagatt gcatctgacc cctatttatg    600
gagatgatga aaccataacc cattatatgg gcat                                 634
```

<210> SEQ ID NO 105  
<211> LENGTH: 20  
<212> TYPE: DNA  
<213> ORGANISM: Artificial  
<220> FEATURE:  
<223> OTHER INFORMATION: Primer
<400> SEQUENCE: 105

```
accaccatgg agtgggacag                                              20
```

<210> SEQ ID NO 106
<211> LENGTH: 21
<212> TYPE: DNA
<213> ORGANISM: Artificial
<220> FEATURE:
<223> OTHER INFORMATION: Primer

<400> SEQUENCE: 106

```
ttcaatcgcg aacgtgaaca t                                            21
```

<210> SEQ ID NO 107
<211> LENGTH: 388
<212> TYPE: DNA
<213> ORGANISM: Zea mays
<220> FEATURE:
<221> NAME/KEY: misc_feature
<222> LOCATION: (188)..(188)
<223> OTHER INFORMATION: n is a, c, g, or t
<220> FEATURE:
<221> NAME/KEY: misc_feature
<222> LOCATION: (219)..(219)
<223> OTHER INFORMATION: n is a, c, g, or t

<400> SEQUENCE: 107

```
ctgaacaaga tcgaccaaac agttcattca ccagctagaa aatgtgttca aataggagtg    60
gcagaaaaat aacacggttt accagattat actgtcacaa actgttaccg aacacttaaa   120
acaaagacta gatgttcccc aaaactgatg acaaagcaca gctcctcagt acttgatagg   180
ggcaagantc tccaactgag accccaactt ctcctcggnt gccttctcgg ccttgacacg   240
cagcttggcc aattgcttct tcctctcgta ggcaaccttg ggccttctcc ttgctctttc   300
tcctcaagtt ccctgatggt gtcatggtag ttccacccgg cctccttaga gagctcgccg   360
aggaggcagt acttgtgtcc aggctgta                                     388
```

<210> SEQ ID NO 108
<211> LENGTH: 21
<212> TYPE: DNA
<213> ORGANISM: Artificial
<220> FEATURE:
<223> OTHER INFORMATION: Primer

<400> SEQUENCE: 108

```
cgaccaaaca gttcattcac c                                            21
```

<210> SEQ ID NO 109
<211> LENGTH: 19
<212> TYPE: DNA
<213> ORGANISM: Artificial
<220> FEATURE:
<223> OTHER INFORMATION: Primer

<400> SEQUENCE: 109

```
ctcctcggcg agctctcta                                               19
```

<210> SEQ ID NO 110
<211> LENGTH: 161748
<212> TYPE: DNA
<213> ORGANISM: Zea mays
<220> FEATURE:
<221> NAME/KEY: misc_feature
<222> LOCATION: (3611)..(3710)
<223> OTHER INFORMATION: n is a, c, g, or t
<220> FEATURE:

```
<221> NAME/KEY: misc_feature
<222> LOCATION: (7624)..(7723)
<223> OTHER INFORMATION: n is a, c, g, or t
<220> FEATURE:
<221> NAME/KEY: misc_feature
<222> LOCATION: (13118)..(13217)
<223> OTHER INFORMATION: n is a, c, g, or t
<220> FEATURE:
<221> NAME/KEY: misc_feature
<222> LOCATION: (25477)..(25576)
<223> OTHER INFORMATION: n is a, c, g, or t
<220> FEATURE:
<221> NAME/KEY: misc_feature
<222> LOCATION: (70085)..(70184)
<223> OTHER INFORMATION: n is a, c, g, or t
<220> FEATURE:
<221> NAME/KEY: misc_feature
<222> LOCATION: (94587)..(94686)
<223> OTHER INFORMATION: n is a, c, g, or t
<220> FEATURE:
<221> NAME/KEY: misc_feature
<222> LOCATION: (117477)..(117576)
<223> OTHER INFORMATION: n is a, c, g, or t
<220> FEATURE:
<221> NAME/KEY: misc_feature
<222> LOCATION: (128130)..(128229)
<223> OTHER INFORMATION: n is a, c, g, or t
<220> FEATURE:
<221> NAME/KEY: misc_feature
<222> LOCATION: (143525)..(143624)
<223> OTHER INFORMATION: n is a, c, g, or t
<220> FEATURE:
<221> NAME/KEY: misc_feature
<222> LOCATION: (151880)..(151979)
<223> OTHER INFORMATION: n is a, c, g, or t
<220> FEATURE:
<221> NAME/KEY: misc_feature
<222> LOCATION: (155542)..(155641)
<223> OTHER INFORMATION: n is a, c, g, or t
<220> FEATURE:
<221> NAME/KEY: misc_feature
<222> LOCATION: (159499)..(159598)
<223> OTHER INFORMATION: n is a, c, g, or t

<400> SEQUENCE: 110
cagcttcggt agtggtggtc atgattaatg acttatggtg ccgcaacgaa aactgagagc      60
ctcctgtgaa tgcgcacata ggactgtgcc actcatcgga tgctggtatc aaggtctgtg     120
gtcatgatcc attgtggaag tacactgatg tgtgatcttc cgtggagtcc tcccttgaaa     180
caatttctat gttgtttgtc aagtgatcaa gcaacatcta tcatctctgt ggatcaaaag     240
ggcataccac tttcatgtgt gatctcttat ctcttgactt tgatggtgac ttcacacata     300
caagttccct ttacatcctt tgtgtaaagg tgaagccttg gagcttttta gtgttgcaag     360
acaaccaatt agttcccaaa atggagattt gtttcccctg ctgctgaaat gcaagaattt     420
gttcattcgc tctcttattt aatccatgta ttccctaacc aagtcggttc atcttgtata     480
gaagaaacgg atgaacaacg tgaccaaatg gatttctacc caagtgcatg atttcctgtt     540
agcaaatgtg aactctcaac ccttggatta ccaatggtac tgagaggact tgctcaatgt     600
caaaagtagt ttaacaagtt ggttttacta acttgtaact gctttgtgaa cgaaggtcga     660
gtttagagat cgtttcatcg agttatctaa actcgctatg gtccaaacca tcctaaggaa     720
gtactttcaa gaatcgagat taagtcggcc agtaaccacc taaacatcgc tctagtcatg     780
cctcgatcgt ctcacgtgtg cttttccagc atgtgtgatc aagtagatcc atgattagtg     840
cttgataaaa tggattggtt gcgaaggcag catttacaga tccctctgct ggtaattttt     900
ttcaagtctt tatcattttt cttggacttg gattctctgg ctaacacgag ttaactgtga     960
tgttattcga catccacact cgtctcgtgt gctatgaact taccgtgacc acttgttggt    1020
```

```
aaatctcttt ctgtgtgttt tacccaagag gttgcatctg attctgtttg tgtaaagttg    1080
catatctacc actcgctcaa cagactcaga tattacagtg tcatcagaaa aagtaaactg    1140
cacacatgga accttatgtg tacttctggc agacatcgtc tctattggtg gacatttcta    1200
aattagccta aggcgacaca tgttatgtcc actagaggaa cgacattttg agacactcga    1260
ctttgtttgg aattgtctca tgattatcgc tgatatggac atgggttaca tgcttctcta    1320
ctcttagaag tctttcgttt tgaatctcgg gacgagattc ttttaagggg ggagggctgt    1380
aacaccccag gtgtttattt tccgctcaac aacgagttcg gatttaagca cgcaatatca    1440
gtggataaaa cggattttaa attttaatca tcgtcgctta tcgcgatttt aatatcgcat    1500
cggtgtcgtt tgtcgcgagt gcgacatcgt ttttattttt ttatctgtcc gggctcttcc    1560
taaattttcg taatgttcgg aacctagctg ttccgaaaat cggtgcgtcc gatgagtatt    1620
taaaatccat cgctcgcgcg aacacgaatt cggaagcccg aactcactcg aatgatctta    1680
ttccgagcaa ataatttga acttgacgac taaaatgttc agggtaaaat aatccgaatc     1740
gcgcattgtc tgagaaagat cgtgcgcggg gatatgatct aatttgttct ttagcccgca    1800
atgtaggata accaaatcaa ctgtgttttg gtgacggata agtttttatc tgatttcaat    1860
taaatgtaac accgattaaa acattgtaac taaaatcatt tttaattta gtcctcttac     1920 atctttccaa attctagtcc caatctccag ctgataattg tattttatt caaattttcg     1980 agtaaaagaa aacgaaggaa gaaatatct gcaaccgctc ttctctctaa ttttatccat    2040
cgctttcccc ttccatatct gaagtcacta gcctggatat tttctccacg tagttctcct    2100
cttcctcacg tctccttctc tcttatccat tggacgctag ctcgctggaa aatctcacgc    2160
acgtctctcc tccagcctta cccagcgacc agcatttctt ccatccatca gcatccaaag    2220
gcagccggca gccggctgtg ctcgtcggac cctccgagca cctctgtgcc cgacgacctg    2280
accaagctcg tctccagctt gcgtccatcc tgtgctcagt ttccatccac tagcaccgtg    2340
tctctggtcc tgctcgtcgt ggacatcgtc ggctctagtt ccttgctcga gctcgccctt    2400
tgcgcagacc gcgtctcccc tcaccttgcc gcggtcgggc tggccgtcgt cgtcagcttg    2460
tgtccatgcc gacgaatttg tcgaactgct cactgcatct ctttaatctc gtcgcctgat    2520
ttttctgtac cgcgccgcgc aaccctaga aataaaatc acgccgccga gcgctcctat      2580
ccttatcccg ccaccgccct tggtctccta caaatctcca gcgcgcaggt tcttctcca     2640 cgcacgcccg gcagcaagcc gcagccgagc agctccttcc catctcccct ctgctcgctg    2700
gctgaatccc cagccgctcg gctctgcttt tctcccatgg ccggcgctcc ctgcttggtt    2760
ccgtctgtcg cgccgtcgtc ttactgctcg cctttgcgtc gcgcgcatag cgttctgttg    2820
ttcttgcacg cgcgaagctc tttgctcgtc aacgcttcag cctggatttc gctttgtcgc    2880
ccagctcggc tctacatgac tacatctccc atgactgtct actctagctc accgaagttc    2940
ctgcgcgcgt cgagttttct ctactctagc tcgccgtagt tcctgcgcgc gtcgagtttt    3000
cgtgtggagc tctctgctca cgcgcaactc gctctttctt tgttgccgcg cacacgaatt    3060
ttatctgctc gtcacagcgt gtcgagttcc cacgccatca tcgcttctgt cgcaagctcg    3120
ttggtcacag ttgtcttgac cgcgttaact cgcgactgtg gtcgtgttca tcgaattcgc    3180
caacgctttg ttgccgattt gactgtcgtc gcttcgcgtg ttgtcgagtc gtcgtttttc    3240
ctgtcttgtg ctcgcacggt ttcctgctcg ccagcgtgcc ctctcggctc gctcggcttt    3300
aatttccaat cacgtcgtcg atctcgtcgt ttgccgtcga gttgtcaaac acgtcatctc    3360
```

-continued

```
cggctcgatc cccacctcac cagcttaccc cagacttcaa tcgaaggtca tcgtcgctcg   3420
tgcgttcccc aagaaaaccc aagaatcggg tgaagacgaa gttagcagcg caatattccc   3480
taagcgctcg acaaatgcgt ggatcgaaaa atcactgccc gatctcacgg attcgtgtca   3540
gctgttgaaa cggtaagctg atgaattgtt tagaatagtt tataaagctg atgaaatggt   3600
tagaataaat nnnnnnnnnn nnnnnnnnnn nnnnnnnnnn nnnnnnnnnn nnnnnnnnnn   3660
nnnnnnnnnn nnnnnnnnnn nnnnnnnnnn nnnnnnnnnn nnnnnnnnnn ctgattcgtt   3720
gtcgccagct cgctttacat gactacatct ccatgactgt ctacttagct cacgtagtct   3780
gcgcgcgtcg agtttctcta ctctagctcg cgtagtcagc gcgcgtcgag tttcgtgtgg   3840
agctctctgc tcacgagcac tcgctctatc ttgtgccgcg cacacgaatt tatctgctcg   3900
tcacagcgtg tcgagttccc acgccatcat cgcttctgtc gcaagctcgt tggtcacagt   3960
tgtcttgacc gcgttaactc gcgactgtgg tcgtgttcat cgaattcgcc aacgctttgt   4020
tgccgatttg actgtcgtcg cttcgcgtgt gtcgagtcg tcgttttttcc tgtcttgtgc    4080
tcgcacggtt tcctgctcgc cagcgtgccc tctcggctcg ctcggcttta atttccaatc   4140
acgtcgtcga tctcgtcgtt tgccgtcgag ttgtcaaaca cgtcatctcc ggctcgatcc   4200
ccacctcacc agcttacccc agacttcaat cgaaggtcat cgtcgtcgt gcgtccccaa    4260
gaaaacccaa gaatcgggtg aagacgaagt tagcagcgca atattcccta agcgctcgac   4320
aaattgcgtg gatcgaaaaa tcactgccga tctcacggat tcgtgtcagc tgttgaaacg   4380
gtaagctgat gaattgttta gaatagttta gtaagctgat gaattgttta gaatagttcg   4440
atcgttgaat aagttaatgt gttagtgcga ggctcattag ggtgctcgat aaattgcgta   4500
agtcacgaaa ctctcgtcga cttcgcagtt cttgcgatta tcgagccagg ttcagttata   4560
gcgagttatt tcgctattcc ggtcacttag ctgaattagt ggaccgagta gaattttagt   4620
aggcatatgt gttgataaaa tattttaatc acttataaag atgtagtata atttataagg   4680
caagggatta gttcagaatt taattaatta actgataagt tgtgattagg ctaattatat   4740
ttcttgtgta tagtttgttg ttcgtgatgt ttgcgttagg ttcgagaagc gtaatcatag   4800
cgcgtagtcg catattaata actagtgttt ccgtacaaaa ttgtacaacg cctcgccact   4860
aggtgtttaa tacgctatcg tatagcacta tttagatttg tgctattctt gtttatatgc   4920
attcatgtgc atcgtgcatc tcaattaggt acgataattg atcgcgtgat gcggaagaca   4980
agccaagtcg accccaagcg cgggctaatc cgcaggatga tgctgatgga caaacctgaa   5040
aatggtcgcc aagtggacgt cgtctaacaa cactaaccta gtgttaccca ggcaagcccc   5100
ggtgcatttg ccacctccct tgatgttttt aaaatctttc tcacttgatt gctgcattag   5160
gtgacaggag ttgattgatt aaacaattcc tgcattacct tccttgatct tgattaccct   5220
ccttgaaaac ccgtttttac aaaaaggttt tactatgctt agtattgctt agaaaaacaa   5280
aaggatttgt tttagaaaag atgtttggca agtgggagg gttgttttca aaataaaac     5340
ttgatggtga atccatcatg gatatgatgg attcaacatc ggaaaagatg tacctctgcc   5400
aggtaccaag ttttttgggtt aaaagattaa gctaagaccg ggcgggtgac ttgcacggga  5460
aaggagtctc agtgtagtgt ctccgtctga gtcgattaag gaccttgtcg atgtaggctt   5520
gatgatcgag gacccttttaa ctggtcacat gcctcgtcat gggtaagcct tgcctcgggc  5580
agactaaggc cagaataaga taacacgaaa tgggcgtgga gcggtggcga gagtagcgtg   5640
tacccctccgt ggcaagaggc tggacggtgg tgtaactgtg ctctcggttt gcgtgaacct   5700
gatctggtct taagaaccccc ggtggcgggt tgacatatgc aagggttaag tgctacatat  5760
```

```
gtcgtgtgat tggagatcct cagctgagta taatcgattc ggatcgccgt accttcgcgg    5820
ttatgaagac ttggtcattg ccctacacgt agcattccac taaagatgat gggttttgt     5880 taagaaattg gctagtgcag gaccagtgat tgaactaggg tagaaagaac tctagttaca    5940
ggtaattcta cttaacttga caaataaaac tggattttaa ggatccactt tagtaagcat    6000
ttctgcaaaa cagagtcttt gattattgaa aagccttacc ttgactccca tataaccagc    6060 ataccttga gagtcttttc tttagtcggg taagacttgc tgagtaattc catactcagg     6120
gttttattcc ctgttgtttt tcaggttcta actttgtgct gttgttgatg tgttaagtg     6180 ccggtgggct cggccttctt ataagtctaa gtaacccttc tatacttctt attgaggatg    6240
atcccttgag ctagcatata tatttcaaac ttatactttt gtaatcactc cgataaacta    6300
atgtaaaatt tttgtaacct gtaaaatttg gtagtaagat ttccgctgca acaaatattgg   6360 tgtgtgtgat ttgtgttact taatcctgcg gttctggttg taagtggttt atccgatgtc    6420 cttgggcaa tcggacagat cctgttaagt tatctggtgc acatgcacag ccgtctgagg     6480
tctttgggac aaggacaggt gcatgtgggc ccaataactt gggaggttct gccacagctt    6540
gaagcgtccc caatcctctg ggactcaaat gtgatacaat tactagtccc aggaggctag    6600
taaacacatt tatacatcag atgattcaga tctgcttaaa cgagacaaac ctataaaggt    6660
ggcgatcaac tttaagagtt ggtccacaac tcgggacata tcatcagagt ggggctgaag    6720
cagcccgata tacgcagtga agcaattcag cggtccaaca gccacaggca aggttgggaa    6780
cagtcgtaac tcttacccga tctcttttttt ctgaaaaaca acaaataagc aagggtgagt   6840
acaaacgtac tcagcagccc accttcaccc gcggaatggg gaaatcagat ataatgcatg    6900
gaatatgtag agctcaggat atttgcagaa acagcaatat tttatgcagg gttgttttga    6960
aaaacatttt gtattttgca aagtgcatcc tctccaaaag gagcaggaag ttttttcagta   7020 ttataacaaa atcccctgga ctaaaccatc caggtatctc agcagtttcc cactggtttt    7080
cattttcaaa aacagctact ggacttcccg tccaccatag ctcacggctc aaccgccgga    7140
ccttttaaaa accacttttc aaaagcatct ctttttttg gaaaacaaaa cattaattgc     7200
cataccatac cagactcgtc cattcctgtg gacacagact attcgaatag gttttcaaac    7260
tctgcgcaga ggtgtacact ttacccacta gtccagctct gcgatcccat gatcaatgag    7320
acccgaatcc gactctcttt cttttcccgc atgtcctaac cttaatggtt atcctgaagg    7380
agtcaggcca ccaccatgtc caaaccggac aaaactttcc ccctccttat cctcccggtg    7440
ctccccagcc ttcataaccc tggggttgga ccgtacgagt tcagattgag tgactgccca    7500
cacagtctcg agtggttgta ctattaaaga gtacaggtag tgaagatgac aaaccggtcc    7560
ttatatgagg ggacaatcct tctgctcacg cctaaaccag ctgaggacga atctctagtt    7620
tcannnnnnn nnnnnnnnnn nnnnnnnnnn nnnnnnnnnn nnnnnnnnnn nnnnnnnnnn    7680
nnnnnnnnnn nnnnnnnnnn nnnnnnnnnn nnnnnnnnnn nnnaagctgt taaaaacatt    7740
tagccaccca tcgagcttta tgatggtcaa tagactcatc agcttttctc ttgagtttat    7800
aaacccactt gcaatcaatc aaatttctgt caggtgcggg aggaaccaag tgccatgttt    7860
tattccgcat aagggcagaa aattctaggt ccatggcagc ttttccagtt tgggtcaaac    7920
aatgcaacag acaagctgga gggttcttca caaattgtca aatttccata cgggatcgag    7980
ccatcggtaa atttatatggg cttcacaata ccagtgtgta gcggactgcg gacatctgga   8040
atttgatgtc cggtgcaccg gtatgggcgt gcctggcgtc tgcgcgcgct gcgcgcgcat    8100
```

```
taaatgcacc gcagggagcc gttggcgccg cagggagccg ttgctccgct ggcacaccgg   8160
acagtccggt gcacaccgga cagtccggtg aattttagcg gagcggctgc cgcgcgaacc   8220
cgaggctagc gagttcctga ggccgacctc ccttggcgca ccggacactg tccggtgtac   8280
accggacagt ccggtgaatt atagccgagt cgccttagaa attcccgaag gtggcgagtt   8340
tgagtctgag tccctggtg caccggacag gtactgttca ctgtccggtg gcacaccgga   8400
cagtccggtg cgccagacca ggggtgcctt cggttgcccc tttgctcttt tgttgaatcc   8460
aaaacttggt ctttttattg gctgagtgtg aacctttac tcctgtatac actatacact   8520
tgggcaaaca agttagtcca aaagatttgt gttgggcaat tcaaccacca aaattattta   8580
ggaactaggt gtaagcctaa ttcccttca atatgatcta atttgttctt tagcccgcaa   8640
tgtaggataa ccaaatcaac tgtgttttgg tgacggataa gttttatct gattcaatt   8700
aaatgtaaca ccgattaaaa cattgtaact aaaatcattt ttaattttag tcctcttaca   8760
tctttccaaa ttctagtccc aatctccagc tgataattgt atttttattc aaattttcga   8820
gtaaaagaaa acgaaggaag aaaatatctg caaccgctct tctctctgat tttatccacc   8880
gctttcccct tccatatctg aagtcactag cctggatatt ttctccacgt agttctcctc   8940
ttcctcacgt ctccttctct cttatccatt ggacgctagc tcgctggaaa atctcacgca   9000
cgtctctcct ccagccttac ccagcgacca gcatttcttc catccatcag catccaaagg   9060
cagccggcag ccggctgtgc tcgtcggacc ctccgagcac ctctgtgccc gacgacctga   9120
ccaagctcgt ctccagcttg catccatcct gtgctcagtt tccatccact agcaccgtgt   9180
ctctggtcct gctcgtcgtg gacatcgtcg gctctagttc cttgctcgag ctcgcccttt   9240
gcgcagaccg cgtctcccct caccttgccg cggtcgggct ggccgtcgtc gtcagcttgt   9300
gtccatgccg acgaatttgt cgaactgctc actgcatctc tttaatctcg tcgcctgatt   9360
tttctgtacc gcgccgcgca acccctagaa ataaaaatca cgccgccgag cgctcctatc   9420
cttatcccgc caccgccctt ggtctcctac aaatctccag cgcgcaggtt tcttctccac   9480
gcacgcccgg cagcaagccg cagccgagca gctccttccc atctcccctc tgctcgctgg   9540
ctgaatcccc agccgctcgg ctctgctttt ctcccatggc gcggggttcc ctgcaggctg   9600
ctcgcggtat ccatctcctc tgctcctgct cgtccgtccc tgagctcctg tgccgcggca   9660
cctctgttcg gccgcgcctg atcggatttc ttgtgccgtg gcttcccctc cgagctcgcc   9720
cagctctatt gccgcgccca tggccggcgc tccctgcttg gttccgtctg tcgcgccgtc   9780
gtcttactgc tcgcctttgc gtcgcgcgca tagcgttctg ttgttcttgc acgcgcgaag   9840
ctctttgctc gtcaacgctt cagcctggat ttcgctttgt cgcccagctc ggctctacat   9900
gactacatct cccatgactg tctactctag ctcgccgtag ttcctgcgcg cgtcgagttt   9960
tctctactct agctcgccgt agttcctgcg cgcgtcgagt tttcgtgtgg agctctctgc  10020
tcacgcgcag ctcgctcttt ctttgttgcc gcgcgcacga attttatctg ctcgtcacag  10080
cgtgtcgagt tcccacacca tcatcacttc tgtcgcaagc tcgttggtca cagttgtctt  10140
gaccgcgtta actcgcgact gtggtcgtgt tcatcgaatt cgccaacgct tgttgccga  10200
tttgactgtc gtcgcttcgc gtgttgtcga gccgtcgttt ttcctgtctt gtgctcgcac  10260
ggtttcctgc tcgccagcgt gccctctcgg ctcgctcggc tttaatttcc aatcacgtcg  10320
tcgatctcgt cgtttgccgt cgagttgtca aacacgtcat ctccggctcg atccccacct  10380
caccagctta ccccagactt caatcgaagg tcatcgtcgc tcgtgcgtcc ccaagaaaac  10440
ccaagaatcg ggtgaagacg aagttagcag cgcgatattc cctaagcgct cgacaaattg  10500
```

```
cgtggatcga aaaatcactg ccgatctcac ggattcgtgt cagctgttga aacggtaagc    10560
tgatgaattg tttagaatag ttcggtaagc taatgaattg tttagaatag ttcgatcgtt    10620
gaataagtta atgtgttagt gcgaggctca ttagggtgct cgataaattg cgtaagtcac    10680
gaaactctcg tcgacttcgc agttcttgcg attatcgagc caggtcagt tatagcgagt     10740 tatttcgcta tttcggtcac ttagctgaat tagtggaccg agtagaattt tagtaggcat    10800
atgtgttgat aaaatatttt aatcacttat aaagatgtag tataatttat aaggcaaggg    10860
attagttcag aatttaatta attaactgat aagttgtgat taggctaatt atatttcttg    10920
tgtatagttt gttgttcgtg atgtttgcgt taggttcgag aagcgtaatc attgtgcgta    10980
gtcgcatatt aataactagt gtttctgtac aaaattgtac aacgcctcgc cactaggtgt    11040
ttaatacgct atcgtatagc actatttaga tttgtgctat tcttgtttat atgcattcat    11100
gtgcatcgtg catctcaatt aggtacgata attgatcgcg tgatgcggaa gacaagccaa    11160 gtcgaccccca agcgcgggct aatccgcagg atgatgctga tggacaaacc tgaaaatggt   11220
cgccaagtgg acatcgtcta caacactaa cctagtgtta cccaggcaag ccccggtgca     11280
tttgccacct cccttgatgt ttttaaaatc tttctcactt gattgctgca ttaggtgaca    11340
ggagttgatt gattaaacaa ttcctgcatt accttccttg atcttgatta ccctccttga    11400
aaaccgtttt ttacaaaaag gttttactat gcttagtatt gcttagaaaa acaaaaggat    11460
ttgttttaga aaagatgttt ggcaaagtgg gagggttgtt ttcaaaaata aaacttgatg    11520
gtgaatccat catggctatg atggattcaa catcggaaaa gatgtacctc tgccaggtac    11580 caagttttg ggttaaaaga ttaagctaag accgggcggg tgacttgcac gggaaaggag     11640
tctcggtgta gtgtctccgt ctgagtcgat taaggacctt gtcgatgtag gcttgatgat    11700
cgaggaccct ttaactggtc acatgcctcg tcatgggtaa gccttgcctc gggcagacta    11760
aggccagaat aagataacac gaaatgggcg tggagcggtg gcgagagtag cgtgtaccct    11820
ccgtggcaag aggctggacg gtggtgtaac tgtgctctcg gtttgcgtga acctgatctg    11880
gtcttaagaa ccccggtggc gggttgacat atgcaagggt taagtgctac atatgtcgtg    11940
tgattggaga tcctcagcta agtataatcg attcggatcg ccgtaccttc gtggttatga    12000
agacttggtc actgccctac acgtagcatt ccactaaaga tgatgggttt ttgttaagaa    12060
attggctagt gcaggacaag tgattgaact agggtagaaa gaactctagt tacaggtaat    12120
tctacttaac ttgacaaata aaactggatt ttaaggatcc actttagtaa gcatttctgc    12180
aaaacagagt ctttgattat tgaaaagcct taccttgact cccatataac cagcataccc    12240
ttgagagtct tttctttagt cgggtaagac ttgctgagta attccatact cagggtttta    12300
ttccttgttg ttttcaggt tctaactttg tgctgttgtt gatggtgtta agtgccggtg      12360
ggctcggcct tcttatgagt ctaagtaacc cttctatact tcttattgag gatgatccct    12420
tgagctagca tttatatttc agactagaa ttttgtattc cctccgatag aggtatgaaa     12480
aatttgtgta acctgtcaaa tttgtcaata atatttccgc taccactttg tatccgtgtg    12540
tgagtttcaa gacttaatct cgcggttctg gttgaaattg gtttatccga tgtccttggg    12600
gcaatcggac acatcctgtt aagttatctg gtgcacatgc acagccgtct gaggtctttg    12660
ggacaaggat aggtgcatgt gggcctaata acttgggagg ttctgccaca ggtcgggtt     12720 actccggtga gcaatcccga ccgtgaggag gcggaatccg gtgcaccgag gccagcacaa    12780
gcttcggtga ggggtgaggg acgcctaggg ccaaggcacg ggcacggggc ggggctgaat    12840
```

```
cggtcggaca ccgagcgggc gcggcaaacc accgcgatag agctccagcg aacacaaatt    12900
caccgtagag ggaaaagaat cggggcagga agggcctgaa ggtacttact tacgttaaga    12960
gttctgtcag ggatgcttga ctgttgcttt gggggaggat cttcactggg cggtcgttgt    13020 cttttgttc gtgtgtggat gatgagtgcc acttgcttcc gactggtatg ctctacaaat    13080
ccagtctttc tcaaaatgac attgtttaat ccctgaannn nnnnnnnnnn nnnnnnnnnn    13140
nnnnnnnnnn nnnnnnnnnn nnnnnnnnnn nnnnnnnnnn nnnnnnnnnn nnnnnnnnnn    13200
nnnnnnnnnn nnnnnncac gaaatgggcg tggagcggtg gcgagagtag cgtgtacctc    13260
cgtggcaaga ggctggacgg tggtgtaact gtgctctcgg tttgcgtgaa cctgatctgg    13320
tcttaagaac cccggtggcg ggttgacata tgcaagggtt aagtgctaca tatgtcgtgt    13380
gattggagat cctcagctaa gtataatcga ttcggatcgc cgtaccttcg tggttatgaa    13440
gacttggtca ctgccctaca cgtagcattc cactaaagat gatgggtttt tgttaagaaa    13500
ttggctagtg caggacaagt gattgaacta gggtagaaag aactctagtt acaggtaatt    13560
ctacttaact tgacaaataa aactggattt taaggatcca ctttagtaag catttctgca    13620
aaacagagtc tttgattatt gaaaagcctt accttgactc ccatataacc agcatacact    13680
tgagagtctt ttctttagtc gggtaagact tgctgagtaa ttccatactc agggtttat    13740 tccttgttgt ttttcaggtt ctaactttgt gctgttgttg atggtgttaa gtgccggtgg    13800
gctcggcctt cttatgagtc taagtaaccc ttctatactt cttattgagg atgatccctt    13860
gagctagcat atatatttca aacttatact tttgtaatca ctccgataaa ctaatgtaaa    13920 attttttgtaa cctgtaaaat ttggtagtaa gatgttcgct gcaacaatat tggtgtgtgt    13980
gatttgggat tcgttttctc gcggttctgg ttgtaagtgg tttatccgat gtcctttggt    14040
agatcttaca gatcctgtta agttatctgg tgcacgtttt ttggggtctg aggtctttgg    14100
gacaaggata ggtgcatgtg ggcctaataa cttgggaggt tctgccacag gtcggggtta    14160
ctccggtgag caatcccgac cgtgaggagg cggaatccgg tgcaccgagg ccagcacaag    14220
cttcggtgag gggtgaggga cgcctagggc caaggcacgg gcacggggcg gggctgaatc    14280
ggtcggacac cgagcgggcg cggcaaacca gcgcgataga gctccagcga acacaaattc    14340
accgtagagg gaaaagaatc ggggcaggaa gggcacgggg atggttcctt accttaggag    14400
tgtgctcggg gatgcttgac acgatgctag gagctccggg cagacgacgc ggtgcgcgc    14460 ttctccggcg agcttgagcg gcggcggcta agcgcgagag aggttgagag tgggtgaaat    14520
taggaagggg agggagagcg ggtgtaggcg ggctcaaaa gggagctggg ggcgtgggta    14580
ggcaacgtgg tcggcttcct cggcgtgagt gcgtgtgcgg gtcagcagcg gttgcgggga    14640
agatgagact gacaaggcgg gcccacagag tagaggcacg agcacgtgtg aggaggaaat    14700
gattcagcgc tgatgggctg ggcccactgc acagaggag agcggggcg tgcgcgcgag    14760 ggtgagcggc accataggt cgggcccacc tggcagatgg agagagaggg caggtgcgta    14820
ggctgggctg cttttctatt ttctttttat tctgaatttc tagttccttt tattttatt    14880 ttctctattg aattcaaatc caacgaaacc acaaattcaa atttgaatat ttcaaacatg    14940
tgcatcaacc aaaaacaaag tttaagctca gcatgatgca acaattcatg tctcccctag    15000
gtttgaatat agtaaagaaa aaaaatacat ctcccaaata tataaccaaa actctattag    15060
aaaggaagaa aataggaaat ctacggagat gagaaaagtg gtaacacctg aatttggtag    15120
atattagaga agaaatttta tacccccaaa ttcagggtgt tacataggct ctataatcat    15180
agcgtgtata gatgcatgaa taaataaggt gagcctatga gctatgcgtt tcttccactc    15240
```

```
ctgatacatg ccaatcaagt gtttctttga acaaccttc actggcatgc tttgaggagc    15300
ttgcatagcc cttctgaggt tttgccttg cctttgcctt tgccatagcc attgctactc    15360
tactgccatt ttgtggtggc ttcgtaaaaa ttcccctct catcccctga ttattacagt    15420
gcccatgacc cctttctctg gagggacctt tcttcccttta agactagaag ttggcgtgtg    15480
ctttatgcat gaccgcgtgc cgaatggatg cttctagtag ttctgcatca gaagctcatt    15540
ctgagcctta gcaccaagca acatgttgac gaggtcacat tatttgtgta cttgttgcta    15600
cagtactgct gttggagcac catattggag gggtagaagg tttggagagt tttctcgatc    15660
atctctaagt ctatggctat ctggccacag aaatgtagct gagcgacaat gcgatggatg    15720
acagtgttgt aagcctcaac tgcattgaag tcgagagtgg cccattcatg ttgcgcccgc    15780
gggagcatca catgcttctc cacactgaaa cactcacata gctctgtcca caatatcata    15840
tggtctttca cctctggata ctccatcttc aggcctggat ggatgtggtg cccgacgaag    15900
atcgtaattt ttgctttctc atgaagtttc aggcaagtgt cattcgggcc ctaccagaag    15960
atctcctttc ctagctatat cgcctctagg tgaaacttgc agtcgttagt ctaggtcggt    16020
tagttcttgc cattgaggac aagctccacg aatcaattct gttgtcttca accatagtcc    16080
gtcacacaaa attaacttta ggttaattag gcgtgctaat tatcaataat agaaatttaa    16140
atagataaat tgcatgaccc acgggagccg gtccagggcg tgctgacgag gcgtggctga    16200
agcatatgcc gacgagctgc gccccagctg gccgagcaag cgcgacccag tgcggggtgg    16260
cgccgtgggc tgacgcagcg tgaaccatct cagctcgaga tggcgtgacc agcagcaggg    16320
catgggtgcg tgggtcagtg tgacatcaag gcgcagagtt gggggcgccg acatagtgta    16380
cgactagaag ccggcatgac cgatctattc atgaacgcaa cgtgtgggcc accggtgggg    16440
tgggtgtgta gtgcacgcga ctggcgcacg agcctcgcca tcggggtgat tcgtacgacc    16500
cgcggttagt aggacatcga tggcttttta agtaaaagta atagattgga tatattaagc    16560
aggtcaaatc atcaggattt aacatgctag tgtatacata aatcaatcta caatatgtat    16620
ctgacagtaa gaaatcactc tacaatatgt atctgaccgc gagaaaacaa tctagtttga    16680
acaaaatcta ctaaacaatt gtctagagcg gtcaaaaacg atacccgtg cttctttatt    16740 cagcgaacgg aaacgaagcc tatcatgtaa gacaattagg caaggcggga ggacttgctg    16800
tggtgcaatt tccaaattca gaccttgaac cctctcctca gcaatggagg gcttattctc    16860
tttttgtcga ggcagaagca caaaaaacta tttccttgtt atatagacga ctagagcttc    16920
tcgtttgata ttagcccaca taagatttt tgatagtata aggccatctc caactgatcc    16980
cctattgtat cctctatttt attcctatat taaacgcaac tctgtaaata atatcatcta    17040
aaattctgtg ttacctattt tattggataa gtgagtctaa tattttgatc caaacagcgc    17100
ttaatctctt cccttgctgt aagttctcga cagatttagc tgggttaaaa ttcagactca    17160
aagacatata aattgatggg ctggtgttat ttccacgtgg gggtggaccc ctcacgggcc    17220
gggccgcatt cttggccaac catgggctat ccgcaacatt gcagactccg gaatccggat    17280
tggccgaatg ggcccggcag ccgaaaatga aaaggaaag gatcgaccct ctagcgcgat    17340
cgatccccgt gcgctggggc ccaaattagg agaacctcag taccccacgt gatccacggt    17400
ccgcccgccg cgcaagctgg gccacgggct cgcgggcggg catgcgccgg ttccgcgagc    17460
gaccaccccg ccatccgcgg agcctgccct gcgctgccca ccgctcctcc gcctactccg    17520
gcctcagcta ataacgatgg gtggtgggag ccgagcccct tccctctcct ccctctgcgc    17580
```

```
caccaccctc gccgccgcca agcccccaca gcacccgtc cccttcgccc cggctcaccg    17640
cgcgctcccc caccgcctcg ccgccgccat gtcctcctct tcctccccga ccccgccgc    17700 atcggtggac gccggtgccc cggcccttc ggcgtccaac gccatcgact tcctcacgct    17760
ctgctaccgc ctcaaggtga gcgactgagc gcccctgttt agtcgcttcg catttccacg    17820
ggccggcttg gttgagatgg atggaaatgt gacgcgatgg atgagattgt ggatgtaatt    17880
gcagacgacc aagagggcgg ggtgggtgaa gcgcggggtg caggcgcccg agtcggtggc    17940
cgaccacatg taccggatgg gcgtcatggc gctcgtcgcg gccgatctac ccggcgtcaa    18000
ccgcgacagg tgatcctgac agtttcgctc tcaagtctag ctcggcagta tttagccttc    18060
ttacggttcc gttttcatac actgtttatt tatcccttca attacaggtg tgtcaagatg    18120
gcgattgtgc acgacattgc agaaggtatg gtctcaaaag acttccgtct agacggcttc    18180
actgaagttt tggggctttg tgtgagatga gggatgcaat tttgtgaata tgcgagccta    18240
ttactacctg agatgttggt agatggtaac tagaccactg gactggagac ctgtagtagg    18300
aatgtaggat gtgtgttcaa gtacttgtgc caattagttg gttctttgac ctctgctagc    18360
caaagtgtaa aactttaaac tatgtgcaca ttttcctatt ttcattcaga agcatgctca    18420
gcttagaaat gaacacatga ttttgccctc cgctcatatg gactcttgct gctgttccta    18480
agccagcttg cctgtttctg gaactaactg cctatgagga tgtgggttca gttgactcat    18540
ttcaattgtt ttttctttg gtactccagc aattgttggt gacatcaccc cttctgataa    18600
tgtacccaag gaagagaaga accgcaggga gaaagaagca ttggaccata tgtgcgagct    18660
gcttggtggt ggttcaagag gtgaatactg aaacttgcaa ttgtgataca ttagcatttt    18720
atgctgtagt taattaggca tcttatgcct caaattgtct tttcatgatt tagttatata    18780
tgaaatgaat gtggtgctat tgcacactgg catcatcttt ctagattact caatagtcta    18840
gacttaatga tcccattatg tgtgcatagt accatagttt caaggaaaaa agaacaatat    18900
gtggatgcca atgaattttg tgaatacaat actatagtac ttgcaggtca tatacatatt    18960
ttattttacc cttgaaaagc tattcatctg ttattattat ttcttagatg gtcatttttc    19020
catccgatac ttttcacttc catcagggaa gcagatcata acctggcaat tattttgtag    19080
aaatccagcg ggcagctttt gttcttattt tttgatacat agtttaaata agtattggat    19140
aattcttaga gtattcacat ccctagtta ggtgtcaagg aaactcttgg taacttaaaa    19200
tcactcagat tatttccaga gaaactgtta tttatacttc tctttttctt tttataaggt    19260
gtattagtgt ttgagaattt cattcaaaga tatgctttat ccataatttt cccttgcaat    19320
atatgaactc aatatattat caattactac aaaagcaatg tctcactaaa atgcatgtga    19380
aatatgaatc tatagatta tctttgtgca ataaatatac aaatattttg actagtttca    19440 ttgactttt tgaatcctta cgccctacat tttgaaatgg aggttgaaaa gataagggat    19500 gttttgtag aagccaaaac cgaagagttt atattcagca atgttgatg actatgagtt    19560 ttggaatttg aacatgatat tgtaattgat ggtgataata ttattccatc tctaatgatt    19620
ttctaccttg aagcattatg gatcgtaaat tatttatgct caaatggcta tcatagcatc    19680
caacattttt tccctaagag tttcacaaca tagaattcta gtattctggt tgtgttctca    19740
ttattcatat cattaatcgt taaaaatat tggagagatc cagcatccct tacatgtgaa    19800
gtgaaccttt tagaactaaa taagtatct tagcagcctt ttggaaacag tttttcatgc    19860
aggataaaag gatgttctct gtacaggcga gactaaagag ttcatgtgat ctttgacatg    19920
gtatatataa taaatacttg cctttatctg catgctgttg tcttgcagca caagaaattc    19980
```

```
gtgaactttg gatggagtat gaggagaatg cgtctttgga agcgaaggtt gtcaaagatt    20040
ttgacaaggt acagtttcat atttcaatcc atcaagttgg tggcatgatt gcaacgtctg    20100
tctgaagcta tcagatggta gttcttgtga tcattcaata ggcaatgcat ataactggca    20160
ggatatttaa ctaatgtagg caatcattat gattatggcc cctaacccat atggctccac    20220
ttcttccttt tcctttgcat gctgtaatcc tttgttgcac tgttatattt ccaggttgag    20280
atgatacttc aagctctgga gtatgaaaag ggtgagttca tactggtgct tgaatatttg    20340
aactaacatt tcccatgcac agtagctata aagtacaaac cacaactatt taaatgcatt    20400
catcaaatat tcttgttgta ataaccaaat aaatgtatat agtaaaatca gctcacattt    20460
cacatttcaa atacagcaca tcttttctt tgcatcattt gtgcttatat tgggtaggcc    20520
tggtgtagtg gtgagggcag tctcactaag tcactatgtt gccagttcga aacagcctct    20580
ctgcatttgc aggggaggct tgtctcgatt tatcccatct caagaccccca ctcatgtggc    20640 agcctccgcc ctagatctgc ccatctgtgc ttacaccatt atttaatttg ctccacggcc    20700
ttctgggtgt gagaagtgat acatatgatc aatgtactat cacttaacac ctggtgaact    20760
ccttgttgat agatggggtt aacagtatca cacttacgcc tatgtatttt aaaattttca    20820
gagcaaggac gggaccttga agaattcttc caatcaacag caggtgtgat ttttctcttt    20880
ctgttatgct cttctcaatt ttcatgagta tccagtacat aaatcttgct cttctcaatt    20940
ttcatgacaa tccagtacat aaatcttgct cttctcaatt ttcatgagca tcctgtacat    21000
aaatttgaac agttcattta agctgagaag gatgttgcca ttttttggt cttacactta    21060 aaaatgtttt cctgagataa tataaacatt catcagcaat tcagaacata ttagtgcctg    21120
aatgattatt gctaattgaa aactggacac taccacctat aatggttttc tttaccatga    21180
actgatacat gcctatgcct tttatggttt tctttatca cgtgcttatg tttgatctca    21240
tttttacatt gtattagacc gtgtccagca gttcacccac ccaaaacact gttttgcact    21300
tagattgcac tattcgcaga gtggaatttg aatatgggga tggtaaactt agcctaggct    21360
attagcatta gagtcattgt gtaacaaaac catatccccg cacctaattc ccatgcaggc    21420
aaatttcaga cagacttggg aaaagcatgg gcagcggaga ttgcatcgag aagaaaaaca    21480
aagtgatcaa acgatgctca ttttaccacg tcggttccaa gacaacttgc tggcacagca    21540
tttctgttga actttgcttt tactagatga tacttcgagg tggcattgag acgtagggtt    21600
gccttgggaa tgtgaacttc accacatttc ttggtcctgc cctgaccctg aggcatattg    21660
ggcttgcgat accagggctc tagataagta agataaccca cttgggtat tggttgtaga    21720 tgctcctgcc aagggcagtt agctggatcc aacgggaagg ttcagcacca gctggtggtg    21780
atgtaaaatc cttcacttca tgaattactg taccattacc gtttctcttg ttaatccagc    21840
ctcacggttt cggcctttt taatgtaatt ctattgtttt caagtataat gagcctgaat    21900
atttgctata tccatttttgg ttgttgatga tgacctgaag tgcattcata ttttcatagt    21960
acgtataatg ctgaagccta aagctgacc actgatagtt ccggtgtagc gtcggatcgc    22020
atgtattagg gtctgttcgt tttatttga atccacgtgg attagacgga attgagtgag    22080
ttttgaaagg atcacgatgc ccaagaggag ggtgaattgg acttttctaa aaatcaacac    22140
taattaaaat ctaagcaaga gtccaacttc accccgataa ctatcactaa gagaataata    22200
atagaaatac aacaatgtta agacaatatt tcaaatactt gctaaacaaa tacacaatgt    22260
aaaatgtttt aattaagtgc ggaatgtaaa gcaaggttta gaagactcca atttttctcg    22320
```

```
aggtatcgaa gagtcggcac tctcctctag tcctcgttgg agcaccctcg caagggtatc    22380 actcccctt  ggtcctcgca agaaccaagt gctcacaacg agatgatcct ttgccactcc    22440
agcgcagtgg atccctcacg accgcttaca aacttgagtc gggtcaccaa caagatctcc    22500
acggtgatca ccgagctccc aacgccacca agccgtctag gtgatgacga tcaccaagag    22560
taacaagcca tagactttca cttgaccaag agaagcctaa tgcatgcggt gtatgctcta    22620
ggtggctctc gctagcgcta ataaggtcca aatgcgggat taagattctc aaataacctc    22680
actaggcttt gtggtgcttg caatgctcta ccaatgtgta ggagtaaatg tgggtagcaa    22740
gaccatcaat atagtgggtg gagggggtat aaatagccct cacccaccaa ctagccatta    22800
ccaggaatct gctgcacatg ggcgcaccgg acagtccggt gcgccaacgg tgcgccaacg    22860
gtcgactcca atggctagtt ctgacagcta gccgttgggc agatggcaca ccggacagtc    22920
cactaaaatt caactcgcga acaacgcgct ctcaggtttc tgtgcgcagg gaaccctctt    22980
ccttgggcca ggctgccccc actggcgagg ggtgcaccgg acagtccggt gcacaccgga    23040
cagtccggtg ccccaaagcc agaaacccta gtttctgttt tgtgctgttt tttcaattcg    23100
gttttcgttc taacttgtga gtatgttcta gagtggcacc tagcactata tgtgagtgtg    23160
aatatgcacc aacactacac tagaactctc ttggtcaaac tactcatcga caacccctct    23220
ttatagtacg actaaaacaa aataaaagac ctaactatat cacgagtgtc cgcaactcct    23280
tgacactcgg aatacgaaga ccttcacttt ttgttttgtc gctttagccg tcgcttcaag    23340
ttcttatctc cgagattgtt ttcaccgttg tagtacatct acatgtaatg cgacctaact    23400
taccatttgc ctctgcaaaa cacatgttag tcacatataa aattacattg tcattaatca    23460
ctaaaaccaa ccaggggcct agatgctttc aatctccccc ttttggtga ttgatgacaa     23520 cctacaagat tgtgagagta gtttgttttg aaatttctgt caatagagaa gatggttagt    23580
tatactcaaa aattttgac agaaagagtg tgtaacataa taataagagt gagtgcatac     23640
acattgtaag tttcttgttc atataaaagt gaaatcaaat cgatgaacaa gaactagaga    23700
ctggtgataa catataaggt gaaaacacaa tacacacaca gtcaacataa gcatcgagag    23760
catataaatg agtttgtgag ccaaaatcgt catacaaaag tggatctagt acagagagta    23820
tcaagcacat atattacatc aaaatgactc tatactaact ccctaactcc ccctagctct    23880
cacaactctc atatctctcc cccttttggcg tcaaacacca aaaggaaacc tgaacctaca    23940
gaccagaaga ggaaggaggt ggctggggcg catccgatca cgatcgtggc agaagagcaa    24000
acgccagctg agggtcagag tcagcctcgg atccaggatc taccgtagaa gctggagcta    24060
gtactgactc ggatggaggc tgtgctgcag gagctaccga agctgaagag gtcacagaca    24120
ccgccacaac agcagtggta acagcaggag ctggtggcac tggcggctga gcgctgatgg    24180
agctgatgac cggcgacgag aaaaccaggg tgaccggcag gagcggagag gaagaaggac    24240
caaatgaagg tagaggggt cctgcctgaa gggctagcac aacagcggcc tgaagatcta     24300
gagggggtgc agactgaaca ggaggaatct gagcaccggt atgctgaagt atgtgagtca    24360
tgaaggcccg gttctcagcc ttgtctgcca aaagctgctg ctgcagagtg tcctgtctgt    24420
cctgaatagt ctaaacatc gatagcattc tctcggacat ctgctgttgc accgctgcca    24480
gatgagcctg ctgctgagta agagtctgga ggatcgcagc cagagcaggg tcaatggcag    24540
gaggaacagc agggggcagca cgagaactcc gggcctcatg gtcatgtgag cgtggaggca    24600
caggaggcag aggcggaatc ccaaaatcat catcatcatc atcatcatca tcgtcaggaa    24660
ctgctgcgcc ctaagtctca aactgatgga aacttgtatc ctctgcctga atgtctgtca    24720
```

| | | | | |
|---|---|---|---|---|
| ctggatcagg | tactggtact | ggatcctcag | gggctggatg | gtaggagcca | aataggaggc | 24780 |
| gtgaggcctc | aagggtgccc | tggaactatg | gtggtcggat | cagctgtgcg | aagatgtggc | 24840 |
| agagataatg | agcatttggc | agctgtcgcc | gagcacgaag | accatccaat | accgtgtcct | 24900 |
| cgatctcaca | aataaggaag | tcaacaacat | caaactctga | atgaaagatc | agggcaccga | 24960 |
| ggagccaaag | ctgaatatga | gtggtagcct | ctctataacc | catccacgac | agaagcgtcc | 25020 |
| gtctcatgag | ctgatataag | tacttggcta | ctgtagtgaa | atctgccgga | gaacgtcgcg | 25080 |
| acccatctga | gaagggcggt | cggaacaaag | ccgcgatgtg | agctgtagct | ggagcaactc | 25140 |
| cgtcgtgagg | gcgacgagga | ggatcagagg | taccatagca | caagctatga | agacaagtcg | 25200 |
| atgactcatt | gaatccaaac | agctggcgaa | tctagctagc | atgaagtgta | acatcctctc | 25260 |
| gctcaaagcg | gaacctcatc | cactggtgat | cggggtcgat | ccatactgac | gcattgaaca | 25320 |
| cacggaccca | ctcctcaaca | tatctgccgc | tggtagtcag | aagagtgaga | agtcccagca | 25380 |
| aatatgtgag | atgcatctca | gagtctgcac | cagcggctag | cagaacacag | gaagacccaa | 25440 |
| tagccggtgc | gctcgcagaa | gcaatctggg | ctgaccnnnn | nnnnnnnnnn | nnnnnnnnnn | 25500 |
| nnnnnnnnnn | nnnnnnnnnn | nnnnnnnnnn | nnnnnnnnnn | nnnnnnnnnn | nnnnnnnnnn | 25560 |
| nnnnnnnnnn | nnnnnngttg | atgatcagct | tgattcgtta | ggataaaacc | ctgagtatgg | 25620 |
| aattactcag | caagtcttac | ccgactaaag | aaaagactct | caagggtatg | ctgggtatat | 25680 |
| gggagtcaag | gtaaggcttt | tcaataatca | aagactctgt | tttgcagaaa | tgcttactaa | 25740 |
| tgtggatcct | taaaatccag | ttttatttgt | caagttaagt | agaattacct | gtaactagag | 25800 |
| ttctttctac | cctagttcaa | tcactggtcc | tgcactagcc | aatttcttaa | caaaaaccca | 25860 |
| tcatctttag | tggaatgcta | cgtgtagggc | agtgaccaag | tcttcataac | cacgaaggta | 25920 |
| cggcgatccg | aatcgattat | actcagctga | ggatctccaa | tcacacgaca | tatgtagcac | 25980 |
| ttaacccttg | catatgtcaa | cccgccaccg | gggttcttaa | gaccagatca | ggttcacgca | 26040 |
| aaccgagagc | acagttacac | caccgtccag | cctcttgcca | cggagggtac | acgctactct | 26100 |
| cgccactgct | ccacgcccat | ttcgtgttat | cttattctgg | ccttagtctg | cccgaggcaa | 26160 |
| ggcttaccca | tgacgaggca | tgtgaccagt | taaagggtcc | tcgatcatca | agcctacatc | 26220 |
| gacaaggtcc | ttaatcgact | cagacggaga | cactacaccg | agactccttt | cccgtgcaag | 26280 |
| tcacccgccc | ggccttagct | taatctttta | accaaaaact | tggtacctag | cagaggtaca | 26340 |
| tcttttccga | tgttgaatcc | atcatagcca | tgatggattc | accatcaagt | tttatttttg | 26400 |
| aaaacaaccc | tcccactttg | ccaaacatct | tttctaaaac | aaatccttt | gttttctaa | 26460 |
| gcaatactaa | gcatagtaaa | accttttgt | aaaaacaggt | tttcaaggag | ggtaatcaag | 26520 |
| atcaaggaag | gtaatgcagg | aattgtttaa | tcaatcaact | cctgtcacct | aatgcagcaa | 26580 |
| tcaagtgaga | aagattttaa | aaacatcaag | ggaggtggca | aatgcaccgg | ggcttgcctg | 26640 |
| ggtaacacta | ggttagtgtt | gttagacgac | gtccacttgg | cgaccatttt | caggtttgtc | 26700 |
| catcagcatc | atcctgcgga | ttagcccgcg | cttggggtcg | acttggcttg | tcttccgcat | 26760 |
| cacgcgatca | attatcgtac | ctaattgaga | tgcacgatgc | acatgaatgc | atataaacaa | 26820 |
| gaatagcaca | aatctaaata | gtgctatacg | atagcgtatt | aaacacctag | tggcgaggcg | 26880 |
| ttgtacaatt | tgtacggaa | acactagtta | ttaatatgcg | actacgcgca | atgattacgc | 26940 |
| ttctcgaacc | taacgcaaac | atcacgaaca | acaaactata | cacaagaaat | ataattagcc | 27000 |
| taatcacaac | ttatcagtta | attaattaaa | ttctgaacta | atcccttgcc | ttataaatta | 27060 |

```
tactacatct ttataagtga ttaaaatatt ttatcaacac atatgcctac taaaattcta  27120
ctcggtccac taattcagct aagtgaccgg aatagcgaaa taactcgcta taactgaacc  27180
tggctcgata atcgcaagaa ctgcgaagtc gacgagagtt tcgtgactta cgcaatttat  27240
cgagcaccct aatgagcctc gcactaacac attaacttat tcaacgatcg aactattcta  27300
aacaattcat cagcttaccg tttcaacagt tgacacgaat ccatgagatc ggcagtgatt  27360
tttcgatcca cgcaatttgt cgagcgctta gggaatatcg cgctgctaac ttcgtcttca  27420
cccgattctt gggttttctt ggggacgcac gagcgacgat gaccttcgat tgaagtctgg  27480
ggtaagctgg tgaggtgggg atcgagccgg agatgacgtg tttgacaact cgacggcaaa  27540
cgacgagatc gacgacgtga ttggaaatta agccgagcg agccgagagg gcacgctggc  27600
gagcaggaaa ccgtgcgagc acaagacagg aaaaaacgac ggctcgacaa cacgcgaagc  27660
gacgacagtc aaatcggcaa caaagagttg gcgaattcga tgaacacgac cacagtcgcg  27720
agttaacgcg gtcaagacaa ctgtgaccaa cgagcttgcg acagaagcga tgatggtgtg  27780
agaactcgac acgctgtgac gagcagataa aattcgtgcg cgcggcaaca aagaaagagc  27840
gagctacgcg tgagcagaga gctccacacg aaaactcgac gcgcgcagga actacggcga  27900
gctagagtag agaaaactcg acgcgcgcag gaactacggc gagctagagt agacagtcat  27960
gggagatgta gtcatgtaga gccgagctgg gcgacaaagc gaaatccagg ctgaagcgtt  28020
gacgagcaaa gagcttcgcg cgtgcaagaa caacagaacg ctatgcgcgc gacgcaaagg  28080
cgagcagtaa gacgacggcg cgacagacgg aaccaagcag ggagcgccgg ccatgggcgc  28140
ggcaatagag ctgggcgagc tcggagggga agccacggca caagaaatcc gatcaggcgt  28200
ggccgaacag aggtgccgcg gcacaggagc tcagggacgg acgagcagga gcagaggaga  28260
tggataccgc gagcagcctg cagggaaccc cgcgccatgg gagaaaagca gagccgagcg  28320
gctggggatt cagccagcga gcagagggga gatgggaagg agctgctcgg ctgcggcttg  28380
ctgccgggcg tgcgtggaga agaaacctgc gcgctggaga tttgtaggag accaagggcg  28440
gtggcgggat aaggatagga gcgctcggcg gcgtgatttt tatttctagg ggttgcgcgg  28500
cgcggtacag aaaaatcagg cgacgagatt aaagagatgc agtgagcagt tcgacaaatt  28560
cgtcggcatg gacacaagct gacgacgacg gccagcccga ccgcggcaag gtgaggggag  28620
acgcggtctg cgcaaagggc gagctcgagc aaggaactag agccgacgat gtccacgacg  28680
agcaggacca gagacacggt gctagtggat ggaaactgag cacaggatgg acgcaagctg  28740
gagacgagct tggtcaggtc gtcgggcaca gaggtgctcg gagggtccga cgagcacagc  28800
cggcagccgg ctgcctttgg atgctgatgg atggaagaaa tgctggtcgc tgggtaaggc  28860
tggaggagag acgtgcgtga gattttccag cgagctagcg tccaatggat aagagagaag  28920
gagacgtgag gaagaggaga actacgtgga gaaaatatcc aggctagtga cttcagatat  28980
ggaagggaaa agcggtggat aaaatcgag agaagagcgg ttgcagatat tttcttcctt  29040
cgttttcttt tactcaaaaa tttgaataaa aatacaatta tcagctggag attgggacta  29100
gaatttggaa agatgtaaga ggactaaaat taaaaatgat tttagttaca atgttttaat  29160
cggtgttaca tttaattgaa atcagataaa aacttatccg tcaccaaaac acagttgatt  29220
tggttatcct acattgcggg ctaaagaaca aattagatca tatccccgcg cacgatcttt  29280
ctcagacaat gcgcgattca gattatttta ccctgaacat tttagtcgtc aagttcaaat  29340
taatttgctc gaaataagat cattcgagtg agttcgggct tccgaatttg tgttcgcgcg  29400
agcgatggat tttaaatact catcggacgc accgattttc ggaacagcta ggttccgaac  29460
```

```
attacgaaaa tttaggaaga gcccggacag ataaaaaaat aaaaacgatg tcgcactcgc   29520
gacaaacgac accgatgcga tattaaaata gcgataagcg acaatgatta aaatttaaaa   29580
ttcgttttat ccactgatat tgcgtgctta aatccgaact cgttgttgag cggaaaataa   29640
acacctgggg tgttacacac cccgtccaat ccctggaccg gcggtactta ctcctggcag   29700
ctgtctagga tcatatattg tccccacaga ccaacacgag tcttttgtgc gcactttgtc   29760
ctcactcatg cgcacccgag aaaacttccc ggtcggtcac ccatcccaaa ttgctccaag   29820
ccaagcacgc ttaacttgga ggttctttcg agataggctt ccgaaaaaga agatgcacct   29880
tgttggtatg attacactat taattctatt aagccttggg ccaggacatc ccatcccagg   29940
ggccaggata tcacaatcca cccccttag aagaccgacg tcctcgtcgg tcaaccccaa   30000
tccaggaacc tcccctcttg gccacgtctg tgtgtctagt gccgtcatat gccatgccat   30060
gtgaccactc cgggcccaca tgtgccatgc gccatatacc cgaacccct agcccacaca   30120 cgcccgtgaa accgcgagtg tcggctctga taccacttgt aacacccgt ctaatccctg   30180 gaccggcggt acttactcct ggcagctgtc taggatcata tattgtcccc acagaccaac   30240
acgagtcttt tgtgcgcact ttgtcctcac tcatgcgcac ccgagaaaac ttcccggtcg   30300
gtcacccatc ccaaattgct ccaagccaag cacgcttaac ttggaggttc tttcgagata   30360
ggcttccgaa aaagaagatg caccttgttg gtatgattac actattaatt ctattaagcc   30420
ttgggccagg acatccatc ccaggggcca ggatatcaca ataagtgtcc cgcccagagc   30480 gcccctccg ccattcactc acctccagtc ccgttctcat ggccagaacc ctgccatcga   30540
gttcgtcggg tcccctcac cggtctggcc aactccagcg accccagacc cctgggggtc   30600
cgcgcttgtc tcgtctttgg cgacttcacc gctgcggatg gagcagcgcc ggccgcagtg   30660
ctgttaaccc ccctgacgcc taatcctagc cgtttagcct tgatctagcg gtctagatcg   30720
ctggatatcg cttcacgtgg gtgcccttgc ccctgggccc cacttgtcag tcatctgtgc   30780
cctagcgctg ggcccgactg gtcagctcgt cctcacctcg gatcatcact tggaaacact   30840
atgtagcagc atgaatgcaa caatcatgac acttctagag ctcacaccaa tatagaacca   30900
aaataactct ctactgtttt gataaaggga aaagaaaagt gaataaagga aagggtaaca   30960
cctagatttt gagtatagag caaggaaatt tttatacccc aaaattcagg gtgttacagc   31020
tacgtagtga aaccttgccg actcaccttg gtagtgtttg agggttgat cgacctgagg   31080 caaaaggga tcacgacttg tgggtaaagt gtgcaacctc tgtagagtgt tagaagctag   31140
tatatcagcc atgctcacag ttatgagcag ccttgggagc tcctttgatt agagttactc   31200
tggatacttt tatgatgatg cttaatgatg gtgattatga ttatgaattc ttggtatttc   31260
ctcttggagg gagtaatgtt tgggtttata acttggggtt attgctaaaa catggctctc   31320
tactggtaat aaataccta ccaactaaaa gcaactgctt taagcttaac cccacataca   31380
gctagtccac tttagccaaa caggacattt gttgagtacg ttgaggtgta ctcaccattg   31440
cttaaaaaca ccaaacccca ggttgtcccc attgcaacta gtgctcagga gaagatgaag   31500
gcaacgtgga ggactttcag gagtttcagg acttcgacga gttctagact agattagtgg   31560
caaaccctca gttagctgcc tgtgaaggcc ttatcgtact gcgtttcgtt caaaattttg   31620
attatgacct aagttaatga ctctgtggat gtcttggaca tccactacta gaaatatgct   31680
tatttaagac atacatctta agacaaatat cagtgcattt tatagaagcg tctttttatca   31740 tatggtgctg agtacggtaa gacggttttgt tggatatccg tctttaatga agaaggtttt   31800
```

-continued

```
tgaggcagat atatggttgg aaatgtctta tattgattta atacagtttg atgttgaaaa      31860
ccgtctcaaa taaatatacc ttttgaggca ttaagtttac aagaagtgtc ttttatttg       31920 gttagtatat tagacacttc tgtatatgaa accatctcaa ataaagatat tattagagtc      31980
atctagacta tacaaaattg tcttagatgt tagtgagtat actagaaact tgtaaacata      32040
aaaccgtctc gtacgatatt tttgatagga catattgtga aaaaacatag tcaatagtaa      32100
attctgatta gattgaacta aacatttttt ggaatttaaa atgaactagt tagctgactg      32160
tatgttcgta cggtttctat atatcatata ggtaaaaaat cttgcttaaa taagaatctt      32220
cttcaaataa aattatacgt ttgaaatatg attattttt attttctcat caacagtatg       32280
tttatagtta taatatcgtc tctttgtacg gtataagcaa cctgataagc ggtggttaat      32340
gccacgaata tttctcttta tatacgtatt gcacatatat acaatacgtt ttattaatat     32400
agcggtggtt aatgccatct cctgcgtccg acgcccatcg ccgaggctga gaggcaagat      32460
ccgtcgtctt cagtgccccc agcgcggtgc tccaaactcc caggctatgc ttttgtttat      32520
gttttattgt catttcatga ttcatgacat gacaggctct aggctatgct ttagacattt      32580
aataagtata ttcagctcaa acgaaacggg atctaaacca gagggttaaa ggcatgtttg      32640
gtttgtggct aaatgtgcca cactttgcct aagtttagtc gtccgaattg aataactaac     32700
cttagacgaa aaagttaggc aaagtgtgat aacttaggta gcgaacaaac atgccttaag     32760
tctcacatct agggatggca atttaatgcg tggatagtga tatccgtcgg atattcgacc      32820
cgacggatca ggatatggat atgttttttg acctgcgggt tagacccgta cccgatccga     32880
gataaagcag acatggattt ggatattaaa cctcacccgc gggtaattcg ttggatatcc     32940
gaaattaacc attagtccat tactgtcgat ccacacatgg acaccaatga acaaatcgcc     33000
agcccaccat tgtccattgt gcccaggcgc caagcgccag cccattgccc actaaggcat     33060
cattccgcca aagacccaaa gtggcaaaca cccaaaccga caaacactaa tgatctaatc     33120
cccatccccc agccggcagc ttccgagcaa accaactcat ccggtcggtc atccactcat     33180
cctcatcccc tgcccatctg atccgatcag tcatctcatc ctcatcccct acccgatcgg     33240 atccctgct catccgccga gcaccaccaa gcagcaggct ccagtcgtcg agcaccagca      33300
ggagcacgac acgccgccca gtaggagcac ggccaggagg acgacgcccg catcctgcct     33360
cttctcctgc tactggagcc tctactgcta ggagcacggc taggaggacg acgcccgcat     33420
ccagcaggag caccagcagg aagaggacgc ccatactgct gtcgttgagc gatgatctga    33480 tgcccccat catggctctt ctcctccctc gcggcctcgc ctcgatctgc tgctgccgga      33540
tccgagcgcc gtgcccacgg gtcacgacca gcgatatgca gggatcaaga atccaacttt    33600
gagaaaaatt gcttgagatg taaatggcgc caccggagta ccatcagtac tgtgacggaa     33660
cctcccaagt aattaggccc acctatagtt gtccttgtcc aacagacatc agacacccta     33720
tagatgttcc taaatcactt cacaagttcg gtatcttctt tcttaccttt ccaggaacgt     33780
ttcacccatc ttgcagacat tacagaacat cggagatata gaaatgcaga agcgattaca     33840
taacttacat ttatttaaaa agtaagatca agttacttat tacagaccag agttatccta     33900
gaagtgcaga gtaatattat tacaatacca agggaggcaa aaactcctcc cgatggtttt     33960
taaacaaaag ttctatatgg aggaccaagt cttcccgcgg cttcactctt gttttttcttc    34020 cttgggaacc accttggagc agaagcaaca aaaatttgtc gcttcctcac ctaaaaacaa     34080
cggaggaata aaccatgagt atggaattac tcagcaagtc ttacccgact aaagaaaaga     34140
ctctcaaggg tatgctggtt aagggagtca aggtaaggct tttcaataat caaagactct     34200
```

```
gttttgcaga aatgcttact aaagtggatc cttaaaaatc cagtttttatt tgtcaaatta   34260 agtagaatta cctgtaacta gagttctttc taccctagtt caatcacttg tcctgcacta   34320
gccaatttct taacaaaacc atcatcttta gtggaatgct acgtgtaagt cagtgaccaa   34380
gtcttcataa ccgcgaaggt acggcgatcc gaatcgatta tactcagctg aggatctcca   34440
atcacacgac atatgtagca cttaacccctt gcatatgtca acccgccacc ggggttctta   34500
agaccagatc aggttcacgc aaaccgagag cacagataca ccaccgtcca gcctcttgcc   34560
acggagggta cacgctactc ccgccaccgc tccacgccca ttttgtgtta tcttattctg   34620
gccttagtct gcccgaggca aggcttaccc atgacgaggc atgtgaccag ttaaagggtc   34680
cccgatcagc aggcctacat cgagacggtc cttaatcgac tcagacggag acactacacc   34740
gagactcctt tctcgtgcaa gtcacccgcc cggtctcggc ttaatcattt caaacccaaa   34800
gtttggtacc tggcagaggt acatcttttc cgatgttgaa tccatcaagg cctttgacag   34860
attcaccatc aagtttttatt tttgaaaaca accctcccac ttttgccaaa catcttttgt   34920
aaaacaaatc cttttgtttt tctagagcaa ggctaagcat caaaatcctt ttgtaaaacg   34980
ggtgatcaag gatggtaatc aaattcaagg aaggtaatgc aggaattgtt taagcattca   35040
actcctatca cctaatgcag caatcaagtg agaaagattt taaaagcatc aaggaggtgg   35100
caaatgcacc ggggcttgcc ttcgttagta ggtgagttag gctcggtccc gcagatatcg   35160
aagtagaaac aattgccggc ctgagaatcc gaaggtgggg gtgtcttctc ttcggtcact   35220
tcaatctctt cttcgttttc taaatataac catataggta tatatatata taagaatgaa   35280
tgccatgtaa tgctcatgag agtgcgaaga taataaagat ttattatcta agtcttgaat   35340
acaactttcc ttcacggaac tccgagaact tagggtttcc ggagtcagta aaggagttca   35400
aagggcaggg gggttttagg ttctaagtat caaacaaggt ccaaatcaac ccaaattcta   35460
cccaaggcct ctaaataatg catagaactt atgtaaaaag tttggacatt tttggaaatt   35520
ccatttattt tctaaaaatc caaaaccact accttaaact actttaaata ccttaaaatt   35580
ccttagttaa cctaaaattc atataactat ttttattaaa ttctatggaa ataagaagc   35640 ctaggaaaat tggtttcaca atttttaggat ttttctacaa tttttaaaaa atttccaaag   35700
ctctatagaa aaagaaaagg aaaaagattg aatagtgttg ggctgattct agcccagccg   35760
gcccagtacc aggggaaaac gcgcgcgcgc gccctcgccc tggcgacttt gcacagaggt   35820
cctcggggtt tggctaatta gaactggctt ctatcactat tacactgtgt cgctgacaga   35880
ttgcagagaa gccccctgcag ttctaactct tcgcagaggg aggtcctcga cggcgttcac   35940
gcccagccga actccggcga gtgcctgcac cggccgaacg gggcaacgac tagggttccc   36000
gagcggcgga catcaaattg gacctagccc gagcatttcc cctaacctaa ttccatctat   36060
ggcccaatgg cttgctctgg ccacggtggc cgtgaacatc gcggcaagac agtcgcgttc   36120
ccggcgacca aagggctcct agctcgattg tgtgggtcgg caagcatcat agacttaagg   36180
gaaagcttaa acgagggaga gaaggagacg aactgaccgg aataaggctg gccgaggtga   36240
ggttcggttt cgggtggcgg agaattgatt tggggcgaat tcaaaattcg tgagctcggg   36300
cgaacaattg ctagcaatac gtggtggctg ggtgggtgat gatgttgtga agctctctgc   36360
ggggtcaatt tatagatccc aggggcggtg gcgcttaatt tgagccgaca gtgtgggcgg   36420
ccggagataa ggaagatcat cggcttcgcg atttcgtgtc caccgccgtg gcgggctcac   36480
cggcaatgat gagacaacag tggggagtca cggcgatgcg acagaggtgc tcggatacat   36540
```

```
ggtgtaaggc cgagcgacgg tgatccccgg cgggcttatc tgctcaagcc gcacggcaga    36600
ggggaagtac tggggttca ccggagtgcc gtccagcgca tgcctttacc gagcgatctt    36660
atctggtcac cggcgacgtg aatcacaacg gcggcgacgt gaatctcagc gaagatcagt    36720
cgtcggcggt gagagactac cgcgctggct gtctgatctc cctggtagca ctgtaccatg    36780
gagagttata tttagacagc ctgacagtca agtttggagc ccaattttct ctcaatttca    36840
aataacaact catccagtga cctgcagcaa agttgtagag ctacaatcca gctataactt    36900
tgctacaatg tgctcccaca aaaagtcact ggatcttgct taaaattaag ccctaagttc    36960
atgtcatccc actgttaatc tgaatttcag atttcaagca gtctgacagt ccaactttag    37020
gctcaattat ctccagtatt tcttaacaa ctatgctcac actcttaaga aaagttgttc    37080
tcctatgatt gggctataat tttaatgtgg tgacctaggg aaaaaccct atgatttaaa    37140 agttacaagg ctcaaaagtt gagcccataa cactatttt cagacttagt ataaaatctc    37200
aaatagggtc cttttttgcaa atgaggccaa aacttagggt ttggcttgta aattcacata    37260
tgagtgaccc aaatgactta agatacttat ttaacttggt ttttgcactt tagtccaaaa    37320
gtggactaat tttgcacata agcccctagg gtttggattt agggttttct agggttccga    37380
ttaggttttt tggtatccca gaggtataaa tgtggttcaa ctttattctt gggaatattt    37440
catgactatt tccctagagc ttttaggttt tctcaatttg ggttatatct taccccttta    37500
atccctattt agggttaaat tccctatcta ggttctattt gcaaacact aaaacaatac    37560 aacttgtttg aaattttac ctagtgaatg cactctaggt gtgtcaaaca tatgcaatgc    37620
caatgtttat gatgctatgc tcaagtttta gttgcagtaa caccaggggt gttacatcct    37680 tcccccata aagaatctc gtcccgagat taaaagtcct agggtaagta atggaaaagg    37740
aaacacgaca tacttttatt tccttatttc tggtacaagg caggggtggt tttggaatca    37800
ctcctttatt acaacagcta tacaggcttt acaatttaca agaagctaaa aagcctggga    37860
aattcttatc taaaagtct tgagtttccc atgtagcctc atcttcggaa tgttggttcc    37920
actgtatctt ataaaacttg agagttttct ccgggtaacc ctgtcctttt gatccaagac    37980
tcgaataggg tgctcagaat atgtcaagtc cggttcaagg acaacatctg tcacttcaac    38040
ggttcgatca ggaacccgaa gacacttctt caattgggac acgtgaaaca cattatgcac    38100
agcaaacaag gttcgggta actgaagtcg gtatgccact ggcccatatc tttccaggat    38160
aagaaaagga ccaatatatt atggtgcaag ctttcctttta actccgaaac gcgatactcc    38220
cttcattggt gaaaccttta agtagacata gtatccttca aggaaatata agggcattcg    38280
ccgtttgtct acgtaactct tttgacgagc ttgagctttc ttcaaattat gaattatcct    38340
ttgaactctt tcttcagtct ctttcaccat atcaggcctg aagaagtacc tttcaccagg    38400
ttcagaccaa tttagcggag tacgacatcg tcgtccatat aaagcttcaa agggtgccat    38460
cttgatgctt tcttgatagc tattattata tgaaaattcc gctaacggca acattcatc    38520 ccatttttgt ggaaattcca gaacacatgc ccgcagcata tcttcaagta tttggtttac    38580
tctctcagtc tgtccactgg tttgaggatg gtaggccgaa ctatggagca acttagtacc    38640
caaggatttg tgaagtgctt cccaaaactt ggctacaaat tgaggtccac gatccgacac    38700
tatgggtctt cggaacacca tgcagactaa gaatacgagc aatgtacaaa tgggcataga    38760
cagtaaccgg gtgatctgtc ttgaccggta gaaagtgagc aattttcgta agccgatcaa    38820
ttataaccca gatagaatca tacccttttg tagtcctggg taatcccaca atgaagtcca    38880
tactaatatc ttcccatttc tatgttggga tcggcaaagg ttgtaatgga ccagctatct    38940
```

```
tcatgtgtat ggccttgaca agtctgcaag tgtcacactt agccacatag cgtgcaattt   39000
caattttcat cttcgtccac cagtagtgct gctttagatc atgatacatc ttagtgcttc   39060
ccagatgaat agaatagcga ctaagatgtg cttcatctaa gatttgctgg cggagttctt   39120
cattcttcgg caccactatg cggttattga accatatcac accttgatca tcttctttga   39180
aacatttggc tgttccagcc attatcttct cacgtatgtg cttcataccc tcatcatctt   39240
tttgtgcgtc aattattctt cgtatgatga ttgactccag cttcaaatga tttgaagtcc   39300
catgttgaat cattcccagg tttaatttct ccatctcctg cataatgta atgtcagaag    39360 tcctcactgt taaacaatgg caggaagcct tgcaattgag cgcatctgcc actacatttg   39420
cttttcctgg gtgataatgg atttctaatt cataatcctt gattagctcg agccatcgcc   39480
tctgtctcat attcaattct gactgggtga agatgtattt caagctttta tggtctgtat   39540
aaatatgaca gacattaccc agcaaataat gacgccagat ctttagggca tgaaccacca   39600
cagctaactc cagatcatga gtaggataat gttcctcatg tcggcgcaac tgccttgaag   39660
catatgcaat tactcggcct tcttgcatta gcacacaacc gagtccactg cctgatgcat   39720
cacaatatac atcaaagggc ttggtgatgt ccggttgagc caataccgga gtagtggtta   39780
ctaatgtctt caattgttca aaagcttcat cacactttga agaccaattg aacttaatat   39840
cattcttcaa taaacttgtg attggcttca caagcttaga aaaatctggt atgaatcggc   39900
ggtaatatcc agccagtcca aggaaacttc ggacctgatg aacagtggtc gggggtttcc   39960
actccaaaat gtccttgact ttgctgggat ctaccgcaat ccccctggca gacaatacat   40020
gtcccagaaa ctgaatttcg tccagccaaa acacgcattt gctaaacttg gcatataact   40080
gatgttctct caagcgcgtt aacacgatcc gtaaatgttg ggcgtgctcc tcttcattct   40140
tggaatatat caaaatatcg tcaatgaaga ctaccacaaa cttgtccaac tcgggcataa   40200
ataccgagtt catcaaatac gtgaagtggg caggagcatt tgtcaatccg aaagacatta   40260
ccaggtattc aaataatcca taccgcgtag tgaaggcggt ctttggtata tcttcgggcc   40320
gaatacggat ctggtgatag cccgatctga gatcaatctt ggaaaatacc cttgctccag   40380
tcagttgatc aaataaaatg tcaatccttg gaagagggta cttgtttttg atggtgacct   40440
cattcagggg tcgataatcc acacacattt gtaaagtttg atccttcttt ttgacgaata   40500
tggctggaca accccacggc gatgagcttg gccggataaa tcctttctca agtagatctt   40560
gtaattggat cttcagttct gccaactcat taggaggcat tcggtacgat cttctagata   40620
ctggagccgt accgggtttc aactcaatta caaactctac ctcccgttca ggtggcagtc   40680
cgggcaaatc ctcgggaaag acattgggaa actcgcatac caccggaata tccttgattt   40740
ccggtataat ggcttcataa gctctgccag tagctttggt tggaatgggg ataggcaaaa   40800
gaatttcttc ctggttatga ctcaacctga taattctctg atcagtgttg agagttgctt   40860
tatgtctggc taaccaattc atacccaaaa tgacatatat atcttggcct ttcagaatga   40920
tcatattagt aggaaagtcc catccggcca aggttacggg cacttgatag gccacttctc   40980 tagtaaaatat ttgtcccccct ggtgagtgaa ttttttaaacc cctctttttga ttcatggcat   41040 gagatgcaat gttgctccac aaatttcttg ctgatgaatg tatgcgaagc accagaatca   41100
aagagaataa ctgcgggatg attggccaca agaaacgtac ccatcattac cggctcaccg   41160
tccggtgtag tggccacttg cgtataatat atgcgtcccg tcttctttgt atttttgccc   41220
atattatttt ccttggcttg agatgaattc ccagatcctt gctgattatt tgactggttc   41280
```

| | |
|---|---|
| tgctttggat aagggcaatc cttgataaaa tgcccagatt tgccacaatt gaaacatcca | 41340 |
| gtcgacgagc tgggtaaagc agggaatcga gtgcctgggg cacccggctg acttgatgta | 41400 |
| gtagggcat tattgggacg aataaagact ggctgcttaa aaggaaagga gggtggacga | 41460 |
| gcgaaagaac gattctggtt agaaggccgg atgacgaacc gttgcctgtt caccgggccc | 41520 |
| tgactagacc tgtcacctcc aaaacccttg gatttaccag cgcctgcata cttcgcttct | 41580 |
| actgccagtg ctgtactgac agctcttcca taagtaagat ctatgcaggt tgccatcttc | 41640 |
| ctttgcagtc gatcatttaa tcctctcata aagcaattct tcttcttcaa atcagtgttc | 41700 |
| acttgatcga ttgcatattg tgacaaatga ttgaacttat tgagatactg gttaacagta | 41760 |
| tccctcctt gtttcagctt cataaactct tcttgcttca tgtgaagaac accttctggt | 41820 |
| atatagtgct cgcggaaggc caccttgaat tcttcccaag ttatctaatg attggccggt | 41880 |
| tgaacggcca caaaattacc ccaccaagtg ctggcaggtc cgcgcagttg ctgggctgcg | 41940 |
| aataaaggct tctgggtttc tgaacatcgc agcagtccaa acttttgctc aatcacacga | 42000 |
| agccattcat ctgcttctaa cgggtcttcg gctttgacaa acagcggtgg tcgcgtctct | 42060 |
| gagaagtcca gtaagaggt ttcacggggg ccctgttgat aaccccgccc accttgttgt | 42120 |
| tgcaattgtt gacccgccat ctctctaaga aaacgggtat tatccgcggt tgcatttacc | 42180 |
| aaggccacaa tcgcctcggc cagtgtggga ggaacaggag gtggatttgg ggtagactcc | 42240 |
| ctcccacagg aggtactagc tccgtcctgt gctcgagtct tggaaggcat ctgtggcaac | 42300 |
| aacatttgga aaacaatatg atatgccaag gaaaaaccat ccatttaca ttaccaaaaa | 42360 |
| gagtaatgta cagactcgaa ttttacaac aggatacatt acctattata caatagcaca | 42420 |
| acctattatg caatagtaca aaatattata cattagagca acctgttata caatacacta | 42480 |
| cttctacttc tactacccca ttattcctgc tttccgttgc ttttggcggc ctcgtcgtcg | 42540 |
| ggtgtgggag accattcgtc gactagcctc atagaaggag ggggctgaaa aaggtctaac | 42600 |
| tcaccaccaa gcgcgtgtcc cgcaacatgc gagggtccgg cttccgactc accaggattc | 42660 |
| gtaggctcac tgggatgcag ttgcgaatat aatacatgaa tctcttcatg taaggtattg | 42720 |
| caatatgtct gcagttcatc aacagccaag ttgagctcgg ctactcgagc ttgagctttt | 42780 |
| tgctccttgt cccatgcaag cgaacgggat tgaacaaccc agtcaagtgc caaatcccgg | 42840 |
| tccgcgagct gatctcgcag atggcagata tctcttctca actcatttat gcggtcgcca | 42900 |
| tctatgaccc agatagtcgt tctgcggcgg agtttcgctt ggagtcgact tacttcagct | 42960 |
| tcaagatccc ctataggatc attgcttccg ctactactat tatcatgcct tggggtcagc | 43020 |
| tggtgactcg gcacaccaat cggtccagta tgtttgcgcg ttgttctcct tgtgcgcggc | 43080 |
| ggcattttct aagggggaaa atttgattag tatggttctt agcatgatgc atgtataatt | 43140 |
| acagaatcaa ccttagttga ttcacacctt ctatatgttg cactcttact acctggtctt | 43200 |
| taagatagac tcttcagaat acttaggtaa gaaaggaaga gagtttctag gtaagacttt | 43260 |
| tagaaaatct ttttgaagat gcctcataat atctgcaaag aagggctacg ctccgatacc | 43320 |
| agctgtgacg gaacctccca agtaattaag cccacctaca gttgtccttg tccaacagac | 43380 |
| atcagacacc ctatagatgt tcctaaatta cttcacaagt tcggtatctt ctttcttacc | 43440 |
| tttccaggaa cgtttcaccc gtcttgcaga cattacagaa catcgaagat atagaaatgc | 43500 |
| agaagcgatt acataactta catttattta aaaagtaaga tcaagttact tattacagac | 43560 |
| cagagttatc ctaggagtgc agagtaatat tattacaata ccaagggagg caaaaactcc | 43620 |
| tcccgatagt ttttaaacaa aagtcctata tggaggacca agtcctcccg cggcttcact | 43680 |

```
cttgttttc ttccttggga accaccttgg agcagaagca ataaaaattt gtcgcttcct   43740
cacctaaaaa caacggaggg ataaaccctg agtatggaat tactcagcaa gtcttacccg   43800
actaaagaaa agactctcaa gggtatgctg gttaagggag tcaaggtaag gcttttcaat   43860
aatcaaagac tctgttttgc agaaatgctt actaaagtgg atccttaaaa atccagtttt   43920
atttgtcaaa ttaagtagaa ttacctgtaa ctagagttct ttctacccta gttcaaatca   43980
cttgtcctgc actagccaat ttcttaacaa aaccatcatc tttagtggaa tgctacgtgt   44040
aagtcagtga ccaagtcttc ataaccgcga aggtacggcg atccgaatcg attatactca   44100
gctgaggatc tccaatcaca cgacatatgt agcacttaac ccttgcatat gtcaacccgc   44160
cactggggtt tttaagacca gatcaggttc acacaaaccg agagcacaga tacaccaccg   44220
tccagcctct tgccacggag ggtacacgct actcccgcca ccgctccacg cccatttcgt   44280
gttatcttat tctggcctta gtctgcccga ggcaaggctt acccatgacg aggcatgtga   44340
ccagttaaag ggtccccggt cagcaggcct acatcgagac ggtccttaat cgactcagac   44400
ggagacacta caccgagact ccttcctcgt gcaagtcacc cgcccggtct cggcttaatc   44460
atttcaaacc caaagtttgg tacctggcag aggtacatct tttccgatgt tgaatccatc   44520
aaggcctttg acagattcac catcaagttt tattttcaaa ataacccctc ccacttttgc   44580
caaacatctt ttgtaaaaca aatccttttg tttttctaga gcaaggcaaa gcatcaaaat   44640 cctttgtaa aacgggtgat caaggaaggt aatcaaattc aaggaaggta gtgcaggaat   44700
tgtttaagca ttcaactcct atcacctaat gcagcaatca agtgagaaag attttaaaag   44760
catcaaggag gtggtaaatg caccggggct tgccttcgtt agtaggtgag tcaggctcag   44820
tcccgcagat atcgaagtag aaacaattgc cggcctgaga atccgtaggt ggtggtgtct   44880
tctctttggt cacttcaatc tcttcttcat tttctaaata taaccatata ggtatatata   44940
taagaatgaa tgccatgtaa tgctcatgag agtgcgaaga taataaagat ttattatcta   45000
agtcttgaat acaactttcc ttcacggaac tccgagaact tagggtttcc ggagtcagta   45060
aaggagttca aagggcaggg gggttttagg ttctaagtat caaacaaggt ccaaatcaac   45120
ccaaattcta cccaaggcct ctaaataatg tatagaactt atgtaaaaag tttggacatt   45180
tttggaaatt ccatttattt tctaaaaatc cagaaccact accttaaact actttaaata   45240
ccttaaaatt ccttagttaa cctaaaattc atacaactat ttttattaaa ttctatgaaa   45300
aataagaagc ctaggaaaat tggtttcaca atttaggat ttttctacaa tttttaacaa   45360
atttccaaag ctctacaaaa aaagaaaagg aaaaagattg aatagtgttg ggctgattct   45420
agcccagccg gcccagtact agggaaaac gcgcgcgcgc gctcgcgccc tggcgacttt   45480
gcacagaggt cctcggggtt tggctaatca gaactggctt ctatcactat tacactgtgt   45540
cgctgacaga ttgcagagaa gcccctgtag ttctaactct tcgcagaggg aggtcctcga   45600
cggcgttcac gcccagccga actccggcga gtgcctgcac cggccgaacg gggcaacggc   45660
tagggttccc gagcggcgga catcaaattg gacctagccc gagcatttcc cctaacctaa   45720
ttccatctat ggcccaatgg cttgctctgg ccacggtggc cgtgaacatc gcggcaagac   45780
agtcgcgttc ccggcgacca aagggctcct agctcgattt tgtgggtcgg caagcatcgt   45840
agacttaagg gaaagcttaa atgagggaga gaaggagacg aactgaccag aataaggctg   45900
gccgcagtga ggttgggttt cgggtggcgg agaattgatt tggggcgaat tcaaaattcg   45960
cgagcttggg cgaacaattg ctagcaatac gtggtggctg ggtgggtgat gatgttgtga   46020
```

```
agctctctgc agggtcaatt tatagatccc aggggcggtg gcgcttaatt tgagtggaca    46080
gtgtgggcgg ccggagataa ggaagatcat cggcttcgcg atttcgtgtc caccgccgtg    46140
gcgggctcac cggcaatgat gagacaacag tggggagtca cggcgatgcg acagaggtgc    46200
ccggatacgt ggcgtaaggc cgagcgacgg ggatccccag cgggcttatc tgctcaagcc    46260
gcacggtaga ggggaagtac tgggggttca ccggagtgcc gtccagcgca tgcctttacc    46320
gagcgatctt atctggtcac cggcgacgtg aatcgcaacg cgcggcggcgt gaatctcagc    46380 gaagatcagt catcggcggt gagagactgc cgcgctggtg gtctgatctc cctggtagca    46440
ctgtaccatg gagatttata ttcagacagc ctgacagtca agtttggagc ccagttttct    46500
ctcaatttca ataacaact catccagtga cctacagcaa agttgtagag ctacaatcca    46560
gctataactt tgctacaatg tgctcccaca aaaagtcact gaatcttgct taaaattaag    46620
ccctaagttc atgtcatccc actgttaatc tgaatttcag atttcaagca gtctgacagt    46680
ccaacttcag gctcaattat ctccaatatt ttcttaaaac tatgctcaca ctcttaagca    46740
aagttgttct cctatgattg ggctataatt ttaatgtggt gacctagggc aaaaaccta    46800 tgatttaaaa gttacaaggc tcaaaagttg agcccataac actgttttca gacttagtat    46860
aaaacctcaa atagggtcct ttttgcaaat gaggccaaaa cttagggttt ggcttgtaaa    46920
ttcacatatg agtgacccaa atgacttaag atacttattt aacttggttt ttgcacttta    46980
gtccaaaagt ggtcgaattt tgcacataag cccctagggt ttggatttag ggttttctag    47040
ggttccaatt agggtttttg gtatccgagg ggtataaatg tggttcaact ttattcttga    47100
gaatatttga tgactatttc cctagagctt ttaggttttc tcaatttggg ttatatctta    47160 ccccttttaat ccctatttag ggttaaaattc cctatctagg gttctatttg caaaacacta    47220
aaacaataca acttgtttga aattttttacc tagtgaatgc actctaggtg tgtcaaacat    47280
atgcaatgcc aatgtttatg atgctatgct caagttttag ttgcagtaac accaggggtg    47340
ttacaagtac cttgtgcagg tgaccaagta ctaggccgca cagaactgca aggtacgtat    47400
gcacacatgg ttacatttac tatagaactg gagttatttt ttgatgcaaa ggctgccagg    47460
tcatggcgat ttcacgtccg ttaggctcga gaggtggact caaacatcca agttttgcaa    47520
gttttgatgt tggatgttaa atttctatgc tcaccctcg tttggttatt gatgtactat    47580
ttccatctca tgtcacaaat ttggcataag gaatgggtat tggtggctac tggctgtgtt    47640
tatttccaag tattatacat gtacaatgga acagttgata atagttttgc atgaactatt    47700
ggcattagct atctaaaagg acagaaaggc agacatgagc aacaaatccc gctccatggg    47760
ctgaaactgg gattcgtgat ggtcagctaa gcataccttc gccttcaaat ttgcgtagct    47820
tcttttttat tctgctagtt gtttggtctg ctgttcaaat gccttattat tctgcgagtt    47880
gttttaagac tgggcctcaa tttttttttca aggcagaaag tgctactgcc gctctcactg    47940
tagcggtgtg gtactgggat ccttgccaat aaggtaaaac tctaactgat cttcttacgc    48000
tttgcattga ggaaggagct cttctgggcg gttggataac agagtcgttc tagtgtgttt    48060
ttagggtgag cccgtccaag acgcccgtgc gtcccgtgc ccctcgccag ctgatgtcgt    48120
cctaggtata catacaggag gtgctgacga tggcactgct catatataag taatagagat    48180
agacatgtat gaaaagggtc ttttgttttc aagtagtgtg tagttgctgt tacttttaac    48240
agctaatgca atctggatga gtcacctatg aatgccatac tggaatctgt tgcgcttttg    48300
ttgatcatta ttattttgca atccaggcta ggggattgaa gaagcacttg aagaggctca    48360
atgcgcccaa gcattggatg ctcgacaagc ttggtggagc ttttgtaagt aaacatgtcg    48420
```

```
gggaccataa ttaggggtac ccccaagact cctaatctca gctggtaacc cccatcagca   48480
caaagctgca aaggcctgat gggcgcgatt caggtcaagg ctccgtccac tcaagggaca   48540
cgatcccgcc tcgcccgagc ccagcctcgg gcaaaggcag ccgacccagg aggattcacg   48600
tctcgcccga gggtcccctc aagcaacgga cgcaccttcg gctcgcccga ggcccaggct   48660
tcgcggagaa gcaaccttgg acagatcgcc acgccaacca accgtatcgc aggagcattt   48720
aatgcaagga tcgactgaca ccttatccta acgcgcgctc ctcagtcgat agggccgaag   48780
tgaccgcagt cacttcgccg ctccactgac cgacctgacg ggaaaatagc gccgcctgcc   48840
ctgctccgac tgctgtgcca ctcgacagag tgaggctgac agcagctaag tccagcctcg   48900
ggcgccatga gaagctccgc ctcgcccgac cccagagctc gggctcaacc tcgacgccgg   48960
acgacggact ccgcctcgcc cgaccccagg gctcggactc agcctcgacc tcggaagacg   49020
gactccgcct cgcccgatcc cagggctcgg gctcaacctc gacctcggag gagcctccgc   49080
ctcgcccgac ctcgggctcg gaccgaccac gtcgcagggg gagccatcat taccctaccc   49140
ctagctagct caggctacgg ggaacaagac cgacgtccca tctggctcgc cccggtaaac   49200
aagtaatgat ggcaccccat gtgctccgtg acgacggcgg ctctcagccc cttatggaag   49260
caaggagacg tcagcaagga tccgacagcc ccgacagctg tacttccaca gggctcaaac   49320
gctcctccga cggccacgac atcacatgaa cagggcgcca aaacctctcc gacagccacg   49380
acagcatgta cttagggctc tggctcctct ctgctagaca cgttagcaca ttgctacacc   49440
ccccattgta cacctgggcc ctctccttac gtctataaaa ggaaggtcta gggctctcgt   49500
acgagagggt tggccgcgcg ggagaacggg ctgacgcaca aggctctctc tctctctctc   49560
ccacacgaac gcttgtaacc ccctactgca agcgcatccg ccctgggcac aggacaacac   49620
gaaggccacg ggttcccctt tgctgttttc cccccttgt gtttcgtctc gtgccgaccc   49680
atctggaatg ggacacgcag cgacagttta ctcgtcggtc cagggacccc ccggggtcga   49740
aacgctgaca gttggcacgc caggtagggg cctactgcat ggtgacgaac agcttcccgt   49800
caagttccag atgggtagtc tccagcaacc actccaaccc gggacggtgc tccatttcag   49860
gagtcttgag ttcatgtccc tcgacggcag ctacgacatg acactccttc ctccgccgcg   49920
cgacaacgac aatggcggcc gtcagcccgc ccgtcggcgg cggaatcgac gacgtcttcc   49980
ccacgtggcg gaagagcgat atccgggtct gtcccgtcac cttccccgct gacggaggag   50040
gaggcggggt aggcatggcc aatcaggagg cggcacctcg tcggctgtcg agcgagtcga   50100
cggcgccgac gccccaacgg gggacacgtc gggcgttgac ctcgcgtctg agacgaagac   50160
aagcgtcgtt tccccgcaac acgccaaccc caagcagacg gatgacgcca gcacgctcgc   50220
gaaggacttc ctgggcgtta acctcgtacc tgagacaacg gtgcagtccg tccctgacgc   50280
gacttcgtca ccacccgtcg atcaagaggt accgtccgtt tcccatccca tgccttttag   50340
attcagttgt gacccaccaa gcgatcccgc ttcgtggac gctttcataa aggcatgtcc   50400
aaaccctccg gggtatcata tgcggtcaac ctgggaccga ctgacggccg tctcgaccta   50460
tgggcccccg ggttccgagg aagatgacga gcctgactct ggttgggatt tctccgggct   50520 cgataaccccc agtgtcatgc gggacttcat gaccgcatgt gactactgcc tctccgattg   50580
ctccgatagc agccacagcc tcggcgacga ggactgtggc ccaaggtgcg aatgcttcca   50640
cgtcgatcta gggggtcttg acgaaggcaa ccatcttggt atgccggagg atggtgatcc   50700
ccctaggcct gcgcctcgcg ttgacatcct tcgggagcta gctgtggtcc cagtccctgc   50760
```

```
ggggggtcaa gacgcacggc ttgagcaaat ccgcgaggta caggccaggc tcgacgagga    50820
agcaggacaa cttgtgcagc ttcggcaaaa tatcgggcag gagtgggcag gccgagcacc    50880
ggctggagaa gcgcgtcatc tggcccagga cgtccagcac cgcatcaccg acgatgccag    50940
ggcgaggctg cccccggctt ccagtggggt cggccagaac ctggctgcag cagcgatact    51000
actccgagcg atgccgaaac catccaccac cgaggggtgg cgtatccaag agagctcaa    51060 aaatctccta gaggatgtcg cggtccgacg ggccgagagc tctgcctccc gaaggcaggg    51120 gtaccccgg agcatcgcgc tgcgacttcc cgattcatgc gggaagcctc ggtccacacc    51180
gggcgcacgc gggacacagc gcctgcggcc ccaagacgcc tcggcaacga gcaccgccgc    51240
gaccgtcaag cccacctcga cgagaaggtg cgtcgaggct accacccag gcgtggggga    51300 cgctacgaca gcgtggagga tcggagcccc tcgcccgaac cacccagtcc gcaagctttc    51360
agccgggcca tacaacgggc accgttcccg acctggttct gaaccccgac taccatcacc    51420
aagtactcgg gggagtcgaa gccggaactg tggctcgcgg actaccgct ggcctgccag    51480 ctgagtggga cggacgatga caacctcatc atctgcatcc ttcccctgtt cctctccgac    51540 gccgccgag cctggctgga gcatctatct cctgtgcaga tctccaactg gacgacctg    51600 gtcaaagctt tcgtcggcaa cttccagggc acatacgtgc ccctgggaa ctcctgggat    51660 ctccgaaggt gccgccagca gccgagagaa tccctctggg actacatccg gcgattttcg    51720
aagcagggca ccgagctgcc caacatcacc aactcggatg tcatcggcgc gttcctcacc    51780
ggtaccactt gtcgcgacct ggtgagcaag ctgggtcgca agactccac tagggcgagc    51840 gagctgatgg acatcgccac caagttcgcc tctggtcagg aggcggtcga ggccatcttc    51900
cggaaggaca agcagcctca ggggcgtcag ccggaagacg tccccaaggc gtccgctcag    51960
cgcggcgcga ggaagaaggg caagaagaag tcacaagcaa aacgcgacgt cgccgacaca    52020
gacattgtcg ccgccgccga gcacagaaac cctcggaagc ctcccggagg cgccaacctg    52080
ttcgatagga tggtcaagga gtcgtgcccc tatcatcagg gtcccatcaa gcacacctt    52140 gaggaatgcg tcatgcttcg acgctacttc cacaaggccg ggccaccggc gaaaggtggc    52200
agagcccaca acaacgacaa gaaggaggat cacaaggcag aggagttccc cgaggtccac    52260
gactgcttca tgatctatgg tgggcaagtg gcgaacgcct cgactcggca ccgcaagcaa    52320
gagcgtcggg aggtctgctc agtaaaggtg gcagcgccag tctacctaga ctggtccgac    52380
aagcccatca ccttcgacca gggcgaccac cccgaccgcg tgccgagcct aggaaagtac    52440
cctctcattg tcgaccccgt catcggcaac gtcaggctta ccaaggtcct catggacgga    52500
ggcagcagcc tcaacatcat ctacgccgcg accctcgggc tcctgcagat cgatctgtcc    52560
tcgatccggg ccggtgcgac gccttttcac gggatcatcc ccgggaaacg cgtccaaccc    52620
cttgggcaac tcaatctgtc agtctgcttc gggactccct ccaacttccg aaaggaaacc    52680
ctcacgttcg aggtggtcgg gttccgagga acctaccacg cagtgctggg gagaccatgc    52740
tacgccaagt tcatggccgt ccccaactac acctacctca gctcaagat gtcgggcccc    52800 aacggggtca tcaccatcgg ctccacgtac cgacacacgt acgaatgcga cgtggagtgc    52860
gtggagtacg ccgaggccct cgccgaatcc gaggccctca tcgccgacct ggggagcctc    52920
tccaaggagg cgccagatgc gaagcgccac gccggcaact tcgagccagc tgagacgatt    52980
aagtccgtcc ctctcggccc cagcaacgac gcctccaagc agatccggat cggctccgag    53040
ctcgacccca aataggaagc agtgctcgtc gactttctcc gcgcgaacgc cgaggttttt    53100
gcatggagtc cctcggacat gcctagcata ccgagggatg tcgccgagca ctcgctggat    53160
```

-continued

```
atccgagctg gagcccgacc cgtgaagcag cctctacatc gattcgacga agaaaagcgc   53220
agagccatag gcgaggagat ccacaagctg atggctgcag ggttcattaa agaggtattc   53280
catcccgaat ggcttgtcaa ccctgtgctt gtgagaaata aaggagggaa atggcggatg   53340
tgtgtagact acactggtct aaacaaagca tgtccgaaag ttccctccct ctgcctcgca   53400
tcgatcaaat catggattcc actgctgggt gcgaaaccct gtctttcctc gatgcctact   53460
cagggtatca ccaaatcagg atgaaagagt ccgaccagct cgcgacttct ttcatcacac   53520
cctttggcat gtactgctac gttactatgc cattcggttt gaggaatgcg ggtgcgacat   53580
accaaagatg catgaaccac gtgttcggag agcacattgg tcaacggtt gaggcttacg    53640 tcgatgacat catagtcaag acgaggaaag cctccgacct cctctccgac cttgaaacga   53700
cattcaagtg tctcaaggcg aaaggcgtaa aactcaatcc cgagaagtgt gtcttcggag   53760
tcccccgagg catgctcttg ggttcatcg tctccgagcg gggcatcgag gccaacccgg     53820
agaaaatcgc ggccatcacc aacatggccc catcaagga cttgaaagga gtacagaggg    53880
tcatgggatg ccttgcggct ctgagccgtt tcatctcacg cctcggcgaa agaggcctac   53940
ctctgtaccg cctcttgagg aagaccgagc gcttcacttg gacccccgag gccgaggaag   54000
ccctcgggaa cctaaaggtg ctcctcacaa gcgcgcccat cttggtgccc cctgttgccg   54060
gagaagccct cttggtctac gtcgccgcta ccactcaggt ggtcagcgcc gcgatcatgg   54120
tcgagagacg agaagagggg cacgcattgc ccgtccagag gccggtctac ttcatcagtg   54180
aagtactgtc tgagaccaaa atccgctacc cgcaaattcc agaagctact ttacgcggta   54240
attctgacgc ggcgaaagtt gcgacactac ttcgagtctc atccggtgac tgtggtgtca   54300
tccttccccc tgggagagat catccagtgc cgagaggcct cgggtaggat tgcaaagtgg   54360
gcagtggaga ttatgggcga gacaatctca ttcgcccctc ggaaggccat caagtcccaa   54420
gtcttggcgg actttgtggc tgaatgggtc gacacccagc ttccagcagc tccgatccaa   54480
ctggaactct ggaccatgtt tttcgacggg tcgttgatga aaacaggagc gggcgcgggc   54540
ctgctcttca tctcgcccct cgggaagcac ctccgctacg tgttgcacct ccatttcccg   54600
gcgtccaaca acgtggccga gtacgaggct cggttaacgg gttgcgaatt gccaccgagc   54660
taggggtccg acgcctcgac gctcgcggcg actcgcaact tgtcatcgac aagtcatgaa   54720
gaactcccac tgtcgcgacc cgaagatgga agcctactgc gatgaggttc ggcgcctgga   54780
ggacaagttc tatgggctcg agctcaacca catcgcccga cgatacaacg agactacgga   54840
tgagctggct aagatagcct cggcgcggac aacggttccc ccggacgtct ctccccgaga   54900
cctacatcaa ccctcagtca agaccagcga cacgcccgag cccgagaaag ccttggccct   54960
gcccgaggca ccctcggccc ccgagggtga ggcactgcgc gtcgaggaag agcggtatgg   55020
ggtcacgcct aatcgaaact ggcagaccct gtacctgcaa tatctccacc gaggagagct   55080 accccctcgac agagccgaag ctcggcaact agcgtgggc gccaagtcgt tcgtcttgct    55140
gggtgacggg aaggagctct accaccgcag cccctcaggc gtcctacaac gttgcatatc   55200
catcgccgaa ggtcaggagt tattacaaga aatacactcg ggggcttgcg gtcaccacgc   55260
agcacctcga gccctcgttg gaaatgcctt ccgacgggt ttctactggc caaccgcggt     55320
ggccgacgcc actaggattg tacgcacctg ccaagggtgt caattctatg caaagcagac   55380
ccacctgccc gctcaggctc tgcaaacaat acccatcacc tggccgtttg ctgtgtgggg   55440
tctggacctt gtcagcccct tgcagaaggc acccgggggc tacacgcacc tgctggtcgc   55500
```

```
catcgacaaa ttctccaagt ggatcgaggt cagacccta aacagcatca ggtccgaaca     55560
ggcggtggcg ttcttcacca acatcatcca tcgctttggg gtcccgaact ccatcatcac     55620
cgacaacggc acccagttca ccggtagaaa gttcctactg cgaggattac cacatccggg     55680
tggactaggc cgccgtagct cacccatga cgaatgggca gctagagcgt gccaacgaca      55740
tgattctaca aggactcaag ccacggatct acaacgacct caacaagttc agcaggcgat    55800
ggatgaagga actcccctcg gtggtctgga gtctgagaac gacaccaagc tgagccacgg     55860
gcttcacgcc gttttttcta gtctatgggg ccgaggccat cttgcccaca gactcactgg     55920
gccatcttca cgctgttttt tctagtctat ggggacgagg gcgtacgacg accgaagcaa     55980
tcgaaccaac cgagaagact cactggacca gctggaagag gctcgggaca tggccttact     56040
acactcggcg cggtatcagc agtccctgcg acgctaccac gcccaagggg ttcggtcccg     56100
agacctccag gtgggcgact tggtgcttcg gctacgtcaa gacgcccgag ggtgtcacaa     56160
gctcacgcct ccctaagaag cccggaacat acaagctggc caacagtcaa ggcgaggtct     56220
acatcaacgc ttggaacatc cgacagctac gtcgcttcta cccttaagat gttttcaagt     56280
cgttcataca cctcgtttac atacgccaac aaagtctaac catcaaggaa gggtcagcct     56340
tgcctcggca aagcccgacc ctccctcggg ggctagaagg ggggcacccc ctctacgtca     56400
aaattttcct cgaaaaaagt ctttctgcca gaacatcttt cgtgcttttc gactacttcg     56460
aaagtgggat cctgaaaacg acggagtaca cgtaagcagg caaggacgac cgagccgagg     56520
gactcctacg cctccgggat acggatacct cactcatcac cttctgcgat aagtaactca     56580
cgctcggata agcgatcccg ctggccgaac aagtcttaac gttcgaaagc ttttctgccg     56640
aaacgatttt ttgtgccttc tcgactatat cgataacaga atccaacgga cgagtaagag     56700
tacacgtaag cggcaaggcc gaccgagccg agggactcct acaccttcgg gatacggata     56760
cctcactcat caccttccgt gaaaagtaac tcttgctcgg ataagcaatt ctgttactga     56820
cgaacaagtc ccgatactcg aaacaagggg aaaagaaacg ccgctttaca acacgacgac     56880
ggtatgtttg ggcctcggcg gccgcaaaaa acatacgcac actacagata aattgttcct     56940
gcaggatcag acatcagtgg gggagcagca gcacccctcgg cgtcgactcc accttcggcg     57000
gagtccgacc cagcctcgga cggcgacacg gtcggaggat ctccatctcg aaggaacctg     57060
tcagcaccgc gcctgggcca tcgccgaggt gtccctccagg aacccggccc gagtagacga     57120
ctcgaccgac cgctctgtag cctcagccag ctgtccccg aggacatcag cccggctcat     57180
ggcctcggca acccgactcc ggcgtcggtc ccaccagtgg acggcccgac caggctccgg     57240
ccgatgaagc ttcttttga gccaactccg cctctgtcca cgctgacacc gctgacaccg     57300
ctgcctctag ctccggctca tcgcagagcg gccgagggtt tctttaacta agcaagagaa     57360
gcctcgggcg gcaaggccga ccgatccgag ggactcctac gcctccggga tacggatacc     57420
tcactcgtca ccttccgcac gaggcaactc acacttggtt aagcggttca gctagccgac     57480
aggcgagtcc tagtgctcga aatgaggaaa aaatacggct ttagccaaaa tacacatctt     57540
caggccccga cagccgcaat gaacagacac cggcactcaa ggtgccatta caaacagaac     57600
tctggttccg cccccacagg tacgaacgac cccccacatt ggagggcctg cggggcaact     57660
gaaagctctc ttgtgagttt tggtgtttgg atgacaactc aattaaagga ctaacaagtg     57720
tactaagtgt tgaacaggtg cttaaggtaa agcctacagg gttcaacaca agtgaacaaa     57780
tgtgatggtc caagaactgg attatggata cataatggat atcacaagta agatggacat     57840
tgcacaaagt gagactcggg tgcgtagctc ggagacaact gatcaagcca aggacggagg     57900
```

```
caagaaaagc ttcgaggtac caaatgcacg ggagaaggtc aaggaggctg aggaacccaa    57960
agccaagggt gaagaagaag gcttgcaaag tcaagggtga tcgagttgag aacagctacg    58020
gcacatcaag gatcactaca taaggacgtg acttacagcc aatgaggtaa cagctatagt    58080
tatgtggtgt aagtcataag gctcaagatc aagctctaag gaggagatca aggtcactag    58140
aaggagaaca agtgtcgaaa ccagaactgg aagcagccca aaagagctaa gttcactttg    58200
atctttagtt tggggttgttc ctatgtttgg agatgttcta tgtgaccttt acaggatgtt    58260
ggagccaagc gatgtcaatc tagatcaagt caagctgact tgataaattta tgagtccaac    58320 atcaaagctc aagcatgtga aatgctatag atgtaatgat taatagaagg tatgtttcta    58380
gacttagtac attggttttg gggactaata tacttgtcta agtgttagaa acagaaagaa    58440
gaagaaaagg gaagaggtgc gaaaggcttg gctgtgtaca gccaagactt agttcagtct    58500
ggcacaccgg actgtccggt ggtgcaccgg acagtgtccg gtgcgccagg ctgaactctg    58560
gcgaactggc cgctctcggg aattcaccgg cgatgtatgg ctataattca ccggactgtc    58620
cggtgtgcac cggactgtcc ggtgagccaa cggtcggccg ggccaacggt tggccgcgcg    58680
atctgcgcgg gacacgtggc cgagccaacg gctagatgga ggcaccggat tgtccggtgt    58740
gcaccggaca tgtccggtgc gccaacggct ccaagactgc caacggtcgg cttcgacgta    58800
gaaggaaaga aatcgggcac cggacagtgt ccggtgtgca ccggacagtg tccggtgtgc    58860
accggactgt ccggtgcgcc acccgacaga aggcaagatt tgccttcctg gattgcttcc    58920
aacggcttct aggccccttg tgtctataaa agggacccct aggcgcctcc agcaaaatag    58980
aagtgcagcc aacaagtgta gactccactg gaatcaattc tcactctccc tcttgtgtgt    59040
aactctatag tttgtgtaga aggcacagct ataagcctta gagagaggag tagtgctgct    59100
aagagctaga gcaaggtctt gagcatatcg ttactctacc ggggtgctgc caagaagtct    59160
gtaagcagcc gcggttctgt tgtaacccca ctcaatagtg aaaggctcta tctgtcatac    59220
tgacagatct gagcaaacgg aggaaggagt tgaaatagac tccaagccca ggtgtggcta    59280
actccaacga ggactaggca agcatttcag gcttggccga acctcgggat aaatccttgc    59340
gtctgtgtgc tctgttctgt attgtatcct gactctcttt ctactcgcct ttatatctgc    59400
acttcaatac ttatctgtgg tataagcttt atttgaagtg caggacattt tgagacagga    59460
tcttctattc ggctgcaacc tacttgaaga gtcttctcac tccactgcat actaagtctt    59520
cgagtagagt aagaatttaa gttttaaagt gaaaagtttt attcgcctat tcaccccccc    59580
ccctctaggc gacatccaga tcctgttccc gggtcaaagg gaactttcaa ttggtatcag    59640
agctaggcct ctccagtgtg ggcttagccg tccggagatg acgatgtcgt cacaagaggt    59700
aactgtggaa cttcttttag acgatggctc taattacaag tcttggtctg tctctattta    59760
tagtgctttc atgagtgttg atcctgattt gagacaggtc tttagtagta gtatttttcc    59820
ctccaatatt agtaaaaacc catccaatga agaactaaga tgtctaactc taaatcacca    59880
tgcttgcaac atcttagttg attctctatc tagaggtgcc tattttgcca tcatgagtag    59940
tgatagtgat ctatttgttg atgctcatga tttatggaat aggattaaag aaaaatattt    60000
tgtggcaaac tgtgatgctc ctactcccta tattacttgt gatactaacc attcaaaggg    60060
agaagaacaa gaacgatggc atccaaacga tgaatccacc tcgtcgacag gtttgttctc    60120
cactagtgat aaatgtttta ttgctaacaa tgacggtgga gacgaaagcc atgataagga    60180
gaaatatgag gatgaatctt catcatcaca aggtacattt tcctatattg cttccactga    60240
```

```
cattaatgac agggaaaatg agaccgatga tgtggaggaa gaggagattc accgtttcta    60300
catccatctc aacaaagagg acaaggcact cttggttaag ctgttgagaa ggaacaagga    60360
acaaggcgag acgcttctca ggctagagga gtccctcatc aaaaccaaca acagcctgga    60420
gaagatgacc aaagaacatg agaagctaag gcgctctcat gatgatttgg tccaaaggta    60480
tgaatatgtt ttaattgagc aaagaaatag tcatgatgca ttatctaata ttgctcaact    60540
taaaacggaa aattctatgc ttaagagtca agtagaaaca atgaacttag aaaaacgtgc    60600
tctaggtaaa aagtatgata tgttgtcaaa ttctcataat aaattagttg atgaccatat    60660
catgcttaat gttgctcatg aggttataat tgcaaactta aattcatgtg aacctcattc    60720
tcgcacgtgt gcgcatttga agtgtatatc accatgtgct aaccctgtt gctcaaaaga     60780 aagccaatca ttgattgagc aacaagtttt agggtcacaa aagaaattct gtgggaacaa    60840
gaagcaaaga caactaagga gaagacacat tgctcaactc tctcaagata tccacgggcg    60900
cgtggtgaag aagcttgaga aaggaaaaac tgcagcaagt gttaagctca ataagaagaa    60960
tgttcccaaa gctataaatg aagaaatcaa catgaacaag gaaaaaggta aaaattcaat    61020
tagtcatgtt gtttgcactg atcatctctc catgtcattc aagcacaaaa agggaagagg    61080
aaaaaggagg tgcttcaaat gcaaggagac aggccacctc atcgcgtctt gtccgtacaa    61140
agacaaggat gaaagaacaa ggagttgttt tggatgcaac aataaggacc acatgatcac    61200
ttcatgtccg gtcatgaaga atcaaggata tgcatcctcc aaagtgaccc tcaccaagga    61260
aaatgacaca aaacaagcgt catgtcaagt tgagcgacgc ttctgctaca agtgtggtga    61320
gcaaggtcat ctatccaagg tatgttacaa aggtaagatt cctaaacaag tgaatttgtg    61380
tcaatcttat tcgcatagga gacccaaatc atacacttgt gctagatcta aacgagatc    61440 acctagaact agcacaaagg caatttgggt accaaaggca catttacatg atcattatgt    61500
acccatcccg agatggatac caaactgtgc caactagacc atgcaggtgc ctcgagatgg    61560
actggagacc atgggaaaga ttaagacggt tatctaaaac tctatgctta agctgttaat    61620
tgttttagtg tttattgacc caaggttgaa ttattgtgaa acactaatcc catgttcatc    61680
tcaagagaaa taaggtgtat aggtcctgaa tcattattgg tgaatcaagt aaaggatctt    61740
gatgagaatc tacaacctgc tctccaaagg acggtacccg tgtattttaa gtacataatt    61800
gcaatttagt attgctctta agttggcttg ttgtgctacc tgtccttaga gtagttatgc    61860
tttatgattg cctgtgttaa attgatcata atgatggttg cttaatcatg actggtgcta    61920
taaaggatat atcttttgaa tcattcatgg gtagctattt catttgttat atccacaacg    61980
ataactctct tgatgtatat ggataaacct gtaacttttg taagtcatgc tatgtgcaat    62040 tatgacttt tgtttagtcc atgttcacat gattaccta gtttggtact gtgtgaattt      62100
caaatccatg tcgtgccctt ttgagctatg aggtgcgtaa gcaaaggag ccctaaattg      62160 gcgataacaa gggctctcat aaaggcaaag gtatggaaaa tggagctatg caatttcatt    62220
aaatattctt gaaattccat tcattgtgat catagctatg ttcttgcctt tcaattggta    62280
atatcttggc ttaggtaatt tatgccttta aaatgttgtt tcttttgtgc acctaagaaa    62340
ccttcttaat tataacatgc ttagatattt cgattgtgtt tatctttaat tggtatatac    62400
aatgatagtt aaatatgaag catgtacaag ttgcgtaaat gttagacttc ctgtgagtat    62460
tcaattggct taggtgccac tgaggcgtgc attgttgtat ttagtcaacc tttcatttag    62520
ccttcaattg gtgttatgtg gcgtttcatt tgatattcaa attggcatct ttgggtgatg    62580
aaagtggtag agtatgcctt gaccaaggta tgttgtgatc ccctctaatt ctaaggaagc    62640
```

```
tagaatgtgc aaagtgcaag tcattcaaat acttgatgca caacttgagg gggagcacac   62700
ataacttgtg tcttttgaga ctaactgttt cttgagcaat cttgtatagt ctctaggtgg   62760
aaaagagaag ataagcaaga aatggagcaa tcaggacttg ggtacctctg taagtcaaga   62820
aaattggtat ctcaagttgt gagtaagtgc atattttttag attgctcatg ctctataata   62880
tctggtgata atagatgctt attcttaaat atcatggagc catgataata aatgaacttt   62940
gcaattggta tctttcaatt ggtagccgta atagttcgct tcaattgaca tcttttgata   63000
atcatgagaa tagaagtttc ttcttgtgcc caatactata acttgttcta agtttggtgt   63060
cttagcaaca agaaaaagtt aggagagaga atcaggcaca agtgtggaga agctctcgag   63120
agattaacta ctttcaagat gggaagtaca ctacatcatg gtaaaggtac aaaaggaagt   63180
attaatcttt ttgcatatat gtatcttacc taaatgttga taggacatat gttcaataaa   63240 taaggggag ttttgatagt cgttttttccc cttaacaccc tgctgtccct tgacatcatc   63300
atatgttctt gctgagtat ggttttttggt gtttgatgtc aaaggggag aagttgtgca   63360 ttaaagctta tctcaacctg agaggaaagc ttatcctaat gggtgatgtg ttagtttgag   63420
ctttgccaag tgtgatattc atatgttttct tgcagtatta tacgtgttga tcatatggac   63480
tagactagtg tttttatattc atatgttttct tgcagtatta tacgtgttga tcatatggac   63540
tagaccagtg tttccgctgc gatgaattat ttggcttcta tagtgaaata gatagtcatg   63600
tggttaatgg tgctttaaga ttgctttaaa ttgatatctt agtttaagtt ggtatcttaa   63660
tggtgaatag tggtaggttg atattcctgt gatatatcca ctaatttgaa tggtgtttaa   63720
ctctgattat gtgcatttgt gtgttatagc atcatggttt gattcttgac ataatgcatc   63780
ctaaaaagtg ctaaggtgta gaaatgtttc aattttccta agtatgtgca aattgacgtt   63840
tgtggtcaaa attaggtttt tgaagtaagc acttatttag ggggagcatt ctataatctt   63900
agaattcaaa tttgtgcttc aaatcttatt cttatgtaag cttttaattgt gttgccacca   63960 atcaccaaaa agggggagat tgaaagctct cttgtgagtt ttggtgtttg gatgacaact   64020
caattaaagg actaacaagt atactaagtg ttgaacatgt gcttaaggta aagcctacag   64080
ggttcaacac aagtgaacaa atgtgatggt ccaagaactg gattatggat acataatgga   64140
catcacaagt aagatggaca ttgcacaaag tgagactcgg gtgcgtagct cgaagacaac   64200
tgatcaagcc aaggacggag gcaagaaaag cttcgaggta ccaaatgcat gggagaaggt   64260
caaggaggct gaggaaccca aagccaaggg tgaagaagaa ggcttgcaaa gtcaagggtg   64320
atcgagttga gaacagctac ggcacatcaa ggatcactac ataaggacgt gacttacagc   64380
caatgaggta acagctatag ttatgtggtg taagtcataa ggctcaagat caagctctaa   64440
ggaggagatc aaggtcacta gaaggagaac aagtgtcgaa accagaactg gaagcagccc   64500
aaaagagcta agttcacttt gatctttagt ttgggttgtt cctatgtttg gagatgttct   64560
atgtgacctt tacaggatgt tggagccaag cgatgtcaat ctagatcaag tcaagctgac   64620
ttgataattt atgagtccaa catcaaagct caagcttgtg aaatgctata gatgtaatga   64680
ttaatagaag gtatgtttct agacttagta cattggtttt ggggactaat atacttgtct   64740
aagtgttaga aacagaaaga agaagaaaag ggaagaggtg tgaaaggctt ggctgtgtac   64800
agccaagact tagttcagtc tggcacacca gactgtccgg tggtgcaccg gacagtgtcc   64860
ggtgcgccag gctgaactct ggcgaactgg ccactctcgg gaattcaccg gcgacgtacg   64920
gctataattc accggactgt ccggtgtgca ccggactatc cggtgagcca acggtcggcc   64980
```

```
gggccaacgg ttggccgcgc gatctgcgcg ggacacgtgg ccgagccaac ggctagatgg    65040
aggcaccgga ctgtccggtg tgcaccggac atgtccggtg cgcgaacggc tccaagactg    65100
ccaacggtcg gcttcgacgt agaaggaaag aaatcgggca ccggacagtg tccggtgtgc    65160
accggactgt ccggtgcgcc acccgacaga aggcaagatt tgccttcctg gattgcttcc    65220
aacggctcct aggccccttg tgtctataaa agggacccct aggtgcctcc agcaaaatag    65280
aagtgcagcc aacaagtgta gactccactg gaatcaattc tcactctccc tcttgtgtgt    65340
aactctatag tttgtgtaga aggcacaact ataagcctta gagagaggag tagtgctgct    65400
aagagctaga gcaaggtctt gagcatatcg ttactctacc ggggtgctgc caagaagtct    65460
gtaagcagcc gcggttctgt tgtaaccccca ctcaatagtg aaaggctcta tctgtcatac    65520
tgacagatct gagcaaacgg aggaaggagt gaaatagac tccaagccca ggtgtggcta    65580
actccaacga ggactaggca agcatttcag gcttggccga acctcaggat aaatccttgc    65640
gtctgtgtgc tctgttctgt attgtatcct gactctcttt ctactcgcct ttatatctgc    65700
acttcaatac ttatctgtgg tataagcttt atttgaagtg caggacattt tgagacagga    65760
tcttctattc cgctgcaacc tacttgaaga gtcttctcac tccactgcat actaagtctt    65820
cgagtagagt aagaatttaa gttttaaagt gaaaagtttt attcgcctat tcaccccccc    65880
tctaggcgac atccagatcc tgttcccggg tcaagggaa cttttcagcaa caaaaccta    65940 gacagctcgc cgaggcccgc tctggcagca gcgacaacga cctccgctcc ggacagccaa    66000
acagcagcag cgatgacctc agtgcagacg ctgctgcgac aaggccctcg cccacgtccc    66060
caccatcaaa ctggtggtca ccgtcttggg tgaccaccag cgaggggatg cagccgggcc    66120
gcctgatgaa aatccttgaa gccgagcgat ggctgaaagg taccaacttc cgcgaagttg    66180
cgttcctcca acgacgacaa gacgaaagca acgcgggcgc tccccatccg ggggctcgga    66240
agttggaagg gcgcgatgca tgaagggagt gtgaagacat ggttgccatc caaggggtc    66300 gccctccttt taaaggcgac tctccccact tgcgtcctca gccgtcgcgg actgagtctt    66360
caccaacacg ctccaaggtc ctcccccta cacatggggg ctgggtccca cgcgtcatgc    66420
aagctggccc agggcagaag aagccaaacc gtcgcgcgca gagtgcgtaa ctgcccagcg    66480
gttacaagca ctcctccact ttcgcccaga ccggcgggtg aaagggcgga ccgccatgca    66540
ggcggcatgc aaccgcacca aggggggtgca ccctttcgac tccgacgcgt ccagcacggg    66600
ggcccaggcc cacacgtcat gtaaccggcg cgccggttac tacgcgcgag aaactgcacc    66660
gccacttgtg ctagtaccgc gccttctcga ctgcggaacc ggtgccgcga ctcgaggcaa    66720
ccctgcgcat ggcccaacag tgccaaccga gcacatcgat cacgggtcag tcagccgcgg    66780
gagaaggcgc gatggttgat atggccaaaa gtgggccggc agtaatggcg gcggcaggcg    66840
ggcggaagca gcggtcaagt cgtctgtagg ctcacgtccc ctcctgggac agcgagagag    66900
ccccctccca cggcgtgaag acgacacgcc cgtgttccgt tcctcgaacg gctagcgcac    66960
gcacaacggc tgccccgcga accactcatc ccgtcgcatt aactctgcgg caggacaggc    67020
ggcacctttg gcaggcgaag caggtgacgc ttcacctccg ccttaatgac cgcgtcaaaa    67080
aaggtgcgcc acgtcgtttg atttcgtatc cttttaccct tcctctttct ctctcttgct    67140
atagggaccg ggaaagagga tactccgaaa gggatccttc tccgcgaagg aagcgggccc    67200
cgagccctcc tactaatcag aggttcgaag gctggcccct cggaagggtt cgacagtcgc    67260
cttagagcac tcgggctccg cgccctccta ctgatcagag gttcgaaggc tggccctcg    67320 gaagggttcg acagccgcct cagagcactc gggttccgtg cccactactg gtcagaggtt    67380
```

```
cgaaggctag cccctcggag gggttcgaca gccgcctcaa gccactcgag ctctgcgccc   67440
actactgatc aggggtttgt aggctggccc ccgaaggatt cgccagccgc ctcagagcac   67500
gcagagcgag ggatgactct gggtacgtcc gatacatggc cgaggctcgg gctacgctcc   67560
cgaggtaccc taggacattt ccgagaccaa caggagcgat tctgtaacgg aatcccatca   67620
gagggaggca tcgagccctc ggaccctatc aaacgggacc gggtccggca atcacctgt    67680 aggtactttt ggagcgcgcc tctgggccac tagccgaccc ttatcgaacg gggcacgggc   67740
gtccactcgg atcaaccgtt agcaactcac tggagacacc atgttcgacg ccctctgagg   67800
gcaacatggc gctttccccc ccctcctcct tgcggaaagg cgacgcaggg gcgtatgaaa   67860
aaagccgagt cagtccttgg ccgtcctctc gctctgtgcg gaggctcggg ggctgctctc   67920
gcatgaggga acaaccaaac cagcccgaga acttggaacc tgactatgca cccgggctac   67980
ggccagttcg catgagggaa caaccagacc ggccgaagca tcacgaaacg tgctaagacc   68040
tcgaaggagt caaaccactc ctccgaggcc tcagggcta cacccggcgg gtgcactcgc    68100
gcgcacccac cggaacgaaa cgcaaccgag aaaggccggt cccccttgcaa aaaagtgcga   68160 caaaagcctc caagtgagta ccaacactcc cttcgaggct cggggggctac tgtcggggac   68220 cataattagg ggtaccccca agactcctaa tctcagctgg taaccccccat cagcacaaag   68280 ctgcaaaggc ctgatgggcg caattcaggt caaggctctg tccactcaag ggacacgatc   68340
ccgcctcgcc cgagcctagc ctcagcaaa ggcagccgac ccaggaggat tcacgtcttg     68400
cccgagggtc ccctcaagca acggacgcac cttcggctcg cccgaggccc aagcttcgcg   68460
gagaaggaac cttggccaga tcgccacgcc aaccaaccgt atcgcaggag catttaatgc   68520
aaggatcgac tgacaccttaa tcctgacgcg tgctcctcag tcgacagggc cgaagtgact   68580
gcagtcacat cgccgctcca ctgaccgacc tgacgggaaa atagcatcgc ctgccctgct   68640
ccgactgcta tgccactcga cagagtgagg ctgacagcag ctaagtccag cctcgggcgc   68700
catgggaagc tccgcctcgc ccgaccccag agctcgggct caacctggac gtcggacgac   68760
ggactccgcc tcgcccgacc ccagggctcg gactcaacct cgacctcgaa agacggactc   68820
cggctcgccc gaccccaggg ctcggactca gcctcgacct cggacgatgg actccgcctc    68880
gcccgacccc agggcttgga cttagcctcg acctcggaag acggactctg cctcgcccga   68940
tcctagggct cgggctcaac ctcgacctcg gaggagcctc cgcctcgccc gacctcaggc   69000
tcggaccgac acgtcgcagg gggagccatc attaccctac ccctagctag ctcaggctat    69060
ggggaacaag accggcgtcc catctggctc gccccggtaa acaagtaatg atggcacccc   69120
gcgtgctccg tgacgacggc ggctctcagc cccttacgga agcaaggaga cgtcagcaag   69180
gatccgacag ccccgatagt tgtacttcca cagggctcaa acgctcctcc gacggccacg   69240
acatcacatg aacagggcgc caaaacctct ccgacagcca cgacggcatg tacttagggc   69300
tctgtctcct ctctgctaga catgttagca cattgctaca ccccccattg tacacctggg   69360
ccctctcctt acgtctataa aaggaaggtc cagggctctc gtacgagagg gttggccgcg   69420
cgggagaacg ggctgacgca caaggctctc tctctctccc acacgaacgc ttgtaaccc    69480 ctactgcaag cgcatccgcc ctgggcgcag gacaacacga aggccgcggg ttcccctttg   69540
ctgttttccc cccttttgtgt tctgtctcgc gtcgacccat ctgggctggg acacgcagcg   69600
acaatttact cgtcggtcca gggacccccc ggggtcgaaa cgccgacaaa acaatatttt   69660
ctagctttgg tacctacaat cttctgtact tccccatttg tctaatgctt caggttgttc    69720
```

```
ttttttttct gtagatctat gtaccttatc cttgctatac tgtccatata tgttgtgtgc    69780
atgaaagtct tgcattgaaa atgtcatgtg ctacaatcgt taggactatt aatagatgtt    69840
gctctgtcta tctatccatt tacatcgctg gaaattccca tgcccttcca tagtacgcct    69900
gtgaaattct cactgctttt ctattggttt gtgtgcagtt catgtctctgc aaggtaaggt    69960 ctgttcagtt tggccagaaa ggcatcccct gcctaaacac ctacgacgac cgcaccatcc    70020
gctaccccga cccgctcatc aaggccaacg acaccatcaa gatcgacgaa atcttctaga    70080
attgnnnnnn nnnnnnnnnn nnnnnnnnnn nnnnnnnnnn nnnnnnnnnn nnnnnnnnnn    70140
nnnnnnnnnn nnnnnnnnnn nnnnnnnnnn nnnnnnnnnn nnnntcttat gtatcagctt    70200
gattcgttgc acattgttga gatgggcctc tctttactcg ctaatggaca ataccgctca    70260
agttttggga ccaagcgttc ctcacctcaa cacatcttat caatagaact cctactaagc    70320
ttcttgatta tgacacatcg ctccaccgtc tcttaggtgc tacccagat tactctaatc    70380 tacgcgtctt tggctatgca tgttagccaa atttgcggcc atacaacacc cataaactct    70440
agtttcggtc catttggtgt gcttttctag tctatagcaa ccttcacaag ggttacaagt    70500
gtcttgacat ctcaacgggc cgtgtttata tttcacatga tgttgttttt gatgagacgc    70560
ttttcccttt gctgctctcc atcccacagt cggtgctcga tatacctctg acgtgcttct    70620
tctacccgat cctaataatt ctcgggccaa ctcagatgat cttgtgacta attctcctgc    70680
tgaatccagc atgcttgctc cgattttgtg gcctaaccag cttttgcagc caccaatgat    70740
ccctgctgca aattctgtcc cggctggtgg cctcaatccc ggtgctgatc tgttgctagg    70800
ctccacgcca caccctccg acgcggctac aggtgcgccc agcaacgcgg tgcttcccac    70860
caccacggcc gcatcaatag cagcagccac ttcgggattg cctcgtgccg actctggcgc    70920
ggctggtccc tctctcactg acagccatct gccctcgcca tcagcctcgt gtcctattcc    70980
gcttcctgct aggcgcactc ggctacagag tggtattgtg aagcccagaa agtttacaga    71040
tggcacgatc aggtatggaa atttggcaat ttgtgaagaa ccctccagct tgtctgttgc    71100
attgtttgac ccaaactgga aaagctgcca tggacctaga attttctgcc cttatgcgga    71160
ataaaacatg gcacttggtt cctcccgcac ctgacagaaa tttgattgat tgcaagtggg    71220
tttataaact caagagaaaa gctgatgagt ctattgacca tcataaagct cgattggtgg    71280
ctaaaggttt taaacagcgc tacgacattg actatgatga cacttttagc ctagtagtta    71340
aatttgctac tgtccgcctt attttgtctc ttgctgtctc tcagggttgg agcctctgcc    71400
aactggatgt gcagaacgcg tttcttcatg gtgttctaga ggaagatgtg tgtcggcacc    71460
ctaaaactag ggtaccccctt actactgtat aaagacgcag tacccacacg actatcttta    71520
gtcgcgtggt aaataagctg tatgtgggac cagaccatga ctcgccctag cctcgggcga    71580
ctactctggg ccagcaacag cacctgaccc caccacatgg gcgggttcgg ggccgccatg    71640
tgtccagaga aagtgatgta ctccaaggca tcaacagtga gtccggaccc catgggagag    71700
tgccggacca gtgccagacc cctgtatata cggtccaggc ctccaagttt ggtccaggac    71760
ctccacgtgt acaaaccgga cccctaggat gggatccgaa cccccgtat gggtctgggc    71820 cacccatagt ggggtcccag ggttctagga cagaacatac ccgggccttg attaggaccc    71880
aggtgggggt ccggagccga cacgtgtcta gacctggtct ggtgggatcc ggacctatcc    71940
gcatacactc cttctccctg ctcaggcgga gacccgatgc tgccacgtgg catactcgcg    72000
gcggcataaa ccaacgggtg gaacctggca tgatgcctct gggctacgcg tgccttcgca    72060
ttcattacgg agaagatgtg cgcctgtcca ttccactgac aggcggcatg ctcagtccac    72120
```

```
gatacgtggg ccatgcagtt actcacacgt taccatatcg agggcaatga ctcaccatta   72180
ctcgtatgtt tccaagaaaa gggttactgt ctatcaatgc tgcatggact gcagccatca   72240
tgactcccgc tgattactca tgtgttactc tgtcagcatt agttattcac ataatgtatt   72300
tcttccatta tgctcctggg cccacatgtc ggggctcagc atccttgtat gtgcctccct   72360
taaactataa aagggaaggc acacaacgtt acaagggaca cgctgtacac actcaataca   72420
acatacacac agtggaggta gtgtattacg ctccggcggc ctgaaccact ataatccctc   72480
gtgtcctctt gtgttcatcc cgaattcacc aaacaggcaa ccgcttaggc cccctcctca   72540
tcttaggatt agggcgggtg cattccgcca cccggccgga ggattttccc ttcgacattt   72600
ggtgctccag gtaggggggct ttggctttag gtttttgcct gttttcttgc tcgacacgat   72660
ggttcagatc gtcgagcacc gtggcttgtc tcccgaggac ttcttgatgg aggaagggggc   72720
attatcttcc atgccacgag gctccaaccg cgctgtgcct ggtgctgctg ctatgcacgc   72780
tgcgcagcaa cacacgcccg cacagacctc taggactccg tcgagggcta cctatggtgg   72840
gccattgtct gcagccaggg agttgctgcg taacccacca agttccacgg cctccccggg   72900
ggccatgagg cagtggcgtg aagatgtcga ccgtctcctc ggcatggccc atcctagctc   72960
ggccaggtcc aggcctcgat cattccggca tcagcgcgag gcgtcaacgt ctgtgcattc   73020
accctcagtg aggggggcaca gactaacgac ctgcgagcag aactcaacca caggcgtgca   73080
ggcgaggatg ctcgaatctc tctggagagg gcgcgtgagc gccggcaaaa cttcgagggt   73140
cgcaacctcg accaagactt cactgcaagg gacgcccgaa tccagatggg tgtcccattg   73200
gtcggcgtgg gctgcgccgc actagcagat catctccgcg cggcgacttg gccacccatg   73260
ttccggccac acctgccgga gaagtacgat gggacatcga acctgtcgaa attcctgtag   73320
gtctatgtca ccgccattac ggcagctggt gggaacactg ctgtaatggt aagctatttc   73380
catgtagcct tgaatgtgcc ggcacagacc tggctcatga acctcacccc ggggtcgatc   73440
tactcctggg aagagctctg tgcacggttc acaatgaact tcgccagtgc ttatcagtag   73500
catggcgtgg aggctcatct ccatgcagtg aggcaggaac ccgaggagac tctccgggct   73560
ttcatctccc gcttcaccaa ggtacagggg actatacctc gcatctccga tgcctccatt   73620
atcactgctt tccaacaggg gggtgcgtga taagaagatg ttggagaaat tggcgacgca   73680
tgacgtggaa accgtcacta cgctcttcac tctggccgac aaatgtgcca gagctactga   73740
gggccgtgca tggcactcga cgctgcaaac cagagtcacc caaatgggtg gctcaggtgc   73800
tgccacccag ggtggtggca agaaaaagaa gaagcaccgt gtcacgatag gccgtagtct   73860
ggtgctccag ttgctgtagc tacggctggg gaccgggacg agcgcggcaa gcatccacgg   73920
caacagggaa gtgacattgg gtcatgccct gtccacccca acagtcgcca cagtgcctca   73980
gaatgacgag agatcctgaa gctcgtgaag cgcatcagtg agcggcgcga gcatgcctcc   74040
agggatggct cgccgcctcg gcgccggcct ggcaaggaga aggtcgacga aggtgacctg   74100
gccacgggag aatgggacct cgagaattag gcccccgagc aagtcctcaa ggatatcctc   74160
actggagact ccgactccgg tgatgacaac gaccgccgca agaagctgta cgtaatgtat   74220
ggtggaagct gggagctcac ctcccgtagg aacgtgaagt ccctgcgccg cgaggtcctt   74280
ttggcgaccc caggggtccc gaaggcagcc ccacatcagc ggtggcggag caccactatc   74340
tccttcgggg cacccgactg ccccgaaaac atggcagggg ctggtatact accactcatc   74400
actgcccctg tcatcgccaa catgaagttg catcatgtgc tgattgatgg tggggttggg   74460
```

```
ctcaacgtca tcagccacgc tgcgttcaag cagctgcaga tcccaggatc ccgactagga    74520
ccctctcgca cgttctctgg agtgggccct aaaccggtgt atcccctttgg gagcatcaca   74580 ctcctggtta cattcgggac tgaggataac ttccacacta agaatgtcta gttcgatgtt    74640
gcggaggtta acctcccttt caatgccatc attggcaggc cggccctgta ccggttcatg    74700
tccattgccc attacaggta cttggtcctc aagatgccat cccctgctgg ggtcctcacc    74760
atgcggggcg accgtcccgc tgcgcttgca gctatcgaga agttgcatgc cctagcggca    74820
gaagctgctc gcccggatga cgaggggagg gaccccctcga cttcctgtac caagatgcct   74880
gctaaggtgc ctaaggtgca accatctggg gcagacggcg tccctgtcaa gaccatccgg    74940
ctcaacgggg attcctccca gaccactcgc atcacgggcg atctggagga gaaataggaa   75000
atcgcgctca tcgccttcct ccaggcaaat gccaatgtat tcgcatggga actatcgcag    75060
atgcctggga tccctaggga ggtgatcgag caacatctga agatccaccc tgacgccaaa    75120
ccggtgagtc agaagcctca aagacagtcc atcgagcggc aggatttcat ccgtaaggag    75180
gtccggaagc tgctggacgc tggtttcatc gaagaggtcc atcacccagt atggctggcc    75240
aatctagtca tcgtccccaa ggctaacggg aagctttgga tgtgcatcga ctacaccagc    75300
ctcaataagg cctgtcccaa ggacccatat ccacttccac gaatagatca aatcgtggat    75360
tctacctctg ggtgcaacct cctatccttc ctggatgctt actctagttt ccatcagatc    75420
gagatgtcta ggcaagatag gaagcatacc gcttttgtaa ctgtggatgg actttactgt    75480
tatgttgtaa tgccttacag tctgaaaaac gccttgccaa catttgtacg ggcgatgagt    75540 aatactttg gtgacttgat tagggacagg gtagaggtat acgtcgatga catcgtagtc    75600
aagactaagg gagggtcgac cctagtggaa gacttaaccc tagtctttga caagctgcag    75660
gcaacacgca tgaagctgaa cccggacaag tgcgtctttg tgtctctgc agggaagttg    75720 ctaggattcc tggtttcaca ccggggcatt gaagcaaacc cagagaagat caaagcaata    75780
gagacaatga ggcctccggc ctgaatcaaa gacgtccaga agcttacggg gtcactggcc    75840
gcccttagtc gcttcatctc aagactggtt gagagggcac tacccttctt caagctattg    75900
cggaagtccg acccattctc ttggaccaaa gagacagaac aagccttca agagttgaag    75960 cagcaccatg tgtccctatc aatactggta gctccagagc caggagagcc attatactag    76020
tacattgcag cggctacaga ggcggtgagc atggtgctgg tcgtcgaaag tacgacacaa    76080
catccctagg ggagtcataa agttccccta ggagaaggtg gtggtctgac caccacgatg    76140
ttgacagaag gccaggagtt tgaggactcg ggactgaatg caggggtccg aaccatccag    76200
aagccggtct actacgtcag cgaggtcctc catgaggcaa aagccaggta ccttgagacg    76260
cacaagctta tctatgctat acttgttgtg tccaggaaat tgcgccacta ttttttaggca   76320 cacagagttg tggtggtgac ctccttcccg ttaagggcca ttctccacaa ctcaaacgcc    76380
acaggcaaca tcgccaagtg ggccacggag cttgctgagt tccaactgga gttccagccc    76440
cgccacgctg tcaagagcca ggtcctggct gacttcatcg tggagtggac cccttccccg    76500
agcgctcctg ggggtccaga tcccgattcg gacaccacac tgcggagcc aagggcttcg    76560 gtcttcactg agccccactg gatgcttttc ttcgacggat ccgcctgcca gcagggtggc    76620
agtgctggag ttgtgacacc ccaggtgtca gtttcgtgtt acgtcgcgag atttatccta    76680 atctccggatg ctcagtaaaa atttctattt ctcgctcgcg tatgtccctg attatccaga    76740
ttattcattc atgtttcacc gaattcggag ttactcagtc tcatagaagg ccaatttttgg   76800 agcctgttaa aacttttatc cttggcacaa atgcgaactc aaaaatcatt ctcgaattat    76860
```

```
aaacctcatc tgaagctcaa taaatcaaac tctcgacggc tgttatttga tctgtgtccg    76920
aatccaattt ctcgatgttc gatcgatgtc caactatttt aatccgagtc catactcaca    76980
aacgaaataa tcaatatgtc gtcctctgat caaatcttac tcgactcagc ttagcatctc    77040
tgtatccaat ccgatttcaa aatcaacatc ggcaacgatt tttatatatc acgattcgct    77100
ttctccgact aaaaatccaa aaccgatcaa atctcaggac ggtttatttt cgatttacgc    77160
gtagggaatt attttcaagc aaaatctaaa cagactctcg gctgagttaa tcgcgcaacc    77220
ttccgttcgt ccgaactctt ttcgctctgt ttctcagtag cgacgaattc cgcaggaaca    77280
tttttagtcc ggaaattatt tagcgcgacc caatttagtg ttttgggcca aatccagtcc    77340
agcccgtttg gcccataaga aaccctaccc taatttctcc tctataaata tgggcttccc    77400
taccttgcat tctgaaaatt ttccatttcc accccagccg ccaacaccct tctcttcctc    77460
ctctaccatt ttccagccat gggctccttc aagcacgtag agctggagct ccttccccag    77520
cgcgcagggg cttccatggc cgggcgttcc ttccctccag cgcgtcgaag ctcttctcgt    77580
agcgtcctct gcctttcttc ttccccgctt cacggcagca aggccaccag caggctccct    77640 gctcccgcg ccccccagcca tggcatcctt cactcccta ctgttttct cccagggcgc    77700 agcagcaaat ccatgcagcg gctccatggc cgagcaccct gcccggtgct ccagccggcc    77760
tcctctgccc ctgccatttt ccataggagt cgagctccta cctgcagcag cgcgcccctg    77820
ctctttcctg tccgcgacca gggagcttca gctggcgtga acttcactt gcgcacggcg    77880 gccagcaccc tctccttggg ctccaacagc ttggatgccg aaccccttc ttccttcccc    77940 tggccgagct cgagcttccc atggagccat tcctccctct ctctgttgta catagtgcca    78000
agcagcaact ccatttttccc tggccgcgcc caaggtcggt gaccagcctc cccttccctg    78060
ttcttgccgt ggccgagcca ccacttcccc agccgtagcc ctctcccct ccattgtttc    78120 agcgcctgaa acaaacacct ggccgccatc cacacttgtg ctcgatgaaa tgtgcagcag    78180
ccccgacggc tccgcgtgct gccggcttgc tgttttgttg cgtagtgagc agcacgccgt    78240
gatgccgccg tgtgttcgct gtttttgcgc agccccaaac gtcgtcgtcg ttcaccccgg    78300
tgagaccgcg acgctccttg tttgattccg catcgatgtt attttcctat gattaattat    78360
gtatgtgtgt tgctttgttt tattttttgtg gaggagagaa ccccgtgttt tgcgaggaga    78420
aagcaagtcg cttaacgctc gttggatgtt tggagcgatg cacgaatcgg aatcaccgtc    78480
attcttgcaa acatcatttg ggtttgttta tggtgagccg atgcatgtcg ctctcgatcg    78540
actcgattaa tcattttgta tggatgtgtg taaaatgttc gattatgcgc attggtagga    78600
tcacgtttgc gattggagaa caagaggtta attgatgtgc acgatttgta gttgtctaat    78660
tatgttttgg tcgatgatgt gcatgtggtt atatgtgtgt aactgtataa tttttataaat    78720 ggacgcgtgt agggaagaaa ttgaaataga aaagaactcg agtattttta ttttgatagg    78780
aaaatatgcg atgcgttgtt tgatgcgaaa actaagttac aaaatgtgga ttttgttttg    78840
ggaaatgcat cgatgtgttt atgtgaaaag tgtatttgtt ttaagcaatg tgatgggatt    78900
cataatttta gagggatat atttattgat gtgacgagta gtttagagaa tgctagtttg    78960
cgtagaggat gtatcgttaa gacatgagtg tcagagtcca tttatactag tggtcgcgcc    79020
acatggattg aagtgtctcg agtgcacgcc ataatatggt tgtatgcgag acagggttat    79080
gcgtacgatg agtttagtaa aaattccatc ggtgtcagtt gtgttaagtt gaagtttatt    79140
tgtgcgtata aagtagtaag gtatttaatg cttacgactc ttaatcgatg gtagaaattg    79200
```

```
tcttgactta aatagagagg tggtgacatg ccagagtagt catcgctttc tctatattta   79260
taggtcaagt catgacgatg cgtattatgc gttcgttaaa attatgtttc gtatatagtg   79320
tatgattgtg ctcacgattt cgagtagaca cttcaaataa gtcaagtagc tttgtaatgc   79380
aagatgtgtg atgaagttag tttgttttag gatatgtgtt gaaatgctcc attcctgtga   79440
tagacatgta gggttatttc aaaacgggtc gatgtgtgtg atgatgatat tcatgattta   79500
agtagatgtc ctgaaattat gtggcgaagc ttaggttaag ttgcaagcga tgtgaaatg    79560
ttttcgtaaa gatatatgtg aatgtgaac gagtcattca atgtattcgg tatgtcatgt    79620
agtggtggta tgaaaaatgg gttaggaatc gatcggctaa atgccaagtt cggttagagt   79680
tattgtcggc gtttcgagac cgggggggtcc ctcaggtcga cgagtgagtg ccgcgtgcgc  79740
cagcccagat gggtcgagcg cgtgggcgag cgcgaagggg ggaaaggagc gaggcggccg   79800
gagaccggcg tgagagaggt gggaatcccg cggccttcgt gttcgtcccg cgcccaggtc   79860
gggtgcgctt gcagtagggg gttacaagcg tccacacggg tgagggaagc gagcggcccc   79920
aagagagcgc ctgtcccgtc ctcgtcccgc gcggccaacc ctctctaaga ggaccctggt   79980
ccttcctttt atagacgcaa ggagaggatc caggtgtaca atgggggtgt agcagagtgc   80040
tacgtgtcta gcgagggaga gctagtgccc tgagtacatg ccaatgtggc agccgaagag   80100
atcttggaac ccagctagtg tgatgtcgtg gccgtcggag gagcggcgga gcctggcgga   80160
gggacagctg tcggagcggt tgtgtccttg ctgacgtcct cctgcttccg taagagagct   80220
gagagctgcc gtcgtcacag ggcatgcggg gcgccatcat tgcctatctg gtggagacag   80280
ccagatggga caccggtctt gttctctacg gcccgagtca gctcggggta gggtgatgat   80340
ggcgcttcct gttgacgtgg ctggcctgcg ccctaggttg ggcgacgtgg aggctcctcc   80400
gaagccgagg tcgagtctgt cttccatggc cgaggacgag tccgagcccc tgggtcgggc   80460
gaggcggagg tcgtcggcag aggccagggc ggtgtccgag ccctggggtc gggcgaagcg   80520
gagttcgtcg tcttctgggg ctgagcccga gcccgagccc tggggtcggg cgaagcggag   80580
ttcgtcgtct tccgggtctt agcccgagtc cgagccctgg gtcggttgga gcggagttcg   80640
ccgtcttccg ggtcttagcc cgagtccgag ccctgggtcg gacggagcgg agttcgccgt   80700
cttccgggtc ttagcccgag tccgagccct gggtcgggcg gagcggagtt cgccgtcttc   80760
cggggctgag cccgagtccg agccctgggt cgggcggagc ggagttcgcc gtcttccggg   80820
gctgagcccg agtccgagcc ctgggtcggg cggagcttcc tatggcgcct ttggcagggc   80880
ctggcttcct gtcagtatct ctctgtcaag tggcactgca gtcgaagtgg cgcaggcggc   80940
gctgtccttc tgtcagaccg gtcagtggag cggcgaagtg acggcggtca cttcggctct   81000
gccgagggc gcgcgtcagg ataaaggtgt caggtcacgt ttgcgttaaa tgctcctgcg    81060
acttggtcgg tcggtgcggc gatttagtca gggttgcttc ttagcgaagg cagggcctcg   81120
ggcgagccga agatgtgtcc gccgttagag gggggcctca ggcgagacgg aaatcctccg   81180
gggtcggctg cccttgtccg aggctaggct cgggcgaggc gtgatcgagt cgctcgaatg   81240
gactgatccc tgacttaatc gcacccatca ggcctttgca gctttatgct gatgggggtt   81300
accagctgag aattaggagt cttgagggta cccctaatta tggtcccgga cagtagcccc   81360
cgagcctcga aaggagtgtt agcactcgct tggaggcttt cgtcgcactt ttttgcaagg   81420
gaccagcctt tctcggttgc attttgttc ggtgggtgcg cgcgagcgca cccgccgggt    81480
gtagcccccg aggcctcgga ggagtggttt cactccttcg aggtcttaat gccttgcgta   81540
atgcttcggc tggtctggtt gttccctcat gcgagctggc cgtagcccgg gtgtacggtc   81600
```

```
ggggcccaag ttctcgggct ggtatgttga cgctgtcaac ggtttggccg gagccgggtt   81660
tgcgagagca gccctgagc ctctgcacag ggcaagaggg cgatcaggga cagactcggc    81720 tttttacat atgccctgc gtcgcctttc cgcaaggagg actaggggga gggcgccatg     81780
ttaccctcga tgggcgccga acatggtgtc tccggtgagc tgcaagcagg taatccgagt   81840
ggacgtccgt gccccgttcg ttaggggtcg gctaggggcc cagaggcacg cccaaaagta   81900
cctgcgggtg atctgccgga cccggtcccc tggcgacggg gtccgagggc tcgatgcctc   81960
cctccgatgg gattccatta caagatcgct cccgctggtc tcggaaatgt cctagggtac   82020
ctcaggagcg cagcccgagc cttggttatg tatcgaacgt accctggtc atccctcgct    82080 cggcgtctga ggcggctgtg aaccctt cgg gggccagcct tcgaacccct gatcagtaat   82140
gggcacggag cccgagtagc ctgaggcgac cgtggaaccc ttcggggggc cggccttcga   82200
acctctgacc agtagtgggt gtagggccca cgcgatctga ggcggctgtt gaacccttcg   82260 ggggccagc cttcgaacct ctgatcagta aggaggctcg gagcctggtt ccttcacggg    82320
gaaggatccc tttcgggta tccccctttc ccggtccctg tcgcaagaga tagagaaaga    82380
ggaaaaaggg aaaaggatac gaaaccgaac gacgcgcgcg accttttttg gcgcggttat   82440
ttcggcgaag gcgaagtgtc gcccgctgct cctgccagaa gcgccgcctg tccagccgcg   82500
gagttaatgc gacgaggcga gtagttggcg gggcagccgt tgcgcgtgcg cgagccgttc   82560
gaggaacgga tcacgggcgc gttgtcttca cgccgtgaga gggggttctc ttgctgcccc   82620
cggatgggac gtgagcttgg ctgacgacgt gaccgctgct cccacgcgcc tgccaccgtc   82680
attactgccg gcccactttt ggccgtgttg accgccgcgt caggctggcg ctgctgggtc   82740
gcacgctggg tcgcctcgag tcgcggtatt ggttccgcaa tcgaggaggc gcggtggtgg   82800
cgcaagtggc ggtgcagttg cttgcatgtc gtcgtagtca gagcgggcgg cggcgagccg   82860
ctcgtcagtc ttctgttgct ccgtaggccc acccctatcg agtggggctg ttcgtacctg   82920 cggaggggg aaccggagtt ccgtttgtaa tggcacttcg aatgccggtg tttttgttca    82980
ttgcggcttt cggggcctga acatgtatgt aattccggca cggagccgtg ttttttcctca  83040 tttttgagcg ctaagactcg tctgttgatt atctgaaccg cttcaccaag catgagtcgc   83100
cccgtgtcaa ggtgacgagt gaggtatccg tatcccggag gcgtaggagt ccctcggctc   83160
ggtcggcctt gctgtccgag gctcctctag cttagttaaa gggacccctc ggccgctctt   83220
cgacgagccg aggccagggg tagcgatatc agtgtgaaca gaggcggagt tggctcgaaa   83280
atgaaacctg gttggtcgga gcctagccgg gttgtccgtt ggcgggaccg acgtcgggc    83340 tgatcagccg aggcctcagg tcgggctggc gcccttggga gatggtcggc cgaggcccca   83400
ggggtaaccg gccgagccgc ctgctcgggc cggattcccg gagaagtccc tggcagcgat   83460
tgcccgggcg tggtgatgac atcgtccttc ggagcggaga tcctcggacc gcgtcgccgt   83520
ccgaggctag gtcgggcctc gctgaaggtg tcatcgatgc cgagggtgtt gctgccccct   83580
tccagcgtca agacccgagc ctgtagggtc agattgtctt gtagcgtgtg ccttctgcag   83640
ccgccgaggc cagaatacac gccctcgctg tgttgtaaag ctgcgtctcc tttcctcttg   83700
tttcgagtat cttgacttt ttgtcggtaa cagggatgtt tgtgtgagtg ggagttgctt    83760
ctcgcggaag gtgatgagtg aggtatccgt atcccggagg cgtggaagtc cctcggctcg   83820
gtcggccttg ccgcttacac gtactttcac tcgtccatga ggcctgcca ccgactcagt    83880 cgagaaggct cgaaggattg cttcggcaga agaacttccg aacatgaaga cttgttcggt   83940
```

```
ccgcggaatc actttatccg aacgcgagtt acttatcgca gaaggtgatg agtgaggtat   84000
ccgtatcccg gaggcgtagg agtccctcgg ctcggtccgc cttgactgct tacgtgtact   84060
ccgtcgtttt caggatccac ttttcgaagt agtcaaaaag cacgaaagat attctggcag   84120
aagagacctt ttttcgagga aaatttcgac gcagaggggg ttcccccct tttagccccc    84180 gagggagggt cgggctttgc cgaggcgagg ccgacccttc cttgatgact aaactttgcg   84240
tgggtgcgag gtatatgaac gacctgaaaa catcttaagg gtagaagcga cgtagctgtt   84300
ggatgttcca agcgttgccg tagacctcgc cttgactgtt ggccagcttg tacgttccgg   84360
gcttcagaac tttggcgatg acgaatggcc cctcccaggg gggcgtgagc ttgtgcctcc   84420
ctcgggcgtc ttgccgcagc cgaagcacca ggtcgcccac ctggaggtct cggggtcgga   84480
cccctcgggc gtggtagcgc cgcagggact gctgataccg cgccgagtgt agtaaggcct   84540
tgtcccgagc ctcttccagc tggtccagcg agtcttctcg gctagcttgg ttgctttgat   84600
cgtcgtaggc cctcgtcctc ggggagccgt attctaggtc agtgggcaag acggcctcag   84660
ccccgtagac caggaagaac ggcgtgaaaa cccgtggccc ggctcggcgt cgtcctcagg   84720
ctccagacca ccgaggggag ttccttcatc catcgcttgc cgaacttgtt gaggtcgttg   84780
taaatccgag gcttgagccc ttgtagaatc atgccgctgg cacactctac ttgcccattc   84840
gacatgggat gagctacggc ggcccagtcc acccggatgt ggtgatcctc gcagaagtcc   84900
aagaattttc tgccggtgaa ctgggtgccg ttgtcggtga tgatggagtt caggaccccg   84960
aagcgatgga tgatgttggt gaagaacgtc accgcctgct cggacctgat gctgttcaga   85020
ggtcggacct cgacccactt ggagaatttg tcgatggcga ccagcaggtg cgtgtagccc   85080
ccgggcgcct tctgcaaagg gccgacgagg tccagacccc acacagcgaa gggccaggtg   85140
atgggtattg tctgcagagc ctgagcgggc aggtgggtct actttgcata gaattgacac   85200
ccttcgcagg tgcggacaat tctagtggcg tcagccaccg ccgttggcca gtagaagcct   85260
tgccggaaag cattcccaac gagggctcga ggcgctgcgt gatggccgca agcccccgag   85320
tgtatctctt gcaggagttc ctgaccttcg gcgatggaga tgcatcgctg gaggatgccc   85380
gagggattgc ggtggtagag ctcctgctca tcgcccagca agacgaacga cttggcgcgt   85440
cgcgctatcc gtcgagcctc ggctcggtcg aggggtagct ctccttggcg gagatattgc   85500
aggtacgggg tctgccaatt tcgatcaggc atgcccccac ttcgctcctc ctcgatgcgc   85560
gatgcctcgc cctcggagac cgagggtacc tcgggttgag ctgagggtgc ctcgggccgt   85620
gccgagcgta cctcgggctg gtccgagggc gcctcgggct cggagggtc atcgatcttg    85680 acggagggct aatgcagatc ccgggagaag acgtccgggg aaccgttgtt cgccccgagg   85740
ctatttttgc cagctcgtct gcagtctcgt tgtagcgccg agcgatgtga ttaagctcga   85800
gcccgtagaa cttgtcttcc aggcgccgaa cctcatcgca ataggcctcc atcttcgagt   85860
cgcgatagtg ggagttcttc atgacttggt cgatgacgag ctgcgagtcg ccgcgagcgt   85920
cgaggcgtcg gaccctagc tcgatggcga ttcgcaatcc gttggtcaga gcttcgtact    85980
cagccacatt gttcgacgcc gggaaatgga ggcgtagcac atagcgtagg tgtttcccga   86040
ggggtgagac gaaagagtag cccgcgccgg ctcctgtctt catcaatgac ccgtcgaaaa   86100
acatggtcca gagctccggt tggatcggag ccgtcggtag ctgggtgtcg acccattcgg   86160
ctacgaagtc cgccaagacc tgggacttga tggccttccg aggcgcgaac gagatggtct   86220
cgcccatgat ttccaccgcc cacttcgcaa tcctgcccga ggcctctcgg cactggatga   86280
tctcccccag ggggaaggat gacaccacag ttaccgggtg agactcaaag tagtgtcgca   86340
```

-continued

```
acttccgcct cgtcaggatc actgcataca gcagcttctg aacttgtggg tagcggatct  86400
tggtttcgga cagtacctca ctgacgaagt aaactagcct ctgaatgggc aatgcatgcc  86460
cctcttcttg cctctcgacc acaatcgcgg cgctaaccac ctgagtggtc gcggcgacgt  86520
agaccaagag ggcttttttct ccatcagctg ggggcaccaa gataggcacc ttggtgagga  86580
gcgccttcag gtctacgaga gcttcctcgg cctcaggggt ccaagtgaag cactcggcct  86640
tccttaagag gcggtacaga ggcaggcctc tttcgccgag gcgtgagatg aagcggctca  86700
gggccgcgag acatcccatg accctctgta caccttttaa gtccttgatg ggccccatgc  86760
tggtgatggc tgcgatcttc tccaggttgg cttcgatgcc ccgctcggag acgatgaacc  86820
ccaagagcat gccccggggc accccgaaga cacacttctc gggattgagc ttgacgcctt  86880
ttgccttgag acaccggaat gtcacttcaa ggtcggagag gaggtcggaa gctttccttg  86940
tcttgactat gatgtcatcg acgtaggcct cgaccgtgcg accgatgtgt cgccgaaca   87000
catggttcat gcaccgctgg tacgtcgcac ccgcattcct caaaccgaac ggcatggtga  87060
catagcagta catgccgaag ggcgtgatga agaagtcgc  gagctggtcg gactctttca  87120
tcctgatttg atgataccct gagtaggcat cgaggaaaga cagggtttcg cacccagcag  87180
tggaatccac gatttgatcg atgcgaggca gagggtaagg aaccttcgga catgctttgt  87240
tgagaccagt gtagtctaca cacatccgcc atttcccccc tttctttctc acaagcacag  87300
ggttggcgag ccattcggga tggaatacct ctttgatgaa cccggctgcc attagcttgt  87360
ggatctcctc gcctatcgct ctgcgcttct cctcgtcgaa tcggcgcaga ggctgcttga  87420
ccggtcgggc tccggcccga atatccagcg agtgctcggc gacatccctc ggtatgctag  87480
gcatgtctga gggactccac gcgaagacgt cggcgttcgc gcggagaaag tcgacgagca  87540
ctgcttccta tttgggctcg agcccggaac cgatccggat ctgcttggag gcgtcgccac  87600
tggggtcgag ggggacggcc ttagccgtct ccactggctc gaagttgccg gcatgacgct  87660
tcacgtctgg cacctctttg gagaggctct ccaggtcggc gatgagggcc tcggactcgg  87720
cgagggcctc ggcgtactcc acgcactcca cgtcgcattc gaacgcgtgt ttgtacgtgg  87780
ggccgacggt gatgaccccg ttggggcccg gcatcttgag cttcaggtag gtgtagttgg  87840
ggacggccat gaacttcgcg tagcatggcc tccccagcac cgcgtggtag gttcctcgga  87900
acccgaccac ctcgaacgtc agagtctccc ttccgaagtt ggagggtgtt ccgaaacaga  87960
cagggaggtc gagtcgtccg aggggctgga cgcgcttccc gggaatgatc ccgtggaagg  88020
gcgcagcgcc tgctcggacg gaggacagat cgacgcgcag gagcccgagg gtctcggcgt  88080
tgatgatgtt gaggctgctg cccccgtcca taaggaccttt ggtgagcctg acgtcaccga  88140
tgacagggtc gacgacgagt gggtatttcc ccgggctcgg cacgtggtcg gggtgatcag  88200
cttggtcgaa ggtgatgggc ttgtcggacc agtctaggta ggctggcgcc gccaccttca  88260
ccgagcagac ctcccggcgc tcttgcttgc gatgctgagc cgaggcattc gccacatgcc  88320
cgccgtagat catgaagcag tcgcggacct cgtggaactc tcctacttgg tgatcttcct  88380
tcttgtcgtc gtcgcgggcc ctgccaccct ccgcgggtgg cccggccctg tggaagtggc  88440
gccgaagcat gacgcactcc tcaagggtgt gcttgacggg cccctgatga taggggcacg  88500
gctccttgag catcttgtca aagaggttgg cacctccggg gggctttcga gggttcttgt  88560
actcggcggc ggcgacaagg tccgcgtcgg cggcgtcgcg tttcgcttac gacttcttct  88620
tgcctttctt cttggcgccg cacggagtag acgcctcggg agcatcttcc gacgggcggc  88680
```

```
cctgggctg   cttgtcctttt  cggaagatag   cctcgaccgc   ctcctggcca   gaggcgaact   88740
tggtggcgat  gtccatcagc   tcgctcgccc   tggtgggggt   cttgcgaccc   aacttgctca   88800
ccaggtcgcg  gcaggtggtg   ccggcaagga   acgcgccgat   gacatctgag   tcggtgatgt   88860
tgggcagctc  ggtgcgctgc   ttcgagaatc   gccggatgta   gtcccgaaga   gactctcccg   88920
gctgctgtca  gcagcttcgg   aggtcccagg   aattcccagg   gcgcacatac   gtgccctgga   88980
aatttccggc  gaaggcttgg   accaggtcat   cccagttgga   gatctgcccc   ggaggcaggt   89040
gctccaacca  ggcgcgagcg   tgtcggaga   ggaacagggg   gaggttgcgg   atgatgaggt   89100
tgtcgtcgtc  tgttccaccc   agttggcagg   ccaggcggta   gtccgcgagc   cacaaatccg   89160
gcctcgtttc  ccccgagtac   tttgtgatag   tagtcggggg   tcggaaccgg   gtcgggaacg   89220
gtgcccgccg  gatggcccgg   ctgaaggcct   gcggaccggg   tggttcgggc   gagggactcc   89280
gatcctcccc  gctgtcgtag   cgtcccccac   gcctggggtg   atagcctcag   cgcaccctct   89340
cgtcgaggtg  ggctcgacgg   tcgcagtgat   ggcgctcgtt   gccgaggtgg   cccgggggccg  89400 caggcgcggt  gttgcgcgtg   cgcccggtgt   agaccgagcg   ttcccgcatg   aatcgggaag   89460
tcgcggcatg  aggttccgag   gggtatcctt   gccttcggga   ggcagtgctc   tcggcccgtc   89520
ggaccgtggc  gccttccagg   agattttga    gctctcccta   gattcgccga   ccctcggtgg   89580
tggatggctc  cggcatcgcg   cggaggagca   tcgctgctgc   gaccaggttc   tgaccgaccc   89640
cactggatgc  aggtggtggc   ctgaccctga   cgacatcggc   gacgcggtgc   tggagaccct   89700
ggggcaggtg  acgtatttct   ccggccgggg   gttggcccgc   ccatgcctgc   ccgacgtccc   89760
ggcggatcgg  ctcaagcgct   cctgctccct   cgtcgatcct   ggcctgcgcc   ccgcggactt   89820
gctcgagctg  tgggtcgtaa   ccccccgccg   gaacagggac   cacaactagc   tcccgcggga   89880
tgtcagcgcg  aggcaccggc   ccaggggag    caccgtcctc   cggcatgccg   agatgattgc   89940
cttcggaggg  accccctaga   tcgacgtgga   acattcgcg    gcttgggccg   cagtcctcgt   90000
cgtcgaggct  gcggctaccg   tcggaacagt   cggagaggca   gtagtcacat   gcggtcatga   90060
agttccgctg  gcactagggt   tgccaaatcc   agagaaatcc   caacagatgt   tggggtcgtc   90120
atcttcctcg  gacccagagg   gcccgtaggt   cgagacgtcc   gtcagccggt   cccaaggcga   90180
ccgcaagcga  aaccccagag   ggtttgtact   cgcctctaca   agggcgcccg   ccaaagcaag   90240
attgctagac  gggttgaggc   tgagtacaaa   tgacgtagga   tgggaatcgg   ttggtacctt   90300
ttggtcgtcg  agcggcgatg   aagtcacgtc   gaggactgac   cgcatcgtcg   cctcaggtac   90360
gagggcgatg  tcctgcaagc   ttttcgcaag   cgcgctggcg   tcgtccactt   gctcgggatt   90420
ggcgtgtcgc  ggggagacgg   cgctcgcctt   tgtctcaaac   gcgaggtcga   cgcccaacgc   90480
gccccccgtt  ggggtgctag   ggacgtcgac   tcgctcgaca   gccgacgagg   cgcggcctcc   90540
tgcttggcct  ttgttgcccc   gcctcctcct   ccgttggcgg   gggagaggac   ggggcgagct   90600
cgaatgttgt  tcttccgcca   cgcggggaag   acgtcgtcga   ttccgccgcc   ggcgggcggg   90660
ctgtcggccg  ccatcgtcgt   tgtcgcgcgg   cggtggaagg   agtatcatgt   cgtagctgcc   90720
gtcgagggac  atgaactcaa   gactcccgaa   acggagcacc   gtcccgggtt   ggagaggttg   90780
ttggagactg  cccatctgga   gctcgacggg   aagctgttcg   tcaacacgca   gcaggcccct   90840
acctggcgcg  ccaactgtag   gcgtttcgag   accgggggt    ccctcaggcc   gacgagtgag   90900
tgccgcgtgc  cccagcccag   atgggtcgag   cgcgtgggca   agcgtgaagg   ggggaaagga   90960
gcgaggcggc  cggagaccgg   cgtgagagag   gtgggaatca   cgcggccttc   gtgttcgtcc   91020
cgcgcccagg  tcgggtgcgc   ttgcagtagg   gggttacaag   tgtccacgcg   ggtgagggaa   91080
```

```
gcgagcggcc ccaagagagc gcctgtcccg tcctcgtccc gcgcggccaa ccctctctaa   91140
gagggccctg gtccttcctt ttatagacgc aaggagagga tccatgtgta caatggggt    91200 gtagcagagt gctacgtgtc tagcgaggga gagctagtgc cctgagtaca tgccaatgtg   91260
gcagccggag agatcttgga acccagctag tgtgatgtcg tggccgtcgg aggagcggcc   91320
gagcctggcg gagggacagc tgtcggagcg gttgtgtcct tgccgacgtc ctcctgcttc   91380
cgtaagagag ctgagagctg ccgtcgtcac agggcatgcg gggcgccatc attgcctatc   91440
tggtggagac agccagatgg gacaccggtc ttgttctcta cggtccgagt cagctcgggg   91500
tagggtaatg atggcgcttc ctgttgacgt ggctggcctg cgccctagtc tggggtacg    91560 tggaggctcc tccgaagccg aggtggagtg gatcttccat ggccgagggt cgagtccgaa   91620
gcccactggg tcgggccaag gcggaaggtc gtcggcaaaa gtccagggcg gtgtccgagc   91680
cctgggctcg ggtgaagcgg aattcgtcgt cttctggggc tgagctcgag cccgagccct   91740
ggggtcgggc gaagcggagt tcgtcgtctt ccgggtctta gcccgagtcc gagccctggg   91800 tcggggcggag cggagttcgc cgtcttccgg gtcttagccc gagtccgagc cctgggtcgg   91860
gcagagcgga gttcgccgtc ttccgggtct tagcccgagt ccgagccctg gtcgggcgg    91920 agcggagttc gccgtcttcc ggggctgagc ccgagtccga gccctgggtc gggcggagcg   91980
gagttcgccg tcttccgggg ctgagcccga gtccgagccc tgggtcgggc ggagcttcct   92040
atggcgcctt tggcagggcc tggcttcctg tcaatatcac tctgtcaagt ggcactgcag   92100
tcgaagtggc gcaggcggcg ctgtccttct gtcagaccgg tcagtggagc ggcgaagtga   92160
cggcggtcac ttcggctctg ccggagggcg cgcgtcagga taaaggtgtc aggccacctt   92220
tgcgttaaat gctcctgcga cttggtcggt cggtgcggcg atttagtcag ggttgcttct   92280
tagcgaaggc agggcctcgg gcgagccgaa gatgtgtccg ccgttagagg ggggcctcgg   92340
gcgagacgga aatcctctgg ggtcggctgc ccttgtccga ggctaggctc gggcgaggcg   92400
tgatcgagtc gctcgaatgg actgatccct gacttaatcg cacctatcag gccttgcag    92460 ctttatgctg gtgggggtta ccagctgaga attaggagtc ttgagggtac ccctaattat   92520
ggtctccgac agttatttg atagttggga ttgtggggtg aagtgatggc atgactacgt    92580
agccgtcacg tcatctattg cgtggctatg cttaagcgtg ccttgatata atttagaata   92640
agtcgagtct ctagaacgcg gcaattttta aaagtaaata gaagctgaat ttattgattg   92700 ctgtttggg ctgcacgcac tgttttagtt gtgctgtttg tttgataaac caaatcatgt     92760
tttctataga aaagtcatat agaagagttg tagatgacat gattatcctg cttgtactaa   92820
aatttgacag ccataaacct gattgtttag gagttgtgct tttcacaagc ccagcacctg   92880
aatctgtcaa atttctgaac atatttcaga aattgcaatg attgcttaag ttaatgttga   92940
aattagttat tggtggtcac aaaaagttg tagataactt tattatcgta cttgtgttaa    93000
aatttgacag gcataagtct gattgtttag gagttatgtt tttacaaat tcagtaactg    93060 aatctgtcca ctttctgtac agatttcaaa agctgcattg tttgcttaag ttaatgttag   93120
aatcagccct tgtcaattat aagaaagttg tagaggcttt tcttgtcttg cttgtgttaa   93180
aatttcataa ctataggcct gacggttaa gagttatgaa ttttacaaac tggttgctgt    93240
gttctgtcca ccgtcagaac agatttcgaa aactgtaata tttgatttag ttaaacctgg   93300
aatcacttct tggtgattat aaaagttgtg tagtactttt gctaagcttt tcaaaaagtc   93360
ttagatcact cttttggtg gtctgaagat taagttacat gtgtttgaag tgtgaagact    93420
```

```
gaatctgtcc agttttggac agcacagcct tcatagtata ttttaacctt gatacatgct    93480
aaaccagcct gggatgttta taaataattt gtagaacatt taattagctt tccagaaagt    93540
ctaggatcaa tttgtttgga tgtctgaatc ttcagttatg aattttaaa atcacaagtc     93600
tgaatctgtc caaatctgga cagagctgct gtgattgcac ttttttgacct tgctaagtgt   93660
ttaatcatgc tgtgatgaaa ataccaaaat tgtagagcac tttctaaact ttccagaaag    93720
ttttagtttg ctattttttgg attaatattt taaaagttat gattaaaaca agtagctgct   93780
gtgctgctgt cctaaaaatc tgcacgtgct caaatgaata tttagttcac cattttggct    93840
aaaaacgctt tagtaagcac ttaacggaca tagacttgtg atggctaaac ttaggttaac    93900
atgtgttcca taattaatgt gtttgcttgc tgtagttgat tgtgatagag gagtccatcg    93960
acattgatgc atcggtcctt ttattaaact tgtgtttgtg atgttttttgt gtgatcaata   94020
taagaattaa tgaaaagccg tagcaactaa ataaatgctt gtacatatga tatcgtgttg    94080
cgttggttaa ttgtaggtag tgatcattgt cttttccagtg gtagtgttta cgtgtgccca   94140
atgacacata ataactagt gtttgcgtat agttgttgca gtgtcttact aattaatgtt     94200
tagttcgcca ctgtgtcttg gtatatctta tgttactttt attatattca tacatatgca    94260
tcttgcacct catataggac cgagagatga tgatcgagcc agtgatgtgg tgccaaccac    94320
aagatgccgt tgatggacga cctgaagaat ggacttaacc agtggatgct caccaagcga    94380
gtacctcccc cagcaaacac tacctaagtg ttaaattaaa ggcaagcccc ggttttatgc    94440
ataaccatta tatatgct attttactgc acttaatgtt tgtaggcttg taccgtgcac      94500
ttaagtgtag gagttgaatg aaaccctagt tgcatgaact caggattccc tttgagatgg    94560
atactagtat gctaggtcga gtagctnnnn nnnnnnnnnn nnnnnnnnnn nnnnnnnnnn    94620
nnnnnnnnnn nnnnnnnnnn nnnnnnnnnn nnnnnnnnnn nnnnnnnnnn nnnnnnnnnn    94680
nnnnnnacag tgcacagtgc accggacttt ccggtgagcc taggcagagg tgattttgaa    94740
aattttcaaa ttttttcgatc taaattttaa ccaaaccaaa tcccaactta taatcataca   94800
aaagaacacc tattgggata ggtattggcc ccctcatata ttttcccata attttcaaaa    94860
atattttgcc ataggctagt caattttttag agaaaatagt caaatggtga gatttgcatt   94920
ttagctttga actaggggtt ttcatgaata atttgagttt tgaatactcc cccctaagt     94980
gtagtactac atgcatatct caagaaccaa caatggcata gtaaataaga atttaagtac    95040
taaaagctta aagctaagac ttgtcaagtt tgagcccgag ttaagctttt ttcactcgct    95100
ttgttggcgg ttatcttaac taggttagac aagcctaga tgcaatacaa gaaatttaaa     95160
tatgcaatgc aggcttgaca acactatttt gagatcttta aataaaattt ctgagatcaa    95220
gtatgtttaa ttcatttctc aacatgcaaa agcgggtttt atcaagaggc ttagtgaaaa    95280
tatcctctaa ttgatcttcc gacctcactt cttctaaaat aatgtctcct ttagcaatat    95340
gatctctaag gaagtgatga cgaatatcaa tgtgcttggt gcgagagtgt tgtacaagat    95400
tattagcaat tttaacagca ctctcattgt cacacaacaa aggtaccttt tctagaacta    95460
caccatagtc tagaagagtt tgtttcatat ataaaatctg tgtgcaacaa gcaccagcgg    95520
caatgtattc cgcttcggcg gttgacaagg caacactatt tttctttttg gatgtccata    95580
atagtagtga tctcccaagc aaattacacc cctagaagta cttttctat caattttgca     95640
accggcataa tccgaatcgg aatagccaat taaatcaaaa gtagctcctt tgggatacca    95700
aaggccaaca cttggggtgt gcttgagata cctaagaatt cttttaagag cgcaaatatg    95760
agctttctta ggatttgatt gaaatctagc acacatgcat acactaaaca tgatatcggg    95820
```

```
cctagatgca ataagataca ataaactacc aatcatagaa cggtagagag ttaccatctt   95880
ttcaacaagt gatctccatg ttgaaccttt caacaagtc tttggtatac ttctcttgtg   95940
agaggaagtt accatctttc atttgcttca cttgaaagcc gaggaaatac atcagctcac   96000
caatcattga catctcgaac tccttcgaca tcaactcacc aaattccttg caatgatagc   96060
gatttatcga gccaaagatt atgtcatcaa catatacttg acaaatgaaa atatcaccgt   96120
tatgtttctt tgtgaataga gttgtgtcga cggtcttgat cttgaagccc tttttgatga   96180
ggaagtcgcg aagacgctca taccaagccc ttggagcttg ctttaaccca tatagcgcct   96240
tggacaacct ataagcatgg ttaggatatc tagggtcttc aaacccgggt ggttgctcaa   96300
catatacaag ttcatttatg aagccattta aaaatgcact ttttacatcc atttgataaa   96360 gcttttatc atagcatgat gcatatgcga gtaggataca gatggcttca agtcgagcaa   96420
ccggtgcaaa ggtctctcca aaatctaaac cttcaacttg agagaagccc tttgcaacaa   96480
gtcttgcctt gttcctcaca atcacgcctt gatcatcttg ttttgtttctg aataaccact   96540 ttgttccaat gatccttgca tcttgtggag gcttctccag ggtccaaact tggttacggg   96600
tgaagttgtt tagttgttca tgcatggcat tcacccagtc cggatcctgt agcgcctcat   96660
ctatacagta ggctcaacac aagaaacaaa ggagtgatgt tcaataaaag aagcatgttt   96720
atgtgatcga gtaataaccc cttgtgaagg acttccaatg atttgatctt gtgggtgtgc   96780
ttgaagcagt gatgagtttc tcctatcaac cacttaggaa gaagatcctg gagcatcaac   96840
atcttcggct tgtatccttg cttgttcatg agagacaaat gtatcttcat ttgcatgcct   96900
ctcatctttt tcatcatctt gtggtacact tgatgaagaa ggcctattaa tgttttgcac   96960
ctcttcttca tcttcttttg gtttgatagc tccaattggc atgttcttca tggcttcctt   97020
aagtggctca tcacctacat catcaagatt ttcaagtgct ccttgggagc cattagtctc   97080
atcaaactcc acatcatatg tttattctac cacgccagtg gcatgattga atactcgata   97140
tgctttggac tttaatgaat aacccagaag aaaaccaata tcacaacgtc tttgaaactt   97200
ccctaggtga tggcgtttct tgtaaatgta gcatttgcat ccaaacaccc aaaagaatga   97260
gacgtctggc ttttttcccat ttagcagttc atagagagtc ttcgcaagta gccagtgagg   97320
aaatagcctg tttgatgcat aacatgcagt gttgatagct tcggcccaaa acctctccgg   97380
tgtgttatac tcatcaatca ttgtccttgc aagtgtgatc aaggtcctat tttttccttc   97440
aacaactcca ttttgttgag gtgtatatgt tgctgatact tcatgcttga tcccaatctc   97500
atcacagtat tcatgaatgt tggtgttgtc aaattctttt ccattatcac ttctaatctt   97560
cttgatcttg taatcaaatt cattttgagc tttcttggca aacttcttga atatagatgc   97620
aacttcagat ttatcatgga gaaaacacc caagtgtatc ttgagaaatc atcaactatc   97680
accagacagt agaggttgcc accagcactt gcataagttg ttggtccaaa tagatccatg   97740
tgaagtagtt ccagtggcct tgatgttgac atgaaagctt ttgtaggatg tgtgttagca   97800
acttgctttc cagcttgata agcactacaa ggcttgtcct tttcaaatat aacatccttt   97860
agtcctctaa ccatgtcctt ctttaatact ttcttcagtg tgctcattcc aacatgtgca   97920
agccttctat gccatagtca tccaagagat gctttggtaa agaggcaagt tcttaagtct   97980
gcatcttcag aggtgaaatc cactaagtag agattgttgt atctaaatcc tttgagcacc   98040
atttattcat catccatttt tgatacaata acctctgttg gagtgaataa gcattgaagt   98100
ccaagaacac agagttgacc cactgataat aagttgaatc ttaaaggtgc aaccaagaga   98160
```

```
acatttgaaa ttgatagatc atttgaaatt gccaccttgc caagtccttg aacttttccc   98220
tttgaattgt ccccaaatgt gattttgtct tgtccatcaa cattatcatc aagtgaggtg   98280
aacatccgtg ggttgcctat catatgttat gtgcatccac tatcaataac ccaatggctc   98340
ccaccggtct tgtagttcac ctacatccac agacaaatca agcctaagtt ttgagggccc   98400
tatattgcat aggaccagtg actttctcaa tcaaggactt tgcaacccaa atttgtctag   98460
gtctactctt gcttggtgga cctaggaatg taacttcgac ttttccattt gctacttctt   98520
aaaacataat gagcattgaa ggcaaatggt cttgagtgct ttggcagggg agttggtggt   98580 ttggcttttgc agttgtggga aaaatgacct tcttttccac actcaaagca tttgatatgc   98640
ttatgagtct gatttggctt gtattgagtt gtagctttct tttgcacaaa ggagttatat   98700
ccaataccac tcttgttgtt tttcatgaca gtgttcatga gcaattcatt ttagaggtat   98760
tggcccttgt tgaactttg cacacttgtt gcaagatgtt cattttcacg cttaagtttc   98820
ttgacctcat tttaagcctt tctttatcca ctgccaactc attgttgaag tcattgttct   98880
caatggcaac ctttcctcta gtagttgcat cagtcaagta tctcttcaat ttttggttgt   98940
ctaatgtcaa gacttcaact ttttcagtca attcatcatg tagactagtt tgatcaccct   99000
gactcaaatc atcacatgag gttgctacat caatattaac aacagggtta atagcctcat   99060
gtgtattgca agataaaagt tcattttcaa caagaagatt atcatgatca aatttaatct   99120
tagtatagtc ttccttattt tttactagtc tatctttcaa ctccctatta gcttcattta   99180
acttgtcaca tttatcctta gcatctttta gggaggatgt aagctcattt acagtggatg   99240
acatagtttt gtttttcttct ttcatttcat tactagcttt cataactatg tcatatttag   99300
catttaaaaa ttcattttca tctttcaact tatcacattt agcttttgac ttcctaatga   99360
gttgagtgta ttcattaagc aagtcaacta gttcatcata ggaaggtgaa gcaaattctt   99420
catcactatc actatcacta tcatcaataa tatcattatc attttgtact tttcgttcac   99480
ctctagccat gaggcatagg tgagaagtcg atgatggaga tggtggtggt gaagagaagt   99540
ccccagcgat ggcggtaact ttttcatcat tttcttcttc acttgaagaa gatccacttg   99600
acgactcaat gtcagtgagc caatcaccaa caatgtatgc ctttacattt ttcttttttgt   99660 ggaacctctt atgctttcca tccttcctct tgaagaatct cttttcattt ttctcatcat   99720
cactgtcatc ttcttttcttg cccttgaact tgttcttctt ggacttgtta cattgatgag   99780
caagatgacc aagctctcca cagttgtagc aatccattta agaaatgggc tttcttttgc   99840
tggaaaagaa tttcttctttt cttgagtcaa atttgatgcc ttctctgttg agcttcttta   99900
atatcttggt ggtcttcctc accatcaagg caatgttagc attaagatca tcgtcacttg   99960
aggattcctc ctcaacttgt actttagctt ttccttctct ttcttgatttt tctttgagag  100020 ccaaatcctt tctcttgtaa gatgactcat ccttgtcatt gatgtgcatg tacatctcat  100080
gtgcattgat ctttcccaaa atttgtgtag gagtgacaac tgaaagatcc atctgatgca  100140
gcacagtgac aatgtgtcca tatttatcaa ttgggaggac actgagaatc ttcctcacaa  100200
catccggttg tgaaatttgt gtaagcccca agccatttac ttcctctaca agaatattga  100260
gacgtgagta catagcattg gcattttcat tagcaagcat ttcaaaagaa tttaattttc  100320
tcatagcaat gtgatatctc tcctcacgct caattctagt tccttcatgt agagcacata  100380
tgtccatcca caaatcatga caatttttat ggttttcaac tctattaaac acatctttgc  100440
aaaggcctct aaaagggtg tttttggcct tagcattcca tttctcatag ttcaactctt  100500
cacctacaag atttgtggga tctctaggtt cggggaatct ttgtgtggcg gctttgtaga 100560
```

```
caccaatgtc tatagcctct aaatatgctt ccatacgaat tttccaatat ggaaaatcgt   100620
caccataaaa aacgggagaa ggtccatccc caccggacat cgttactcta gcggttaagc   100680
taatctaaga gcaacaaggc tcttatacca attgaaagga tcacgatgcc caagaggggg   100740
ggttgaattg ggcttttcta aaaatcaaca ctaactaaaa tctaagcaag agcccaactt   100800
caccccgaca actagcacta agagaataat actagaaata caacaatgct aagataatac   100860
ttcaaatact tgctaaacaa atacacaatg taaaatactt gaattaagtg cggaatgtaa   100920
agcaaggttt agaagactcc tccaattttt ctagaggtat caaagagtcg gcactctccc   100980
ctagtcctcg ttggagcacc tgcgtaaggg tatcgctctc ccttggtcat cgcaagaacc   101040
aagtgctcac aacgagatga tcctttgcca ctccggcgcg gtggatccct cacgaccgct   101100
tacaaacttg agtcgggtca ccaacaagat ctccacggtg atcaccgagc tcccaacgcc   101160
accaagccgt ctaggtgatg ccgatcacca agagtaataa gccatagact ttcacttgac   101220
caagagaagc ctaatgcatg cggtgtgtgc tctaggtggc tctcgctagc gttaatgagg   101280
tccaaatgcg ggattaagat tctcaagtca cctcactagg cttttgtggtg cttgcaatgc   101340 tctaccaatg tgtaggagta aatgtgggca gcaagaccat caatatggta ggtggatggg   101400
gtataaatag ccctcaccca ccaactagcc attaccagga atctgctgcg catgggcgca   101460
ccggacagtc cggtgtgcca ccggtgcgcc aacggtcgac tcaaacggct agttctgaca   101520
gctagccgtt ggacagatgg cataccggac agtccgatac gctgtccggt gtgcctctaa   101580
aattcaactc acgaacagcg cgctctcggg tttctgcgcg cagggaaccc tcttccctgg   101640
gccaggctgg gcccactggc aaagggtgca ccggacagtc cggtgcccca aagccagaaa   101700
ccctagcttc tgttttgtgc tgttttttca atttggtttt tgttctaact tgtgagtatg   101760
ttctagagtt acacctagca ctatatgtga gtgtgaatat gcaccaacac tacactagaa   101820
ctcttttggt caaactactt atcgacaacc cctctttata gtacggctaa acaaaaataa   101880
aagacctaac tatatcacga gtgtccgcaa ctccttgaca ctcggaatac gaagaccttc   101940 acttttttgtt tcgtcgcttt agccgttgct tcaagttttt atctccggga ttgttttcac   102000
cattgtagta catctacctg taatgcgacc taacttacca tttgcctctg caaaacacat   102060
gttagtcaca tataaaatta cgttgtcatt aatcactaaa accaaccagg ggcctagatg   102120 cttttctagtt taaatcccca acaagtcaaa attcttttcta ttttttttttg caagttccaa   102180 ttgacatctg aaaggttgta aggtacacgt ttggctctca ttgataacgg gggaaagata   102240
cagtgcaaac caccatataa tgacccactt ctaatcgaat ggacctgtaa cgacgaaata   102300
ccctgtgaga actatggttc actcatgtta attcattgaa attgttgtag tgaattgaca   102360
tggttgggag cctgcttaga gagtatagat tgtcactttt ttttggaccg caacttattt   102420
ttaaaagata ttgcgatcgc ttgtttagta gctgtttcag gccccaatgc agtttctatc   102480
gtgatccatt taagtcactc aacattctca tacttctcat tttgcattaa ttcattccaa   102540
tctccactac tataaaatac tagcttcgat ggtcgtcata cgccatgcac gaagcatgta   102600
gatcaatccg cataccagtg ggcatctata gataggctgt gaaaaccacc caaatcccta   102660
ctagtggaca ttttatctat agatggaccg tgagaaacca cacaagtcta acacgacagg   102720
gaagccaaac gcagcgcagc gctcccacat agaaccacct cactacctaa aggaggacaa   102780
gccatcgagc aagcttttaaa aaagtagtca ggcttcttc aactcatacc tttcctgata   102840
ttttagctaa gataaaagcg taatatttgt ttttatcagt ttagtatctg atatatggac   102900
```

```
catatgttca ctttgatatt tgatattatt tttttattgg tatcaaatat gattgtatgt 102960
cgtcgcagcg cacatgtgtt gtactagtta ttttataaga taatcaagta tttcttaatc 103020
atttaagaca ttttgatgat tatttaaaac attctatttt tttctcagtc attcactcgt 103080
taggtcattc agtacatatt atgttaaatt aagtcattct gttacaattc tagtcatcac 103140
atgtcattta gtcattttat gacttattta aaatatttca tattgtcaac agttgttaca 103200
agactttctt acaaatattt taagtcatcc aatagtttat tcatccagag actcataata 103260
tgtttttaag tcattccttt ctattaaatt gatgtaatta tttttatcac gattggactt 103320
cttttctttta tcacttagaa gccgtgcgag atgaaagtct catgcacggt tttgcatgag 103380
agaaagaagc gaggaattct cttttttgact ctgactcccc cactccaatc gttgcttttc 103440
tttctgttac ttcgaaagta gttgcttcag ctttagccac gcgaattctc gatattcctt 103500
tttatttctc atcaaacgaa tgacatcttc ttctggaaat cctagctatt cttagcatga 103560
tattggagaa tctccttgct attagtcaaa caagcatctg attggagcac aggcgtgtgg 103620
ggggagggat gctcaatggg ttattgaggt gtgatggata gagcatccgg ttagagcgca 103680
gggcacgcag tggatactat ttggcaccac gctcagcgag tatgcgtgta tgcagtcatg 103740
caacccgcat atataggcat aaaaaaccaa aatccctttt tttgttatat tcgtgtttat 103800
gagattttcg aacaaaacta gacactcatg ctatatcttt ttcaatttt tatttaatcg 103860
caatgtccga ccctaataaa tacaatgatt ggtcctaata aatacgatga ctggctctaa 103920
taaaaaatac aatgacttat cttgatagct ataatgagtg accctgataa aatacaatga 103980
ttgaacctaa taatacaata actaaccctg ataaaaatat cctgctaaat acaatgactg 104040
accctaataa aaaaatacaa tgaccgacct tgataactat aatgagtgac tctgatataa 104100
atacaatgac tgatcctaat aatacaatga ttgaccttaa taaatacatt gactgacact 104160
gattaaaata taatgattga tcctgataac tacaataact gaccttgata aaatgtagac 104220
cctaatagaa gaagtacaat gactgatcct gataaaatac aatgactggc cctggtaaaa 104280
aataaaatga ccctaataat tacaatgaat gaccctgata aatacacgac tgatcctagt 104340
aactataatg attgaccttg ataaaagtac aagtgattca ccttgataac tacaaatgat 104400
tgatcctaat aacataaaga taaaggagaa caaatgagag gttggttatg aaataattgg 104460
ggaaatttgg gctagccagt tgcatgggtc cgacctagtc acgaaccagc cagccaggcg 104520
cgtggaataa ccacacaaaa aataggacgt ggggattcaa accatgctct ttcgatacaa 104580
gcgagcgtct tctaccacta taacttatgt ctgtttatgt tatataaagg agagatattg 104640
tatgtgtgca cacatatata cacacataca ctataaaact gatgtcagcc attcacattt 104700
tgttcaacca tccattatct tttgttgagc catttctaat caataccact tgtcgggtat 104760
cataattagg ggtacccaga ttatgcccct aaaacacact taaccccttag accaccttca 104820
agacacattc cccgagatca aaggatcata aaccgcgctt cgcccgaggc cccgctcagg 104880
ggtcaccata ggtccgcttc gctcaagcct gccctcggac atggtgtgct ctagggagaa 104940
ttctcgtccc ggccgaggct ccatctccca gaacaaaagt ctttgcctcg cccgagcaca 105000
tctcgggtaa ggaagacaac cccaatgcaa gactcaacca aagtctgcag ggggcaggag 105060
cattcaatat gcatacctac cccacgtaga gttgcaggtg aacaggagca acaagaccgc 105120
ggtcctgtca agcttcacca actacgatga cgcatgcgac cactattccc acatgccatc 105180
tgtcaaccc tgatgggacg tacaatacga caagagtgca ggatggctct cggacgtgaa 105240
ctctgcctcg ctgaaggcga cctcggcctc gggacaaact tcgcctcgcc tgagcccggc 105300
```

```
ctcgtttacc tgctccccgc gaatactgga gcgggctcgg tcgtgacctc gggcggactt   105360
ctgcctcgcc cgagcccgac tctagcctca atatccacaa cggaaaggcg cccaacgtca   105420
ccatatactg cagagctgac atattactta gggactttt  gccatactca gtactgtgtc   105480
aaccactacg gcatgggcaa ccccttgtc  aggggggctc gggtacgtga ccaagcgctc   105540
agcccttgcc tcggctctca gcagaaatca agcgggcaca agtcaccaaa caagtacaag   105600
accatgcttc ttgaagatct ttgagtgatt tctgcagatt tgaactttt  tcaacttcag   105660 cttcgagttt tgtttcgaaa tctttcttct cttgctcaat gcttttgac  ttcatggaaa   105720 gttcactatt cagtctggcg atctcggctt gagcttctgc cagtgaacct tccattgttt   105780
gaattatgaa gtctttcttt tctagggcag cttcatgatc tttaatcttg ttctctaagc   105840
cctcaattat aacttcgttt ttcttgtcct cgaggtcttg ttgcatcctc aaggttttgc   105900
ttagtagtag gctctgacaa aataaccttc atcagaaaac atcttcatat caaaacaata   105960
aaaagttaag ggaagaattt taccttaaag ttagaataaa ataggctacc gacgatatgc   106020
tgtcgtcggt atctgctgag atcggcttcg agtttcggaa aaccaacact tttcgataaa   106080
gtcctgacaa ctttctcccc agtccggtct caaaggcaac ctaagctctc ttcgtctata   106140
ccaccgaaga gcagtgcccc tggctggtac ccgcaagata tagcaaagtc cctcagctct   106200
tcttttttag cctttagacaa ctcttgtcca attatgtttt gaaagttgat atttctttct   106260
tccgaagcat cttcggcaag ctccttctcc tttcaggca  ctgtagccgg ggtttcctca   106320
gcagctgcag cagtttcttc ctcagccata ttcaaaatta tttcatcaat gtcagtaagc   106380
gtgttttcca aatttgtggc ttcggctgct gcaacttcgg aagtagaagc ttcggctgga   106440
gcagctttgg ctgctgctgt ttttagcact gaggccgacg atggtgtttc ttcaatagcc   106500
tcaatgatag taataatcct tcgctttttt ggttcagcgg gcttctcggc aaccgaaggt   106560
tccttcttct tcttctgtaa aagcttcatc agttccggtc ccagcgggct tagcttatta   106620
ggtagagatt cggtcattac ctttaaaatt tcttctgcgt cagtggcaga aggtgttgag   106680
ggaacttctt ctaaatcagc ttttggcttc ggagctgtag cttttctttt cttcgaaacg   106740
gccaccttcg gctcagggct ggatttttt  tcttttttgc taaattttca tcttctttta   106800
tcattctggc agcttgtctt tgcataacac tgacagctct ttttttgtttt ggcccttcgg   106860 cacctttact taaccgttca tagtctgggt attcaaattt cagagtgttc attactcggt   106920
ttagccttcg tttcggtcgg gtgccgaagg ctgccgtcat caattgatct tctttcttcg   106980
tataattgcc caatatttca ttgcacataa cttcgatcgt atccaaccat tcttggcagg   107040
gttctttgaa gtgtttcttg aacttaaaat gatagggcag tcgaacaagt tcattctttt   107100
tcttctctcc tttaagcttc ggcatactcc attcctttaa cgttgggaat actctattgg   107160
ctaagtattc ctgaaccaaa tccctagttc cgatatgctc ggacacaact ctaaattcac   107220
ccacaacatc tgggcatgat gatcccagcg tcatgcgaca ctgggccta  gttaacccga   107280 aggttaggcc cagtgggctc taaactagct tctccttctt ctcatcaacc ttaacataaa   107340
accattcagt tttccaaccg gttgtccatt tggtgcggta gctaaccaac ggtgtcttca   107400
tgtctttgcg gtaggcaaaa ttatagcagc cgaagttctc gtgcagtcca tcttctctag   107460
ccttcgtctg atagtgaagt tcgtgcaccc ggtagaaggc ttcggcaagc ggctccactc   107520
cttggcttcg aagagcccag ataaagacgc taagcctaac gatagcgtta ggagtcagct   107580
gatgaaaata aatttcgaaa ttttccaaaa catccacaat catcccatgc agaggaaacc   107640
```

-continued

```
tcagtcctgc tttaaagaaa cttctgaaaa ctaccacctc atcattttct agcttcggag 107700
tgatttattc tccgccaaaa cgaattagct tcttctcggc ttccccgaag tagcctagct 107760
tcgtcatcat gggcatatcg gcctcagaga cggtagactt tccaaattcc aagtggctgg 107820
gtttagatgg catgacgaaa taatctatct cctcttcatc agcctcacct tcttcaatgt 107880
cagcctgctc ggtttcggca gcacgtgcac cttcgtcaga aacaccctct agcacaacca 107940
agcctgattg tctcattact tcggagattg gggcggtctc ggcagcttcg gcctcctccc 108000
cgtcgcgtgt gactctagca gttgaacgca ccctggccat ttgatgctga atttctcgcg 108060
gttttgacaa agttgattac tttttgattt tgccgaagct ccctcttttg acgaagctaa 108120
agaacaagac gatgctctaa ttgagaatac gaagaataag cttcggctat ggtcaaattt 108180
ttcagcagca caacaatacg atagtaatga atgctgtggt aacttcacac ctacccgtct 108240
gtttatatag tgctacaggt gggaaggtga atcatcaagc cacctgcacc cgccgaacag 108300
tcgctcgcat tcactgaacg gtggaccgca tggcgcgaga aggagaatca ccagatcgtg 108360
cgtacccgtc ctatggtggg accacctcgc actaggaata cttaaatcgt ttctcgacaa 108420
cgagctcagg gaaggtgttt tcggaccttt cggcattccg aagcctaaaa gaattttttca 108480 cgggtcgagc tcgttacaaa aaatgatctg gcaccgtgaa ggggctactg ttgggggtct 108540
gtttcgtcgc cgaaggtcct gtgagaaaaa acaccttcgg aaggccagaa caggaatgat 108600
gccgaagcta ccaatcagag agcttcgtag cgtatttcca gatgcaccga cttaaagatg 108660
aaatgacgaa ttgggcccat gataatctat gttatgattg taatcatttg tagaggacat 108720
gaatgtaaat ttacacaggc tgcgccctgt gcctataaat aggtgaacag taccctcgta 108780
ctgttcacgc tttcgcatct tacttttatc tttgccttct atcaagctca aggtataaat 108840
gtaatttgat attattctta tgttcttatg attatttaat aataaatatt tatgttaaga 108900
tgttatataa ttgtttatgt tgtcttccta tgtttcataa gcttcatcct ttgtttatac 108960
atgtcatact tatgaaggta tgtccttcat aaccttcgtc cgaagatcgt tatctcctaa 109020
gggaaataat gcttcgaagg acgaaggaca ttaacattta acattttgtg ttgccttgtt 109080
cttaactcat agcatttgag aacaagtccc caacaattat tatgatatcc tcgccactaa 109140
caagtgaatt tttgggagaa ggactaaaat gcagtcaacg ataatgtata agactttgga 109200
gcaaaaacaa agacaagaga cataaatatc caatacaaaa ggaaaccaga gaggtagtgg 109260
tatttttttc tttcttggtg gctaagcatc gctcaccctg tgatgcaaaa atctaccaga 109320
gacaagtata gccaagacca tcaaataaag agacaattta gcaaacaatc caaatcaaga 109380
tcagtgtttt tatgtaaaat agagcatttt tatcatctcc aattgcattg acaattataa 109440
atatgatgaa attgagaaat agataggctg agtaccctag ctcagcctca tctttggcag 109500
aggcatcacc atcaacatct tcaaagtcac aatcttggaa gagtttcttt gccctttttt 109560
ggcaggggaa gggtgggtaa gtcctatcag tagattgcaa tcaacaatag gataagatct 109620
catatgtatt atggaaacaa ataagtagat ttttgcgtta caaaggttac cttttttata 109680
ccactcttct gtgtcccggt tatagaacca ccccaggttc acactagcat caaagatctg 109740
tagcaacccg cgatcaagca catagattac cattatattt tagacatggt gtctcatgtt 109800 atttttatttt caagtactat gtaaattcaa tgaaatgcta agattaatat ggcaagaaca 109860
tttgacagaa attagcatca tactgctggt gacattggaa tgagagaatt tccatcatct 109920
cttagtatta gctaaaggaa tgagttccaa ggcgaaaaga ggcttcagtt agaagaaaaa 109980 tttacctttag gtataagggc atcaccatca gtttctgtg tttctgttga cctcgcaaag 110040
```

```
caacttgcag aaactgcact catgatgtgc agattcatat catcttccac agatttaaga  110100
ataaaatatg agtgtacaaa aaatcaaatt ggtagtcaaa catgcgaact gtattctgtt  110160
gtttgagtga tttcacaaat tactgtcaaa tgtgagttag aatatacctt agaagtggtc  110220
ctggcattcc tgctttgtgg tgtcactgtt ggttcagtga ttttcatcaa cattttgttg  110280
ttggtattct cgaagcatgg ctagcctctg aagctggtag ttaaggcatc acttttttga  110340
agagtcccctt gcatattgct tgttgtaact tgagagacca tgatcagtgt tgattgtgat  110400
cctgctggtg acatttccat aatctagctc aaccccctag ctgatataaa acagatcaac  110460
cataaatcaa ataacata ttgcaacaaa caattacaca atcatgattt ctatagcaga  110520
atattatatt gtgttcatga gttgtaactg ttagatgaag ttacgatatt ctagaagttt  110580
cttgtgcatg taatctttag ccaaccgaat caatctccta tagatagaaa ggatatattc  110640
taggctgtgc atagatagaa actccaacaa tagattgatt cggttacctt attgtataag  110700
ttgttgcacc cagccttgtg cctatataaa catgcaatcc ttggccacct agtgtggtag  110760
aacgcttcaa ctgtgacacc ccagtgtcac gtagggtttt tcctagagtt gactccaacc  110820
attatcacat gtgaaccaaa aagaggaatg aacataaaaa aattaagaac aaggtttaag  110880
tgagtctttt tcatcttaag aaattctcct taatcatgcc atgcacctca aggtaagaag  110940
aactctcaaa ccctaattaa tcctaagtgg accatttaag cacataaagg gaatttggga  111000
aaagacttgg gaaaatacaa aattttggta agaaccaaat aacaaagttt tagtgcacta  111060
aataaccaac aaaatatagt aagaaagttt tgccatttga attttccaaa atcccaaatc  111120
agcccatgaa ccaatgccct atggggaaat tcagaaattc agaaaactga atttcaaacc  111180
cttttcccaaa gttcagatgt gttccctgtt ttccaaaact cgaatccaca aagtccaaat  111240
atcaaagtgg cgccaaaata ccctaggaac actttggaga agtttgagat caaacccgaa  111300
tcgtttgaca cgacttgaca taagttttgt ctcggtttgg acagtgctaa cagagctatc  111360
ttcaggccat catatcttct cacctaggcc atatcttcac tcgggactca cacacgacag  111420
gaagaccttg gcacggtgaa gagacgctac acaggatcct tggcaagata tgcacgtttt  111480
ggtcggccaa caggcgtttg aactcgggca gaatcacact tccacgtgtt cgatcgcgtg  111540
ctcaagcgct tggccgcgca ctggctgccc tctgatcgcg cgccatgcac ggtcggcttc  111600
tgtccccgc gcctgcactc agccatgcct gagggcgcct ataagtaccc tggatgcaca  111660
atggtctgcc cttcactccg cctcacgcct cgagcaagaa ctccaactcc gcgagctctc  111720
ccccgcccgc catcaccgcc cgagcctcgg ccaccgcggc cagctccctc cagccacttc  111780
caagctgcac cagtcactcg gttagcttcg ccagtggccc gtgaagcttt ccaagtcctc  111840
ggacccaaca gagtttcacc agagacccag gatcgacctc gctggacttc ggtcaccgc  111900
agccgcgcgt agaccgagca atccggtgat tcattctcaa attcctcgcg cgcatgtctt  111960
ccttgaccctc tggtgaagct ccctaacctg ttcaattgga ctatcgcgcc gtgagcaggc  112020
cggatccctc gccgccgacg agctccccgc ctgtgcacgt ggaccaacct actccgacca  112080
ccaccgccga cgatccgcac ctcgacgtga tcgccagaga ccccggacct cacccgaccc  112140
ctcaccggag caacctcgcc gccggtaagc ccctccgccc ttttcttcca ctgcggtcac  112200
tattccatta ggggaaggat cgcgggttcg atttcgcaaa accctagggg ttttctgcag  112260
agtcatagac tcagataaat agtgaaccaa ggacctgtct gtaatacact taaaacccttt  112320
cgccagggac cccagtgcaa aaccctttt cctttatcca tttctgttta ttcttttaa  112380
```

```
attcagtaaa ggacttagga aatttgtatc ttgagaaata ttcaaccaaa tttagtcaaa   112440
ccaattttac tagattcaaa atattatgaa ctatcacata aaatattga accctgtgct   112500 ttctgtttta aattttggag tttagaatta attaaagaaa ctgaccaaac cttattaaaa   112560
tgaagaaaat tagttatgct tctgtgctga acttaagaaa atttgtagaa gttcaaaccc   112620
cacttagaca ctgtttaaaa atattgagca ccctagtatt gaagatttaa acagggttat   112680
ctattaaaag ccataattgt ccaaaactta ggaaaataag aaaggtacta gaaaataatg   112740
aacagtggat gcaaatattt ttcctagccc acttaagtaa tgaagaacct agaaaaaata   112800
aaaggaacac tagtccagag caaattcaag gtgaaatgtt ttattaggca ctaataaagc   112860
tagaagggca attattagaa atatgagaac aatttcaaaa ttggtaagaa aaattcagta   112920
gacttgtaac cactaggaca ccactacaaa aatgataaat acctagccca tcattttaag   112980
tgggttgaac aaataaaact tgatattgag ccatattcca attaaatcat aagcaagcca   113040
aaaagtgtgc aacaatgggc gaataaattt ttactagatt attaatgaaa tagatcacca   113100
gagcaaaatg caaaacctat tcaaactaca agtaatacc cattgcccct acttcatgaa   113160
aaaggccatt taattcaaga aattcctacc acccttccct taagaaaaag gttaccaaat   113220
tttagaatga ttgctcttgc gcaaagaaga agataggaaa aattggaaat ctgttgtttg   113280
atatttttca agtatagtgg tagtagaaag cacccctttg gctagaaact ttagaaaatc   113340
ataataaaat aactaataaa tattagtggc tgaaaatttg tacaaaatca tgttataaca   113400
tctaaatgcc agcaaaaata agtcttaaag aataacccac tgttaaaaga gagttgtagt   113460
tcaaaacatc cccttttgccc taacacttgc taattttgta cagagagaac ccctcacttt   113520
ttaagcccca aattttgaga cagaaaatta taccagta agaagctact gtaatgtttg   113580
cagaatttct ggaaatttat taagctatct tgtagttcaa acccaccta aaagcataaa   113640 aggaataaag aagggaggaa ttagaaagat taataagtat taccccaaca tggcagctaa   113700
gaatcttgtt aaaatatcca taagatataa agaagaaaat cagtagaaca ctaaaaatgg   113760
gttaaccatt cagtaatcaa cttgacccta agttggtgag tgtaccacca aaaatctcca   113820
gtagtgagaa tgaggtctac cctattaaat tgatcatcct ccatcaaatt ttaattgcta   113880
aattaaatat catgccatgc atatatctta ctcattgcat tcattagatt gcaacctcgc   113940
tgatggagag tacgtgctca tccctgagca aggagctgtc cacgaggaag accaggagca   114000
agctcccgag actgccatcg aggatctccc cgcagcccca tcatttggag gcaagccccg   114060
gttttatgca taaccaattt atatatgcta ctttactaca cttagtgttt gtaggcttgt   114120
aatgtgcact taagtgtagg agttgcttga aacccttagt tgcatgaact caggattcct   114180
ttttgagatg gatactagta tgctaggtcg agtagctgct ttactaatta ggatctcggt   114240
agaagtcgag tgatttttct agcaatcgcg cgaggtcagg aattgattgt attcatcttg   114300
ataatgggat ctatgatggt ctatggtctt ggatccaggg tggatgcctt gtccatgaga   114360
caggaaaatg aattaaggat taatgtgtgg atacctgagt caagcgtttg aacgtactaa   114420
acacatgtcg ggaaatatgg taaccggtaa acctagtacc tgattgaagc tgggcgcgga   114480
cttttctcct cactcgtcct gagactgggc tccctatgct agctttggtg ggtacaagtg   114540
cggtcactgc acggcggcag cccgggtcag tgagcattg tatgccaagg cggtgagccc   114600
tggccgcgaa aggggaatcg atggggacgg agtgccctga catgtcgtgt gtttaggttt   114660
accttgcaag gttaatactc gatttgaatc gtctgcttct cgcagctaat gagactgctt   114720
gaccccttgt actacattga gtaagaagtg aaatgaggat tacatgagat aacttgttga   114780
```

```
ttgtattaaa tgattgttac catgtatgct tagaaagagc aaacttagct acaataatga   114840
tactagaaat ggaaaagata aagttgacct tagatacaac tagtgctttt ggcaaaccaa   114900
acccctcaac caaacagcta catggtctag aggtagaaga gtagattcct cacaccgggt   114960
aagtctagct gagtattagt atacttagcc ttgcttgtgg cataatttt gcaggtacgc    115020 tctaggatat ggttgacggt gtaacttggc ctacaaccct gtcaccgggt tggacggtcg   115080
agtgggatgc tgctccggca ggagaggagc aggagaagta gtgggccagg ccttgcccta   115140
ttcctcgctt ttgacgacat cgattatccg ctgcagttta ttttgtgaac ttttctcagc   115200
tacttgaaaa actctgattt atgtaataac tccagtactt taatttgagg ttttcctgtt   115260
ttattgtatt tcttctgtga ctcaccttcg agtgagcttg tggtatttga tcctggataa   115320
gtggctttat tagactagat ctgagggact gatggcttat tccgatttaa gtgcattgcg   115380
gcctttaagg cgtgacttgg gcacttaaac tggaataatc cggcggttc tgccacatca    115440 accattccaa tctacatggt accatagcca ggtcctctac aacacatcca tcatggcgag   115500
tagattctca aattccacca ccatcccctc ctccttctcg atcccggtca ccgaaaaact   115560
caccaaaacc aactaccgcc tatggagtgc ccaaatccta ccgcccatcc aatctgcaca   115620
gctctacggt ctgctcatcg gcaaagaaaa gatgctggtt aagactgtct ctgtgatgac   115680
taacgacgcc tatatggaga cgcccaatcc cgagtacatc aactgggtga ctcacgatca   115740
agcgctgctg ggatatatcc tctcctctct gatgcgtgag gtcttgatgg gtgtcacgac   115800
agccacgacc tcggccgacg tctggagctc cctcgcggct atgtacggat cttgcacacg   115860
tgcgcgttct gtcaacacgc gcattgcgct cgccaccacg aagaaaggca cgaccacaat   115920
ggccggattc taatccaaga tgaagagtta tgccgatgag atgtcggcgt ccggccaacc   115980
tctgggcgat gaggagttcg tcgcctatgt cctcaccgac cttgatgaag aaatctacaa   116040
cccgcttgtg tcgtccatcg tcacttgcgt cgagccaatc tcctctgcca agttatactc   116100
gcagatgctc agctatgagc ttcggcttgc gaagcagtcc ggcggcaggt acgctgctca   116160
tggatcagcc aatacggcta ctcgtggccg tggtggctcc tggcatgatg gttctccaaa   116220
atcacggtcg cggacgctcg cgcggaaatg gccatggcta tccttcgtcg tcttcgcgcg   116280
gcaactacag caacaacaac tacttcaggc gcagttccgg tccaccgaca gatcaatccg   116340
gtggccagtc ttgtccacgc tgctaggtct accttaaagt cggtcacaga gctaatatct   116400
gttggtaccg cttttatgaa gaattcactc ctgatgatcg ggttgcggcc atggcatcat   116460
cctccactgc tgctgatcca aactggtacc ttgacttcgg tgtgactgat cacatcaccg   116520
acgagctgga aaagctaaca gcatgatcgt tacaatggca atgatcagat tcgggcggct   116580
aatggtgcag gtatggagat tactcacatt ggttattctg ttttgcccac ttccttccgc   116640
cctctgcacc taaatcatgt ccttcgtgtc cctcataccc ataaaaatct tgtttccatt   116700
catcgtttca atcttgataa taacacccttt attgagttcc atccgttctt tttcttgatt   116760
aaggatcagg ccacgaggca agtgctggtg cgcggaccat gtaggggtgg cctctaccca   116820
ttgacatctc ttgcacacct acccagaagc acgaccttgc cgcaataaag ccatcctatg   116880
agcgttggca ttgcagatta ggtcatccat cgcgtgtatat tgtcgctcgt gtcattagaa   116940
ataataattt agtgtgttca ggcttagatt cctcggagta tgtttgtgat gcctgccttc   117000
gtgctaaggc ccatcagttg ccttatccta agtcgaccag tcagtctgct gctcctttag   117060
atctggtgtt tttcgatgtc tggggacccg ccattgattc tttttgtaat aaaaggtatt   117120
```

```
atgtcagctt cattgatgat tatagtaaat ttacttggat ctatcttctt cgccataagt 117180
ctgaggtgtt tcagttcttc aaagaatttc aaagccttgt tgagcgcttg ctcaatagaa 117240
aaatcattgc tatgcaaacc gattggggtg gcgaatttga gcggcttatc tccttttttc 117300
ttatcactcg gcgtccctca tcgtgtctac tgccccatg ctctgcaaca atgaggact 117360
cctatcgtga attaatcgcg cttgtttata tgatcctttc tttatttctg aacatagtca 117420
taaactttat tctctttgga cgaccggtcc taccgctctt ggcaatattg ctcagcnnnn 117480
nnnnnnnnnn nnnnnnnnnn nnnnnnnnnn nnnnnnnnnn nnnnnnnnnn nnnnnnnnnn 117540
nnnnnnnnnn nnnnnnnnnn nnnnnnnnnn nnnnnngaaa tctagagtaa tcgttctcat 117600
cgcctaattt atgttttaaa aaattaggca tgtgagtttt aacaaatgca tgtgtcatcc 117660
tctctatatc ctccgtgata cttttaatcc gattatcaaa agaaatttta atagatggaa 117720
tatcatcggc tgacctggca tcacctattg tggggagctg ttgcagcacg ctaacatat 117780
actcggcgtt tatctccctc tcttggacgg tcttctggtg gcagtctacc ttgaagtgcg 117840
agaggtacca cttgtccgcc accttgagca cctgatcctt ttgtcggtgg gctcctcgt 117900
ctatttctt catgtcatct tctaattttt tatgctcagc ggccgataaa ttagtcagcc 117960
ttgtgttgct gtttggagaa gcactgttga gatctttaga atcggccatg taagcctgat 118020
tttgtagatc tgcaacttct tccccagcgg agtcgccaaa agtatgttg acgccttttt 118080
ggagcgccaa acactcaaca agaaccgtgg cggtgccctc tggtcaggcg cggacggtct 118140
gcagccttgg gccggacgat ccgcagcctt gggccggacg tccgcgacc tgggcgcagg 118200
agtggtgtct tccctgcgtc acaccggacg gtccgcagct ctgggccgga cggtccgcga 118260
cctggcgaca gggtcgtctt cctactcctt gctggaatct agatctcgtc cctgggggg 118320
aaagatctta aggtgctccg ggtcgacagg tcacccgggg cgtccccaga cgacgtgag 118380
tcgcctagga attaagagat caaatcgagg aagaagtctt ggatggacaa ctagatcttg 118440
ccccccggga ggggtgagat cctagggtcg tcttgggatc ggcaggccac ccaagacgga 118500
tctagacgac gtagagtcga ataggggtgg aggtggatat gtggaagact acaactagaa 118560
ctatgctaca tctactccta gggcaggaaa agtaaataag gtaattggtt cgattggaat 118620
gtgttcgggg gttctcaatc ggccgtaccc ctttatattt ataggggagg aggtctggac 118680
cttttcctaa gagatagcca acaaactccc acgtgattag atggataacc acgcacgaga 118740
taaggataaa catccgagtt aatctaatct cgggacacgc ggaccgtccg ggcccatggg 118800
ccggaccgtc cgctcatttt ggtgtccaac agctacgtag tcatgccatc acttcacccc 118860
acaatcccaa ctatcaaaat aactctaacc gaacttggca tttagccgat cgattcctaa 118920
ctcattttc ataccaccac tacacgacat accgaataca ttgaatgact cgttcacatt 118980
ccacatatat ctttacgaaa acatttccac atcgcttgca acttaaccta agcttcgcca 119040
cataatttca ggacatctac ttaaatcatg aatatcatca tcacacacat cgacccgttt 119100
tgaaataacc ctacatgtct atcacaggaa tggagcattt caacacatat cctaaaacaa 119160
actaacttca tcacacatct tgcattacaa agctacttga cttatttgaa gtgtctactc 119220
gaaatcgtga gcacaatcat acactatata cgaaacataa ttttaacgaa cgcataatac 119280
gcatcgtcat gacttgacct ataaatatag agaaagcgat gactactctg gcatgtcacc 119340
acctctctat ttaagtcaag acaatttcta ccatcgatta agagtcgtaa gcattaaata 119400
ccttactact ttatacgcac aaataaaactt caacttaaca caactgacac cgatggaatt 119460
tttactaaac tcatcgtacg cataaccctg tctcgcatac aaccatatta tggcgtgcac 119520
```

```
tcgagacact tcaatccatg tggcgcgacc actagtataa atggactccg acactcatgt   119580
cttaacgata catcctctac gcaaactagc attctctaaa ctactcgtca catcaataaa   119640
tatatcccct ctaaaattac gaatcccatc acattgctta aaacaaatac acttttcaca   119700
taaacacatc gatgcatttt ccaaaacaaa atccacattt tgtaacttag ttttcgcatc   119760
aaacaacgca tcgcatattt tcctatcaaa ataaaaatac tcgagttctt ttgtatttca   119820 tttcttccc tacacgcgtc catttataaa attatactt tacacacata taaccacatg   119880
cacatcatcg accaaaacat aattagacaa ctacaaatcg cgcacatcaa ttaacctctt   119940
gttctccaat cgcaaacatg atcctaccaa tgcgcataat cgaacatttt acacacatc    120000 atacaaaatg attaatcgag tcgatcgaga gcgacatgca tcggctcacc ataaacaaac   120060
ccaaacgatg tttgcaagaa tgacggtgat tccgattcgt gcatcgctcc aaacatccga   120120
cgagcgttaa gcgacttgct ttctcctcgc aaaacacggg gttctctcct ccacaaaaat   120180 aaacaaagc aacacacata cataattaat cataggaaaa taacatcgat gcggaatcga    120240
acaaggagcg tcgcggtctc accggggtga acgacgacga cgtttggggc tgcgcaaaaa   120300
cagcgaacac acggcggcat cacggcgtgc tgctcactgc gcaacaaaac agcaagccgt   120360
cagcgcgcgg agccgtcggg gctgctgcac atttcatcga gcacaagtgt ggatggcggc   120420
caggtgtttg tttcaggcgc tgaaacaatg gaggggggaga gggctacggc tggggaagtg   120480
gtggctcggc cacagcaaga acaggaagg ggaggctggt cgccgacctt gggcgcgggc    120540
agggaaaatg gagttgctgc ttggcgctat gtacaacaga gagagggagg aatggcgcca   120600
tgggaagctc gagctcggcc aggggaagga agaaaggggt tcggcatcca agctgttgga   120660
gcccaaggag agggtgctgg ccgccgtgcg caagtgaagt ttcacgccag ctgaagctcc   120720
ctggtcgcgg ataggaaaga gcaggggcg cctgctgcag gtaggagctc ggctcctgtg    120780
gaaaatggca ggggcagagg aggccggctg gagcaccggg cagggcgctc ggccatggag   120840
ccgctgcatg ggatttgctg ctgcgccctg ggagaaaaac agtaggggag tgaaggatgc   120900
catggctggg ggcgcgggga gcaggagcc tgctggtggc cttgctgctg tgaagcaggg    120960
aagaagaaag gcagaggacg ccacgggaag agcttcggcg cgctggaggg aaggaacgcc   121020
cggccatgga agcccctgcg cgctggggaa ggagctccag ctctacgtgc ttgaaggagc   121080
ccacggctgg aaaatggtag aggaggaaga gaagggtgtt ggcggctggg gtggaaatgg   121140
aaaattttca gaatgcaagg gagggaagcc catatttata gaggagaaat tagggtaggg   121200
tttcttatgg gccgaatggg ctggactgga tttggcccaa aacactaaat tgggtcgcgc   121260
taaatatttt ccggactaaa aatgttcctg cggaattcgt cgctactgag aaacagagcg   121320
aaaagagttc ggacgaacgg aaggttgcgc gattaactcg gccgagagtc tgtttagatt   121380
tcgcttgaaa ataattccct acgcgtaaat cgaaataaa tcgtcctgag atttgatcgg    121440
ttttggattt ttagtcggag aaagcgaatc gtgatatata aaaatcgttg ccgatgttga   121500
ttttgaaatc ggattggata cagagatgct aagctgagtc gagtaagatt tgattagagg   121560
acgacatatt gattatttcg tttgtgagta tggactcgga ttaaaatagt tggacatcga   121620
tcgaacatcg agaaattgga ttcggacaca gatcaaataa cagtcgtcga gagtttgatt   121680
taatgagctt cagatgaggt ttataattcg agaatgattt ttgagttcgc atttgtgccg   121740
acgataaaag ttttaacagg ctccaaaatt ggccttctgt gagactgagt aactccgaat   121800
tcggtgaaac gtgaatgaat aatctggata atcagggaca tacgcgagcg agaaatagaa   121860
```

```
attttttactg agcatccgag attaggataa atctcgcgac gtaacacgaa actgacacct   121920
ggggtgtcac agccttcccc ccttaaaaag aatctcgtcc cgagattcga atgaggatat   121980
ttatgggtgg agaagcatgt aactcccaga ctgaagatag atgcaaattc atgagagggt   122040
atctgacaag atactggaga cagatttggt tagaatatcg cgacatatcg agacaaaatg   122100
cagcgatcat tctgagagtg tccacaaaaa aatagcacat cagtatagtc tcgtaatgga   122160
tcacgactat taaccgcgat actagcgcgt gccgagcagc tcaaccatgt gtgcaccata   122220
gtaggctctc ggtttcgtcg cggcaccatc agtcgttagt catgacatca ttaccaaacg   122280
caaccaataa gaaattcaca tagcactgat agttggagcc catgagagta tggctcagaa   122340
aataagaatg tgatcagagt tgaagcagag attattggca aaagatcatc acatgagaat   122400
tttcttcaac tcatagagtt attttatgat catcacgggg attagcaggc cagcgattag   122460
tacgagattt gatatgagaa ggaagcactc cagagatcat gttgatgaac ttgtagagac   122520
atgagagaac cacaagatga caacaacatc ccttgaacca aatggataca ctgtttagag   122580
ataaagttga taaacatcgt catgatcctc agagaacgag tatgagaatg accagaattg   122640
agagacttag gtagatcaac attcgatact tgagaacggg ttatagtaga taacaagata   122700 ataggggcaga atcatgaaag atcagagatt cggatgataa ggtcacaaca tgattcacaa   122760
ggaaaaagat cactagatcc atgcgaaagg agaggtaggc aacaagatca gctggatgat   122820
caacaggaat gctatgaagt tttaggggca aggaatttat ggaaagaaac atggccttga   122880
tagggtttgc gcaactagac accaaacaac aaatttttt tgacgtaacc agtgcacaag   122940
gaagctttgg tcgatctagg agtcaagcta tgggaatcta caagctgtgc aggtgtaact   123000
tcaagggtaa aacccacaag ggctagaaaa cgccaacaca agcatttttt taaaagcggg   123060
ttcacttgct aaactcaagg ttgtttggag gagtcttttt atgaacagaa caagcaacaa   123120
aatgttttgc aaaaagggtt gaacaattac aatactacct agatagcaag acaagagaag   123180
cacataacat aacctagtaa agactatcat gacacacaag ataagacatt ttttttgcag   123240
ttcctagcaa tacagcacat tattcacaat tttttttatt atttgaataa aggtgagaga   123300
agcatgttgg tgcacaaaag acaattataa tgcgacaatc atgatgcatg ctcattctag   123360
tcgtcttctc agacctaact acttttttcgg ttgcttctac agcatcctta ttaatagtag   123420
tagtagcctt tatggcctat ataaatagcc acctagctac ccatctattt cctaaggctt   123480
cacgtcctaa gtctatcctt atcgtcctga catctatcca acattggttt ctagcaagtt   123540
ttacttttag aaaaggttgg taatcatgac ttattgactt ctctgtgatg gtattcgctc   123600
cgataccagc tgtggcggaa ccgcccgaat tattcaaact taagtgccca agtcccgcct   123660
tagaggctag accacactta aataggaata aaccgtcagt ccctcggatc tagtccgata   123720
aagccactta tccaggatcg aataccacta gctcactcga aggtgagaca cagagaaata   123780
caataaaaca taataccaca aatttaataa gtatcattag tgattacatt atcggagttt   123840
cagaaataat aaccataaat tttaatgcag cagaaataac taacggagaa gaaccgagta   123900
acatggcgaa gcctggccac tctactcctc ctggtcctct cttgcggaag cagtaaccca   123960
ctcgaccatc tatcccggtg gtagggatgg aggccaagtc acaccatcaa ccaatcatcc   124020
taatgaatat ctgcaaaaat tatgccacaa gcaaggctga gtatacatta ctcaactaga   124080
cttacccggt gtgaggagtc tacttctcta cctctagaca tgcagctgtt tggctgaggg   124140
gtttggtttg ccaaaagcac tagctgagtc taaaatcaag ttttagcttt tcaagtttta   124200
gtatgatcct ttttgactag atgtgtacct agctaatcat acatgatatc aagaattttt   124260
```

```
atcaaacaac atcttttgcc aatcacctca tttccactta ttactcaatg cagtacaatg   124320
gatcaagaag tctcattagc tgcgagaagc agacgattcg aatcaagttt ttaaaccttg   124380
caaggtaaac ctaaacacac gacatgtagg ggcactccgt ccccacacac atcaaccgtc   124440
cccatcgatt ccctggcaac agaaaggggc tcaccgcctt ggcgtacaat gcctcactga   124500
ccccgactgc cgtcgtgcag tgaccgcact tgtacccacc ataaccggaa tgggagacca   124560
cgtctcaggt cgcctgagga gggcaatctg cgggcaggtt cactcaggta ctaggcttac   124620
cgatttacca tatttctcgg catgtgttta gtacgttcaa acgcttgaca caggtatccg   124680
cacgttaatc cttattccaa tttcatctcg tagaccacgc gtccccatgg acccgtgtcc   124740
acagaccatc accattatgt tatcaaagtg gatacaacca attcctgacc tcgcgcgagt   124800
gctagaaaaa tcactcgact tctaccgaga tccctaatta gcaaagcagc tactcaacct   124860
agcatactag tatccatctc aaagggaatc ctgagttcat gcaactaggg tttcattcaa   124920
ctcctacact taagtgcatg gtacaagcct acaaacatta agtgcagtaa aatagcatat   124980
atataacagt tatgcataaa accggggctt gcctttaatt taacacttag gtagtgtttg   125040
ctgggggagg tactcgcttg gcgagcatcc actggttaag tccattcttt aggtcgtcca   125100
tcaacggcat cttgtggttg gcaccacatc actggctcga tcatcatctc tcggtcctat   125160
atgaggtgca agatgcatat gtatgaatat aataaaagta acataagata taccaagaca   125220
cagtggcgaa ctaaacatta attagtaaga cactgcaaca actatacgca aacactagtt   125280
atttatgtgt cattgggcac acgtaaacac taccactgga aagacaatga tcactaccta   125340
caattaacca acgcaacacg atatcatatg tacaagcatt tatttagttg ctacggcttt   125400
tcattagttc ttctattgat cacacaaaag catcacaaac acaagtttaa taaaggaccg   125460
atgcatcaat gtcgatggac tcctctatca caatcaacta tagcaagcaa gcacattaat   125520
catggaacac atgttaacct aagtttagcc atcacaagtc tatgtccgtt aagtgctaac   125580
taagcgtttt tagccaaaat ggtgaactaa atattcattt gagcacgtgc agattttttg   125640
gacagcagca cagcagttac ttgttttaat aataactttt caaatattaa tccaaaaata   125700
gcaaactaaa actttctgga aagtttagaa agtgctctac aattttggta ttttcatcac   125760
agcatgatta aacacttagc aaggtcaaaa agtgcaatca caacagctct gtccagattt   125820
ggacagattc agacttgtga ttttaaaaat tcataactga agattcagac atccaaacaa   125880
attgatccta gactttctgg aaagctaatt aaatgttcta caaattattt ataaacatcc   125940
caggctggtt tagcatgtat caaggttaaa atatactatg aaggctgtgc tgtccaaaac   126000
tggacagatt cagtcttcac acttcaaaca catgtaactt aatcttcaga ccaccaaaaa   126060
gagtgatcta agacttttg aaaatcttag caaaagtact acacaacttt cataatcacc   126120
aagaagtgat tccaggttta actaaatcaa atattacagt tttcgaaatc tgttctgacg   126180
gtggacagaa cacagcaacc agtttgtaaa attcataact cttaaaccgt caggcctata   126240
gttatgaaat tttaacacaa gcaagataag aaaagcctct acaactttc ttataatcta   126300 caagggctga ttctaacatt aacttaagca aacaatgcag cttctgaaat ctgtacagaa   126360
agtggacaga ttcagttact gaatttgtaa aaaacataac tcctaaacaa ttagacttat   126420
gcctgtcaaa ttttaacaca agtacgataa taaagttatc tacaactttc ttgtgaccac   126480
caataactaa tttcaacatt aacttaagca accattgcaa tttctgaaat atgttcagaa   126540
atttgacaga ttcaggtgct gggcttgtga aaagcacaac tcctaaacaa tcaggtttat   126600
```

```
ggctgtcaaa ttttagtaca agcaagataa tcatgtcatc tacaactctt ctatatgact    126660
tttctacaga aaacatgatt tggtttatca aacaaacagc acaactaaaa cagtgcgtgc    126720
agcccaaaac agcaatcaat aaattcagct tctgtttact tttaaaaatt gccgcgttct    126780
agagactcga cttattctaa attatatcaa ggcacactta agcatagcca cacaatagat    126840
gatgtgacgg ctactgttga cgcctttttg gagcgccaaa cactcaacaa gaaccgtggc    126900
ggtgccctct ggtcaggcgc ggacggtccg cagccttggg ccggacggtc cgcagccttg    126960
ggtcggacgg tccgcgacct gggcgcagga gcggtgtctt ccctgcgtca caccggacgg    127020
tccgcagctc tgggccggac ggtccgcgac ctggcgacag ggtcgtcttc ctactccttg    127080
ctggaatcta gatctcgtcc cctgggggga aagatcttaa ggtgctccgg gtcgacaggt    127140 cacccgggc gtccccagac gacgtggagt cgcctaggaa ttaagagatc aaatcgagga    127200
agaagtcttg gatggacaac tagatcttgc ccccgggag gggtgagatc ctagggtcgt    127260
cttgggatcg gcaggccacc caagacggat ctagacgacg tagagtcgaa taggggtgga    127320
ggtggatatg tggaagacta caactagaac tatgctacat ctactcctag ggcaggaaaa    127380
gtaaataagg taattggttc gattgacaag ttttcggggt ttctctcact gccgacccttt   127440 tttatcataa ctgagcacca ggtctgaaac tcaaacctct ccgaaaggga agcgtatcac    127500
ctgatccgag ctggataagc tccgactatc gacggatgac atagcatcac aactgatctc    127560
gggacagcag gtgctgccgg ttccctggac caagcaagcc catatcattt gatgtccacc    127620
agatgccccc tgccgcaagc gcgcaaaaag ctgcacccgg gagcctgaat tacactccga    127680
aaagcgtgag cccgtgattg ccttttcatg tcaaaggatc gatacggatc gatgggagat    127740
cacgcccgat gggcctggat tgcttctgtt accttggcga gcgtttggtg cagaggccat    127800
cctctggaac ggattccact gcaccatggc tgatggaata tcctgcgtca tgcagaccat    127860
tgatggaggt gggtccccag cccagatagt gaagcgcgaa ctcgcatggt gtccacatgg    127920
attgaccgca ccgtcccgca gcttgaaata gaagcccggt cccgaaggag acatgtcggg    127980
gagctcggcg gctgtcccta ctggacggct gctagctgca aaatggggg ttggccgctc    128040 ctacgggacg ttccgcacgc gtctctcgtg cgaccggacg caatggccat cggatagtgt    128100
tgctctggac tggttcatga ttagcacccn nnnnnnnnn nnnnnnnnnn nnnnnnnnnn    128160
nnnnnnnnnn nnnnnnnnnn nnnnnnnnnn nnnnnnnnnn nnnnnnnnnn nnnnnnnnnn    128220
nnnnnnnnng aattctttat tcctaagtta atttgatcct catgcttact tggttcaca    128280 taaaataatg gttcttggtt tggcattttt aagagaaacc gtaggtgaca ctagggtgtc    128340
acagccttcc cccttaaag gaatctcgtc ccgagattcg ggccagagtc ctcccagggt    128400
gaagcgaagg gtgagactta taggaaaagg gtggggattg ttatgcttca aatcatggta    128460
catcttggtg cttcccggat gcatagagaa tttggagaga tgagcctcat ccaaaatttt    128520
cttcttgaga tcctggtcct taggaattac caatctgctt ttgaaccata acacacccttt   128580 ctcatcctgg cggaaacaat tatacttctc aaccttctga tggagattct tcttgataat    128640
ttgcactccc ttgtcactga gctgggccat gataatctgg tcttgcaagg ctggctcaac    128700
agcaatgtga gacaaagaac cagaaggaat cacttcaatt tgcatcttgc tcaactcatc    128760
acacaaggtg ttaacacgag aatccatcag aatacagttg cactgcaact tccgactcaa    128820
ggcatctgct accacattag ctttccctgg gtgataatgt acctccaggt cataatcctt    128880
gatcagctct agccatcttc tctgcctcat gttgagatca gcctgagtaa aaatgtactt    128940
aaggctctta tgatcagtga agatgttgca gtgggttccc attagatagt gcctccacat    129000
```

```
cttcaatgca tgaaccactg ctgctaactc aaggtcatga gtaggataat tttgctcatg 129060
aggcctgagt gctcttgagg cataagcaat gactcggttg tcttgcatca agacacaacc 129120
tagcccggtg ccagaggcat cacaatatac atcaaaaggc ttgctgctgt cgggttgcgc 129180
caatactggt gctgtggtca gatgctgcct taatgcatgg aaggcatctt cgcacttctg 129240
actccacaca aatttgactt ctttcttcag caactcagta ataggcttcg caattcgaga 129300
gaagtccgga ataaatcttc ggtaataacc agccaatccc agaaaactcc gaatctggcg 129360
aacagtcgtt ggtggcctcc agttcatcac ctcttgcact ttatcaggat caacagctat 129420
tccagcctga gagatagtgt gacccaagaa tttgatttcc tttagccaaa atcacattt  129480 ggataacttg gcataaaggt ggtgatctcg cagacgttga agtactacat gcaaatgccc 129540
ggcatgttct tcttcgttcc ttgagtacac cagaatatca tcgatgaaaa ccaccacgaa 129600
cttgtccaat tctggcatga aaacagaatt catcagatac atgaaatatg ctggtgcatt 129660
cgtcagcccg aatgacatca ccaagaattc atatagccca tatctggttg agaatgccgt 129720
cttcggaata tcacttgctc gtattttgat ctgatggtag ccagagcgaa ggtctatctt 129780
ggaaaacacc ttggccccga ccaactggtc aaagagaaca tcaatacgag gcaaaggata 129840
cttgttcttg atagttaccg cattaagagg gcggtaatct atacacaacc tcaagctttc 129900
atccttcttc ttcacaaaca gtgctggaca gccccaaggc gaagtgcttg ggcgaataaa 129960
tcccttatcc agcaactctt gcaactgctt cttcaactct gccaactcag cgggtggcat 130020
tcggtagggc ctcttggaaa ttggggccgt tcccggttgc aactcgatgg cgaactcaat 130080
atcccggtcc agtggcattc ttggcaattc atcaggaaag acatctgcat actcacagac 130140
cactgggatc ttcttcaggg gtaattccgt catagagaaa gcacatgact gagaagaacc 130200
ctgactaggc agaatcaaag tgaaattccc gcagaaggga gaattaactt ccacggtacg 130260
actggctacg tcgagcacaa cttggtgcaa ggtcatccaa tttgctccta gaataatgtc 130320
cacattttcc aatcccaaca caagaagagt ggttttgata atgtggcttc ccagttgaat 130380
aggcacactt tggtttaatt gattagttgc aattttaccc ccaggtgtga ctatcatgaa 130440 tgacccttt gagtgagaga atggaagttt gcaattagca ctgaacttt ggctaatgaa 130500 actatgagat gcaccagaat caaacagaat taaagcaggt tgattataaa ctgaaaaggt 130560
accggtcatg atgggagctc cttctggcac ttcctctaga gcagtgaagt tgagcttccc 130620
ttgcctgact tgtaccttct gctttcttcc cttgtcttga tttggtgctg gcatctgcct 130680
ctgctggttc ctgggacaat tcttggcata gtggcccaca ttgccacaag tgaaacactt 130740
gttcccattg ccctggcgga actgctgctg ctgcggaggc tgattgtttc ttggggcggg 130800
agctggatag cggttgggtg ccggctgctg ctgctgctga ggtggcctga tcacccatct 130860
gcctgcctgc tgctgaaaac ccctgctctg attgtgagaa acaatccgga acctctgagc 130920
ctgagcggat ggtgctgcca ttggtgcctt tctcttcttc tctgcccggt gagcaacaat 130980
gcaatcctcc tgagagatgg ccatgttgac caactcattg aagctatcgg cccggacagt 131040
gttgagtcgt tcccgcagct tggtattgag acccctgcgg aagcgatccc tcttcttttc 131100
atcagaatca gcatgatacc ctgcatactg gcataagtcg ttgaaggctt gcgcatactg 131160
cagtaccgtg cgggttcctt gattgagggc caggaattcg ttcaacttcc gatcaagaat 131220
gccagctgga atgtggtgcc ctctgaaggc agtcttgaat tcctcccaag atacttcacg 131280
atcaccgggg agcatagcac ggaagtgatc ccaccaagtc cgagcagggc cgcgaagctg 131340
```

```
ctgtgcggcg aagcgagcct tggcctcatc agggcagtct cctgtgagga ggggaaactt 131400
ggactcgacg acgcgaagcc acacgtcggc gtccaatgga tcctctgcct tggtgaacaa 131460
gggcggctgc gtgctcagaa actcctggta tgttgccata gccggaggtc gctgatgctg 131520
gcctccacca ggatgctgag ggtggggctg gcgctgcaag agctgtcgca gaatctcatt 131580
ctgctgggcc atcagctcct gcactgtggg agctggagga ggtggcgggg gagcttgctc 131640
attttgcccg cgacgctgcc tcgctgccat ctgaaaacag agattgtcgc cattgttatc 131700
ccaattcaca tttccgaacg acaagatatc atctcatatg aaggaaaat gccataatca 131760
taatattagg ttcgaatgaa gataacatgg tgacaaggat cccacagata tcaaaagttt 131820
acagggttac attaatcagg ggaaggtacc cacaagccta gtccaaaatg tgataccact 131880
aagctcgcat aggtttctat ccgcctaaaa atgtcaaagc gactgcttaa ccctgagcgg 131940
tggaagcgac actggatacg ggtgaaggag gtatcgcgga ggtagtccca ttggcaccag 132000
gggctggtcc tagctcctcg ggagcctctt ctccctcgct tcctgcttca ttggcctcca 132060
tctccaggtg gtgcatgtcc aagtggtcat ttgcttcctc gagttccctc tgcacgtcgt 132120
gaagctggtt ctccaagaca tcaatagtgt tatctcggat ctccacttgc tgctccaggg 132180
tggtaatacg ctggttcagc ctctccacct gcagatcctt ttccaccaac tctgtggata 132240
ggtcgaccac aaaatcttcc cgactgtcga gggtgagctt ggctgcctga gcggtattgg 132300
caagaagtgt catagcatcg ctctgaaggg cctgaaggcg gtacagcgca ctcatgcact 132360
gaacagtgac cctcccaacc aagtcaggat acattgccca cacatccttc acatggctca 132420
cgcggttaca ccacatggga tcatccttct tctcagcggg gaagagtccc aaggggtgca 132480
tcaccatctc caggggatgg tagccacaaa aagtcgtcag agtcttcatg gctgctgcct 132540
caacggtgtc gtccgtcctg agtccaatcg tctcagagtc aagagaacgc caacccggct 132600
gaagggatg agcctccaaa gttagccaga cccgacaacg aggtacccga tgctcctcat 132660
acaactgcac cgtgtacaaa gggggcgtag ggtaaccggc ggaattaagc acttcccaca 132720
aaatggaagg gaagccatcg cgagaaagga agtcagaact gaaacgagag tctcctccac 132780
tggcgggggt gggtgaattc atctgcggaa gggaatcaaa gataaagatt atggtggaag 132840
gaaaaagaaa aagagagccc ggatgatttc gaagaaaagg gggttagctc aattttaatt 132900
cctctttatg ttttataatg catgcatgcg gaaagaaacg ttgcctctca aaaggaaaat 132960
agggtgcctt tttagggcat cctaaaatat aagtattggc ccacagggcc taattagtta 133020
gccacctatt tctccctcta tgcctaaggc ctttcgtcct aggtctagcg gtctagtcct 133080
gacgatccgt agtagcttct aggcaggttt tagattttga aaattggtat tcatggttta 133140
ttgcccttct ctgtggtgga atttgctctg ataccagctg tggcagaacc gcccgaatta 133200
ttccagctta agtgcctaag tcacgcctca ggggccgtaa cacacttaaa tcggaataac 133260
ccgtcagtcc ctcagatcta gtctgatgaa gccacttaac caggatcaaa tcccacaatc 133320
tcactcgaag gtgagtcaca gaagaaatac aataaaacag gaaacctcaa attaagtact 133380
gagttattac ataaatcgga gttttgagt agcgaataaa gttcataaat taaagtgcag 133440
cggataatcg atgtcgtcgg taatgaggaa atgggcaagg cctagcccac tactcctcat 133500
gctcctctcc tgccggagca acatcccact cgaccgtcca accggtggc agggtggtag 133560
gccaagtcac accatcaact acatcctgca tggtacctgc aaaaatggtg ccacaagcaa 133620
ggctgagtat actaatactc agctagactt aaccggtgtg aggagtctac tcctctacct 133680
ctagactatg cagctgtttg gctgaggggt ttggtttgcc aaaagcacta gctgtttcta 133740
```

```
aaatcaactt ttagcttttc aaattctacc atcattaact tagctagatt tgctccttct    133800
aagcatacat ggtaacaatc aattagttca gtcaacaagt tatctcatat aatccacatt    133860
tcacttctta ctcgatgcag tacaaggaat caagcagtct cattagctgc gagaagcaga    133920
cgattcgaat cgagttttta aaccttgcaa ggtaaaccta aacacacggc atgtcagggt    133980
actccgaccc cacacatgac aaccgtcccc atcgattccc cgttcgcgtc caggcctcac    134040
cgccttggca tacaatgctc cactgacccc gactgccgtc atgcagtggc cgcacttgta    134100
cccaccatag ctagcatggg agaccctgtc tcaggtcgca tgagggataa agtccgcgcc    134160
cggcttcact caggtactag gtttaccggt taccatttttt cccggcatgt gcttagtacg    134220
ttcaaaagct tgactcaggt atccacacat taatccttaa ttcattttttc ccgtctcatg    134280
gacatggcat cctccctgga cccaagtcca cggactaaca tatacccccat tatcaagatg    134340
aatacaatca attcctgacc tcgcgcgagt gctagaaaaa tcactcgact tctaccgaga    134400
tcctgattag caagcagcta ctcgacctag catactagta ttcatctcaa aaaggaatcc    134460
taagttcatg caactagagg tttcaagcaa ctcctacact taagtgcaca ttgcaatcct    134520
acaagcatta agtgtagtaa agtagcatat aataacatgg ttatgcataa aaccggggct    134580
tgccttcaat tgctggggct gcggggagat cctcaatagc agcctctgaa gcctgctcct    134640
ggtcctcctc ttggataggt ccttgctcag ggatgagcac gtactctccg tcggcaagat    134700
tacaatctaa tgaatgcaat gcgtaagata tatgcatgat atgatatgtg ctttagaatt    134760
tataacttta aagatgtatg atcttttgat ttaaaaccag ttaactttac ttatgtaaaa    134820
cccctttagtg gtatacttgg taaattgggt tagtcttatt gggatgaggt ttatttcttc    134880
ttctctttttc ttttattctc tttaatgttt tggagtaggt ttgaactaca agttgctttt    134940
ataaaattcc aaaaattctg caaaaattac agtggcttgt tactggtgta tggttctctg    135000
tctcaaaatt tggggttcag aaagtgaatg gttttctctg gacaaaatta ccaaatttta    135060
gggcagaagg ggtactttga actacaacta ttatttaata gtgggtaatt ctcaaaaact    135120
tatttttgct ggcttttagg tgttataaca tgacttgata caaatttcta gtcattaata    135180
cccctttaatt ctttccctaa gattttctta aggtttctag ccaaaggggt gctttctact    135240
accactatac ttgaaaaaca tcaaacaaca gagttcttat ttttcttagc tagtattttg    135300
tgcaagagca atcattctgg agtttggctt ccttttgcct aagggaaggg gtggtttgca    135360
ttatttgagc taaatggcct tcctcacaaa ttactagcaa aaggcatggg ttcacttctt    135420
tttcatgggt ttgtattttt ctctggtggt ttatctcatc atggacttag caaaattttg    135480
gttgcccatt atcacattat ttggggttgc tcatgattta gtgggaaaat gccttattat    135540
cattctgtat ttatttttccc tacttaaaaa gttaggctgg ggtgctctgt attttttgtag    135600
tggggctctg gtggttataa gttcactgga ttttttgttaa ccactttggt tatagttttg    135660
caattctaat aattgatttt cagtctacat aatgctaatt aaagcatctt aattagaaac    135720
tggtccaaat taatggtctc tgcattttttc ctaggttctc tgctgcataa gtaatctagg    135780
aaaaatatta ctaatcactg ttcattaatc tctaaggcct ttctgatttt ctctaagttt    135840
tggacaaaat ggctttaaat gaataactac atcataatct ctaatgctag ggctcctact    135900
atttttaaac agtgtctaat taaggtataa gcatctacaa attttcttaa gctcagcaca    135960
aaagaaaaac taattttcct taattaaaca aggtttaggg ggtttctgtt tttaatttta    136020
aactctaaaa tttagaacag aaagcatatg gttcactatt tttaaatgat aggtcataaa    136080
```

```
attccagagc tagcaaaatt ggtttgacag cttttcatta agatttcatc aagttatgga   136140
ttttctaagt tctctggtca ttttaaaaag aaataacaaa attgattaaa tggaaatcca   136200
ctttgcactg gggtccctgg cggttttcta agttttcctc gcaattcagt ccttaggtta   136260
ctattctcat gagtcgctga cattacgaaa aaccccctcgg gttctacaga acctaacccg   136320
aggtccttct tctaccttaa acagtagccg cggcgaagaa aagggcggag gggcttaccg   136380
gcggcgagac tgttccggtg aagtggccga gggtgaaggg gaggtcgcgg ggatcacaac   136440
ggtgtgcgga acaccgtcgg agatggccgg agtcggtcgg tccacgcgcg caggcgggga   136500
tgctcgtcgg cggcgaggag accggcctgg tcgcggcgag atagttcaat caaataggtc   136560
atggaggtcc acgggatgcc agagaagaca tgagcgaaag gaatcgggcg ggagactcac   136620
tggatagctt ggtccacgcg cggcggcgga agaccgaagt ccggtgaggt tgattcttcg   136680
ggcctcccgg tgaagttccg gtcgggtccg agggcttggc aagcttcacg ggctactggc   136740
ggagctagcc gagcactggt tgggctggag ggtggctgga gtgggctggc cacggcggcc   136800
gtagttctgg cggcaatggc gggcggaaat gagctcgccg gagctaagga acagtggctg   136860
gccggtgagg gtgagtgcgg ggcgaagaga ggtgcgcccg gggaggcttt ataggcgcgg   136920
gcgggcacgg ccgagggcgt gggcgcgcgg cggacttgac cggacgccgg ggcgagcgcg   136980
cgcgcgggtt gggcgagctc tggcgtgccg accagggtcg aacacgtgtg cccgtgcgtt   137040
ctgcccaagc tctggcgcgt gtggtcgctc atccgagcct gctctcgcct tggtcagtgc   137100
acaaaacctc ttctcctccc tacaagctac cattcttgtg tggaggtcat aggattttgc   137160
ctactggttg cagagatatg gagccaggaa atctggtctg tctccctgcc caaacccgag   137220
gcaaatccca gttttgtcg tgtctagggc tcgcgtccca atgccatctt ctggcacaag   137280
acagaggggt tagttagaca caattttgtc aatgggggcca ttaggattcg agttagggat   137340
caaggtgaac atccctgatc tttggctcaa ggtctgaatt tcagaattct gaaattcaga   137400
attcccaatg agtcccaaca aaagaagctt gatttggggg tttcttgaa ttattttggc   137460
taagctttct caatctatct tgttgcttat caaatatact ttaacttata taattggctc   137520
aactcaaaat tttaaacttt tcattcccct ttgcttattt tcttgaattt tgttcatggg   137580
gttcacttag ggttcttaat tagggttgca cattcttatc ctttaagaga ctcaattgtc   137640
ttgatcatga cacttttaag catatacttg gtgaattctt tcttacttaa gttattttga   137700
tgctcatgct tactttggtt cacataaaat aatggtcctt ggtttggctt tttaagagaa   137760
accctaggtg acactggggt gtcacaggag gcacatacaa ggatgctgag cctcgacatg   137820
cgggcctagg agcataatgg aagaaataga ttatgtaaat aactaatgct gacagagtaa   137880
cgcatgacca aacttggagg cctgaccgt atatacaggg gtctggcatg ggttcggcac   137940
tctcctatgg gggtccggac tcactattga tgccttggag tacatcactt tctctggaca   138000
catggcggcc ccggacccgc ccatgtggtg gggtcaggtg ctgttgctgg cctagagtag   138060
tcgcccgagg ctagggcgag tcatggtttg gtcccacata cagctctttt accacgcgac   138120
taaagatagt cgcgtgggta ctgcgtattt atacagtagt aaggggtacc cttgtttcag   138180
ggtgccgaaa gtggccccg gacccacctt aggggaggat gcgagcctgc atgtgggcc   138240
aaagcttgta ctttgcttca acgtgacctg atcggtgatt ggcatgccgt tttagcgcgt   138300
ctgcagacac gcccgctgtc aatccgcctt cagtcacgtc aactgccata tctgtctctg   138360
cagctgacta acccatggcc ccatgcctgg tggtttcgtc gggccacgcg tgggacgcct   138420
cgttgccgct gcataacctt ttgtcttctg cagcggcccc gaggaggtgc gctatcgtgc   138480
```

```
gcggcagttc gcatggcgat tcgctctttc cgcactcgaa atccagcaca caatctgtat  138540
gacttgtgga cccgggccac cgtgtcatag agtgggctgc ctgggtccta tgtgcgcatc  138600
gggcgagatt tcctgtggca attcaagggc gcacggaagg gtttccctga caaggactc   138660 aggtttcctt gaaaaaggat tcaccccgcg tgcagcagtt accttttcgc attctctccc  138720
aatcgcctgc accccttgtc cttcgtgctc ctctgttcca cgctcgcgcc gccgcacacg  138780
ccatggcctc gcttggtcat cctgactgct ttcagtctaa ggaggcgctc aacctggtgc  138840
gcggcctgct tggatggagc gcgccagggc tcgccggaag ttccgcgccg gcgccgtccc  138900
tcatggcgat ctcaccgccg gggagttcgt gctgttcacc tcctacatct tctacgggtt  138960
ggcgttgccg attctcgccc ttcttcttgc tgctgctgga ggagtttggg cttcagcttc  139020
aacacctcac accccactcc gtcctccagg cagccatctt cgtccacctc tgtgagatgt  139080
tcgtaggtgt ggcccctgt  acttccctct tccgctgctt cttcgtgctg gtcaagttcg  139140
ggaagactag ggaccacatc ggtgcctact acttccagac gaggccagat ccagccgtcg  139200
tatacatccc cacctttggc ggtgcgaggt gggaaaactg gcgcaacgat tgggtgattg  139260
ccagcgccga ggccaacgac cgcctcgtcc tgccgagcga tgggccagcg ctcgaccgca  139320
agcagtggag gactaagccg tccctcttgc tagagttcct gcctgtattg gacagaatca  139380
agggcttggc tacgggcggc ctgccatcaa tgcacgtggt cggcgatctc ctgaagcacc  139440
ggatcgcgcc gctgcagagg agaccgcgta tgtgctgttg gttcaccggc ccaaacgaca  139500
tcgataggat ccaacgcagg ccgggcaccg ttctgtcctg ggacgagcta gcagtcctga  139560
tgggagggat tattggggaa acttttgtcc ctgagtccct gatactcccc cagaacatcc  139620
ctgcgctctg cgacgatcca ggcctgagga tggtgatctt ggccacgttg ccgaccctcg  139680
acgagagcgg catggcggtt cgctagaccg gtggccggga cccctccgt gggatccaga  139740 tttctaatgc accgattgga ggttcccagc ccactggtgc ggctcccagc accaaccccg  139800
ccgtggcccc tagccccttg acaaaggca aggggctgc gagcagtgcc tccgcccag    139860 gtagctccga gggggtcgga ggaggagagg caacgcaggc catgtcgcgc tgatgggtcg  139920
ctcatttcgg agccccccc agaagcgtca gagggctgca ggtggggccg aggaagctag   139980
ctcccaggcc cacggcgcgc agaggcgcgt cagtcctcac ccccaggggc accagcagca  140040
gcaacagcaa cagcaacagc gatagcaaca gcaggagcgg tgatcgcccc gcttccaggg  140100
tcactagaaa gtctagggcc ccaagtaagc gtagccccctt ttccatgagt ctaatcatca  140160
tgccgaccag ttttaaccca tcatctgttc gctagggctt cttccttcgc cgctcccaag  140220
gtcatgcctc ctccaccaga taccaggccc accgacgggt ctggctctca acagcaggaa  140280
cctgctgaga gtggtgccgg cggcccaccc ccagctgctg ccaagacagc accagcggct  140340
tctcatgccc cagccggggg tccggtggca gcgtcaggcg gcgtcgcagt ggcgaaggag  140400
gtcccagctg ggggatccgc gcccgctctc gacactgggg gtgacgcagt aggcatgtcc  140460
agctccaacc ccccgcctgc tccggaggag atggaggtgg tgtttgggcg gcgactccgg  140520
tcgggtgccg agcaagaagc ggcgccagtc cccctccctc gcataatgtc tcgtgcccac  140580 taggtccttta gtgacactgg ggcagcaatc ttgcgggagt gggaggcgct tgaggctgag  140640
caccagcgcc taagtgactg gcgcacccaa ctggaggagc gcaccagaac ggcgtcccaa  140700
caattcatct ccgagcggtc ccaactcgag caggaccata aggagtacaa gagggaccctc 140760 cagagggtgt gcgccaggga gctggaggcg tcccggaggg agaagaaggt gaccaggaag  140820
```

```
gaggaggtcg tgacccagcg ggagaccctc acaacagagt accaggccaa gctgagtgcc   140880
ctggaccaga ctctggaagc ccagcgggcc cagcaggtca gggtcgtgga gaggctgcaa   140940
aagtggtagc aggagctcga gggcaaggct agcaatgcca ccctcgccga ggaaaatctt   141000
aaggcgaagg agcagtcctt ggaccggtgg gagacggacc tcgccaggca agagacggat   141060
ctcagcttca gggaagaaat gctcacccgg cgaggcgagt tgctggccaa gcacaagctc   141120
gaggcagagg agaaagagag gaagctggag gagcagatcc gctagttcaa tgcagcgcag   141180
gcggcaccgg gtccccaagc gatggaggcc accaggaagg cccttgaaga tctccaagcg   141240
gagcaccgcg tcgaggtcca gtgtattgtc gcgtgggccg gcgaggcaag cacggcacta   141300
gtgccactag ggatgagccc catcccaatg tcggagctac cagcgtcgat ctctgatgcg   141360
ctcccggtgc tggactctac cgccgatcgc ctccgtcgcc tggatcagat cctcggggcc   141420
cgcctagagg cagagggcag caagctctgt cgggcagtgg ttgaataagt cctaacatgc   141480
ttccggagtc acgaccccac catatccttg gcgctagtga tcgctggtcc ggtagccgcc   141540
atagaagacg ccgcctggga gagtgtacaa gacgccgtgg agctggtggc cgagcgcttc   141600
cagcacgatc ctgctgacga cctatagaga caaagcaagg gttccactgg gaagcggttg   141660
taataacttt tgattttgta agatattata agaaccgcta atgaggtagc attggaactt   141720
aaacttattt gtatgttatt tgtccttgtt atgtgtagtg tcatcaactt ccccttggta   141780
cttggccccc tgggaggtag gctcgacgtg tcgaggctgg ataccagtat accaaagata   141840
aaattggtgg tccggcccct aggaggtagt ctctacagtt tgagactacc tactactgga   141900
ctgggacctg gacttgtaca cagcttcggc tttaaagtgt taggagcaca ccataggatc   141960
catcgtctgg tatctgccat cctttgattt atgcaacagg acctgcagga tttagcctgg   142020
gaagccaagc cgtatgcctg gacccatagg atcacagttc caaatactag ggcacccgtt   142080
atagagtggt ggagcatgca ggcttagggt acggaaccat gctaagcggc tacacaactc   142140
cggacccctc caggaggcta gcgcccattc tctagaactg gtccgcagtt tgccggaccc   142200
cctgtagcag taaaggggtc ttgaactgca agcctgtcta ctcaattcgg atgtcatcat   142260
accaacaagg gtgggaaact atatgggtgg gttagataaa aaataatgca tgtaaaccga   142320
agtagaataa aaccatcaca aaatcacatc tagggggtaa atccttttcct tataactcga   142380 tatacatggg tgtagaccaa cagatgggct tacgagggcg ggcctcaccg aattgacata   142440
cacatatgcg taacctagtt acaaaggaag aaaactcaac cccccagttt tgctattatg   142500
gatagaactt acagagatgc tctatattcc agggattggg aagaggcact ccttctgttg   142560
tggcaaggcg gacacaccat ggtcggcata tttctgtcac cttgaagggt ccttcccaac   142620
tgggggagag tttgtggagc ccttctcggt tcagtactcg ccttaggact aggtccccga   142680
ccctgagctc cctactatgc acaaaccgtt ggtggtagcg cctgagcgct tggttgtacc   142740
gtgcatttcg gatcaccgct tgccatctgc gttcgtcgat gaagtccatg tcctcacgtc   142800
gtagctattc ctgcatagac tcatcgaaag actggactca tggggagccc ataatgattt   142860
ccgggagaag gcaggcttcg gccccgtaga ccaagaagaa cggggtctcc ccggtagctc   142920
ggctgggtgt ggtccggttc ccccatagta cggacggaag ctcattggcc caattggcac   142980
catgcttttt taagcagtcg taggtgtgtg ccttgagtcc cctaaggatt tctgtgtttg   143040
ccctctcagc ctggtcgttg ctcctgggat gagacacaga tgtaaagcag agctgggtgc   143100
caatgccctc gcaatactct tggaagagtc gacttttgaa ctgggtccca ttgtccgtaa   143160
tgatatggct tgggacccca aatctgcata caatcgaatt gaggaaggca acagcagcac   143220
```

```
cttgggtgat actgaccata ggggtggcct ccgaccactt tatgaatttg tagatggcga   143280
caaagagaaa acggtacccg ccgacagccc taggaaatgg tcccaggata tccaccccc    143340 atacggcgaa tggccaagag ggtggaatca tttgcagagc ctgagctggt gtgtgtgtgt   143400
gtctgctttg catgaaactg acatgcttcg caggacttca ccaactcggc tccctcctag   143460
agagcagttg gccagtagaa gccatgccag aagaacgaat caagctgatt ctcagagttg   143520
aaaannnnnn nnnnnnnnnn nnnnnnnnnn nnnnnnnnnn nnnnnnnnnn nnnnnnnnnn   143580
nnnnnnnnnn nnnnnnnnnn nnnnnnnnnn nnnnnnnnnn nnnnaattct tagaaaattc   143640
gtcctcaaac ccaagagaca ttaaagggat tcttgagacg ggctcaaaat gagttcggct   143700
taagggtcaa gaaataaga agcgacaacg gaacggagtt caagaactct caaattgaaa   143760
gctttcttga ggaagaggga atcaagcatg agttctcttc tccctacacc cctcaacaaa   143820
atggtgtagt ggagaggaag aatcgaactc tattggacat ggcaaggacc atgctcgatg   143880
agtacaaaac ttcggatcgg ttttgggccg aggcggtcaa caccgcctgc tacgccatca   143940
accgattgta tctacaccga atcctcaaga agacatcata tgaactccta accggtaaaa   144000
agcccaacat ttcatacttt agagtttttg gtagcaaatg cttttattct gttaaaagag   144060
gtagaaaatc taaatttgct cctaaaactg tagaaggttt tttacttggt tatgactcaa   144120
acacaagggc atatagggtc tttaacaagt ccactggact agttgaagtc tcatgtgacg   144180
ttgtgtttga tgaaactaac ggctctcaag tagagcaagt tgatcttgat gagataggtg   144240
atgaagaggc tccatgcatc gcattaagga acatgtccat tggggatgtg tgtcctaagg   144300
aatccgaaga gcctccaaat gcacaagatc aaccatcctc ctccatgcaa gcatctccac   144360
caactcaaga tgaggaagaa gctcaagtcg atgaagaaga agatcaatca aatgagccac   144420
ctcaagatga tggcaatgat caaggggag atgcaaataa tcaagaaaag gaggatgagc    144480
aagaaccaag ggcgccacac ccaagagtcc accaagcaat acaacgagat cacccgtcg     144540 acaccatcct cggcgacatt cataaggggg taacaactag atctcgtatt gcacatttt    144600 gtgaacatta ctcgtttgtt tcctctattg agccacacag ggtagaggaa gcactacaag   144660
attcggattg ggtggtggca atgcaagagg agctcaacaa cttcacaagg aatgaggtat   144720
ggcatttggt tccacgtcct aaccaaaatg ttgtaggaac caaatgggtc ttccgcaaca   144780
agcaagatga gcatggtgtg gtgacaagga acaaagctcg acttgtggcc aagggatact   144840
cccaagtcga aggtttggat ttcggtgaaa cctatgcacc cgtagctagg cttgagtcaa   144900
ttcgcatttt attggcatat gctacttacc atggctttaa gctttatcaa atggacgtga   144960
aaagtgcctt cctcaatgga ccaatcaagg aagaggtcta tgttgagcaa cctcccggct   145020
ttgaagacag tgagtaccct aaccatgtct ataggctctc taaggcgctt tatgggctca   145080
agcaagcccc aagagcatgg tatgaatgcc taagagattt cctatttct aatagcttca    145140 aagtcggcaa ggccgatcct acactcttta ctaaaactct tgaaaatgac ttgtttgtat   145200
gccaaattta tgttgatgat attatatttg gtctactaa cgagtctaca tgtgaagagt     145260
ttagtaggat tatgacacag aaattcgaga tgtctatgat gggggagttg aagtatttct   145320
taagatttca agtaaagcaa ctccaagagg gcactttcat tagccaaaca aagtacactc   145380
aagacatcct aagcaagttt ggaatgaagg atgccaagcc catcaaaaca cccatgggaa   145440
ccaatgggca tctcgacctc gacacgggag gtaagtccgt ggatcaaaag gtataccggt   145500
cgatgattgg ttcattgctt tatttatgtg catctcgacc ggacattatg ctctccgttt   145560
```

```
gcatgtgtgc aagattccaa tccgaccta aggaatccca ccttacggcc gtaaaacgaa 145620
tcttgagata tttggcttat acacctaagt ttgggctttg gtaccctcgg ggatccacgt 145680
ttgatttgat tggttattcg gatgccgatt gggcggggtg caaaattaat aggaagagca 145740
catcggggac ttgccagttc ttgggaagat ccttggtgtc ttgggcttca agaagcaaa 145800
actcggtcgc tctttccacc gccgaagccg agtacattgc cgcaggacat tgttgcgcgc 145860
aattgctctg gatgaggcaa accctgcggg actatggtta caaattaacc aaagtccctt 145920
tgctatgtga taatgagagt gcaatcaaaa tggccgacaa tcccgtcgag catagccgca 145980
ctaagcacat agccattcgg tatcattttc ttagggatca ccaacaaaag ggggatatcg 146040
agatttctta cattaatact aaagatcaat tagccgatat ctttaccaag ccacttgatg 146100
aacaatcttt taccagactt aggcatgagc tcaatattct tgattctaga aatttctttt 146160
gctagcttgc acacatagct catttgaata cccttgatca tatctctttt atatgctatg 146220
actaatgtgt tttcaagtct atttcaaacc aagtcatagg tatattggaa gggaattgga 146280
gtcttcggcg aagacaaagg cttccactcc gtaactcatc cttcgccatc actccaacca 146340
tctctctatt ctttggggga gaaatgagca tcaaagaaaa ggacttcgtc tttggtataa 146400
tcttaactca tttacttatg accaaaggag aagaaattac ttcgagggct ctaatgattc 146460
cgttttggc gattcatgcc aaaaaggggg agaaaggagc ccaaagcaaa aggaccgcac 146520
caccaccaat ttcaaaaact tagtgttttc caagaaatat ttatcaattg gcatcctatc 146580
gtgttcaaaa ggggggagaaa gtagtatttc aaaaatgata tatcaaaacc ctcttgaaca 146640
ctaagaggag gatttaattt aggggggagtt ttgtttagtc aaaggaaaag catttgaaac 146700
aggggggagaa aacttcaaaa tcttgaaaat gctttgcaaa aatcttattc attcacctt 146760
gactatttgc aaaagatctt tgaaatggac ttacaaaaga atttgcaaaa acaaaacatg 146820
tggtgcaaac gtggtccaaa atgctaaata agaaagaaa cattccatgc atatcttgta 146880
agtagttata ttggctcaat tccaagcaac ctttacactt acattatgca aactagttca 146940
attatgcact tctatatttg ctttggtttg tgttggcatc aatcaccaaa aaggggggaga 147000
ttgaaaggga attaggctta cacctagttc ctaaataatt ttggtggttg aattgcccaa 147060
cacaaatctt ttggactaac ttgtttgccc aagtgtatag tgtatacagg agtaaaaggt 147120
tcacactcag ccaataaaaa gaccaagttt tggattcaac aaaagagcaa aggggcaacc 147180
gaaggcaccc ctggtctggc gcaccggact gtccggtgtg ccaccggaca gtgaacagta 147240
cctgtccggt gcaccagggg actcagactc aaactcgcca ccttcgggaa tttctaaggc 147300
gactcggcta taattcaccg gactgtccgg tgtacaccgg acagtgtccg gtgcgccaag 147360
ggaggtcggc ctcaggaact cgctagcctc gggttcgcgc ggcagccgct ccgctaaaat 147420
tcaccggact gtccggtgtg caccggactg tccggtgtgc cagcggagca acggctccct 147480
gcggcgccaa cggctccctg cggtgcattt aatgcgcgcg cagcgcgcgc agacgccagg 147540
cacgcccata ccggtgcacc ggacatcaaa cagtacatgt ccggtgtgca ccggacaccc 147600
aggcgggccc acaagtcgga agcttcaacg gctagaatcc aacggcagtg atgacgtggc 147660
aggggcaccg gactgtccgg tgtgcaccgg actgtccggt gcgccatcga gcagacgcct 147720
ccagccaacg gtcaagtttg gtggttgggg ctataaatac cccaaccacc ccaccattca 147780
tagcatccaa gttttccact tcccaactac tacaagagct aggcattcaa ttctagacac 147840
atacaaagag atcaaatcct ctccaattca tcacaaagcc ctagtgacta gtgagagtga 147900
tttgtcgtgt tcatttgagc tcttgcgctt ggattgcttc ttttctttct cacttgttct 147960
```

```
tgagatcaaa actccattgt aatcaaggca agaggcacca attgtgtggt ggcccttgcg   148020
gggaagtttt gttcccggct ttgatttgag aagagaagct cactcgatcc gtggatcgtt   148080
tgagagaggg aagggttgaa agagacccgg cctttgtggc ctcctcaacg gggagtaggt   148140
ttgcaagaac cgaacctcgg taaaacaaat ctccgtgtct cacttgctca ttcgcttggg   148200
atttgttttg cgccctctct tgcggactca ttccttatta ctaacgctaa ccccggcttg   148260
tagttgtgtt tatatttgca aatttcagtt tcgccctatt cacccccctc taggcgacta   148320
tcaattggta tcggagcccg gtgcttcatt agagcctaac cgctcgaagt gatgtcggga   148380
gatcacgcca agaaggagat ggagaccggc gaaaggccca ctacaagcca cgggagcact   148440
tcatcggaag agtctcgcac caaaaggagg gagaagaaga agagctcctc caacaaaggg   148500
aaggagaaga aatcttcttc tcaccacaaa gagaagaagg aaaaatcttc ttcccacaag   148560
ccgcatcgga aaggcgacaa gcacaaaagg atgaggaagg tggtctacta cgagaccgac   148620
acttcatcaa catcgacctc cgactccgat gcgccctccg tcacttctaa gcgcaagag   148680 cgcaagaagt atagtaagat ccccctacgc taccctcgca tttccaaaca tacacccttta  148740 cttccgtcc cattaggcaa accaccaact tttgatggtg aagattacgc taggtggagc   148800
gatttaatgc gatttcatct aacctcgctc cacaaaagca tatgggatgt tgttgagttt   148860
ggcgcgcagg taccatccgt aggggatgag gactatgatg aggatgaggt ggcccaaatc   148920
gagcacttca actctcaagc aacaacaata ctcctcgcct ctctaagtag agaggagtat   148980
aacaaagtac aagggttgaa gagcgccaag gagatttggg atgtactcaa aaccgcgcac   149040
gagggagacg agctcaccaa gatcaccaag cgggaaacga tcgaggggga gctcggtcgg   149100
ttccggcttc acaaaggaga ggagccacaa cacatgtaca accggctcaa gactttggtg   149160
aaccaagtgc gcaacctcgg gagcaagaag tgggacgatc acgaagtggt aaatgttatt   149220
ttaagatctc tcattttttct taatcccact caagttcaat tgattcgtgg taatcctaga   149280
tatactaaaa tgaccccga ggaagttatc gggcattttg taagttttga gtgcatgata   149340
gaaggctcga ggaaaatcaa cgagcttggc gactcatccg aagcccaacc cgttgcattc   149400
aaggcaacgg aggagaagaa ggaggagtct acaccaagtc gacaaccaat agacgcctcc   149460
aagcttgaca atgaggagat ggcgctcgtc attaagagct tccgccaaat cctcaaacaa   149520
aggaggggga aagactacaa gtcccgctcc aagaaggttt gctacaaatg tggtaagccc   149580
ggtcatttta ttgctaaatg tccaatatct agtgacagtg accgaggcga cgacaagaag   149640
gggagaagaa aggagaagaa gaggtattac aagaagaagg gcggcgatgc ccatgttgt   149700 cgcaaatggg actccgacga gagctcaagc gactcctccg acgacgagga tgccgccaac   149760
atcgccgtca ccaagggact tctcttcccc aacgtcggcc acaagtgcct catggcaag   149820 gacggcaaaa agaagaaggt taaatccaac tcctccacta aatatgaatc gtctagtgat   149880
gataatgcta gtgatgagga ggaaaatttg cgtatcctct ttgccaacct taacatagct   149940
caaaaggaaa aattaaatga attagtcagt gctattcatg aaaaggatga ccttttggat   150000
tcccaagagg attgtctaat taagaaaaac aagaaacatg ttaaggttag aaaggcttat   150060
gctctagaag ttgagaaatg tgaaaaattg tctagtgagc taagcacttg ccgtgagatg   150120
attgacaacc ttagaaatga aaatgctagt ttaaatgcta aggttgattc tcatatttgt   150180 aatgttttcaa ttcccaatcc tagagataat aatgatgagt tgcttgctag gattgaagaa   150240
ttaaacattt ctcttgctag ccttagatta gagaatgaaa atttgattgc taaggctaaa   150300
```

```
gattttgatg tttgcaaagt tacaatttcc gatcttagag ataagaatga tattcttcat 150360
gctaagattg ttgaacttaa ttcttgcaaa ccctctacat ctattgatga gcatgtatct 150420
atttgtacta gatgtagaga tgttgatgtt aatgctattc ttgatcatat ggctttaatt 150480
aaacaacaaa atgatcatat agcaaaatta gatgctaaaa ttgccgagca caacctagag 150540
aatgagaaat ttaaatttgc tcgtagcatg ctttataatg ggagacgccc tgacattaag 150600
gatggcattg gcttccaaag gggagacaat gtcaaactta atgcccctct aaaaacttg  150660
tctaactttg ttaagggcaa ggctcccatg cctcaggata acgagggtta cattttgtac 150720
cctgccggtt atcccgagag caaaattagg aaaattcatt ctaggaagtc tcactctggc 150780
cctaatcatg cttttatgta taagggtgag acatctagct ctaggcaacc aacccgtgcc 150840
aagttgccta gaaagaaaac tcctattgca tcaaatgatc atgctatttc atttaaaact 150900
tttgatgctt cttatgtgct tacaaacaaa tccggcaaag tagttgccaa atatgttggg 150960
ggcaagcaca aggggtcaaa gacttgtgtt tgggtaccca agttattgt gtctaatgcc  151020
aaaggaccca aaccatttg gtacctaaa gtcaagaact aaatttgttt ttgtaggttt   151080
atgcatccgg gggctcaagt tggatactcg acagcggtg cacaaaccca catgaccggg   151140
gagaaaagga tgttctcctc atatgagaaa aaccaagatc cccaacgagc tatcacattc 151200
ggggatggaa atcgaggttt ggtcaaagga ttgggtaaaa ttgctatatc acctgaccat 151260
actatttcca atgtttttct tgttgattca ttagattaca acttgctttc tgtttcccaa 151320
ttgtgtcaaa tgggctacaa ctgtcttttt actgatgtag gtgtcactgt ctttagaaga 151380
agtgacgatt caatagcatt taagggtgtg ttagaggggtc agctatactt agtagatttt 151440
gatagagctg aactcgacac atgcttaatt gccaagacta acatggggttg gctctggcac 151500
cgccgactag cccatgttgg gatgaagaat cttcataagc ttctaaaggg agaacacatt 151560
ttaggattaa caaatgttca ttttgagaaa gacaggattt gtagcgcatg ccaagccggg 151620
aagcaagttg gcactcatca tccacacaag aacataatga caagtgacag gccactggag 151680
ctcctccaca tggattatt cggcccgatc gcttacataa gtatcggcgg gagtaagtac 151740
tgtctagtta ttgtgatga ttattctcgc ttcacttggg tattcttttt acaggaaaaa 151800
tctctaaccc aagagacatt aaagggattc ttgagacggg ctcaaaatga gacgaatctc 151860
agatcgtctg tatagattan nnnnnnnnnn nnnnnnnnnn nnnnnnnnnn nnnnnnnnnn 151920
nnnnnnnnnn nnnnnnnnnn nnnnnnnnnn nnnnnnnnnn nnnnnnnnnn nnnnnnnnng 151980
catcttgcaa cctcacagac cgtggcgtgc tctggtcagg cgcggacggt cccagccttg 152040
ggcggacgtc cgagccttgg gtcggacggt ccgcgacctg ggcgaggagc ggtgtcttcc 152100
ctgcgtcaca ccgcacgtcc gcagctctgg gccggacgtc cgcgacctgg cgacagggtc 152160
gtcttcctac tccttgctgg aatctagatc tcgtccctg ggggaaagat cttaaggtgc  152220
tccgggtcga caggtcaccc ggggcgtccc cagacgacgt ggagtcgcct aggaattaag 152280
agatcaaatc gaggaagaag tcttggatgg acaactagat cttgccccc ggaggggtga  152340
gatcctaggg tcgtcttggg atcggcaggc cacccaagac ggatctagac gacgtagagt 152400
tgaatagggg tggaggtgga tatgtggaag actacaacta gaactatgct acatctactc 152460
ctagggcagg aaaagtaaat aaggtaattg gttcgattgg aatgtgttcg ggggttctca 152520
atcggccgta cccctttata tttatagggg aggaggtctg gaccttttcc taagagatag 152580
ccaacaaact cccacgtgat tagatggata accacgcacg agataaggat aaacatccga 152640
gttaatctaa tctcgggaca cgcggaccgt ccgggcccat gggccggacc gtccgctcat 152700
```

```
tttggtgtcc aacatatgcc ccctgcctt ttggtggagc atggcgaacc aaaagcatta 152760
gcgaaaactt cggaaacaat tgacctcatg aggttttttt ttccgaagta aggactcagc 152820
tcgatgcaag tcatcggctc ttgcgatcag ataatataaa tacttgatgg gactttaatg 152880
cacagaggcc gtttcggatc gcatcctctt cagccatgtc tatctgatca acctgtcaat 152940
aggcaaaaac ttgtggtgcc ccccagccca aataagcaaa cggattgggc cagtaataca 153000
aattcatcgc cgtaccaccc cacacatgag taggacaaca catcggcgat ggatagaatg 153060
ggacgcacca tgctatccct ggaggaggat gataaggcga tattggttgt gctacccttt 153120
gggtccgttt agtcggcttt tgctttcgca cagatcgccc tattgacttt gtttgtttta 153180
ttggccggtt gtgtggaacg gccttcttca tatatttggc aagcaactga ccaaaagtag 153240
ggccgactct actgagtcgt ccagacgtct tagtagtgtt ttgtttccta acacttgtgt 153300
tggaacgttg tggtccgatg gtctgaggtt gctgcttctg accatctgcg gaccgtccgg 153360
ccatcatagc cggactgtcc gcgcctgtct cggactgttc ggccttagta cccggatcgt 153420
ccggcgtacg catgacaggc gaccgtgatc gggtgtccga tcgtgcttgc ccccggtgc 153480
ctccggtctt tcttttgtcc ggagccttca gagtaaccat tctgcgtgac atatttggtg 153540
tgcgaggatc accaatgacg atattttat ttttactttt atcggccgca caaggccgaa 153600
ttatggcctt tttgctcatg ggctctaatg tggtgacagg aacaggtggc ctgtcaattt 153660
tcacctcttt ttgaaacctc aaccggcctt cgtttatagc cgattgtatt tgccgacgga 153720
agacggcaca atcattggtg ttatggagaa aggagccatg ccatttgcaa taaacacgcc 153780
cttttaattg ttcaaccgga ggaattacat gtgacaattt aatattacca tgtttaagca 153840
actcatcaaa tattttatca catttagtaa tattaaatgt gaacttaacc ttttcctttt 153900
gtttcgagtg cgggtaagag cgaacagaag gtttggcctt agtgggccaa acaagctcag 153960
ggacatgtga ctttttagt tcttggggct tgggtggccg attatattta tgtcggcctt 154020
ccgcactagg tggatcacag gtgacttctg gtgccccgga cggtccgact tgcacagtcg 154080
gacggtctgc gggtggatcg gacggtccgg tactatcctc ggacagtccg gtcacgtcag 154140
gcaacacctg tgacccttgt ggtgggctct gtgtaactcc agactgtccg gcgtagggtg 154200
ccggacggtc cgacagaggg ccggacggtc cgcaattgtg tgcggacggt ccggctgtgc 154260
ccagggttga ctcaccattt agcaaagatg gtgatgacgg tcgtcctaga tatgagtcca 154320
tcggcatacc agaatatggc tggggaaacc catttgccgc cgatgtgttt ggcgcaattg 154380
tttcatcgcc taatttatgt gataaaaaat taggcatgtg agttttttcct aatgcatgtg 154440
tcatcctctc tatatcctcc gtgatacttt taatccgatt atcaaaagaa attttaatag 154500
atggaatatc atcggctgac ctggcatcac ctattgtggg gagctgttgc agcacggcta 154560
acatatactc ggcgtttatc tccctctctt ggacggtctt ctggtggcag tctaccttga 154620
agtgcgagag gtaccacttg tccgccacct tgagcacctg atccttttgt cggtgggcct 154680
cctcgtctat tttcttcatg tcatcttcta attttttatg ctcagcggcc gataaattag 154740
tcagccttgt gttgctgttt ggagaagcac tgttgagatc tttagaatcg gccatgtaag 154800
cctgattttg tagatctgca acttcttccc cagcggagtc gccaaaaagt atgttgacgc 154860
cttttttggag cgccaaacac tcaacaagaa ccgtggcggt gccctctggt caggcgcgga 154920
cggtccgcag ccttgggccg gacggtccgc agccttgggc cggacggtcc gcgacctggg 154980
cgcaggagcg gtgtcttccc tgcgtcacac cggacggtcc gcagctctgg gccggacggt 155040
```

-continued

```
ccgcgacctg gcgacagggt cgtcttccta ctccttgctg gaatctagat ctcgtccct  155100
gggggaaag atcttaaggt gctccgggtc gacaggtcac ccggggcgtc cccagacgac  155160
gtggagtcgc ctaggaatta agagatcaaa tcgaggaaga agtcttggat ggacaactag  155220
atcttgcccc ccgggagggg tgagatccta gggtcgtctt gggatcggca ggccacccaa  155280
gacggatcta gacgacgtag agttgaatag gggtggaggt ggatatgtgg aagactacaa  155340
ctagaactat gctacatcta ctcctagggc aggaaaagta aataaggtaa ttggttcgat  155400
tggaatgtgt tcggggggttc tcaatcggcc gtaccccttt atatttatag gggaggaggt  155460
ctggaccttt tcctaagaga tagccaacaa actcccacgt gattagatgg ataaccacgc  155520
acgagataaa gaaaacccc cnnnnnnnnn nnnnnnnnnn nnnnnnnnnn nnnnnnnnnn  155580
nnnnnnnnnn nnnnnnnnnn nnnnnnnnnn nnnnnnnnnn nnnnnnnnnn nnnnnnnnnn  155640
ngaattccaa gatttaaata gaagtctttt ataatgagag attaaataaa agaccctcat  155700
ataatttaaa ccaacccttg ttgaataaca tgattagaga tattctccaa aagaattaag  155760
cttaaaaaac cttaataaat actatacaca caaaaaaatc ctctatctta aaaattatga  155820
acataatttt aaatggacta tacattcaaa gaagtaattt ttactctatg tgtgtgcatt  155880
gcatacttaa aatatttgga taaaataaac aaaactaaac agatatatgt aattattgca  155940
tatcatgccg gagttttgga ttgagcattt agattagagt ttaaaataag ggaaagaaat  156000
atgaaaggga agataaaaca gaaaatcatt aaagaataaa gaaaaagggg aagctttctg  156060
cgctatgggc cggatctctg gcttctcggc ccagtttctt tccttcgtta gcgggcccaa  156120
ctctatttcc ctgctccggc gcagcccgct cctgcccact ctcgcgcctg cagccgcgtc  156180
tggcatgtgg gccatggccg tcaagtctat cctcccatg gcgatcctgc tcgtccgctg  156240
caagctcgcc tcctgtaaac tgtgcaacga ccttcgtgcc atggtgcacc cgcccactgc  156300
tagccgtacc cctggccata taacggac gctccaacct cggccatggg tgcagctcta  156360
gtttcctctc cttcagcatc gtgggctacg ctcggtctgc cgatcgggag agaaggcgcc  156420
atcaccatcg tcgtaaggga gaaggagaac acaggggggtg aattgccacc gacgggggtt  156480
cccgggcacg ccggtattgc ggtctcggcg tcggggttggg tcatccgtgg gacgcgtgca  156540
ggattctaga aggcacctcg tgcgagaaca acgaccagtg catgcttcgc tggtgacccg  156600
cggcgccacg gagcaactgc gtggtgggggt caacacttga aacaccgtga tccttggtaa  156660
gaacagccct agcatacttg gagcctcctc ctctccgtga ttcacgtacc cacgctcgat  156720
actaggaaat ggggagccgg gcgggatatc actggtggtg tggtggggca tggccgcggc  156780
gtgcccgcac cagtgctctg ctttccgtcg tgaggtggaa ggaaatgcag cagccgttag  156840
atcatgggtg agcgatcacg atcagggcat ggctgggcct cgcgtgaacc gtggatctgg  156900
gaggtatcgg ctgtgattag atcacacgta acgtttcatc cgaatcgatc cgggtcgtct  156960
gatctggatc ttgcatatga ggatcgatct ctattatttt aagcgtgggc cgtttatcgt  157020
agatccgacg atctaggatg cgtaccggtt cggcgggcaa atcttctact ctgggcgctt  157080
ggctgatgat ccaaggaatt agtcacgtgt accccttcac cgtgactaac ttataaagga  157140
gacccccagac ttcttgcaaa tcagcccgca gtccgggtat aggtagaaat cattgcggat  157200
aagtcctaaa tattatatgg agccccctga tctttttatag aatagtgtcc ccaatccaga  157260
aatatttaat aattatagaa ttaaatccta aaacttaata aatacatatc tctttcattt  157320
taactctgat ttaatgtatt catgttgcgt tagcttcgta ataattttgc ctacgcttct  157380
gtaaaattat tttagcaaat agcatgtttc caaaaaataa atattcattt aatatatgct  157440
```

```
tagtagatta ttcctactaa tcaaagttag tttgtctatg attataaggt aactaaaata    157500
ttatgtctac tctagtatga tgtagattaa agttatttct ttaatatctt tatcacataa    157560
tttataaaat caacataaag acctagtctc atatttaatc acataggtct tccgaaaacc    157620
acatcttgtt aaccgtaact ccgaatttag tggttctcga acctaggatc tcgttgtggt    157680
gcgtagatca ttattatgca gtttgttctt tatgtttggt gtgatgttaa ttttgcctat    157740
accatgtttg tttgtattgc tatgattagc agcgaggtta cgagaatctt gaagaccaag    157800
ctggtaccta ggaatcttga gtctcagcca agttgtgccc ttgatcactt ttctttacct    157860
aataatgttc ctattaatca ctgtgacatg ctcaggttaa tttgatggga cccaataggt    157920
tttcctagta ttgtttatcc cctaccttgc aaacaaaagc actattgggt agtattgcta    157980
ttgctctacc tggttttggg aaattaatgt tacattatga tcatgttaca attcttttgt    158040
tattttaatt attgttcatg ataagattgc tatgttaatt ggaacatgga gcaaccaccc    158100
aggaaaacag tgctaccaca agggtggtat gggacgccct tggctgacta attaagaaag    158160
ctagtggaag actaccttac ccgaaagggg caagggcggt agaggagcat gcgtataggg    158220
aggttctcga gtcgatcatg ctgcgatggc ttttggacg agggattcct atattttcct    158280
tcttagaaac cgtagcgggt tttcggaagc tagtggaagt ttgtaaaggc ctcgtagtgg    158340
taacctacct tgtcttctcg gtagagatga atgagaagtc gcgatccctt ggcaaatagg    158400
taacatgact tgtgggtaaa gatgtgcaac ctgtgcagac tgtaaaactg ttatatcagc    158460
cgtgctcacg gtcatgagca gctcggaccc tcacatgagt aaattatgga actaaactta    158520
aattgtcata tgcattgcat tgtgggtgtt gttattaatt taatctctta tttatttggg    158580
tcggtatcta cttatactta gtaactgcta ataaaatttt gaccaacttt aaaagtcatg    158640 ctcatctttta cccatctcct ttggtaagcc ttacacttca catgagctcc cacctttggt    158700
gagttcatac acattattcc ccacaacttg ttgagcgatg aacgtatgtg agctcaccct    158760
tgctgtactc aaatccccct ggtcaagaac aggtaccgca agatgaggag catgaaggat    158820
gtcgcgatga gttcatgaga ggtctaggcc gtcgtctcac agtaaacttt gggttgatgg    158880
atcgtcgtca tcgtatgatg taattattta gttattttgt gcagaacttc tattatatag    158940
taaagatgtg acatttgttt ctataccatg agtcatcata tgtgtgagac tcgatcccag    159000
cacttggtga atttcgcgcc tgggttttgg accctaaaa ccgggtgtg acatgctgct    159060 gttgagggaa ctgcctctgg aattgctact ggtgcgaaca ttggttctgg tgttggtatc    159120
cctgagggtg gatctacttg aactgctagg gtggattgcc agaaacggga gacgactgct    159180
gctcctggcc tagggtccac caatcttgcg cttttggtct tccatctcct ggcgcttcct    159240
ctcagtcatt attgccctat caatcagatg ttggaaggta gggaatgtgt ggttcatcaa    159300
ctagtagtgc agggtcaac caaccctctc ggaaacctgt agtacctctt agcatcaatg    159360
ttgacatcct cgggtgcatt gtgagatagt tgcaggaatt tgtccatgta ctcactgaca    159420
gacaggggcc cttgcttcag tgccagaaat tcttccttcc tcactatcat caaaccttgt    159480
agaacgtggt acccgcagnn nnnnnnnnnn nnnnnnnnnn nnnnnnnnnn nnnnnnnnnn    159540
nnnnnnnnnn nnnnnnnnnn nnnnnnnnnn nnnnnnnnnn nnnnnnnnnn nnnnnnnncg    159600
cgcggaggcc ggtttgtcgg tgccggtttc tttcacgcaa cacgcccgct ccttttttgcc    159660 tcggtgggtc ggcctgtcag cgcagaaccg ctcgttcgcg tattcaccct cgctggcaag    159720 cggacccccac ctgtcagcca cctcccctttt ccctaaccac ccgctcgcgc accccgccgt   159780
```

```
ggatgcacac atgtcgcgtg ttttcggcc actccccca cgcgcctgac ttttttggag    159840
cccacactca ctcgctcact cccctcgctc agtagcgtcc cacagccgac ccctcgcac    159900
ctctctctcg caccgagcgc acagccgtgg agcactgccg tagtccaccg tccgttccgt    159960
ggccgtcgtc gagttcctgt cgcgtccatt gccctactga tcttcgcctc ctcgccagca    160020
acacgagaca ccctctggtt ttccccagcc cctctatttc ccttggttcg ctcaccggac    160080
ctatcaccat gcagccgagt ctccgccacc gtccaccagg ccctcgcgg tgtcctcgcc    160140
gttgctcaag cgctctagag tcatctctcg acgtaaccaa cccacccatg cccttaattt    160200
cccatttact gccctgttgt ccatgcaatc gctcgccaga gttaagctgc gccgccgtgg    160260
ggctgctttg cctcggaccg tgctctctgg tgcctctacg ccggtgtcgt gcccatggct    160320
gagcccgccg tgtcaccctg agctcgcctg agccttttcc cagcgccag accctcacca    160380
tggccgcgcc acgccgcgaa attgggcggc ggcgccatga gcagcctagc aaccccgccc    160440
gagcttgcca tcagatttca ggcatccatc tgagatctaa cgacctggct tcaattaaac    160500
tcgatctgat cccagctgtc cgatggagat ctggccactc ggatccgcca cctcacccgc    160560
gccctgcagc taggcccggc cagacagtcc gcctcgcccc taggtcgctg actatcctgg    160620
cccacctgtt agctcgtgct cgtgctcgcg ctcaaatcta atcctggccg ttgatctgtg    160680
atcatgcagt cgagatcagc tgatacccct ttgcgtggta gttttgttaa aaaggccctc    160740
ggctttctga gaatcaaccc atcgtccctg gttttcgcac gcatgcccct gtacttttgc    160800
agaaaggccc ctaatctttt aggttatcac ataattagac ctagttttgt attttgaatt    160860
ccaaaacttg tttatttcat atcttttgca tatgaactcc aaattgagtg attcaaattg    160920
caaaatgttt gtaaggttat tctctacctg tttaaattat aaccttttac tgtctgcatg    160980
tgctaatttt atgcctagac tataggttag tgtaactgat ggcttattta ttaataagaa    161040
ggataaaagg aaaaccataa tggtagttag atgtttaact ttgtgggtta ataatatgta    161100
atatatgaac ctatccctgg tataattctt ttgtctcatt aagataaatg aaattaagtt    161160
atgtaatcta ttgagataag taatacttag agaaccacaa acctatatgt gtattggtcc    161220
accctagacc ctaggcttcg cttgagtttg ttactttctt ttgaattagt gttcacttga    161280
ttgtatattt ttggtgtatt gtttctttat cattatcgaa atgtgttgaa tgcatgatcg    161340
ctttgcgtag acaacaagca gtctatggtt cctgagtgtg ttgccgaaga tcttcctggg    161400
caacaacctg gtgaaggcaa gtgtcctctg acctattatg tcctacttac ttcataattc    161460
actgtccccc tttacttaat tgaaacctaa ggtttgacta gtctgtattt atcttgtcct    161520
tgtttacctt ttgggttatt atggtaagct tcaagctatt gctccacttt aatcaacaaa    161580
catgatgcga atatttatga tatgatgttg ttattatgat tacgatgatg ttcttatggc    161640
actttaggag actcaggcta ttttcctgag tacctttcct ttggacctgc tcgttgagtg    161700
accacccgtg ataacagaac gaatcaagct gattcatcag cggccggg               161748
```

<210> SEQ ID NO 111
<211> LENGTH: 1348
<212> TYPE: DNA
<213> ORGANISM: Zea mays

<400> SEQUENCE: 111

```
tacaagaata ttgagacgtg agtacatagc attggcattt tcattagcaa gcatttcaaa     60
agaatttaat tttctcatag caatgtgata tctctcctca cgctcaattc tagttccttc    120
atgtagagca catatgtcca tccacaaatc atgacaattt ttatggtttc taactctatt    180
```

```
aaacacatct ttgcaaaggc ctctaaaaag ggtgtttttg gccttagcat tccatttctc      240
atagttcaac tcttcaccta caagatttgt gggatctcta ggttcgggga atctttgtgt      300
ggcggctttg tagacaccaa tgtctatagc ctctaaatat gcttccatac gaattttcca      360
atatggaaaa tcgtcaccat aaaaaacggg agaaggtcca tccccaccgg acatcgttac      420
tctagcggtt aagctaatct aagagcaaca aggctcttat accaattgaa aggatcacga      480
tgcccaagag gggggttga attgggcttt tctaaaaatc aacactaact aaaatctaag       540
caagagccca acttcacccc gacaactagc actaagagaa taatactaga aatacaacaa      600
tgctaagata atacttcaaa tacttgctaa acaaatacac aatgtaaaat acttgaatta      660
agtgcggaat gtaaagcaag gtttagaaga ctcctccaat ttttctagag gtatcaaaga      720
gtcggcactc tcccctagtc ctcgttggag cacctgcgta agggtatcgc tctcccttgg     780
tcatcgcaag aaccaagtgc tcacaacgag atgatccttt gccactccgg cgcggtggat      840
ccctcacgac cgcttacaaa cttgagtcgg gtcaccaaca agatctccac ggtgatcacc      900
gagctcccaa cgccaccaag ccgtctaggt gatgccgatc accaagagta ataagccata      960
gactttcact tgaccaagag aagcctaatg catgcggtgt gtgctctagg tggctctcgc     1020
tagcgttaat gaggtccaaa tgcgggatta agattctcaa gtcacctcac taggctttgt     1080
ggtgcttgca atgctctacc aatgtgtagg agtaaatgtg ggcagcaaga ccatcaatat     1140
ggtaggtgga tggggtataa atagccctca cccaccaact agccattacc aggaatctgc     1200
tgcgcatggg cgcaccggac agtccggtgt gccaccggtg cgccaacggt cgactcaaac     1260
ggctagttct gacagctagc cgttggacag atggcatacc ggacagtccg atacgctgtc     1320
cggtgtgcct ctaaaattca actcacga                                        1348
```